US012576082B2

(12) United States Patent
Chen et al.

(10) Patent No.: US 12,576,082 B2
(45) Date of Patent: Mar. 17, 2026

(54) METTL16 INHIBITORS AND USES THEREOF

(71) Applicant: City of Hope, Duarte, CA (US)

(72) Inventors: Jianjun Chen, Temple City, CA (US); Xiaolan Deng, Temple City, CA (US); Li Han, Monrovia, CA (US); Hongzhi Li, Diamond Bar, CA (US); Rui Su, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 1043 days.

(21) Appl. No.: 17/632,963

(22) PCT Filed: Aug. 20, 2020

(86) PCT No.: PCT/US2020/047185

§ 371 (c)(1),
(2) Date: Feb. 4, 2022

(87) PCT Pub. No.: WO2021/035045

PCT Pub. Date: Feb. 25, 2021

(65) Prior Publication Data

US 2022/0339155 A1 Oct. 27, 2022

Related U.S. Application Data

(60) Provisional application No. 62/889,431, filed on Aug. 20, 2019.

(51) Int. Cl.
*A61K 31/519* (2006.01)

(52) U.S. Cl.
CPC .................................. *A61K 31/519* (2013.01)

(58) Field of Classification Search
CPC .............................. A61K 31/519; A61P 35/00
USPC .......................................................... 514/267
See application file for complete search history.

(56) References Cited

U.S. PATENT DOCUMENTS

| | | | |
|---|---|---|---|
| 4,118,561 A * | 10/1978 | Ledig |
| 2004/0039000 A1 | 2/2004 | Gangjee |
| 2014/0378486 A1 | 12/2014 | Xiao et al. |

FOREIGN PATENT DOCUMENTS

| | | | |
|---|---|---|---|
| GB | 1579678 A | 11/1980 |
| WO | WO-2019/226773 A1 | 11/2019 |

OTHER PUBLICATIONS

Ianniello et al. 'N6-Methyladenosine (M6A): A Promising New Molecular Target in Acute Myeloid Leukemia', Frontiers in Oncology, Apr. 9, 2019 (Apr. 9, 2019), vol. 9, pp. 1-11. (Year: 2019).*
Hewitt et al., Controls for Immunohistochemistry, J Histochem Cytochem. Oct. 2014;62(10):693-697. doi: 10.1369/0022155414545224 (Year: 2014).*
Taconic Printed White Paper https://www.taconic.com/resources/advantage-application-of-genetically-engineered-mouse-models-for-predicting-human-efficacy-and-metabolism) (Year: 2025).*
Srinivasan, B. et al. (May 2015, e-published Mar. 6, 2015). "Insights into the slow-onset tight-binding inhibition of *Escherichia coli* dihydrofolate reductase: detailed mechanistic characterization of pyrrolo [3,2-f] quinazoline-1,3-diamine and its derivatives as novel tight-binding inhibitors," *FEBS J* 282(10):1922-1938.
Extended European Search Report mailed on Sep. 11, 2023, for EP Patent Application No. 20853634.2, 8 pages.
Ianniello, Z. et al. (Apr. 9, 2019). "$N^6$-Methyladenosine ($M^6A$): A Promising New Molecular Target in Acute Myeloid Leukemia," *Frontiers in Oncology* vol. 9, Article 251, 11 pages.
International Search Report mailed on Nov. 20, 2020, for PCT Application No. PCT/US2020/047185, filed Aug. 20, 2020, 2 pages.
Wang, S. et al. (2018). "Novel Insights On $M^6a$ RNA Methylation In Tumorigenesis: A Double-Edged Sword," *Molecular Cancer* 17:101, 10 pages.
Written Opinion mailed on Nov. 20, 2020, for PCT Application No. PCT/US2020/047185, filed Aug. 20, 2020, 5 pages.

* cited by examiner

*Primary Examiner* — Jeffrey H Murray
*Assistant Examiner* — Grace Ching Hsu
(74) *Attorney, Agent, or Firm* — Mintz, Levin, Cohn, Ferris, Glovsky and Popeo, P.C.

(57) ABSTRACT

The disclosure provides, inter alia, METTL16 inhibitors and methods of treating cancers that overexpress METTL16.

11 Claims, 44 Drawing Sheets

METTL16 INHIBITORS AND USES THEREOF

CROSS-REFERENCE TO RELATED APPLICATIONS

This application claims priority to U.S. Application No. 62/889,431 filed Aug. 20, 2019, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant nos. CA214965 and CA236399 awarded by the National Institutes of Health. The government has certain rights in this invention.

BACKGROUND

Many advances in cancer therapy focused on the process of DNA methylation, including the discovery of mutations in enzymes that methylate DNA (e.g., DNMT3A mutations) and the process of DNA demethylation (e.g., TET2 and IDH1/2 mutations). Anti-cancer agents, such as DNA methyltransferase inhibitors (e.g., decitabine and 5-azacitidine) are known to treat cancer by impacting DNA methylation. While these treatments focus on DNA methylation, it has been known that RNA residues can also be modified, but the significance of RNA modifications is limited. Studies have identified that METTL16, which places a methylation mark on RNA known as $N^6$-methyladenosine, may impact cancer. The $N^6$-methyladenosine modification is placed on RNAs, and plays a role in regulating mRNA translation to produce proteins. In fact, METTL16 expression is unregulated in many types of cancers, and may be required for the survival and growth of the majority of types of cancer cells.

There is a need in the art for new and useful therapies that exploit the involvement of METTL16 in cancer survival and growth. The disclosure is directed to these, as well as other, important ends.

SUMMARY

The disclosure provides methods of treating cancer in a patient in need thereof by administering to the patient an effective amount of a METTL16 inhibitor. In aspects, the METTL16 inhibitor is compound of Formula (I), (II), (III), (IV), (V), (VI), (VIA), (VIB), (VII), (VIIA), (VIII), (A), (B), (C), (D), (E), (F), (G), (H), or a pharmaceutically acceptable salt of any one of the foregoing. In aspects, the methods further comprise detecting an expression level of METTL16 in a biological sample from the patient prior to and/or during and/or after administering the METTL16 inhibitor to the patient. In aspects, method comprises administering to the patient an effective amount of a pharmaceutical composition comprising the METTL16 inhibitor and a pharmaceutically acceptable excipient. In aspects, the cancer expresses an elevated level of METTL16. In aspects, the cancer is leukemia (e.g., acute myeloid leukemia, acute lymphocytic leukemia, chronic myeloid leukemia), glioma, glioblastoma, lung cancer, pancreatic cancer, liver cancer, thymoma, lymphoma, prostate cancer, head and neck cancer, fibrosarcoma, adrenocortical carcinoma, breast cancer, cervical cancer, ovarian cancer, bladder cancer, colorectal cancer, melanoma, multiple myeloma, thyroid cancer, cholangiocarcinoma, kidney cancer, or stomach cancer.

The disclosure provides METTL16 inhibitors, including compounds of Formula (I), (II), (III), (IV), (V), (VI), (VIA), (VIB), (VII), (VIIA), (VIII), (A), (B), (C), (D), (E), (F), (G), (H), or a pharmaceutically acceptable salt of any one of the foregoing. The disclosure provides pharmaceutical compositions comprising the METTL16 inhibitors and a pharmaceutically acceptable excipient.

These and other embodiments and aspects of the disclosure are described herein.

BRIEF DESCRIPTION OF THE DRAWINGS

FIG. 1A provides expression levels of METTL16 mRNA across the TCGA tumor types using the cBioPortal database. Each spot represents a single patient sample. White spots represent those analyzed without gene sequencing, black spots represent results of normal gene sequencing and dark spots represent missense mutations. See Cerami et al. The cBio Cancer Genomics Portal: An Open Platform for Exploring Multidimensional Cancer Genomics Data. Cancer Discovery. May 2012 2; 401; Gao et al. Integrative analysis of complex cancer genomics and clinical profiles using the cBioPortal. Sci. Signal. 6, pl1 (2013). FIG. 1B provides expression patterns of METTL16 expression levels in cancer samples and normal controls, based on the GEPIA2 database. Each dot represents a single sample. For each cancer type, the gray dot represents cancer samples, while the black dot indicates the healthy controls. See Tang, Z. et al. (2019) GEPIA2: an enhanced web server for large-scale expression profiling and interactive analysis. Nucleic Acids Res, 10.1093/nar/gkz430. FIG. 1C provides a comparison of METTL16 expression levels between acute myeloid leukemia (AML) samples (n=173) and normal control samples (n=70) based on the GEPIA2 database. See Tang, Z. et al. (2019) GEPIA2: an enhanced web server for large-scale expression profiling and interactive analysis. Nucleic Acids Res, 10.1093/nar/gkz430. FIG. 1D provides a comparison of METTL16 expression levels between human AML samples and normal controls (Ctrl) as detected by RNA-seq. See Su et al, Cell, 172:90-105 (2018). FIG. 1E provides a qRT-PCR analysis of METTL16 expression levels in human AML sample and healthy controls (mononuclear cells (MNCs), CD34+ cells and CD34 cells) $*p<0.05$; $**p<0.01$; t test. Error bars, mean±SD (n≥3). See Su et al, Cell, 172:90-105 (2018).

FIG. 10 shows that METTL16 is the most essential gene in the METTL family for human cancers as detected by CRISPR-Cas screening

FIGS. 12A-12B show the METTL16 abundance in the CD34+ and CD34− cells of bone marrow mononuclear cells (BMMNCs) collected from AML patients and healthy controls. FIG. 12C show CD34 (left panel) and METTL16 (right panel) levels in individual AML patient BMMNC samples and healthy control samples.

FIGS. 13A-13C show METTL16 levels in CD34+ cells versus CD34− cells of individual primary AML BMMNC samples. FIG. 13D shows the statistical results for the level of METTL16 in CD34+ cells versus CD34− cells of primary AML BMMNC samples. In each individual primary AML sample, METTL16 level is significantly higher ($p<0.05$; paired t-test) in CD34+ immature leukemia stem/initiating cells (LSCs/LICs) than in CD34− bulk AML cells.

FIGS. 14A-14C are immunoblot showing knockdown efficiency of METTL16 in AML cell line cells. FIGS. 14D-14E show the effect of METTL16 knockdown on cell growth in AML cell line cells.

FIG. 17A provides Kaplan-Meier curves showing the effect of Mettl16 knockout on MLL-AF9-induced primary leukemogenesis. FIG. 17B provides WBC count in the PB of recipient mice. FIG. 17C is the spleen weight. $p<0.01$; *$p<0.001$. FIGS. 17D-1F show the engraftment in PB, in BM and in spleen of recipient mice. $p<0.01$; *$p<0.001$; ****$p<0.0001$.

FIG. 18A provides bioluminescence imaging of AML xenografts upon METTL16 depletion. 0.1×10^6 MA9.3ITD cells labeled with firefly-luciferase were injected into NRGS mice. The unit of radiance is 'photons/second/$cm^2$/steradian'. FIG. 18B shows Kaplan-Meier survival curves of NSGS mice transplanted with MA9.3ITD AML cells that were transduced with shNS (n=7) or METTL16 shRNAs. $p<0.01$; *$p<0.001$ from log-rank test. FIG. 18C shows the spleen weight of recipients. *$p<0.01$.

FIG. 20A shows METTL16 gene expression in liver cancers (n=517) and normal control (n=214) from GENT2. Minimum, first quartile, median, third quartile, and maximum were displayed in the violin plots. P value derived from two-sided t-test. FIG. 20B shows METTL16 expression in 39 paired normal and cancer liver tissues (GSE57957). Minimum, first quartile, median, third quartile, and maximum were displayed in the violin plots. P value derived from paired t-test. The raw data were derived from GENT2 (Gene Expression database of Normal and Tumor tissues, http://gent2. appex.kr/gent2/). The FC in x-axis represents the ratio of Cancer/Normal. Thus, Log 2(FC)>0 indicates M16 in overexpressed in this cancer type; while Log 2(FC)<0 indicated the levels of M16 are lower in tumors compared with normal controls.

FIG. 22A shows the effect of METTL16 knockdown on cell growth in SNU475 cells. FIG. 22B shows the effect of METTL16 knockdown on migration and invasion of SNU475 cells.

FIGS. 23A-23C are longitudinal bioluminescence imaging of liver tumor xenografts upon METTL16 depletion. Equal amounts of HepG2 cells labeled with firefly-luciferase were injected into NSG mice and the tumors were monitored from 4 to 32 days after implantation. "photons/second/$cm^2$/steradian" is the unit of radiance. FIG. 23D shows total photon flux of the xenograft models upon METTL16 knockout. All data are plotted as mean±s.e.m. (n=8). *, P<0.001 from two-way ANOVA. FIG. 23E shows average growth curves of liver tumors with METTL16 depletion. NSG immune-deficient mice were injected with HepG2 cells upon METTL16 knockout subcutaneously. All data are plotted as mean±s.e.m. (n=8). *, P<0.001 from two-way ANOVA.

FIG. 24A provides tumor images at the endpoint of the xenograft models implanted with HepG2 liver cancer cells upon METTL16 depletion. FIG. 24B provides tumor weight of the xenografts from HepG2 cells with METTL16 knockout at the endpoints (day 33 post inoculation). Data are mean±s.d. (n=8). ***, P<0.001 from two-sided t-test.

DETAILED DESCRIPTION

Definitions

Figure 1A:
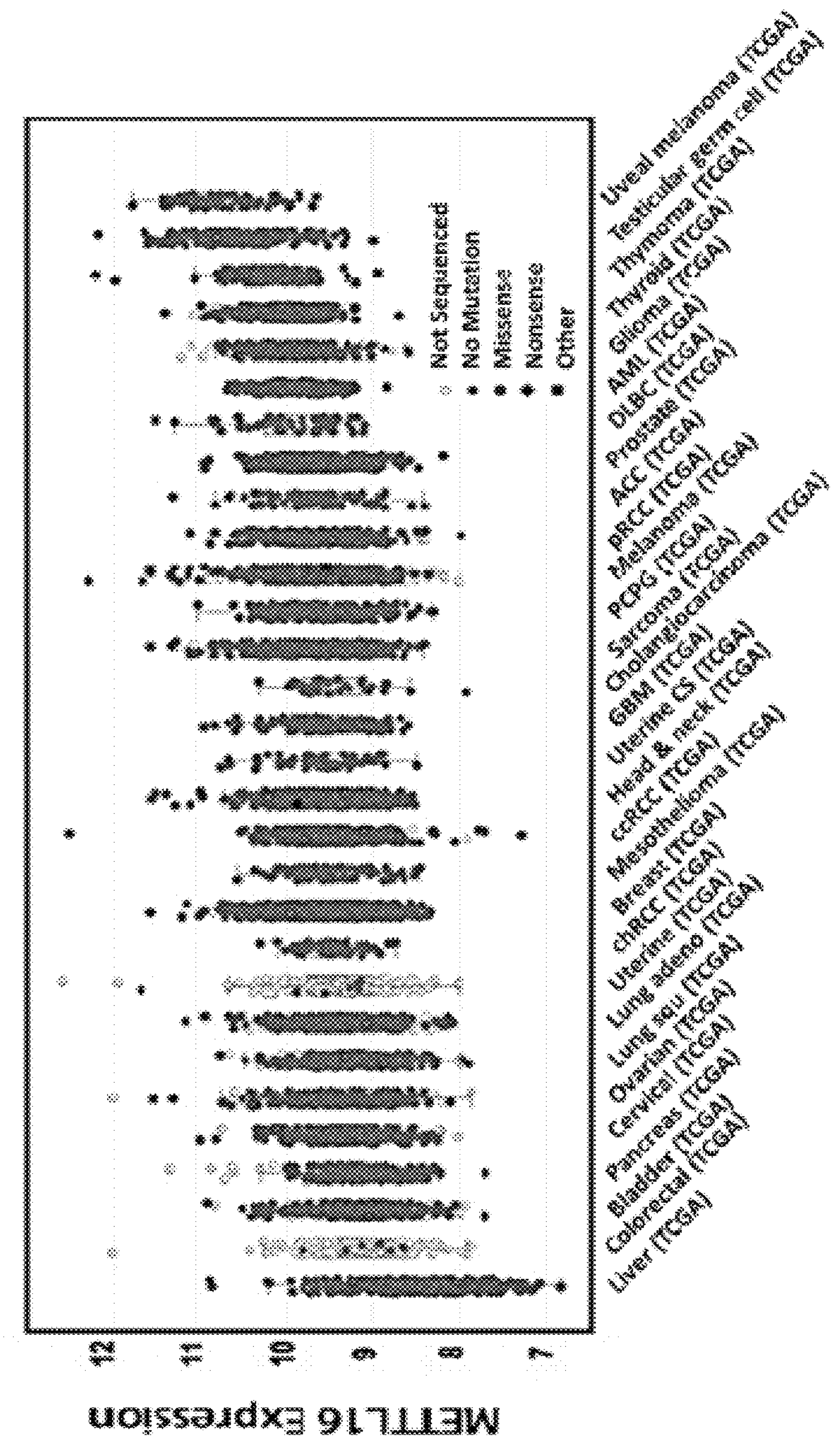
FIGS. 1A-1E show expression levels of METTL16 in cancers.
Figure 1B:
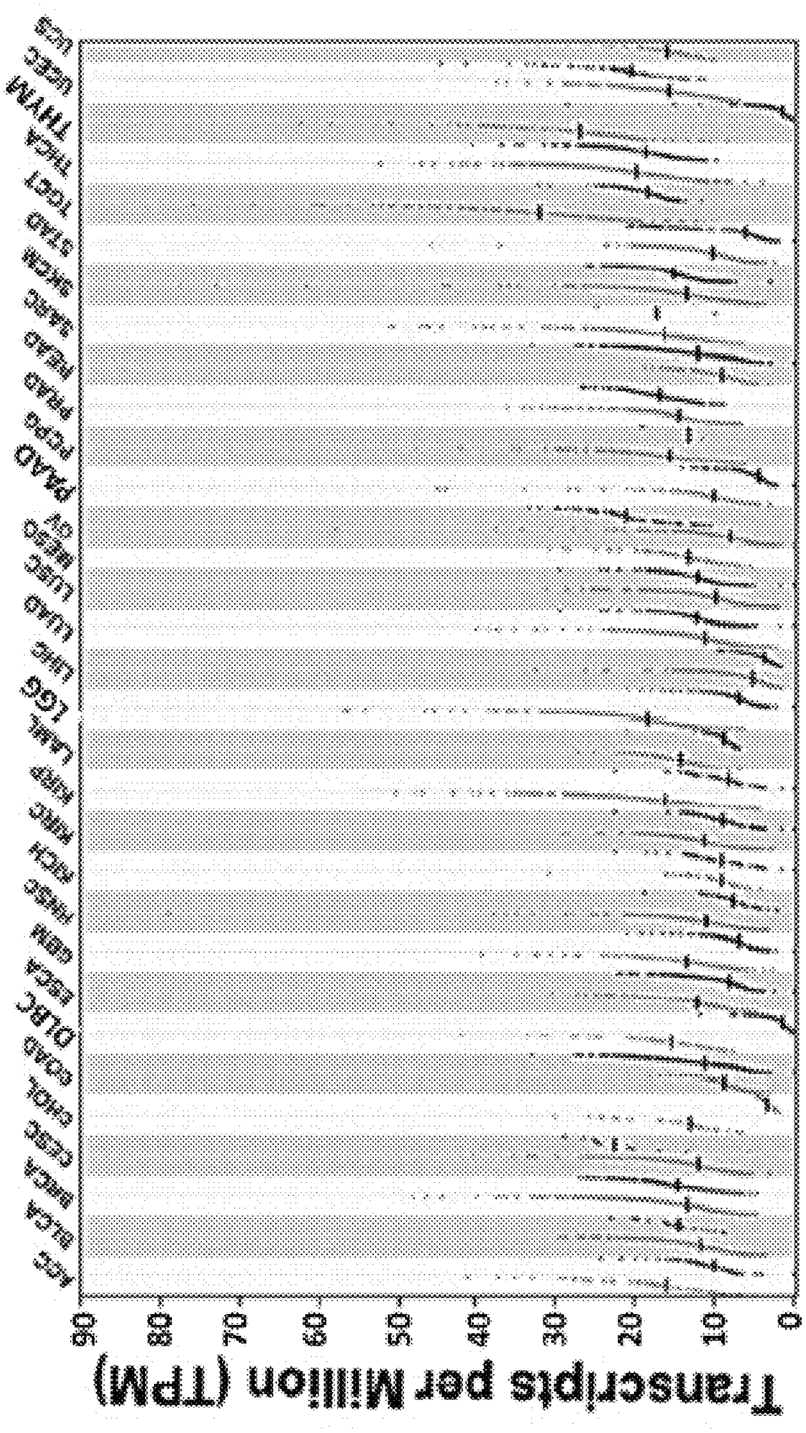
Figure 1C:
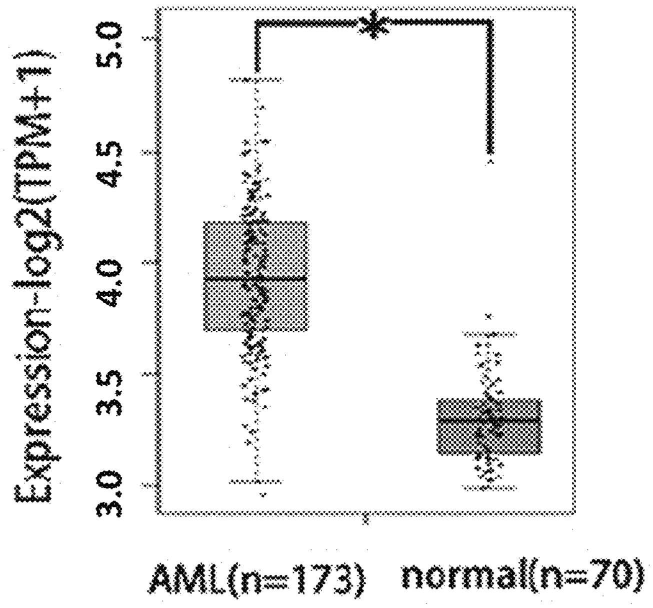
Figure 1D:
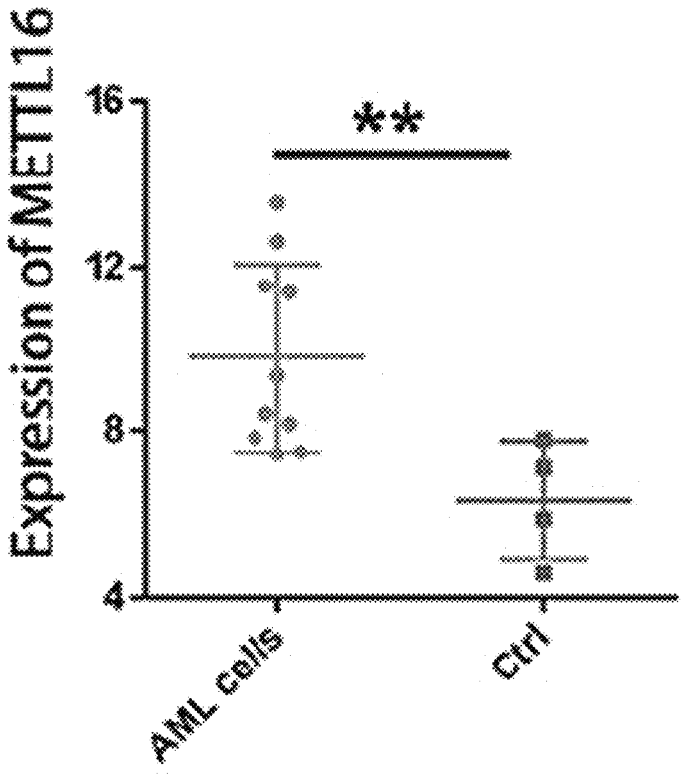
Figure 1E:
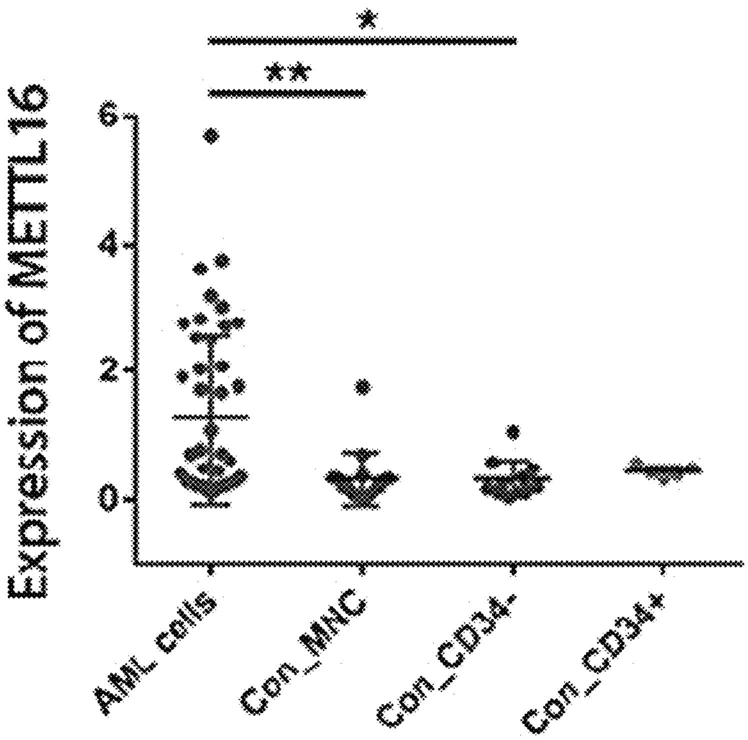

Unless defined otherwise, technical and scientific terms used herein have the same meaning as commonly understood by a person of ordinary skill in the art. See, e.g., Singleton et al., Dictionary of Microbiology and Molecular Biology, 2nd ed., J. Wiley & Sons (New York, NY 1994); Sambrook et al., Molecular Cloning, A Laboratory Manual, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

"METTL16" or "Methyltransferase Like 16" as provided herein include any of the recombinant or naturally-occurring forms of METTL16 or variants or homologs thereof that maintain METTL16 activity (e.g. within at least 50%, 80%, 90%, 95%, 96%, 97%, 98%, 99% or 100% activity compared to METTL16). In aspects, the variants or homologs have at least 90%, 95%, 96%, 97%, 98%, 99% or 100% amino acid sequence identity across the whole sequence or a portion of the sequence (e.g., a 50, 100, 150, or 200 continuous amino acid portion) compared to a naturally occurring METTL16 protein. In aspects, METTL16 is the protein identified as UniProtKB No. Q86W50, a homolog, or functional fragment thereof.

"An elevated level of METTL16" as referred to herein is an elevated level of METTL16 genes, proteins, RNA, or the like, expressed in a subject when compared to a control. METTL16 levels can be measured from biological samples, such as a tumor sample (e.g., resected, biopsy) or a blood sample (e.g., peripheral blood) obtained from a subject.

An "inhibitor" refers to a compound that reduces activity when compared to a control, such as absence of the compound or a compound with known inactivity. A METTL16 inhibitor refers to a compound that inhibits expression of METTL16. In aspects, the METTL16 inhibitor is a compound of Formula (I), (II), (III), (IV), (V), (VI), (VIA), (VIB), (VII), (VIIA), (VIII), (A), (B), (C), (D), (E), (F), (G), (H), or a pharmaceutically acceptable salt of any of the foregoing.

The term "inhibition," "inhibit," "inhibiting" and the like in reference to a protein-inhibitor interaction means negatively affecting (e.g. decreasing) the activity or function of the protein relative to the activity or function of the protein in the absence of the inhibitor. In aspects, inhibition means negatively affecting (e.g. decreasing) the concentration or levels of the protein relative to the concentration or level of the protein in the absence of the inhibitor. In aspects, inhibition refers to reduction of a disease or symptoms of disease. In aspects, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In aspects, inhibition refers to a reduction of activity of a target protein resulting from a direct interaction (e.g. an inhibitor binds to the target protein). In aspects, inhibition refers to a reduction of activity of a target protein from an indirect interaction (e.g. an inhibitor binds to a protein that activates the target protein, thereby preventing target protein activation).

"Biological sample" refers to any biological sample taken from a subject. Biological samples include blood, plasma, serum, tumors, tissue, cells, and the like. In aspects, the biological sample is a blood sample. In aspects, the biological sample is a peripheral blood sample. In aspects, the biological sample is a tumor sample. In aspects, the biological sample is a primary tumor sample. In aspects, the biological sample is a metastatic tumor sample. In aspects, the biological sample is a resected tumor sample. In aspects, the biological sample is a tumor biopsy sample. In aspects, the biological sample is a resected tumor sample from a primary tumor. In aspects, the biological sample is a resected tumor sample from a metastatic tumor. In aspects, the biological sample is a tumor biopsy sample from a primary tumor. In aspects, the biological sample is a tumor biopsy sample from a metastatic tumor. Biological samples can be taken from a subject by methods known in the art, and can be analyzed by methods known in the art.

The term "expression" or "expresses" includes any step involved in the production of the protein including, but not limited to, transcription, post-transcriptional modification, translation, post-translational modification, and secretion. Expression ("level of expression") can be detected using conventional techniques for detecting a protein. In aspects, determining the level of expression of the one or more proteins includes calculating the mean of Log 2 of the amount of the one or more proteins in a biological sample. The resulting value can then be compared to other values obtained in the same manner (e.g., based on level of the same proteins in a control). In aspects, protein level is determined by high-performance liquid chromatography (HPLC); mass spectrometry (MS), e.g., liquid chromatography-mass spectrometry; enzyme-linked immunosorbent assay (ELISA); protein immunoprecipitation; immunoelectrophoresis; Western blot; protein immunostaining; immunofluorescence; or mass cytometry. In aspects, determining the level of expression of the one or more genes includes calculating the mean of Log 2 of the expression of the one or more genes in a biological sample. In aspects, gene expression is determined by Nanostring counts. In aspects, gene expression is determined by number of transcripts detected in the sample. One skilled in the art could use other methods for quantifying gene expression (e.g., mRNA levels), such as RNAseq or quantitative PCR. In aspects, the level of RNA expression is detected by any known methodology, including but not limited to rtPCR, RNA sequencing, nanopore sequencing, microarray, hybridization-based sequencing, hybridization-based detection and quantification (e.g., NanoString).

"Control," "suitable control," or "control experiment" is used in accordance with its plain ordinary meaning and refers to an experiment in which the subjects or reagents of the experiment are treated as in a parallel experiment except for omission of a procedure, reagent, or variable of the experiment. In aspects, the control is used as a standard of comparison in evaluating experimental effects. In aspects, a control is the measurement of the activity of a protein in the absence of a compound as described herein (including embodiments and examples). For example, a test sample can be taken from a patient suspected of having a given disease (cancer) and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. In aspects, a control is a negative control. In aspects, such as embodiments relating to detecting the level of expression of a gene/protein or a subset of genes/proteins, a control comprises the average amount of expression (e.g., protein or mRNA) in a population of subjects (e.g., with cancer) or in a healthy or general population. In aspects, the control comprises an average amount (e.g. amount of expression) in a population in which the number of subjects (n) is 5 or more, 10 or more, 25 of more, 50 or more, 100 or more, 1000 or more, 5000 or more, or 10000 or more. In aspects, the control is a standard control. In aspects, the control is a population of cancer subjects. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "treating" or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In aspects, treating is preventing. In aspects, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, cats, monkeys, goat, sheep, cows, and other non-mammalian animals. In aspects, a patient is human.

A "effective amount," as used herein, is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). In these methods, the effective amount of the compounds described herein is an amount effective to accomplish the stated purpose of the method. An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. For any compound described herein, the therapeutically effective amount can be initially determined from cell culture assays. Target concentrations will be those concentrations of active compound(s) that are capable of achieving the methods described herein, as measured using the methods described herein or known in the art. As is well known in the art, therapeutically effective amounts for use in humans can also be determined from animal models. For example, a dose for humans can be formulated to achieve a concentration that has been found to be effective in animals.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's disease, and Non-Hodgkin's lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In aspects, "cancer" refers to any cancer that overexpresses METTL16. In aspects, "cancer" refers to any cancer that overexpresses METTL16 when compared to a control.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

The chemical structures and formulae set forth herein are constructed according to the standard rules of chemical valency known in the chemical arts. Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom. A heteroalkyl moiety may include two optionally different heteroatoms. A heteroalkyl moiety may include three optionally different heteroatoms. A heteroalkyl moiety may include four optionally different heteroatoms. A heteroalkyl moiety may include five optionally different heteroatoms. A heteroalkyl moiety may include up to 8 optionally different heteroatoms. The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In aspects, monocyclic ring systems are cyclic hydrocarbon groups containing from 3 to 8 carbon atoms, where such groups can be saturated or unsaturated, but not aromatic. In aspects, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In aspects, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]-heptane, bicyclo[2.2.1]heptane, bicyclo[2.2.2]octane, bicyclo[3.2.2]nonane, bicyclo[3.3.1]nonane, and bicyclo[4.2.1]nonane. In aspects, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkyl is attached to the parent molecular moiety through any carbon atom contained within the monocyclic cycloalkyl ring. In aspects, cycloalkyl groups are optionally substituted with one or two groups which are independently oxo or thia. In aspects, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkyl is attached to the parent molecular moiety through any carbon atom contained within the base ring. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term “cycloalkenyl” is used in accordance with its plain ordinary meaning. In aspects, a cycloalkenyl is a monocyclic, bicyclic, or a multicyclic cycloalkenyl ring system. In aspects, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In aspects, bicyclic cycloalkenyl rings are bridged monocyclic rings or a fused bicyclic rings. In aspects, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In aspects, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkenyl is attached to the parent molecular moiety through any carbon atom contained within the monocyclic cycloalkenyl ring. In aspects, cycloalkenyl groups are optionally substituted with one or two groups which are independently oxo or thia. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkenyl is attached to the parent molecular moiety through any carbon atom contained within the base ring. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term “heterocyclyl” as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydro-benzofuran-2-yl, 2,3-dihydrobenzofuran-3-yl, indolin-1-yl, indolin-2-yl, indolin-3-yl, 2,3-dihydro-benzothien-2-yl, decahydroquinolinyl, decahydroisoquinolinyl, octahydro-1H-indolyl, and octahydrobenzofuranyl. In aspects, heterocyclyl groups are optionally substituted with one or two groups which are independently oxo or thia. In certain aspects, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In aspects, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "∿∿" and "-" denotes the point of attachment of a chemical moiety to the remainder of a molecule or chemical formula.

The term "oxo" means an oxygen that is double bonded to a carbon atom.

The term "alkylarylene" as an arylene moiety covalently bonded to an alkylene moiety (also referred to herein as an alkylene linker). In aspects, the alkylarylene group has the formula:

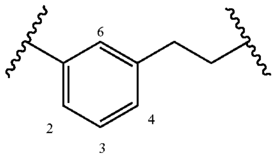

or

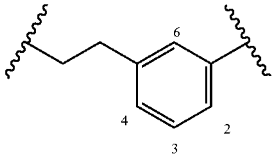

.

An alkylarylene moiety may be substituted (e.g., with a substituent group) on the alkylene moiety or the arylene linker (e.g., at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In aspects, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', —NR'R", —SR', halogen, —SiR'R"R'", —OC(O)R', —C(O)R', —$CO_2$R, —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —$CO_2$R, —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted hetero-cycloalkyl, substituted or unsubstituted aryl, and substituted or unsubstituted heteroaryl. When a compound described herein includes more than one R group, for example, each of the R groups is selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, -—OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In embodiments, each substituted group described in the compounds herein is substituted with at least one substituent group. In aspects, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In aspects, at least one or all of these groups are substituted with at least one size-limited substituent group. In aspects, at least one or all of these groups are substituted with at least one lower substituent group.

In embodiments, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In aspects, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some aspects, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In aspects, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In aspects, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group is optionally different. In aspects, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group is optionally different. In aspects, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group is optionally different. In aspects, if the substituted moiety is substituted with a plurality of groups selected from substituent groups, size-limited substituent groups, and lower substituent groups; each substituent group, size-limited substituent group, and/or lower substituent group is different.

Certain compounds of the disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the disclosure do not include those that are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain compounds contain both basic and acidic functionalities that allow the compounds to be converted into either base or acid addition salts.

The compounds may exist as salts, such as with pharmaceutically acceptable acids. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the disclosure provides compounds which are in a prodrug form. Prodrugs of the compounds described herein are those compounds that readily undergo chemical changes under physiological conditions to provide the compounds disclosed herein. Prodrugs of the compounds described herein may be converted in vivo after administration. Additionally, prodrugs can be converted to the compounds of the disclosure by chemical or biochemical methods in an ex vivo environment, such as, for example, when contacted with a suitable enzyme or chemical reagent.

Certain compounds can exist in unsolvated forms as well as solvated forms, including hydrated forms. In general, the solvated forms are equivalent to unsolvated forms and are encompassed within the scope of the disclosure. Certain compounds may exist in multiple crystalline or amorphous forms. In general, all physical forms are equivalent for the uses contemplated by disclosure and are intended to be within the scope of the disclosure.

Compounds

The disclosure provide a compound of Formula (I) or a pharmaceutically acceptable salt thereof:

(I)

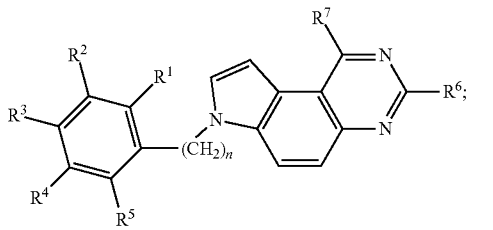

where the substituents are as defined herein.

The disclosure provide a compound of Formula (II) or a pharmaceutically acceptable salt thereof:

(II)

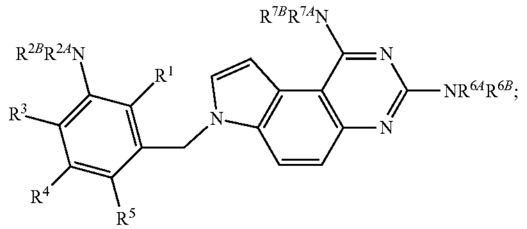

where the substituents are as defined herein.

The disclosure provide a compound of Formula (III) or a pharmaceutically acceptable salt thereof:

(III)

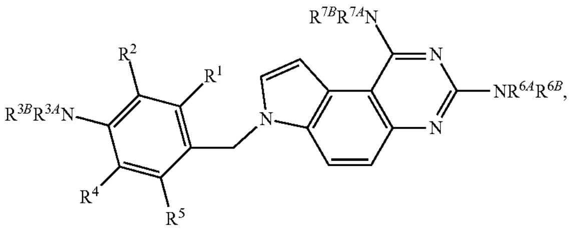

where the substituents are as defined herein.

The disclosure provide a compound of Formula (IV) or a pharmaceutically acceptable salt thereof:

(IV)

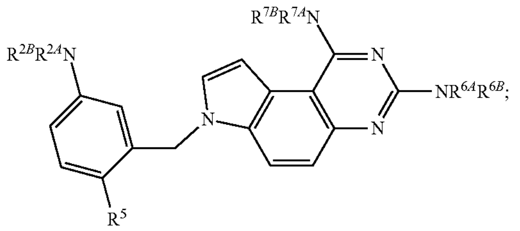

where the substituents are as defined herein.

The disclosure provide a compound of Formula (V) or a pharmaceutically acceptable salt thereof:

(V)

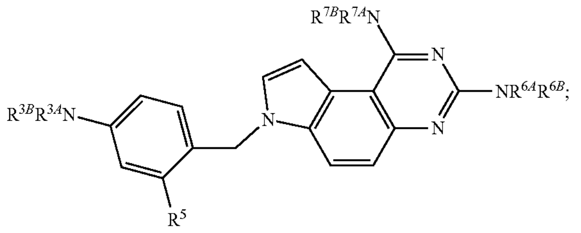

where the substituents are as defined herein.

The disclosure provide a compound of Formula (VI) or a pharmaceutically acceptable salt thereof:

(VI)

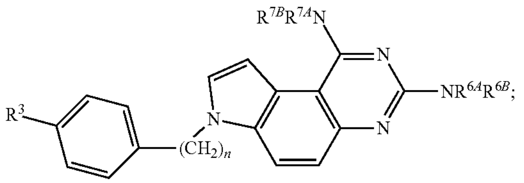

where the substituents are as defined herein.

In embodiments, the compound of Formula (VI) is a compound of Formula (VIA) or a pharmaceutically acceptable salt thereof:

(VIA)

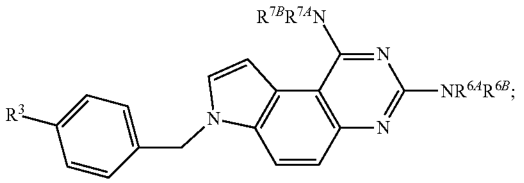

where the substituents are as defined herein.

In embodiments, the compound of Formula (VI) is a compound of Formula (VIB) or a pharmaceutically acceptable salt thereof:

(VIB)

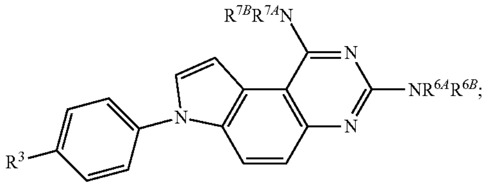

where the substituents are as defined herein.

The disclosure provide a compound of Formula (VII) or a pharmaceutically acceptable salt thereof:

(VII)

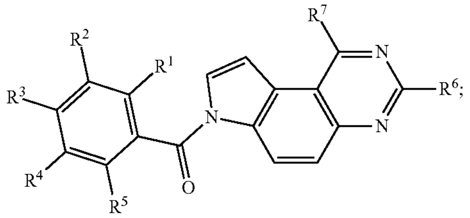

where the substituents are as defined herein.

In embodiments, the compound of Formula (VII) is a compound of Formula (VIIA) or a pharmaceutically acceptable salt thereof:

(VIIA)

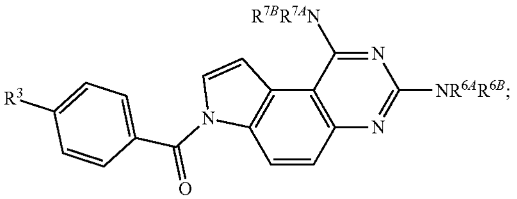

where the substituents are as defined herein.

The disclosure provides a compound of Formula (VIII) or a pharmaceutically acceptable salt thereof:

(VIII)

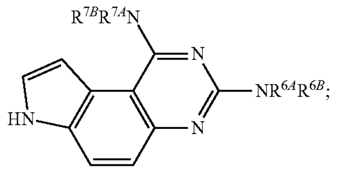

where the substituents are as defined herein.

The substituents for the compounds of Formula (I), (II), (III), (IV), (V), (VI), (VIA), (VIB), (VII), (VIIA), and (VIII) are set forth below.

In embodiments, n is an integer from 0 to 6. In aspects, n is an integer from 0 to 3. In aspects, n is an integer from 1 to 3. In aspects, n is 1 or 2. In aspects, n is 0 or 1. In aspects, n is 2 or 3. In aspects, n is 0. In aspects, n is 1. In aspects, n is 2. In aspects, n is 3. In aspects, n is 4. In aspects, n is 5. In aspects, n is 6.

In embodiments, $R^1$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, $—OR^{1A}$, $—NR^{1A}R^{1B}$, $—COOR^{1A}$, $—CONR^{1A}R^{1B}$, $—NO_2$, $—SR^{1A}$, $—SO_3R^{1A}$, $—SO_4R^{1A}$, $—SO_2NR^{1A}R^{1B}$, $—NHNR^{1A}R^{1B}$, $—ONR^{1A}R^{1B}$, $—NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^1$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, $—OR^{1A}$, $—NR^{1A}R^{1B}$, $—COOR^{1A}$, $—CONR^{1A}R^{1B}$, $—NO_2$, $—SR^{1A}$, $—SO_3R^{1A}$, $—SO_4R^{1A}$, $—SO_2NR^{1A}R^{1B}$, $—NHNR^{1A}R^{1B}$, $—ONR^{1A}R^{1B}$, $—NHC(O)NHNR^{1A}R^{1B}$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

In aspects, $R^1$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^1$ is $R^{21}$-substituted or unsubstituted alkyl (e.g., $C_1$-$C_8$ alkyl, $C_1$-$C_6$ alkyl, or $C_1$-$C_4$ alkyl). In aspects, $R^1$ is $R^{21}$-substituted alkyl (e.g., $C_1$-$C_8$ alkyl, $C_1$-$C_6$ alkyl, or $C_1$-$C_4$ alkyl). In aspects, $R^1$ is an unsubstituted alkyl (e.g., $C_1$-$C_8$ alkyl, $C_1$-$C_6$ alkyl, or $C_1$-$C_4$ alkyl). In aspects, $R^1$ is $R^{21}$-substituted or unsubstituted heteroalkyl (e.g., 2 to 8 membered heteroalkyl, 2 to 6 membered heteroalkyl, or 2 to 4 membered heteroalkyl). In aspects, $R^1$ is $R^{21}$-substituted heteroalkyl (e.g., 2 to 8 membered heteroalkyl, 2 to 6 membered heteroalkyl, or 2 to 4 membered heteroalkyl). In aspects, $R^1$ is an unsubstituted heteroalkyl (e.g., 2 to 8 membered heteroalkyl, 2 to 6 membered heteroalkyl, or 2 to 4 membered heteroalkyl). In aspects, $R^1$ is $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^1$ is $R^{21}$-substituted cycloalkyl (e.g., $C_3$-$C_8$ cycloalkyl, $C_3$-$C_6$ cycloalkyl, or $C_5$-$C_6$ cycloalkyl). In aspects, $R^1$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^1$ is $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^1$ is $R^{21}$-substituted heterocycloalkyl (e.g., 3 to 8 membered heterocycloalkyl, 3 to 6 membered heterocycloalkyl, or 5 to 6 membered heterocycloalkyl). In aspects, $R^1$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^1$ is $R^{21}$-substituted or unsubstituted aryl (e.g., $C_6$-$C_{10}$ aryl, $C_{10}$ aryl, or phenyl). In aspects, $R^1$ is $R^{21}$-substituted aryl (e.g., $C_6$-$C_{10}$ aryl, $C_{10}$ aryl, or phenyl). In aspects, $R^1$ is an unsubstituted aryl (e.g., $C_6$-$C_{10}$ aryl, $C_{10}$ aryl, or phenyl). In aspects, $R^1$ is $R^{21}$-substituted or unsubstituted heteroaryl (e.g., 5 to 10 membered heteroaryl, 5 to 9 membered heteroaryl, or 5 to 6 membered heteroaryl). In aspects, $R^1$ is $R^{21}$-substituted heteroaryl (e.g., 5 to 10 membered heteroaryl, 5 to 9 membered heteroaryl, or 5 to 6 membered heteroaryl). In aspects, $R^1$ is an unsubstituted heteroaryl (e.g., 5 to 10 membered heteroaryl, 5 to 9 membered heteroaryl, or 5 to 6 membered heteroaryl).

In aspects, $R^1$ is $—CX^1_3$. In aspects, $R^1$ is $—CHX^1_2$. In aspects, $R^1$ is $—CH_2X^1$. In aspects, $R^1$ is $—OCX^1_3$. In aspects, $R^1$ is $—OCH_2X^1$. In aspects, $R^1$ is $—OCHX^1_2$. In aspects, $R^1$ is —CN. In aspects, $R^1$ is $—SR^{1A}$. In aspects, $R^1$ is $—SOR^{1A}$. In aspects, $R^1$ is $—SO_2R^{1A}$. In aspects, $R^1$ is $—SO_3R^{1A}$. In aspects, $R^1$ is $—SO_4R^{1A}$. In aspects, $R^1$ is $—SONR^{1A}R^{1B}$. In aspects, $R^1$ is $—SO_2NR^{1A}R^{1B}$. In aspects, $R^1$ is $—NHC(O)NR^{1A}R^{1B}$. In aspects, $R^1$ is —N(O). In aspects, $R^1$ is $—N(O)_2$. In aspects, $R^1$ is $—NR^{1A}R^{1B}$. In aspects, $R^1$ is $—C(O) R^{1A}$. In aspects, $R^1$ is $—C(O)—OR^{1A}$. In aspects, $R^1$ is $—C(O)NR^{1A}R^{1B}$. In aspects, $R^1$ is $—OR^{1A}$. In aspects, $R^1$ is $—NR^{1A}SO_2R^{1B}$. In aspects, $R^1$ is $—NR^{1A}C(O)R^{1B}$. In aspects, $R^1$ is $—NR^{1A}C(O)OR^{1B}$. In aspects, $R^1$ is $—NR^{1A}OR^{1B}$. In aspects, $X^1$ is independently —F. In aspects, $X^1$ is independently —Cl. In aspects, $X^1$ is independently —Br. In aspects, $X^1$ is independently —I.

In aspects, $R^1$ is hydrogen. In aspects, $R^1$ is oxo. In aspects, $R^1$ is halogen. In aspects, $R^1$ is $—CCl_3$. In aspects, $R^1$ is $—CBr_3$. In aspects, $R^1$ is $—CF_3$. In aspects, $R^1$ is $—CI_3$. In aspects, $R^1$ is $—CHCl_2$. In aspects, $R^1$ is $—CHBr_2$. In aspects, $R^1$ is $—CHF_2$. In aspects, $R^1$ is $—CHI_2$. In aspects, $R^1$ is $—CH_2Cl$. In aspects, $R^1$ is $—CH_2Br$. In aspects, $R^1$ is $—CH_2F$. In aspects, $R^1$ is $—CH_2I$. In aspects, $R^1$ is —CN. In aspects, $R^1$ is —OH. In aspects, $R^1$ is $—NH_2$. In aspects, $R^1$ is —COOH. In aspects, $R^1$ is $—CONH_2$. In aspects, $R^1$ is $—NO_2$. In aspects, $R^1$ is —SH. In aspects, $R^1$ is $—SO_3H$. In aspects, $R^1$ is $—SO_4H$. In aspects, $R^1$ is $—SO_2NH_2$. In aspects, $R^1$ is $—NHNH_2$. In aspects, $R^1$ is $—ONH_2$. In aspects, $R^1$ is $—NHC(O)NHNH_2$. In aspects, $R^1$ is $—NHC(O)NH_2$. In aspects, $R^1$ is $—NHSO_2H$. In aspects, $R^1$ is —NHC(O)H. In aspects, $R^1$ is —NHC(O)OH. In aspects, $R^1$ is —NHOH. In aspects, $R^1$ is $—OCCl_3$. In aspects, $R^1$ is $—OCF_3$. In aspects, $R^1$ is $—OCBr_3$. In aspects, $R^1$ is $—OCI_3$. In aspects, $R^1$ is $—OCHCl_2$. In aspects, $R^1$ is $—OCHBr_2$. In aspects, $R^1$ is $—OCHI_2$. In aspects, $R^1$ is $—OCHF_2$. In aspects, $R^1$ is $—OCH_2Cl$. In aspects, $R^1$ is $—OCH_2Br$. In aspects, $R^1$ is $—OCH_2I$. In aspects, $R^1$ is $—OCH_2F$. In aspects, $R^1$ is $—N_3$. In aspects, $R^1$ is $—OCH_3$. In aspects, $R^1$ is $—CH_3$. In aspects, $R^1$ is $—CH_2CH_3$. In aspects, $R^1$ is unsubstituted propyl. In aspects, $R^1$ is unsubstituted isopropyl. In aspects, $R^1$ is unsubstituted butyl. In aspects, $R^1$ is unsubstituted tert-butyl. In aspects, $R^1$ is —F. In aspects, $R^1$ is —Cl. In aspects, $R^1$ is —Br. In aspects, $R^1$ is —I.

In aspects, $R^1$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)NHNH$_2$, —N$_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In aspects, $R^1$ is substituted or unsubstituted alkyl (e.g., $C_1$-$C_8$ alkyl, $C_1$-$C_6$ alkyl, or $C_1$-$C_4$ alkyl). In aspects, $R^1$ is substituted alkyl (e.g., $C_1$-$C_8$ alkyl, $C_1$-$C_6$ alkyl, or $C_1$-$C_4$ alkyl). In aspects, $R^1$ is an unsubstituted alkyl (e.g., $C_1$-$C_8$ alkyl, $C_1$-$C_6$ alkyl, or $C_1$-$C_4$ alkyl). In aspects, $R^1$ is substituted or unsubstituted heteroalkyl (e.g., 2 to 8 membered heteroalkyl, 2 to 6 membered heteroalkyl, or 2 to 4 membered heteroalkyl). In aspects, $R^1$ is substituted heteroalkyl (e.g., 2 to 8 membered heteroalkyl, 2 to 6 membered heteroalkyl, or 2 to 4 membered heteroalkyl). In aspects, $R^1$ is an unsubstituted heteroalkyl (e.g., 2 to 8 membered heteroalkyl, 2 to 6 membered heteroalkyl, or 2 to 4 membered heteroalkyl). In aspects, $R^1$ is substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^1$ is substituted cycloalkyl (e.g., $C_3$-$C_8$ cycloalkyl, $C_3$-$C_6$ cycloalkyl, or $C_5$-$C_6$ cycloalkyl). In aspects, $R^1$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^1$ is substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^1$ is substituted heterocycloalkyl (e.g., 3 to 8 membered heterocycloalkyl, 3 to 6 membered heterocycloalkyl, or 5 to 6 membered heterocycloalkyl). In aspects, $R^1$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^1$ is substituted or unsubstituted aryl (e.g., $C_6$-$C_{10}$ aryl, $C_{10}$ aryl, or phenyl). In aspects, $R^1$ is substituted aryl (e.g., $C_6$-$C_{10}$ aryl, $C_{10}$ aryl, or phenyl). In aspects, $R^1$ is an unsubstituted aryl (e.g., $C_6$-$C_{10}$ aryl, $C_{10}$ aryl, or phenyl). In aspects, $R^1$ is substituted or unsubstituted heteroaryl (e.g., 5 to 10 membered heteroaryl, 5 to 9 membered heteroaryl, or 5 to 6 membered heteroaryl). In aspects, $R^1$ is substituted heteroaryl (e.g., 5 to 10 membered heteroaryl, 5 to 9 membered heteroaryl, or 5 to 6 membered heteroaryl). In aspects, $R^1$ is an unsubstituted heteroaryl (e.g., 5 to 10 membered heteroaryl, 5 to 9 membered heteroaryl, or 5 to 6 membered heteroaryl).

$R^{21}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). In aspects, $R^{21}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{21}$ is independently oxo. In aspects, $R^{21}$ is independently halogen. In aspects, $R^{21}$ is independently —CCl$_3$. In aspects, $R^{21}$ is independently —CBr$_3$. In aspects, $R^{21}$ is independently —CF$_3$. In aspects, $R^{21}$ is independently —CI$_3$. In aspects, $R^{21}$ is independently —CHCl$_2$. In aspects, $R^{21}$ is independently —CHBr$_2$. In aspects, $R^{21}$ is independently —CHF$_2$. In aspects, $R^{21}$ is independently —CHI$_2$. In aspects, $R^{21}$ is independently —CH$_2$Cl. In aspects, $R^{21}$ is independently —CH$_2$Br. In aspects, $R^{21}$ is independently —CH$_2$F. In aspects, $R^{21}$ is independently —CH$_2$I. In aspects, $R^{21}$ is independently —CN. In aspects, $R^{21}$ is independently —OH. In aspects, $R^{21}$ is independently —NH$_2$. In aspects, $R^{21}$ is independently —COOH. In aspects, $R^{21}$ is independently —CONH$_2$. In aspects, $R^{21}$ is independently —NO$_2$. In aspects, $R^{21}$ is independently —SH. In aspects, $R^{21}$ is independently —SO$_3$H. In aspects, $R^{21}$ is independently —SO$_4$H. In aspects, $R^{21}$ is independently —SO$_2$NH$_2$. In aspects, $R^{21}$ is independently —NHNH$_2$. In aspects, $R^{21}$ is independently —ONH$_2$. In aspects, $R^{21}$ is independently —NHC(O)NHNH$_2$. In aspects, $R^{21}$ is independently —NHC(O)NH$_2$. In aspects, $R^{21}$ is independently —NHSO$_2$H. In aspects, $R^{21}$ is independently —NHC(O)H. In aspects, $R^{21}$ is independently —NHC(O)OH. In aspects, $R^{21}$ is independently —NHOH. In aspects, $R^{21}$ is independently —OCCl$_3$. In aspects, $R^{21}$ is independently —OCF$_3$. In aspects, $R^{21}$ is independently —OCBr$_3$. In aspects, $R^{21}$ is independently —OCI$_3$. In aspects, $R^{21}$ is independently —OCHCl$_2$. In aspects, $R^{21}$ is independently —OCHBr$_2$. In aspects, $R^{21}$ is independently —OCHI$_2$. In aspects, $R^{21}$ is independently —OCHF$_2$. In aspects, $R^{21}$ is independently —OCH$_2$Cl. In aspects, $R^{21}$ is independently —OCH$_2$Br. In aspects, $R^{21}$ is independently —OCH$_2$I. In aspects, $R^{21}$ is independently —OCH$_2$F. In aspects, $R^{21}$ is independently —N$_3$. In aspects, $R^{21}$ is independently —OCH$_3$. In aspects, $R^{21}$ is independently —CH$_3$. In aspects, $R^{21}$ is independently —CH$_2$CH$_3$. In aspects, $R^{21}$ is independently unsubstituted propyl. In aspects, $R^{21}$ is independently unsubstituted is independently propyl. In aspects, $R^{21}$ is independently unsubstituted butyl. In aspects, $R^{21}$ is independently unsubstituted tert-butyl. In aspects, $R^{21}$ is independently —F. In aspects, $R^{21}$ is independently —Cl. In aspects, $R^{21}$ is independently —Br. In aspects, $R^{21}$ is independently —I.

In aspects, $R^{21}$ is independently $R^{22}$-substituted or unsubstituted alkyl (e.g., $C_1$-$C_8$ alkyl, $C_1$-$C_6$ alkyl, or $C_1$-$C_4$ alkyl). In aspects, $R^{21}$ is independently $R^{22}$-substituted alkyl (e.g., $C_1$-$C_8$ alkyl, $C_1$-$C_6$ alkyl, or $C_1$-$C_4$ alkyl). In aspects, $R^{21}$ is independently an unsubstituted alkyl (e.g., $C_1$-$C_8$ alkyl, $C_1$-$C_6$ alkyl, or $C_1$-$C_4$ alkyl). In aspects, $R^{21}$ is independently $R^{22}$-substituted or unsubstituted heteroalkyl (e.g., 2 to 8 membered heteroalkyl, 2 to 6 membered heteroalkyl, or 2 to 4 membered heteroalkyl). In aspects, $R^{21}$ is independently $R^{22}$-substituted heteroalkyl (e.g., 2 to 8 membered heteroalkyl, 2 to 6 membered heteroalkyl, or 2 to 4 membered heteroalkyl). In aspects, $R^{21}$ is independently an unsubstituted heteroalkyl (e.g., 2 to 8 membered heteroalkyl, 2 to 6 membered heteroalkyl, or 2 to 4 membered heteroalkyl). In aspects, $R^{21}$ is independently $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{21}$ is independently $R^{22}$-substituted cycloalkyl (e.g., $C_3$-$C_8$ cycloalkyl, $C_3$-$C_6$ cycloalkyl, or $C_5$-$C_6$ cycloalkyl). In aspects, $R^{21}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{21}$ is independently $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{21}$ is independently $R^{22}$-substituted heterocycloalkyl (e.g., 3 to 8 membered heterocycloalkyl, 3 to 6 membered heterocycloalkyl, or 5 to 6 membered heterocycloalkyl). In aspects, $R^{21}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{21}$ is independently $R^{22}$-substituted or unsubstituted aryl (e.g., $C_6$-$C_{10}$ aryl, $C_{10}$ aryl, or phenyl). In aspects, $R^{21}$ is independently $R^{22}$-substituted aryl (e.g., $C_6$-$C_{10}$ aryl, $C_{10}$ aryl, or phenyl). In aspects, $R^{21}$ is independently an unsubstituted aryl (e.g., $C_6$-$C_{10}$ aryl, $C_{10}$ aryl, or phenyl). In aspects, $R^{21}$ is independently $R^{22}$-substituted or unsubstituted heteroaryl (e.g., 5 to 10 membered heteroaryl, 5 to 9 membered heteroaryl, or 5 to 6 membered heteroaryl). In aspects, $R^{21}$ is independently $R^{22}$-substituted heteroaryl (e.g., 5 to 10 membered heteroaryl, 5 to 9 membered heteroaryl, or 5 to 6 membered heteroaryl). In aspects, $R^{21}$ is independently an unsubstituted heteroaryl (e.g., 5 to 10 membered heteroaryl, 5 to 9 membered heteroaryl, or 5 to 6 membered heteroaryl).

$R^{22}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $R^{23}$-substituted or unsubstituted alkyl (e.g., $C_1$-$C_8$ alkyl, $C_1$-$C_6$ alkyl, or $C_1$-$C_4$ alkyl), $R^{23}$-substituted or unsubstituted heteroalkyl (e.g., 2 to 8 membered heteroalkyl, 2 to 6 membered heteroalkyl, or 2 to 4 membered heteroalkyl), $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23}$-substituted or unsubstituted aryl (e.g., $C_6$-$C_{10}$ aryl, $C_{10}$ aryl, or phenyl), or $R^{23}$-substituted or unsubstituted heteroaryl (e.g., 5 to 10 membered heteroaryl, 5 to 9 membered heteroaryl, or 5 to 6 membered heteroaryl). In aspects, $R^{22}$ is independently oxo, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{22}$ is independently $R^{23}$-substituted or unsubstituted alkyl (e.g., $C_1$-$C_8$ alkyl, $C_1$-$C_6$ alkyl, or $C_1$-$C_4$ alkyl). In aspects, $R^{22}$ is independently $R^{23}$-substituted alkyl (e.g., $C_1$-$C_8$ alkyl, $C_1$-$C_6$ alkyl, or $C_1$-$C_4$ alkyl). In aspects, $R^{22}$ is independently an unsubstituted alkyl (e.g., $C_1$-$C_8$ alkyl, $C_1$-$C_6$ alkyl, or $C_1$-$C_4$ alkyl). In aspects, $R^{22}$ is independently $R^{23}$-substituted or unsubstituted heteroalkyl (e.g., 2 to 8 membered heteroalkyl, 2 to 6 membered heteroalkyl, or 2 to 4 membered heteroalkyl). In aspects, $R^{22}$ is independently $R^{23}$-substituted heteroalkyl (e.g., 2 to 8 membered heteroalkyl, 2 to 6 membered heteroalkyl, or 2 to 4 membered heteroalkyl). In aspects, $R^{22}$ is independently an unsubstituted heteroalkyl (e.g., 2 to 8 membered heteroalkyl, 2 to 6 membered heteroalkyl, or 2 to 4 membered heteroalkyl). In aspects, $R^{22}$ is independently $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{22}$ is independently $R^{23}$-substituted cycloalkyl (e.g., $C_3$-$C_8$ cycloalkyl, $C_3$-$C_6$ cycloalkyl, or $C_5$-$C_6$ cycloalkyl). In aspects, $R^{22}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{22}$ is independently $R^{23}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{22}$ is independently $R^{23}$-substituted heterocycloalkyl (e.g., 3 to 8 membered heterocycloalkyl, 3 to 6 membered heterocycloalkyl, or 5 to 6 membered heterocycloalkyl). In aspects, $R^{22}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{22}$ is independently $R^{23}$-substituted or unsubstituted aryl (e.g., $C_6$-$C_{10}$ aryl, $C_{10}$ aryl, or phenyl). In aspects, $R^{22}$ is independently $R^{23}$-substituted aryl (e.g., $C_6$-$C_{10}$ aryl, $C_{10}$ aryl, or phenyl). In aspects, $R^{22}$ is independently an unsubstituted aryl (e.g., $C_6$-$C_{10}$ aryl, $C_{10}$ aryl, or phenyl). In aspects, $R^{22}$ is independently $R^{23}$-substituted or unsubstituted heteroaryl (e.g., 5 to 10 membered heteroaryl, 5 to 9 membered heteroaryl, or 5 to 6 membered heteroaryl). In aspects, $R^{22}$ is independently $R^{23}$-substituted heteroaryl (e.g., 5 to 10 membered heteroaryl, 5 to 9 membered heteroaryl, or 5 to 6 membered heteroaryl). In aspects, $R^{22}$ is independently an unsubstituted heteroaryl (e.g., 5 to 10 membered heteroaryl, 5 to 9 membered heteroaryl, or 5 to 6 membered heteroaryl).

In aspects, $R^{22}$ is independently oxo. In aspects, $R^{22}$ is independently halogen. In aspects, $R^{22}$ is independently $—CCl_3$. In aspects, $R^{22}$ is independently $—CBr_3$. In aspects, $R^{22}$ is independently —$CF_3$. In aspects, $R^{22}$ is independently —$CI_3$. In aspects, $R^{22}$ is independently $CHCl_2$. In aspects, $R^{22}$ is independently —$CHBr_2$. In aspects, $R^{22}$ is independently —$CHF_2$. In aspects, $R^{22}$ is independently —$CHI_2$. In aspects, $R^{22}$ is independently —$CH_2Cl$. In aspects, $R^{22}$ is independently —$CH_2Br$. In aspects, $R^{22}$ is independently —$CH_2F$. In aspects, $R^{22}$ is independently —$CH_2I$. In aspects, $R^{22}$ is independently —CN. In aspects, $R^{22}$ is independently —OH. In aspects, $R^{22}$ is independently —$NH_2$. In aspects, $R^{22}$ is independently —COOH. In aspects, $R^{22}$ is independently —$CONH_2$. In aspects, $R^{22}$ is independently —$NO_2$. In aspects, $R^{22}$ is independently —SH. In aspects, $R^{22}$ is independently —$SO_3H$. In aspects, $R^{22}$ is independently —$SO_4H$. In aspects, $R^{22}$ is independently —$SO_2NH_2$. In aspects, $R^{22}$ is independently —$NHNH_2$. In aspects, $R^{22}$ is independently —$ONH_2$. In aspects, $R^{22}$ is independently —NHC(O)$NHNH_2$. In aspects, $R^{22}$ is independently —NHC(O)$NH_2$. In aspects, $R^{22}$ is independently —$NHSO_2H$. In aspects, $R^{22}$ is independently —NHC(O)H. In aspects, $R^{22}$ is independently —NHC(O)OH. In aspects, $R^{22}$ is independently —NHOH. In aspects, $R^{22}$ is independently —$OCCl_3$. In aspects, $R^{22}$ is independently —$OCF_3$. In aspects, $R^{22}$ is independently —$OCBr_3$. In aspects, $R^{22}$ is independently —$OCI_3$. In aspects, $R^{22}$ is independently —$OCHCl_2$. In aspects, $R^{22}$ is independently —$OCHBr_2$. In aspects, $R^{22}$ is independently —$OCHI_2$. In aspects, $R^{22}$ is independently —$OCHF_2$. In aspects, $R^{22}$ is independently —$OCH_2Cl$. In aspects, $R^{22}$ is independently —$OCH_2Br$. In aspects, $R^{22}$ is independently —$OCH_2I$. In aspects, $R^{22}$ is independently —$OCH_2F$. In aspects, $R^{22}$ is independently —$N_3$. In aspects, $R^{22}$ is independently —$OCH_3$. In aspects, $R^{22}$ is independently —$CH_3$. In aspects, $R^{22}$ is independently —$CH_2CH_3$. In aspects, $R^{22}$ is independently unsubstituted propyl. In aspects, $R^{22}$ is independently unsubstituted isopropyl. In aspects, $R^{22}$ is independently unsubstituted butyl. In aspects, $R^{22}$ is independently unsubstituted tert-butyl. In aspects, $R^{22}$ is independently —F. In aspects, $R^{22}$ is independently —Cl. In aspects, $R^{22}$ is independently —Br. In aspects, $R^{22}$ is independently —I.

$R^{23}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{23}$ is independently an unsubstituted alkyl (e.g., $C_1$-$C_8$ alkyl, $C_1$-$C_6$ alkyl, or $C_1$-$C_4$ alkyl). In aspects, $R^{23}$ is independently an unsubstituted heteroalkyl (e.g., 2 to 8 membered heteroalkyl, 2 to 6 membered heteroalkyl, or 2 to 4 membered heteroalkyl). In aspects, $R^{23}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{23}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{23}$ is independently an unsubstituted aryl (e.g., $C_6$-$C_{10}$ aryl, $C_{10}$ aryl, or phenyl). In aspects, $R^{23}$ is independently an unsubstituted heteroaryl (e.g., 5 to 10 membered heteroaryl, 5 to 9 membered heteroaryl, or 5 to 6 membered heteroaryl).

In aspects, $R^{23}$ is independently oxo. In aspects, $R^{23}$ is independently halogen. In aspects, $R^{23}$ is independently —$CCl_3$. In aspects, $R^{23}$ is independently —$CBr_3$. In aspects, $R^{23}$ is independently —$CF_3$. In aspects, $R^{23}$ is independently —$CI_3$. In aspects, $R^{23}$ is independently —$CHCl_2$. In aspects, $R^{23}$ is independently —$CHBr_2$. In aspects, $R^{23}$ is independently —$CHF_2$. In aspects, $R^{23}$ is independently —$CHI_2$. In aspects, $R^{23}$ is independently —$CH_2Cl$. In aspects, $R^{23}$ is independently —$CH_2Br$. In aspects, $R^{23}$ is independently —$CH_2F$. In aspects, $R^{23}$ is independently —$CH_2I$. In aspects, $R^{23}$ is independently —CN. In aspects, $R^{23}$ is independently —OH. In aspects, $R^{23}$ is independently —$NH_2$. In aspects, $R^{23}$ is independently —COOH. In aspects, $R^{23}$ is independently —$CONH_2$. In aspects, $R^{23}$ is independently —$NO_2$. In aspects, $R^{23}$ is independently —SH. In aspects, $R^{23}$ is independently —$SO_3H$. In aspects, $R^{23}$ is independently —$SO_4H$. In aspects, $R^{23}$ is independently —$SO_2NH_2$. In aspects, $R^{23}$ is independently —$NHNH_2$. In aspects, $R^{23}$ is independently —$ONH_2$. In aspects, $R^{23}$ is independently —NHC(O)$NHNH_2$. In aspects, $R^{23}$ is independently —NHC(O)$NH_2$. In aspects, $R^{23}$ is independently —$NHSO_2H$. In aspects, $R^{23}$ is independently —NHC(O)H. In aspects, $R^{23}$ is independently —NHC(O)OH. In aspects, $R^{23}$ is independently —NHOH. In aspects, $R^{23}$ is independently —$OCCl_3$. In aspects, $R^{23}$ is independently —$OCF_3$. In aspects, $R^{23}$ is independently —$OCBr_3$. In aspects, $R^{23}$ is independently —$OCI_3$. In aspects, $R^{23}$ is independently —$OCHCl_2$. In aspects, $R^{23}$ is independently —$OCHBr_2$. In aspects, $R^{23}$ is independently —$OCHI_2$. In aspects, $R^{23}$ is independently —$OCHF_2$. In aspects, $R^{23}$ is independently —$OCH_2Cl$. In aspects, $R^{23}$ is independently —$OCH_2Br$. In aspects, $R^{23}$ is independently —$OCH_2I$. In aspects, $R^{23}$ is independently —$OCH_2F$. In aspects, $R^{23}$ is independently —$N_3$. In aspects, $R^{23}$ is independently —$OCH_3$. In aspects, $R^{23}$ is independently —$CH_3$. In aspects, $R^{23}$ is independently —$CH_2CH_3$. In aspects, $R^{23}$ is independently unsubstituted propyl. In aspects, $R^{23}$ is independently unsubstituted is independently propyl. In aspects, $R^{23}$ is independently unsubstituted butyl. In aspects, $R^{23}$ is independently unsubstituted tert-butyl. In aspects, $R^{23}$ is independently —F. In aspects, $R^{23}$ is independently —Cl. In aspects, $R^{23}$ is independently —Br. In aspects, $R^{23}$ is independently —I.

In aspects, $R^{1A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{1A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, substituted or unsubstituted aryl, or $R^{21}$-substituted or unsubstituted heteroaryl.

In aspects, $R^{1A}$ is independently $R^{21}$-substituted or unsubstituted alkyl (e.g., $C_1$-$C_8$ alkyl, $C_1$-$C_6$ alkyl, or $C_1$-$C_4$ alkyl). In aspects, $R^{1A}$ is independently $R^{21}$-substituted alkyl (e.g., $C_1$-$C_8$ alkyl, $C_1$-$C_6$ alkyl, or $C_1$-$C_4$ alkyl). In aspects, $R^{1A}$ is independently an unsubstituted alkyl (e.g., $C_1$-$C_8$ alkyl, $C_1$-$C_6$ alkyl, or $C_1$-$C_4$ alkyl). In aspects, $R^{1A}$ is independently $R^{21}$-substituted or unsubstituted heteroalkyl (e.g., 2 to 8 membered heteroalkyl, 2 to 6 membered heteroalkyl, or 2 to 4 membered heteroalkyl). In aspects, $R^{1A}$ is independently $R^{21}$-substituted heteroalkyl (e.g., 2 to 8 membered heteroalkyl, 2 to 6 membered heteroalkyl, or 2 to 4 membered heteroalkyl). In aspects, $R^{1A}$ is independently an unsubstituted heteroalkyl (e.g., 2 to 8 membered heteroalkyl, 2 to 6 membered heteroalkyl, or 2 to 4 membered heteroalkyl). In aspects, $R^{1A}$ is independently $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{1A}$ is independently $R^{21}$-substituted cycloalkyl (e.g., $C_3$-$C_8$ cycloalkyl, $C_3$-$C_6$ cycloalkyl, or $C_5$-$C_6$ cycloalkyl). In aspects, $R^{1A}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{1A}$ is independently $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{1A}$ is independently $R^{21}$-substituted heterocycloalkyl (e.g., 3 to 8 membered heterocycloalkyl, 3 to 6 membered heterocycloalkyl, or 5 to 6 membered heterocycloalkyl). In aspects, $R^{1A}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{1A}$ is independently $R^{21}$-substituted or unsubstituted aryl (e.g., $C_6$-$C_{10}$ aryl, $C_{10}$ aryl, or phenyl). In aspects, $R^{1A}$ is independently $R^{21}$-substituted aryl (e.g., $C_6$-$C_{10}$ aryl, $C_{10}$ aryl, or phenyl). In aspects, $R^{1A}$ is independently an unsubstituted aryl (e.g., $C_6$-$C_{10}$ aryl, $C_{10}$ aryl, or phenyl). In aspects, $R^{1A}$ is independently $R^{21}$-substituted or unsubstituted heteroaryl (e.g., 5 to 10 membered heteroaryl, 5 to 9 membered heteroaryl, or 5 to 6 membered heteroaryl). In aspects, $R^{1A}$ is independently $R^{21}$-substituted heteroaryl (e.g., 5 to 10 membered heteroaryl, 5 to 9 membered heteroaryl, or 5 to 6 membered heteroaryl). In aspects, $R^{1A}$ is independently an unsubstituted heteroaryl (e.g., 5 to 10 membered heteroaryl, 5 to 9 membered heteroaryl, or 5 to 6 membered heteroaryl).

In aspects, $R^{1A}$ is independently —$CCl_3$. In aspects, $R^{1A}$ is independently —$CBr_3$. In aspects, $R^{1A}$ is independently —$CF_3$. In aspects, $R^{1A}$ is independently —$CI_3$. In aspects, $R^{1A}$ is independently —$CHCl_2$. In aspects, $R^{1A}$ is independently —$CHBr_2$. In aspects, $R^{1A}$ is independently —$CHF_2$. In aspects, $R^{1A}$ is independently —$CHI_2$. In aspects, $R^{1A}$ is independently —$CH_2Cl$. In aspects, $R^{1A}$ is independently —$CH_2Br$. In aspects, $R^{1A}$ is independently —$CH_2F$. In aspects, $R^{1A}$ is independently —$CH_2I$. In aspects, $R^{1A}$ is independently —CN. In aspects, $R^{1A}$ is independently —OH. In aspects, $R^{1A}$ is independently —COOH. In aspects, $R^{1A}$ is independently —$CONH_2$. In aspects, $R^{1A}$ is independently —$OCCl_3$. In aspects, $R^{1A}$ is independently —$OCF_3$. In aspects, $R^{1A}$ is independently —$OCBr_3$. In aspects, $R^{1A}$ is independently —$OCI_3$. In aspects, $R^{1A}$ is independently —$OCHCl_2$. In aspects, $R^{1A}$ is independently —$OCHBr_2$. In aspects, $R^{1A}$ is independently —$OCHI_2$. In aspects, $R^{1A}$ is independently —$OCHF_2$. In aspects, $R^{1A}$ is independently —$OCH_2Cl$. In aspects, $R^{1A}$ is independently —$OCH_2Br$. In aspects, $R^{1A}$ is independently —$OCH_2I$. In aspects, $R^{1A}$ is independently —$OCH_2F$. In aspects, $R^{1A}$ is independently —$OCH_3$. In aspects, $R^{1A}$ is independently —$CH_3$. In aspects, $R^{1A}$ is independently —$CH_2CH_3$. In aspects, $R^{1A}$ is independently unsubstituted propyl. In aspects, $R^{1A}$ is independently unsubstituted isopropyl. In aspects, $R^{1A}$ is independently unsubstituted butyl. In aspects, $R^{1A}$ is independently unsubstituted tert-butyl. In aspects, $R^{1A}$ is independently hydrogen.

In aspects, $R^{1B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{1B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, substituted or unsubstituted aryl, or $R^{21}$-substituted or unsubstituted heteroaryl.

In aspects, $R^{1B}$ is independently $R^{21}$-substituted or unsubstituted alkyl (e.g., $C_1$-$C_8$ alkyl, $C_1$-$C_6$ alkyl, or $C_1$-$C_4$ alkyl). In aspects, $R^{1B}$ is independently $R^{21}$-substituted alkyl (e.g., $C_1$-$C_8$ alkyl, $C_1$-$C_6$ alkyl, or $C_1$-$C_4$ alkyl). In aspects, $R^{1B}$ is independently an unsubstituted alkyl (e.g., $C_1$-$C_8$ alkyl, $C_1$-$C_6$ alkyl, or $C_1$-$C_4$ alkyl). In aspects, $R^{IB}$ is independently $R^{21}$-substituted or unsubstituted heteroalkyl (e.g., 2 to 8 membered heteroalkyl, 2 to 6 membered heteroalkyl, or 2 to 4 membered heteroalkyl). In aspects, $R^{1B}$ is independently $R^{21}$-substituted heteroalkyl (e.g., 2 to 8 membered heteroalkyl, 2 to 6 membered heteroalkyl, or 2 to 4 membered heteroalkyl). In aspects, $R^{IB}$ is independently an unsubstituted heteroalkyl (e.g., 2 to 8 membered heteroalkyl, 2 to 6 membered heteroalkyl, or 2 to 4 membered heteroalkyl). In aspects, $R^{1B}$ is independently $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{1B}$ is independently $R^{21}$-substituted cycloalkyl (e.g., $C_3$-$C_8$ cycloalkyl, $C_3$-$C_6$ cycloalkyl, or $C_5$-$C_6$ cycloalkyl). In aspects, $R^{1B}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{1B}$ is independently $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{1B}$ is independently $R^{21}$-substituted heterocycloalkyl (e.g., 3 to 8 membered heterocycloalkyl, 3 to 6 membered heterocycloalkyl, or 5 to 6 membered heterocycloalkyl). In aspects, $R^{1B}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{1B}$ is independently $R^{21}$-substituted or unsubstituted aryl (e.g., $C_6$-$C_{10}$ aryl, $C_{10}$ aryl, or phenyl). In aspects, $R^{1B}$ is independently $R^{21}$-substituted aryl (e.g., $C_6$-$C_{10}$ aryl, $C_{10}$ aryl, or phenyl). In aspects, $R^{1B}$ is independently an unsubstituted aryl (e.g., $C_6$-$C_{10}$ aryl, $C_{10}$ aryl, or phenyl). In aspects, $R^{1B}$ is independently $R^{21}$-substituted or unsubstituted heteroaryl (e.g., 5 to 10 membered heteroaryl, 5 to 9 membered heteroaryl, or 5 to 6 membered heteroaryl). In aspects, $R^{1B}$ is independently $R^{21}$-substituted heteroaryl (e.g., 5 to 10 membered heteroaryl, 5 to 9 membered heteroaryl, or 5 to 6 membered heteroaryl). In aspects, $R^{1B}$ is independently an unsubstituted heteroaryl (e.g., 5 to 10 membered heteroaryl, 5 to 9 membered heteroaryl, or 5 to 6 membered heteroaryl).

In aspects, $R^{1B}$ is independently $—CCl_3$. In aspects, $R^{1B}$ is independently $—CBr_3$. In aspects, $R^{1B}$ is independently $—CF_3$. In aspects, $R^{1B}$ is independently $—CI_3$. In aspects, $R^{1B}$ is independently $—CHCl_2$. In aspects, $R^{1B}$ is independently $—CHBr_2$. In aspects, $R^{1B}$ is independently $—CHF_2$. In aspects, $R^{1B}$ is independently $—CHI_2$. In aspects, $R^{1B}$ is independently $—CH_2Cl$. In aspects, $R^{1B}$ is independently $—CH_2Br$. In aspects, $R^{1B}$ is independently $—CH_2F$. In aspects, $R^{1B}$ is independently $—CH_2I$. In aspects, $R^{1B}$ is independently —CN. In aspects, $R^{1B}$ is independently —OH. In aspects, $R^{1B}$ is independently —COOH. In aspects, $R^{1B}$ is independently $—CONH_2$. In aspects, $R^{1B}$ is independently $—OCCl_3$. In aspects, $R^{1B}$ is independently $—OCF_3$. In aspects, $R^{1B}$ is independently $—OCBr_3$. In aspects, $R^{1B}$ is independently $—OCI_3$. In aspects, $R^{1B}$ is independently $—OCHCl_2$. In aspects, $R^{1B}$ is independently $—OCHBr_2$. In aspects, $R^{1B}$ is independently $—OCHI_2$. In aspects, $R^{1B}$ is independently $—OCHF_2$. In aspects, $R^{1B}$ is independently $—OCH_2Cl$. In aspects, $R^{1B}$ is independently $—OCH_2Br$. In aspects, $R^{1B}$ is independently $—OCH_2I$. In aspects, $R^{1B}$ is independently $—OCH_2F$. In aspects, $R^{1B}$ is independently $—OCH_3$. In aspects, $R^{1B}$ is independently $—CH_3$. In aspects, $R^{1B}$ is independently $—CH_2CH_3$. In aspects, $R^{1B}$ is independently unsubstituted propyl. In aspects, $R^{1B}$ is independently unsubstituted isopropyl. In aspects, $R^{1B}$ is independently unsubstituted butyl. In aspects, $R^{1B}$ is independently unsubstituted tert-butyl. In aspects, $R^{1B}$ is independently hydrogen.

In aspects, $R^2$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, $—OR^{2A}$, $—NR^{2A}R^{2B}$, $—COOR^{2A}$, $—CONR^{2A}R^{2B}$, $—NO_2$, $—SR^{2A}$, $—SO_3R^{2A}$, $—SO_4R^{2A}$, $—SO_2NR^{2A}R^{2B}$, $—NHNR^{2A}R^{2B}$, $—ONR^{2A}R^{2B}$, $—NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^2$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, $—OR^{2A}$, $—NR^{2A}R^{2B}$, $—COOR^{2A}$, $—CONR^{2A}R^{2B}$, $—NO_2$, $—SR^{2A}$, $—SO_3R^{2A}$, $—SO_4R^{2A}$, $—SO_2NR^{2A}R^{2B}$, $—NHNR^{2A}R^{2B}$, $—ONR^{2A}R^{2B}$, $—NHC(O)NHNR^{2A}R^{2B}$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In aspects, $R^2$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, $—OR^{2A}$, $—NR^{2A}R^{2B}$, $—COOR^{2A}$, $—CONR^{2A}R^{2B}$, $—NO_2$, $—SR^{2A}$, $—SO_3R^{2A}$, $—SO_4R^{2A}$, $—SO_2NR^{2A}R^{2B}$, $—NHNR^{2A}R^{2B}$, $—ONR^{2A}R^{2B}$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^2$ is $R^{24}$-substituted or unsubstituted alkyl (e.g., $C_1$-$C_8$ alkyl, $C_1$-$C_6$ alkyl, or $C_1$-$C_4$ alkyl). In aspects, $R^2$ is $R^{24}$-substituted alkyl (e.g., $C_1$-$C_8$ alkyl, $C_1$-$C_6$ alkyl, or $C_1$-$C_4$ alkyl). In aspects, $R^2$ is an unsubstituted alkyl (e.g., $C_1$-$C_8$ alkyl, $C_1$-$C_6$ alkyl, or $C_1$-$C_4$ alkyl). In aspects, $R^2$ is $R^{24}$-substituted or unsubstituted heteroalkyl (e.g., 2 to 8 membered heteroalkyl, 2 to 6 membered heteroalkyl, or 2 to 4 membered heteroalkyl). In aspects, $R^2$ is $R^{24}$-substituted heteroalkyl (e.g., 2 to 8 membered heteroalkyl, 2 to 6 membered heteroalkyl, or 2 to 4 membered heteroalkyl). In aspects, $R^2$ is an unsubstituted heteroalkyl (e.g., 2 to 8 membered heteroalkyl, 2 to 6 membered heteroalkyl, or 2 to 4 membered heteroalkyl). In aspects, $R^2$ is $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^2$ is $R^{24}$-substituted cycloalkyl (e.g., $C_3$-$C_8$ cycloalkyl, $C_3$-$C_6$ cycloalkyl, or $C_5$-$C_6$ cycloalkyl). In aspects, $R^2$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^2$ is $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^2$ is $R^{24}$-substituted heterocycloalkyl (e.g., 3 to 8 membered heterocycloalkyl, 3 to 6 membered heterocycloalkyl, or 5 to 6 membered heterocycloalkyl). In aspects, $R^2$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^2$ is $R^{24}$-substituted or unsubstituted aryl (e.g., $C_6$-$C_{10}$ aryl, $C_{10}$ aryl, or phenyl). In aspects, $R^2$ is $R^{24}$-substituted aryl (e.g., $C_6$-$C_{10}$ aryl, $C_{10}$ aryl, or phenyl). In aspects, $R^2$ is an unsubstituted aryl (e.g., $C_6$-$C_{10}$ aryl, $C_{10}$ aryl, or phenyl). In aspects, $R^2$ is $R^{24}$-substituted or unsubstituted heteroaryl (e.g., 5 to 10 membered heteroaryl, 5 to 9 membered heteroaryl, or 5 to 6 membered heteroaryl). In aspects, $R^2$ is $R^{24}$-substituted heteroaryl (e.g., 5 to 10 membered heteroaryl, 5 to 9 membered heteroaryl, or 5 to 6 membered heteroaryl). In aspects, $R^2$ is an unsubstituted heteroaryl (e.g., 5 to 10 membered heteroaryl, 5 to 9 membered heteroaryl, or 5 to 6 membered heteroaryl).

In aspects, $R^2$ is $—CX^2_3$. In aspects, $R^2$ is $—CHX^2_2$. In aspects, $R^2$ is $—CH_2X^2$. In aspects, $R^2$ is $—OCX^2_3$. In aspects, $R^2$ is $—OCH_2X^2$. In aspects, $R^2$ is $—OCHX^2_2$. In aspects, $R^2$ is —CN. In aspects, $R^2$ is $—SR^{2A}$. In aspects, $R^2$ is $—SOR^{2A}$. In aspects, $R^2$ is $—SO_2R^{2A}$. In aspects, $R^2$ is $—SO_3R^{2A}$. In aspects, $R^2$ is $—SO_4R^{2A}$. In aspects, $R^2$ is $—SONR^{2A}R^{2B}$. In aspects, $R^2$ is $—SO_2NR^{2A}R^{2B}$. In aspects, $R^2$ is $—NHC(O)NR^{2A}R^{2B}$. In aspects, $R^2$ is —N(O). In aspects, $R^2$ is $—N(O)_2$. In aspects, $R^2$ is $—NR^{2A}R^{2B}$. In aspects, $R^2$ is —C(O)$R^{2A}$. In aspects, $R^2$ is —C(O)—$OR^{2A}$. In aspects, $R^2$ is —C(O)$NR^{2A}R^{2B}$. In aspects, $R^2$ is —$OR^{2A}$. In aspects, $R^2$ is —$NR^{2A}SO_2R^{2B}$. In aspects, $R^2$ is —$NR^{2A}$C(O)$R^{2B}$. In aspects, $R^2$ is —$NR^{2A}$C(O)$OR^{2B}$. In aspects, $R^2$ is —$NR^{2A}OR^{2B}$. In aspects, $X^2$ is independently —F. In aspects, $X^2$ is independently —Cl. In aspects, $X^2$ is independently —Br. In aspects, $X^2$ is independently —I.

In aspects, $R^2$ is hydrogen. In aspects, $R^2$ is oxo. In aspects, $R^2$ is halogen. In aspects, $R^2$ is —$CCl_3$. In aspects, $R^2$ is —$CBr_3$. In aspects, $R^2$ is —$CF_3$. In aspects, $R^2$ is —$CI_3$. In aspects, $R^2$ is —$CHCl_2$. In aspects, $R^2$ is —$CHBr_2$. In aspects, $R^2$ is —$CHF_2$. In aspects, $R^2$ is —$CHI_2$. In aspects, $R^2$ is —$CH_2Cl$. In aspects, $R^2$ is —$CH_2Br$. In aspects, $R^2$ is —$CH_2F$. In aspects, $R^2$ is —$CH_2I$. In aspects, $R^2$ is —CN. In aspects, $R^2$ is —OH. In aspects, $R^2$ is —$NH_2$. In aspects, $R^2$ is —COOH. In aspects, $R^2$ is —$CONH_2$. In aspects, $R^2$ is —$NO_2$. In aspects, $R^2$ is —SH. In aspects, $R^2$ is —$SO_3H$. In aspects, $R^2$ is —$SO_4H$. In aspects, $R^2$ is —$SO_2NH_2$. In aspects, $R^2$ is —$NHNH_2$. In aspects, $R^2$ is —$ONH_2$. In aspects, $R^2$ is —NHC(O)$NHNH_2$. In aspects, $R^2$ is —NHC(O)$NH_2$. In aspects, $R^2$ is —$NHSO_2H$. In aspects, $R^2$ is —NHC(O)H. In aspects, $R^2$ is —NHC(O)OH. In aspects, $R^2$ is —NHOH. In aspects, $R^2$ is —$OCCl_3$. In aspects, $R^2$ is —$OCF_3$. In aspects, $R^2$ is —$OCBr_3$. In aspects, $R^2$ is —$OCI_3$. In aspects, $R^2$ is —$OCHCl_2$. In aspects, $R^2$ is —$OCHBr_2$. In aspects, $R^2$ is —$OCHI_2$. In aspects, $R^2$ is —$OCHF_2$. In aspects, $R^2$ is —$OCH_2Cl$. In aspects, $R^2$ is —$OCH_2Br$. In aspects, $R^2$ is —$OCH_2I$. In aspects, $R^2$ is —$OCH_2F$. In aspects, $R^2$ is —$N_3$. In aspects, $R^2$ is —$OCH_3$. In aspects, $R^2$ is —$CH_3$. In aspects, $R^2$ is —$CH_2CH_3$. In aspects, $R^2$ is unsubstituted propyl. In aspects, $R^2$ is unsubstituted isopropyl. In aspects, $R^2$ is unsubstituted butyl. In aspects, $R^2$ is unsubstituted tert-butyl. In aspects, $R^2$ is —F. In aspects, $R^2$ is —Cl. In aspects, $R^2$ is —Br. In aspects, $R^2$ is —I.

In aspects, $R^2$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In aspects, $R^2$ is substituted or unsubstituted alkyl (e.g., $C_1$-$C_8$ alkyl, $C_1$-$C_6$ alkyl, or $C_1$-$C_4$ alkyl). In aspects, $R^2$ is substituted alkyl (e.g., $C_1$-$C_8$ alkyl, $C_1$-$C_6$ alkyl, or $C_1$-$C_4$ alkyl). In aspects, $R^2$ is an unsubstituted alkyl (e.g., $C_1$-$C_8$ alkyl, $C_1$-$C_6$ alkyl, or $C_1$-$C_4$ alkyl). In aspects, $R^2$ is substituted or unsubstituted heteroalkyl (e.g., 2 to 8 membered heteroalkyl, 2 to 6 membered heteroalkyl, or 2 to 4 membered heteroalkyl). In aspects, $R^2$ is substituted heteroalkyl (e.g., 2 to 8 membered heteroalkyl, 2 to 6 membered heteroalkyl, or 2 to 4 membered heteroalkyl). In aspects, $R^2$ is an unsubstituted heteroalkyl (e.g., 2 to 8 membered heteroalkyl, 2 to 6 membered heteroalkyl, or 2 to 4 membered heteroalkyl). In aspects, $R^2$ is substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^2$ is substituted cycloalkyl (e.g., $C_3$-$C_8$ cycloalkyl, $C_3$-$C_6$ cycloalkyl, or $C_5$-$C_6$ cycloalkyl). In aspects, $R^2$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^2$ is substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^2$ is substituted heterocycloalkyl (e.g., 3 to 8 membered heterocycloalkyl, 3 to 6 membered heterocycloalkyl, or 5 to 6 membered heterocycloalkyl). In aspects, $R^2$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^2$ is substituted or unsubstituted aryl (e.g., $C_6$-$C_{10}$ aryl, $C_{10}$ aryl, or phenyl). In aspects, $R^2$ is substituted aryl (e.g., $C_6$-$C_{10}$ aryl, $C_{10}$ aryl, or phenyl). In aspects, $R^2$ is an unsubstituted aryl (e.g., $C_6$-$C_{10}$ aryl, $C_{10}$ aryl, or phenyl). In aspects, $R^2$ is substituted or unsubstituted heteroaryl (e.g., 5 to 10 membered heteroaryl, 5 to 9 membered heteroaryl, or 5 to 6 membered heteroaryl). In aspects, $R^2$ is substituted heteroaryl (e.g., 5 to 10 membered heteroaryl, 5 to 9 membered heteroaryl, or 5 to 6 membered heteroaryl). In aspects, $R^2$ is an unsubstituted heteroaryl (e.g., 5 to 10 membered heteroaryl, 5 to 9 membered heteroaryl, or 5 to 6 membered heteroaryl).

$R^{24}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{25}$-substituted or unsubstituted alkyl (e.g., $C_1$-$C_8$ alkyl, $C_1$-$C_6$ alkyl, or $C_1$-$C_4$ alkyl), $R^{25}$-substituted or unsubstituted heteroalkyl (e.g., 2 to 8 membered heteroalkyl, 2 to 6 membered heteroalkyl, or 2 to 4 membered heteroalkyl), $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., $C_6$-$C_{10}$ aryl, $C_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl). In aspects, $R^{24}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{24}$ is independently oxo. In aspects, $R^{24}$ is independently halogen. In aspects, $R^{24}$ is independently $—CCl_3$. In aspects, $R^{24}$ is independently $—CBr_3$. In aspects, $R^{24}$ is independently $—CF_3$. In aspects, $R^{24}$ is independently $—CI_3$. In aspects, $R^{24}$ is independently $—CHCl_2$. In aspects, $R^{24}$ is independently $—CHBr_2$. In aspects, $R^{24}$ is independently $—CHF_2$. In aspects, $R^{24}$ is independently $—CHI_2$. In aspects, $R^{24}$ is independently $—CH_2Cl$. In aspects, $R^{24}$ is independently $—CH_2Br$. In aspects, $R^{24}$ is independently $—CH_2F$. In aspects, $R^{24}$ is independently $—CH_2I$. In aspects, $R^{24}$ is independently —CN. In aspects, $R^{24}$ is independently —OH. In aspects, $R^{24}$ is independently $—NH_2$. In aspects, $R^{24}$ is independently —COOH. In aspects, $R^{24}$ is independently $—CONH_2$. In aspects, $R^{24}$ is independently $—NO_2$. In aspects, $R^{24}$ is independently —SH. In aspects, $R^{24}$ is independently $—SO_3H$. In aspects, $R^{24}$ is independently $—SO_4H$. In aspects, $R^{24}$ is independently $—SO_2NH_2$. In aspects, $R^{24}$ is independently $—NHNH_2$. In aspects, $R^{24}$ is independently $—ONH_2$. In aspects, $R^{24}$ is independently $—NHC(O)NHNH_2$. In aspects, $R^{24}$ is independently $—NHC(O)NH_2$. In aspects, $R^{24}$ is independently $—NHSO_2H$. In aspects, $R^{24}$ is independently —NHC(O)H. In aspects, $R^{24}$ is independently —NHC(O)OH. In aspects, $R^{24}$ is independently —NHOH. In aspects, $R^{24}$ is independently $—OCCl_3$. In aspects, $R^{24}$ is independently $—OCF_3$. In aspects, $R^{24}$ is independently $—OCBr_3$. In aspects, $R^{24}$ is independently $—OCI_3$. In aspects, $R^{24}$ is independently $—OCHCl_2$. In aspects, $R^{24}$ is independently $—OCHBr_2$. In aspects, $R^{24}$ is independently $—OCHI_2$. In aspects, $R^{24}$ is independently $—OCHF_2$. In aspects, $R^{24}$ is independently $—OCH_2Cl$. In aspects, $R^{24}$ is independently $—OCH_2Br$. In aspects, $R^{24}$ is independently $—OCH_2I$. In aspects, $R^{24}$ is independently $—OCH_2F$. In aspects, $R^{24}$ is independently $—N_3$. In aspects, $R^{24}$ is independently $—OCH_3$. In aspects, $R^{24}$ is independently $—CH_3$. In aspects, $R^{24}$ is independently $—CH_2CH_3$. In aspects, $R^{24}$ is independently unsubstituted propyl. In aspects, $R^{24}$ is independently unsubstituted isopropyl. In aspects, $R^{24}$ is independently unsubstituted butyl. In aspects, $R^{24}$ is independently unsubstituted tert-butyl. In aspects, $R^{24}$ is independently —F. In aspects, $R^{24}$ is independently —Cl. In aspects, $R^{24}$ is independently —Br. In aspects, $R^{24}$ is independently —I.

In aspects, $R^{24}$ is independently $R^{25}$-substituted or unsubstituted alkyl (e.g., $C_1$-$C_8$ alkyl, $C_1$-$C_6$ alkyl, or $C_1$-$C_4$ alkyl). In aspects, $R^{24}$ is independently $R^{25}$-substituted alkyl (e.g., $C_1$-$C_8$ alkyl, $C_1$-$C_6$ alkyl, or $C_1$-$C_4$ alkyl). In aspects, $R^{24}$ is independently an unsubstituted alkyl (e.g., $C_1$-$C_8$ alkyl, $C_1$-$C_6$ alkyl, or $C_1$-$C_4$ alkyl). In aspects, $R^{24}$ is independently $R^{25}$-substituted or unsubstituted heteroalkyl (e.g., 2 to 8 membered heteroalkyl, 2 to 6 membered heteroalkyl, or 2 to 4 membered heteroalkyl). In aspects, $R^{24}$ is independently $R^{25}$-substituted heteroalkyl (e.g., 2 to 8 membered heteroalkyl, 2 to 6 membered heteroalkyl, or 2 to 4 membered heteroalkyl). In aspects, $R^{24}$ is independently an unsubstituted heteroalkyl (e.g., 2 to 8 membered heteroalkyl, 2 to 6 membered heteroalkyl, or 2 to 4 membered heteroalkyl). In aspects, $R^{24}$ is independently $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{24}$ is independently $R^{25}$-substituted cycloalkyl (e.g., $C_3$-$C_8$ cycloalkyl, $C_3$-$C_6$ cycloalkyl, or $C_5$-$C_6$ cycloalkyl). In aspects, $R^{24}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{24}$ is independently $R^{25}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{24}$ is independently $R^{25}$-substituted heterocycloalkyl (e.g., 3 to 8 membered heterocycloalkyl, 3 to 6 membered heterocycloalkyl, or 5 to 6 membered heterocycloalkyl). In aspects, $R^{24}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{24}$ is independently $R^{25}$-substituted or unsubstituted aryl (e.g., $C_6$-$C_{10}$ aryl, $C_{10}$ aryl, or phenyl). In aspects, $R^{24}$ is independently $R^{25}$-substituted aryl (e.g., $C_6$-$C_{10}$ aryl, $C_{10}$ aryl, or phenyl). In aspects, $R^{24}$ is independently an unsubstituted aryl (e.g., $C_6$-$C_{10}$ aryl, $C_{10}$ aryl, or phenyl). In aspects, $R^{24}$ is independently $R^{25}$-substituted or unsubstituted heteroaryl (e.g., 5 to 10 membered heteroaryl, 5 to 9 membered heteroaryl, or 5 to 6 membered heteroaryl). In aspects, $R^{24}$ is independently $R^{25}$-substituted heteroaryl (e.g., 5 to 10 membered heteroaryl, 5 to 9 membered heteroaryl, or 5 to 6 membered heteroaryl). In aspects, $R^{24}$ is independently an unsubstituted heteroaryl (e.g., 5 to 10 membered heteroaryl, 5 to 9 membered heteroaryl, or 5 to 6 membered heteroaryl).

$R^{25}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl). In aspects, $R^{25}$ is independently oxo, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{25}$ is independently $R^{26}$-substituted or unsubstituted alkyl (e.g., $C_1$-$C_8$ alkyl, $C_1$-$C_6$ alkyl, or $C_1$-$C_4$ alkyl). In aspects, $R^{25}$ is independently $R^{26}$-substituted alkyl (e.g., $C_1$-$C_8$ alkyl, $C_1$-$C_6$ alkyl, or $C_1$-$C_4$ alkyl). In aspects, $R^{25}$ is independently an unsubstituted alkyl (e.g., $C_1$-$C_8$ alkyl, $C_1$-$C_6$ alkyl, or $C_1$-$C_4$ alkyl). In aspects, $R^{25}$ is independently $R^{26}$-substituted or unsubstituted heteroalkyl (e.g., 2 to 8 membered heteroalkyl, 2 to 6 membered heteroalkyl, or 2 to 4 membered heteroalkyl). In aspects, $R^{25}$ is independently $R^{26}$-substituted heteroalkyl (e.g., 2 to 8 membered heteroalkyl, 2 to 6 membered heteroalkyl, or 2 to 4 membered heteroalkyl). In aspects, $R^{25}$ is independently an unsubstituted heteroalkyl (e.g., 2 to 8 membered heteroalkyl, 2 to 6 membered heteroalkyl, or 2 to 4 membered heteroalkyl). In aspects, $R^{25}$ is independently $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{25}$ is independently $R^{26}$-substituted cycloalkyl (e.g., $C_3$-$C_8$ cycloalkyl, $C_3$-$C_6$ cycloalkyl, or $C_5$-$C_6$ cycloalkyl). In aspects, $R^{25}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{25}$ is independently $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{25}$ is independently $R^{26}$-substituted heterocycloalkyl (e.g., 3 to 8 membered heterocycloalkyl, 3 to 6 membered heterocycloalkyl, or 5 to 6 membered heterocycloalkyl). In aspects, $R^{25}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{25}$ is independently $R^{26}$-substituted or unsubstituted aryl (e.g., $C_6$-$C_{10}$ aryl, $C_{10}$ aryl, or phenyl). In aspects, $R^{25}$ is independently $R^{26}$-substituted aryl (e.g., $C_6$-$C_{10}$ aryl, $C_{10}$ aryl, or phenyl). In aspects, $R^{25}$ is independently an unsubstituted aryl (e.g., $C_6$-$C_{10}$ aryl, $C_{10}$ aryl, or phenyl). In aspects, $R^{25}$ is independently $R^{26}$-substituted or unsubstituted heteroaryl (e.g., 5 to 10 membered heteroaryl, 5 to 9 membered heteroaryl, or 5 to 6 membered heteroaryl). In aspects, $R^{25}$ is independently $R^{26}$-substituted heteroaryl (e.g., 5 to 10 membered heteroaryl, 5 to 9 membered heteroaryl, or 5 to 6 membered heteroaryl). In aspects, $R^{25}$ is independently an unsubstituted heteroaryl (e.g., 5 to 10 membered heteroaryl, 5 to 9 membered heteroaryl, or 5 to 6 membered heteroaryl).

In aspects, $R^{25}$ is independently oxo. In aspects, $R^{25}$ is independently halogen. In aspects, $R^{25}$ is independently $—CCl_3$. In aspects, $R^{25}$ is independently $—CBr_3$. In aspects, $R^{25}$ is independently $—CF_3$. In aspects, $R^{25}$ is independently $—CI_3$. In aspects, $R^{25}$ is independently $—CHCl_2$. In aspects, $R^{25}$ is independently $—CHBr_2$. In aspects, $R^{25}$ is independently $—CHF_2$. In aspects, $R^{25}$ is independently $—CHI_2$. In aspects, $R^{25}$ is independently $—CH_2Cl$. In aspects, $R^{25}$ is independently $—CH_2Br$. In aspects, $R^{25}$ is independently $—CH_2F$. In aspects, $R^{25}$ is independently $—CH_2I$. In aspects, $R^{25}$ is independently —CN. In aspects, $R^{25}$ is independently —OH. In aspects, $R^{25}$ is independently $—NH_2$. In aspects, $R^{25}$ is independently —COOH. In aspects, $R^{25}$ is independently $—CONH_2$. In aspects, $R^{25}$ is independently $—NO_2$. In aspects, $R^{25}$ is independently —SH. In aspects, $R^{25}$ is independently $—SO_3H$. In aspects, $R^{25}$ is independently $—SO_4H$. In aspects, $R^{25}$ is independently $—SO_2NH_2$. In aspects, $R^{25}$ is independently $—NHNH_2$. In aspects, $R^{25}$ is independently $—ONH_2$. In aspects, $R^{25}$ is independently $—NHC(O)NHNH_2$. In aspects, $R^{25}$ is independently $—NHC(O)NH_2$. In aspects, $R^{25}$ is independently $—NHSO_2H$. In aspects, $R^{25}$ is independently —NHC(O)H. In aspects, $R^{25}$ is independently —NHC(O)OH. In aspects, $R^{25}$ is independently —NHOH. In aspects, $R^{25}$ is independently $—OCCl_3$. In aspects, $R^{25}$ is independently $—OCF_3$. In aspects, $R^{25}$ is independently $—OCBr_3$. In aspects, $R^{25}$ is independently $—OCI_3$. In aspects, $R^{25}$ is independently $—OCHCl_2$. In aspects, $R^{25}$ is independently $—OCHBr_2$. In aspects, $R^{25}$ is independently $—OCHI_2$. In aspects, $R^{25}$ is independently $—OCHF_2$. In aspects, $R^{25}$ is independently $—OCH_2Cl$. In aspects, $R^{25}$ is independently $—OCH_2Br$. In aspects, $R^{25}$ is independently $—OCH_2I$. In aspects, $R^{25}$ is independently $—OCH_2F$. In aspects, $R^{25}$ is independently $—N_3$. In aspects, $R^{25}$ is independently $—OCH_3$. In aspects, $R^{25}$ is independently $—CH_3$. In aspects, $R^{25}$ is independently $—CH_2CH_3$. In aspects, $R^{25}$ is independently unsubstituted propyl. In aspects, $R^{25}$ is independently unsubstituted isopropyl. In aspects, $R^{25}$ is independently unsubstituted butyl. In aspects, $R^{25}$ is independently unsubstituted tert-butyl. In aspects, $R^{25}$ is independently —F. In aspects, $R^{25}$ is independently —Cl. In aspects, $R^{25}$ is independently —Br. In aspects, $R^{25}$ is independently —I.

$R^{26}$ is independently oxo, halogen, $—CF_3$, $—CCl_3$, $—CI_3$, $—CHF_2$, $—CHBr_2$, $—CHCl_2$, $—CH_2F$, $—CH_2Br$, $—CH_2Cl$, $—OCF_3$, $—OCBr_3$, $—OCCl_3$, $—OCI_3$, $—OCHF_2$, $—OCHBr_2$, $—OCHCl_2$, $—OCH_2F$, $—OCH_2Br$, $—OCH_2Cl$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{26}$ is independently an unsubstituted alkyl (e.g., $C_1$-$C_8$ alkyl, $C_1$-$C_6$ alkyl, or $C_1$-$C_4$ alkyl). In aspects, $R^{26}$ is independently an unsubstituted heteroalkyl (e.g., 2 to 8 membered heteroalkyl, 2 to 6 membered heteroalkyl, or 2 to 4 membered heteroalkyl). In aspects, $R^{26}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{26}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{26}$ is independently an unsubstituted aryl (e.g., $C_6$-$C_{10}$ aryl, $C_{10}$ aryl, or phenyl). In aspects, $R^{26}$ is independently an unsubstituted heteroaryl (e.g., 5 to 10 membered heteroaryl, 5 to 9 membered heteroaryl, or 5 to 6 membered heteroaryl).

In aspects, $R^{26}$ is independently oxo. In aspects, $R^{26}$ is independently halogen In aspects, $R^{26}$ is independently $—CCl_3$. In aspects, $R^{26}$ is independently $—CBr_3$. In aspects, $R^{26}$ is independently $—CF_3$. In aspects, $R^{26}$ is independently $—CI_3$. In aspects, $R^{26}$ is independently $—CHCl_2$ In aspects, $R^{26}$ is independently $—CHBr_2$. In aspects, $R^{26}$ is independently $—CHF_2$. In aspects, $R^{26}$ is independently $—CHI_2$. In aspects, $R^{26}$ is independently $—CH_2Cl$. In aspects, $R^{26}$ is independently $—CH_2Br$. In aspects, $R^{26}$ is independently $—CH_2F$. In aspects, $R^{26}$ is independently $—CH_2I$. In aspects, $R^{26}$ is independently —CN. In aspects, $R^{26}$ is independently —OH. In aspects, $R^{26}$ is independently $—NH_2$. In aspects, $R^{26}$ is independently —COOH. In aspects, $R^{26}$ is independently $—CONH_2$. In aspects, $R^{26}$ is independently $—NO_2$. In aspects, $R^{26}$ is independently —SH. In aspects, $R^{26}$ is independently $—SO_3H$. In aspects, $R^{26}$ is independently $—SO_4H$. In aspects, $R^{26}$ is independently $—SO_2NH_2$. In aspects, $R^{26}$ is independently $—NHNH_2$. In aspects, $R^{26}$ is independently $—ONH_2$. In aspects, $R^{26}$ is independently $—NHC(O)NHNH_2$. In aspects, $R^{26}$ is independently $—NHC(O)NH_2$. In aspects, $R^{26}$ is independently $—NHSO_2H$. In aspects, $R^{26}$ is independently —NHC(O)H. In aspects, $R^{26}$ is independently —NHC(O)OH. In aspects, $R^{26}$ is independently —NHOH. In aspects, $R^{26}$ is independently —$OCCl_3$. In aspects, $R^{26}$ is independently —$OCF_3$. In aspects, $R^{26}$ is independently —$OCBr_3$. In aspects, $R^{26}$ is independently —$OCI_3$. In aspects, $R^{26}$ is independently —$OCHCl_2$. In aspects, $R^{26}$ is independently —$OCHBr_2$. In aspects, $R^{26}$ is independently —$OCHI_2$. In aspects, $R^{26}$ is independently —$OCHF_2$. In aspects, $R^{26}$ is independently —$OCH_2Cl$. In aspects, $R^{26}$ is independently —$OCH_2Br$. In aspects, $R^{26}$ is independently —$OCH_2I$. In aspects, $R^{26}$ is independently —$OCH_2F$. In aspects, $R^{26}$ is independently —$N_3$. In aspects, $R^{26}$ is independently —$OCH_3$. In aspects, $R^{26}$ is independently —$CH_3$. In aspects, $R^{26}$ is independently —$CH_2CH_3$. In aspects, $R^{26}$ is independently unsubstituted propyl. In aspects, $R^{26}$ is independently unsubstituted isopropyl. In aspects, $R^{26}$ is independently unsubstituted butyl. In aspects, $R^{26}$ is independently unsubstituted tert-butyl. In aspects, $R^{26}$ is independently —F. In aspects, $R^{26}$ is independently —Cl. In aspects, $R^{26}$ is independently —Br. In aspects, $R^{26}$ is independently —I.

In aspects, $R^{2A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{2A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In aspects, $R^{2A}$ is independently $R^{24}$-substituted or unsubstituted alkyl (e.g., $C_1$-$C_8$ alkyl, $C_1$-$C_6$ alkyl, or $C_1$-$C_4$ alkyl). In aspects, $R^{2A}$ is independently $R^{24}$-substituted alkyl (e.g., $C_1$-$C_8$ alkyl, $C_1$-$C_6$ alkyl, or $C_1$-$C_4$ alkyl). In aspects, $R^{2A}$ is independently an unsubstituted alkyl (e.g., $C_1$-$C_8$ alkyl, $C_1$-$C_6$ alkyl, or $C_1$-$C_4$ alkyl). In aspects, $R^{2A}$ is independently $R^{24}$-substituted or unsubstituted heteroalkyl (e.g., 2 to 8 membered heteroalkyl, 2 to 6 membered heteroalkyl, or 2 to 4 membered heteroalkyl). In aspects, $R^{2A}$ is independently $R^{24}$-substituted heteroalkyl (e.g., 2 to 8 membered heteroalkyl, 2 to 6 membered heteroalkyl, or 2 to 4 membered heteroalkyl). In aspects, $R^{2A}$ is independently an unsubstituted heteroalkyl (e.g., 2 to 8 membered heteroalkyl, 2 to 6 membered heteroalkyl, or 2 to 4 membered heteroalkyl). In aspects, $R^{2A}$ is independently $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{2A}$ is independently $R^{24}$-substituted cycloalkyl (e.g., $C_3$-$C_8$ cycloalkyl, $C_3$-$C_6$ cycloalkyl, or $C_5$-$C_6$ cycloalkyl). In aspects, $R^{2A}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{2A}$ is independently $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{2A}$ is independently $R^{24}$-substituted heterocycloalkyl (e.g., 3 to 8 membered heterocycloalkyl, 3 to 6 membered heterocycloalkyl, or 5 to 6 membered heterocycloalkyl). In aspects, $R^{2A}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{2A}$ is independently $R^{24}$-substituted or unsubstituted aryl (e.g., $C_6$-$C_{10}$ aryl, $C_{10}$ aryl, or phenyl). In aspects, $R^{2A}$ is independently $R^{24}$-substituted aryl (e.g., $C_6$-$C_{10}$ aryl, $C_{10}$ aryl, or phenyl). In aspects, $R^{2A}$ is independently an unsubstituted aryl (e.g., $C_6$-$C_{10}$ aryl, $C_{10}$ aryl, or phenyl). In aspects, $R^{2A}$ is independently $R^{24}$-substituted or unsubstituted heteroaryl (e.g., 5 to 10 membered heteroaryl, 5 to 9 membered heteroaryl, or 5 to 6 membered heteroaryl). In aspects, $R^{2A}$ is independently $R^{24}$-substituted heteroaryl (e.g., 5 to 10 membered heteroaryl, 5 to 9 membered heteroaryl, or 5 to 6 membered heteroaryl). In aspects, $R^{2A}$ is independently an unsubstituted heteroaryl (e.g., 5 to 10 membered heteroaryl, 5 to 9 membered heteroaryl, or 5 to 6 membered heteroaryl).

In aspects, $R^{2A}$ is independently —$CCl_3$. In aspects, $R^{2A}$ is independently —$CBr_3$. In aspects, $R^{2A}$ is independently —$CF_3$. In aspects, $R^{2A}$ is independently —$CI_3$. In aspects, $R^{2A}$ is independently —$CHCl_2$. In aspects, $R^{2A}$ is independently —$CHBr_2$. In aspects, $R^{2A}$ is independently —$CHF_2$. In aspects, $R^{2A}$ is independently —$CHI_2$. In aspects, $R^{2A}$ is independently —$CH_2Cl$. In aspects, $R^{2A}$ is independently —$CH_2Br$. In aspects, $R^{2A}$ is independently —$CH_2F$. In aspects, $R^{2A}$ is independently —$CH_2I$. In aspects, $R^{2A}$ is independently —CN. In aspects, $R^{2A}$ is independently —OH. In aspects, $R^{2A}$ is independently —COOH. In aspects, $R^{2A}$ is independently —$CONH_2$. In aspects, $R^{2A}$ is independently —$OCCl_3$. In aspects, $R^{2A}$ is independently —$OCF_3$. In aspects, $R^{2A}$ is independently —$OCBr_3$. In aspects, $R^{2A}$ is independently —$OCI_3$. In aspects, $R^{2A}$ is independently —$OCHCl_2$. In aspects, $R^{2A}$ is independently —$OCHBr_2$. In aspects, $R^{2A}$ is independently —$OCHI_2$. In aspects, $R^{2A}$ is independently —$OCHF_2$. In aspects, $R^{2A}$ is independently —$OCH_2Cl$. In aspects, $R^{2A}$ is independently —$OCH_2Br$. In aspects, $R^{2A}$ is independently —$OCH_2I$. n aspects, $R^{2A}$ is independently —$OCH_2F$. In aspects, $R^{2A}$ is independently —$OCH_3$. In aspects, $R^{2A}$ is independently —$CH_3$. In aspects, $R^{2A}$ is independently —$CH_2CH_3$. In aspects, $R^{2A}$ is independently unsubstituted propyl. In aspects, $R^{2A}$ is independently unsubstituted isopropyl. In aspects, $R^{2A}$ is independently unsubstituted butyl. In aspects, $R^{2A}$ is independently unsubstituted tert-butyl. In aspects, $R^{2A}$ is independently hydrogen.

In aspects, $R^{2B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{2B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In aspects, $R^{2B}$ is independently $R^{24}$-substituted or unsubstituted alkyl (e.g., $C_1$-$C_8$ alkyl, $C_1$-$C_6$ alkyl, or $C_1$-$C_4$ alkyl). In aspects, $R^{2B}$ is independently $R^{24}$-substituted alkyl (e.g., $C_1$-$C_8$ alkyl, $C_1$-$C_6$ alkyl, or $C_1$-$C_4$ alkyl). In aspects, $R^{2B}$ is independently an unsubstituted alkyl (e.g., $C_1$-$C_8$ alkyl, $C_1$-$C_6$ alkyl, or $C_1$-$C_4$ alkyl). In aspects, $R^{2B}$ is independently $R^{24}$-substituted or unsubstituted heteroalkyl (e.g., 2 to 8 membered heteroalkyl, 2 to 6 membered heteroalkyl, or 2 to 4 membered heteroalkyl). In aspects, $R^{2B}$ is independently $R^{24}$-substituted heteroalkyl (e.g., 2 to 8 membered heteroalkyl, 2 to 6 membered heteroalkyl, or 2 to 4 membered heteroalkyl). In aspects, $R^{2B}$ is independently an unsubstituted heteroalkyl (e.g., 2 to 8 membered heteroalkyl, 2 to 6 membered heteroalkyl, or 2 to 4 membered heteroalkyl). In aspects, $R^{2B}$ is independently $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{2B}$ is independently $R^{24}$-substituted cycloalkyl (e.g., $C_3$-$C_8$ cycloalkyl, $C_3$-$C_6$ cycloalkyl, or $C_5$-$C_6$ cycloalkyl). In aspects, $R^{2B}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{2B}$ is independently $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{2B}$ is independently $R^{24}$-substituted heterocycloalkyl (e.g., 3 to 8 membered heterocycloalkyl, 3 to 6 membered heterocycloalkyl, or 5 to 6 membered heterocycloalkyl). In aspects, $R^{2B}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{2B}$ is independently $R^{24}$-substituted or unsubstituted aryl (e.g., $C_6$-$C_{10}$ aryl, $C_{10}$ aryl, or phenyl). In aspects, $R^{2B}$ is independently $R^{24}$-substituted aryl (e.g., $C_6$-$C_{10}$ aryl, $C_{10}$ aryl, or phenyl). In aspects, $R^{2B}$ is independently an unsubstituted aryl (e.g., $C_6$-$C_{10}$ aryl, $C_{10}$ aryl, or phenyl). In aspects, $R^{2B}$ is independently $R^{24}$-substituted or unsubstituted heteroaryl (e.g., 5 to 10 membered heteroaryl, 5 to 9 membered heteroaryl, or 5 to 6 membered heteroaryl). In aspects, $R^{2B}$ is independently $R^{24}$-substituted heteroaryl (e.g., 5 to 10 membered heteroaryl, 5 to 9 membered heteroaryl, or 5 to 6 membered heteroaryl). In aspects, $R^{2B}$ is independently an unsubstituted heteroaryl (e.g., 5 to 10 membered heteroaryl, 5 to 9 membered heteroaryl, or 5 to 6 membered heteroaryl).

In aspects, $R^{2B}$ is independently —$CCl_3$. In aspects, $R^{2B}$ is independently —$CBr_3$. In aspects, $R^{2B}$ is independently —$CF_3$. In aspects, $R^{2B}$ is independently —$CI_3$. In aspects, $R^{2B}$ is independently —$CHCl_2$. In aspects, $R^{2B}$ is independently —$CHBr_2$. In aspects, $R^{2B}$ is independently —$CHF_2$. In aspects, $R^{2B}$ is independently —$CHI_2$. In aspects, $R^{2B}$ is independently —$CH_2Cl$. In aspects, $R^{2B}$ is independently —$CH_2Br$. In aspects, $R^{2B}$ is independently —$CH_2F$. In aspects, $R^{2B}$ is independently —$CH_2I$. In aspects, $R^{2B}$ is independently —CN. In aspects, $R^{2B}$ is independently —OH. In aspects, $R^{2B}$ is independently —COOH. In aspects, $R^{2B}$ is independently —$CONH_2$. In aspects, $R^{2B}$ is independently —$OCCl_3$. In aspects, $R^{2B}$ is independently —$OCF_3$. In aspects, $R^{2B}$ is independently —$OCBr_3$. In aspects, $R^{2B}$ is independently —$OCI_3$. In aspects, $R^{2B}$ is independently —$OCHCl_2$. In aspects, $R^{2B}$ is independently —$OCHBr_2$. In aspects, $R^{2B}$ is independently —$OCHI_2$. In aspects, $R^{2B}$ is independently —$OCHF_2$. In aspects, $R^{2B}$ is independently —$OCH_2Cl$. In aspects, $R^{2B}$ is independently —$OCH_2Br$. In aspects, $R^{2B}$ is independently —$OCH_2I$. In aspects, $R^{2B}$ is independently —$OCH_2F$. In aspects, $R^{2B}$ is independently —$OCH_3$. In aspects, $R^{2B}$ is independently —$CH_3$. In aspects, $R^{2B}$ is independently —$CH_2CH_3$. In aspects, $R^{2B}$ is independently unsubstituted propyl. In aspects, $R^{2B}$ is independently unsubstituted isopropyl. In aspects, $R^{2B}$ is independently unsubstituted butyl. In aspects, $R^{2B}$ is independently unsubstituted tert-butyl. In aspects, $R^{2B}$ is independently hydrogen.

In embodiments, $R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —NHC(O)$NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —NHC(O)$NHNR^{3A}R^{3B}$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

In aspects, $R^3$ is hydrogen, halogen, —$CF_3$, —$CBr_3$, —$CCl_3$, —$CI_3$, —$CHF_2$, —$CHBr_2$, —$CHCl_2$, —$CH_2F$, —$CH_2Br$, —$CH_2Cl$, —$OCF_3$, —$OCBr_3$, —$OCCl_3$, —$OCI_3$, —$OCHF_2$, —$OCHBr_2$, —$OCHCl_2$, —$OCH_2F$, —$OCH_2Br$, —$OCH_2Cl$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^3$ is $R^{27}$-substituted or unsubstituted alkyl (e.g., $C_1$-$C_8$ alkyl, $C_1$-$C_6$ alkyl, or $C_1$-$C_4$ alkyl). In aspects, $R^3$ is $R^{27}$-substituted alkyl (e.g., $C_1$-$C_8$ alkyl, $C_1$-$C_6$ alkyl, or $C_1$-$C_4$ alkyl). In aspects, $R^3$ is an unsubstituted alkyl (e.g., $C_1$-$C_8$ alkyl, $C_1$-$C_6$ alkyl, or $C_1$-$C_4$ alkyl). In aspects, $R^3$ is $R^{27}$-substituted or unsubstituted heteroalkyl (e.g., 2 to 8 membered heteroalkyl, 2 to 6 membered heteroalkyl, or 2 to 4 membered heteroalkyl). In aspects, $R^3$ is $R^{27}$-substituted heteroalkyl (e.g., 2 to 8 membered heteroalkyl, 2 to 6 membered heteroalkyl, or 2 to 4 membered heteroalkyl). In aspects, $R^3$ is an unsubstituted heteroalkyl (e.g., 2 to 8 membered heteroalkyl, 2 to 6 membered heteroalkyl, or 2 to 4 membered heteroalkyl). In aspects, $R^3$ is $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^3$ is $R^{27}$-substituted cycloalkyl (e.g., $C_3$-$C_8$ cycloalkyl, $C_3$-$C_6$ cycloalkyl, or $C_5$-$C_6$ cycloalkyl). In aspects, $R^3$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^3$ is $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^3$ is $R^{27}$-substituted heterocycloalkyl (e.g., 3 to 8 membered heterocycloalkyl, 3 to 6 membered heterocycloalkyl, or 5 to 6 membered heterocycloalkyl). In aspects, $R^3$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^3$ is $R^{27}$-substituted or unsubstituted aryl (e.g., $C_6$-$C_{10}$ aryl, $C_{10}$ aryl, or phenyl). In aspects, $R^3$ is $R^{27}$-substituted aryl (e.g., $C_6$-$C_{10}$ aryl, $C_{10}$ aryl, or phenyl). In aspects, $R^3$ is an unsubstituted aryl (e.g., $C_6$-$C_{10}$ aryl, $C_{10}$ aryl, or phenyl). In aspects, $R^3$ is $R^{27}$-substituted or unsubstituted heteroaryl (e.g., 5 to 10 membered heteroaryl, 5 to 9 membered heteroaryl, or 5 to 6 membered heteroaryl). In aspects, $R^3$ is $R^{27}$-substituted heteroaryl (e.g., 5 to 10 membered heteroaryl, 5 to 9 membered heteroaryl, or 5 to 6 membered heteroaryl). In aspects, $R^3$ is an unsubstituted heteroaryl (e.g., 5 to 10 membered heteroaryl, 5 to 9 membered heteroaryl, or 5 to 6 membered heteroaryl).

In aspects, $R^3$ is $—CX^3_3$. In aspects, $R^3$ is $—CHX^3_2$. In aspects, $R^3$ is $—CH_2X^3$. In aspects, $R^3$ is $—OCX^3_3$. In aspects, $R^3$ is $—OCH_2X^3$. In aspects, $R^3$ is $—OCHX^3_2$. In aspects, $R^3$ is —CN. In aspects, $R^3$ is $—SR^{3A}$. In aspects, $R^3$ is $—SOR^{3A}$. In aspects, $R^3$ is $—SO_2R^{3A}$. In aspects, $R^3$ is $—SO_3R^{3A}$. In aspects, $R^3$ is $—SO_4R^{3A}$. In aspects, $R^3$ is $—SONR^{3A}R^{3B}$. In aspects, $R^3$ is $—SO_2NR^{3A}R^{3B}$. In aspects, $R^3$ is $—NHC(O)NR^{3A}R^{3B}$. In aspects, $R^3$ is —N(O). In aspects, $R^3$ is $—NO_2$. In aspects, $R^3$ is $—NR^{3A}R^{3B}$. In aspects, $R^3$ is $—C(O)R^{3A}$. In aspects, $R^3$ is $—C(O)—OR^{3A}$. In aspects, $R^3$ is $—C(O)NR^{3A}R^{3B}$. In aspects, $R^3$ is $—OR^{3A}$. In aspects, $R^3$ is $—NR^{3A}SO_2R^{3B}$. In aspects, $R^3$ is $—NR^{3A}C(O)R^{3B}$. In aspects, $R^3$ is $—NR^{3A}C(O)OR^{3B}$. In aspects, $R^3$ is $—NR^{3A}OR^{3B}$. In aspects, $X^3$ is independently —F. In aspects, $X^3$ is independently —Cl. In aspects, $X^3$ is independently —Br. In aspects, $X^3$ is independently —I.

In aspects, $R^3$ is hydrogen. In aspects, $R^3$ is oxo. In aspects, $R^3$ is halogen. In aspects, $R^3$ is $—CCl_3$. In aspects, $R^3$ is $—CBr_3$. In aspects, $R^3$ is $—CF_3$. In aspects, $R^3$ is $—CI_3$. In aspects, $R^3$ is $—CHCl_2$. In aspects, $R^3$ is $—CHBr_2$. In aspects, $R^3$ is $—CHF_2$. In aspects, $R^3$ is $—CHI_2$. In aspects, $R^3$ is $—CH_2Cl$. In aspects, $R^3$ is $—CH_2Br$. In aspects, $R^3$ is $—CH_2F$. In aspects, $R^3$ is $—CH_2I$. In aspects, $R^3$ is —CN. In aspects, $R^3$ is —OH. In aspects, $R^3$ is $—NH_2$. In aspects, $R^3$ is —COOH. In aspects, $R^3$ is $—CONH_2$. In aspects, $R^3$ is $—NO_2$. In aspects, $R^3$ is —SH. In aspects, $R^3$ is $—SO_3H$. In aspects, $R^3$ is $—SO_4H$. In aspects, $R^3$ is $—SO_2NH_2$. In aspects, $R^3$ is $—NHNH_2$. In aspects, $R^3$ is $—ONH_2$. In aspects, $R^3$ is $—NHC(O)NHNH_2$. In aspects, $R^3$ is $—NHC(O)NH_2$. In aspects, $R^3$ is $—NHC(O)CH_3$. In aspects, $R^3$ is $—NHC(O)CH_2CH_3$. In aspects, $R^3$ is $—NHC(O)(CH_2)_2CH_3$. In aspects, $R^3$ is $—NHSO_2H$. In aspects, $R^3$ is —NHC(O)H. In aspects, $R^3$ is —NHC(O)OH. In aspects, $R^3$ is —NHOH. In aspects, $R^3$ is $—OCCl_3$. In aspects, $R^3$ is $—OCF_3$. In aspects, $R^3$ is $—OCBr_3$. In aspects, $R^3$ is $—OCI_3$. In aspects, $R^3$ is $—OCHCl_2$. In aspects, $R^3$ is $—OCHBr_2$. In aspects, $R^3$ is $—OCHI_2$. In aspects, $R^3$ is $—OCHF_2$. In aspects, $R^3$ is $—OCH_2Cl$. In aspects, $R^3$ is $—OCH_2Br$. In aspects, $R^3$ is $—OCH_2I$. In aspects, $R^3$ is $—OCH_2F$. In aspects, $R^3$ is $—N_3$. In aspects, $R^3$ is $—OCH_3$. In aspects, $R^3$ is $—CH_3$. In aspects, $R^3$ is $—CH_2CH_3$. In aspects, $R^3$ is unsubstituted propyl. In aspects, $R^3$ is unsubstituted isopropyl. In aspects, $R^3$ is unsubstituted butyl. In aspects, $R^3$ is unsubstituted tert-butyl. In aspects, $R^3$ is —F. In aspects, $R^3$ is —Cl. In aspects, $R^3$ is —Br. In aspects, $R^3$ is —I.

In aspects, $R^3$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In aspects, $R^3$ is substituted or unsubstituted alkyl (e.g., $C_1$-$C_8$ alkyl, $C_1$-$C_6$ alkyl, or $C_1$-$C_4$ alkyl). In aspects, $R^3$ is substituted alkyl (e.g., $C_1$-$C_8$ alkyl, $C_1$-$C_6$ alkyl, or $C_1$-$C_4$ alkyl). In aspects, $R^3$ is an unsubstituted alkyl (e.g., $C_1$-$C_8$ alkyl, $C_1$-$C_6$ alkyl, or $C_1$-$C_4$ alkyl). In aspects, $R^3$ is substituted or unsubstituted heteroalkyl (e.g., 2 to 8 membered heteroalkyl, 2 to 6 membered heteroalkyl, or 2 to 4 membered heteroalkyl). In aspects, $R^3$ is substituted heteroalkyl (e.g., 2 to 8 membered heteroalkyl, 2 to 6 membered heteroalkyl, or 2 to 4 membered heteroalkyl). In aspects, $R^3$ is an unsubstituted heteroalkyl (e.g., 2 to 8 membered heteroalkyl, 2 to 6 membered heteroalkyl, or 2 to 4 membered heteroalkyl). In aspects, $R^3$ is substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^3$ is substituted cycloalkyl (e.g., $C_3$-$C_8$ cycloalkyl, $C_3$-$C_6$ cycloalkyl, or $C_5$-$C_6$ cycloalkyl). In aspects, $R^3$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^3$ is substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^3$ is substituted heterocycloalkyl (e.g., 3 to 8 membered heterocycloalkyl, 3 to 6 membered heterocycloalkyl, or 5 to 6 membered heterocycloalkyl). In aspects, $R^3$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^3$ is substituted or unsubstituted aryl (e.g., $C_6$-$C_{10}$ aryl, $C_{10}$ aryl, or phenyl). In aspects, $R^3$ is substituted aryl (e.g., $C_6$-$C_{10}$ aryl, $C_{10}$ aryl, or phenyl). In aspects, $R^3$ is an unsubstituted aryl (e.g., $C_6$-$C_{10}$ aryl, $C_{10}$ aryl, or phenyl). In aspects, $R^3$ is substituted or unsubstituted heteroaryl (e.g., 5 to 10 membered heteroaryl, 5 to 9 membered heteroaryl, or 5 to 6 membered heteroaryl). In aspects, $R^3$ is substituted heteroaryl (e.g., 5 to 10 membered heteroaryl, 5 to 9 membered heteroaryl, or 5 to 6 membered heteroaryl). In aspects, $R^3$ is an unsubstituted heteroaryl (e.g., 5 to 10 membered heteroaryl, 5 to 9 membered heteroaryl, or 5 to 6 membered heteroaryl).

$R^{27}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In aspects, $R^{27}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{27}$ is independently oxo In aspects, $R^{27}$ is independently halogen. In aspects, $R^{27}$ is independently —$CCl_3$. In aspects, $R^{27}$ is independently —$CBr_3$. In aspects, $R^{27}$ is independently —$CF_3$. In aspects, $R^{27}$ is independently —$CI_3$. In aspects, $R^{27}$ is independently —$CHCl_2$. In aspects, $R^{27}$ is independently —$CHBr_2$. In aspects, $R^{27}$ is independently —$CHF_2$. In aspects, $R^{27}$ is independently —$CHI_2$. In aspects, $R^{27}$ is independently —$CH_2Cl$. In aspects, $R^{27}$ is independently —$CH_2Br$. In aspects, $R^{27}$ is independently —$CH_2F$. In aspects, $R^{27}$ is independently —$CH_2I$. In aspects, $R^{27}$ is independently —CN. In aspects, $R^{27}$ is independently —OH. In aspects, $R^{27}$ is independently —$NH_2$. In aspects, $R^{27}$ is independently —COOH. In aspects, $R^{27}$ is independently —$CONH_2$. In aspects, $R^{27}$ is independently —$NO_2$. In aspects, $R^{27}$ is independently —SH. In aspects, $R^{27}$ is independently —$SO_3H$. In aspects, $R^{27}$ is independently —$SO_4H$. In aspects, $R^{27}$ is independently —$SO_2NH_2$. In aspects, $R^{27}$ is independently —$NHNH_2$. In aspects, $R^{27}$ is independently —$ONH_2$. In aspects, $R^{27}$ is independently —NHC(O)$NHNH_2$. In aspects, $R^{27}$ is independently —NHC(O)$NH_2$. In aspects, $R^{27}$ is independently —NHC(O)$CH_3$. In aspects, $R^{27}$ is independently —$NHSO_2H$. In aspects, $R^{27}$ is independently —NHC(O)H. In aspects, $R^{27}$ is independently —NHC(O)OH. In aspects, $R^{27}$ is independently —NHOH. In aspects, $R^{27}$ is independently —$OCCl_3$. In aspects, $R^{27}$ is independently —$OCF_3$. In aspects, $R^{27}$ is independently —$OCBr_3$. In aspects, $R^{27}$ is independently —$OCI_3$. In aspects, $R^{27}$ is independently —$OCHCl_2$. In aspects, $R^{27}$ is independently —$OCHBr_2$. In aspects, $R^{27}$ is independently —$OCHI_2$. In aspects, $R^{27}$ is independently —$OCHF_2$. In aspects, $R^{27}$ is independently —$OCH_2Cl$. In aspects, $R^{27}$ is independently —$OCH_2Br$. In aspects, $R^{27}$ is independently —$OCH_2I$. n aspects, $R^{27}$ is independently —$OCH_2F$. In aspects, $R^{27}$ is independently —$N_3$. In aspects, $R^{27}$ is independently —$OCH_3$. In aspects, $R^{27}$ is independently —$CH_3$. In aspects, $R^{27}$ is independently —$CH_2CH_3$. In aspects, $R^{27}$ is independently unsubstituted propyl. In aspects, $R^{27}$ is independently unsubstituted isopropyl. In aspects, $R^{27}$ is independently unsubstituted butyl. In aspects, $R^{27}$ is independently unsubstituted tert-butyl. In aspects, $R^{27}$ is independently —F. In aspects, $R^{27}$ is independently —Cl. In aspects, $R^{27}$ is independently —Br. In aspects, $R^{27}$ is independently —I.

In aspects, $R^{27}$ is independently $R^{28}$-substituted or unsubstituted alkyl (e.g., $C_1$-$C_8$ alkyl, $C_1$-$C_6$ alkyl, or $C_1$-$C_4$ alkyl). In aspects, $R^{27}$ is independently $R^{28}$-substituted alkyl (e.g., $C_1$-$C_8$ alkyl, $C_1$-$C_6$ alkyl, or $C_1$-$C_4$ alkyl). In aspects, $R^{27}$ is independently an unsubstituted alkyl (e.g., $C_1$-$C_8$ alkyl, $C_1$-$C_6$ alkyl, or $C_1$-$C_4$ alkyl). In aspects, $R^{27}$ is independently $R^{28}$-substituted or unsubstituted heteroalkyl (e.g., 2 to 8 membered heteroalkyl, 2 to 6 membered heteroalkyl, or 2 to 4 membered heteroalkyl). In aspects, $R^{27}$ is independently $R^{28}$-substituted heteroalkyl (e.g., 2 to 8 membered heteroalkyl, 2 to 6 membered heteroalkyl, or 2 to 4 membered heteroalkyl). In aspects, $R^{27}$ is independently an unsubstituted heteroalkyl (e.g., 2 to 8 membered heteroalkyl, 2 to 6 membered heteroalkyl, or 2 to 4 membered heteroalkyl). In aspects, $R^{27}$ is independently $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{27}$ is independently $R^{28}$-substituted cycloalkyl (e.g., $C_3$-$C_8$ cycloalkyl, $C_3$-$C_6$ cycloalkyl, or $C_5$-$C_6$ cycloalkyl). In aspects, $R^{27}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{27}$ is independently $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{27}$ is independently $R^{28}$-substituted heterocycloalkyl (e.g., 3 to 8 membered heterocycloalkyl, 3 to 6 membered heterocycloalkyl, or 5 to 6 membered heterocycloalkyl). In aspects, $R^{27}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{27}$ is independently $R^{28}$-substituted or unsubstituted aryl (e.g., $C_6$-$C_{10}$ aryl, $C_{10}$ aryl, or phenyl). In aspects, $R^{27}$ is independently $R^{28}$-substituted aryl (e.g., $C_6$-$C_{10}$ aryl, $C_{10}$ aryl, or phenyl). In aspects, $R^{27}$ is independently an unsubstituted aryl (e.g., $C_6$-$C_{10}$ aryl, $C_{10}$ aryl, or phenyl). In aspects, $R^{27}$ is independently $R^{28}$-substituted or unsubstituted heteroaryl (e.g., 5 to 10 membered heteroaryl, 5 to 9 membered heteroaryl, or 5 to 6 membered heteroaryl). In aspects, $R^{27}$ is independently $R^{28}$-substituted heteroaryl (e.g., 5 to 10 membered heteroaryl, 5 to 9 membered heteroaryl, or 5 to 6 membered heteroaryl). In aspects, $R^{27}$ is independently an unsubstituted heteroaryl (e.g., 5 to 10 membered heteroaryl, 5 to 9 membered heteroaryl, or 5 to 6 membered heteroaryl).

$R^{28}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $R^{29}$-substituted or unsubstituted alkyl (e.g., $C_1$-$C_8$ alkyl, $C_1$-$C_6$ alkyl, or $C_1$-$C_4$ alkyl), $R^{29}$-substituted or unsubstituted heteroalkyl (e.g., 2 to 8 membered heteroalkyl, 2 to 6 membered heteroalkyl, or 2 to 4 membered heteroalkyl), $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29}$-substituted or unsubstituted aryl (e.g., $C_6$-$C_{10}$ aryl, $C_{10}$ aryl, or phenyl), or $R^{29}$-substituted or unsubstituted heteroaryl (e.g., 5 to 10 membered heteroaryl, 5 to 9 membered heteroaryl, or 5 to 6 membered heteroaryl). In aspects, $R^{28}$ is independently oxo, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{28}$ is independently $R^{29}$-substituted or unsubstituted alkyl (e.g., $C_1$-$C_8$ alkyl, $C_1$-$C_6$ alkyl, or $C_1$-$C_4$ alkyl). In aspects, $R^{28}$ is independently $R^{29}$-substituted alkyl (e.g., $C_1$-$C_8$ alkyl, $C_1$-$C_6$ alkyl, or $C_1$-$C_4$ alkyl). In aspects, $R^{28}$ is independently an unsubstituted alkyl (e.g., $C_1$-$C_8$ alkyl, $C_1$-$C_6$ alkyl, or $C_1$-$C_4$ alkyl). In aspects, $R^{28}$ is independently $R^{29}$-substituted or unsubstituted heteroalkyl (e.g., 2 to 8 membered heteroalkyl, 2 to 6 membered heteroalkyl, or 2 to 4 membered heteroalkyl). n aspects, $R^{28}$ is independently $R^{29}$-substituted heteroalkyl (e.g., 2 to 8 membered heteroalkyl, 2 to 6 membered heteroalkyl, or 2 to 4 membered heteroalkyl). In aspects, $R^{28}$ is independently an unsubstituted heteroalkyl (e.g., 2 to 8 membered heteroalkyl, 2 to 6 membered heteroalkyl, or 2 to 4 membered heteroalkyl). In aspects, $R^{28}$ is independently $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{28}$ is independently $R^{29}$-substituted cycloalkyl (e.g., $C_3$-$C_8$ cycloalkyl, $C_3$-$C_6$ cycloalkyl, or $C_5$-$C_6$ cycloalkyl). In aspects, $R^{28}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{28}$ is independently $R^{29}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{28}$ is independently $R^{29}$-substituted heterocycloalkyl (e.g., 3 to 8 membered heterocycloalkyl, 3 to 6 membered heterocycloalkyl, or 5 to 6 membered heterocycloalkyl). In aspects, $R^{28}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{28}$ is independently $R^{29}$-substituted or unsubstituted aryl (e.g., $C_6$-$C_{10}$ aryl, $C_{10}$ aryl, or phenyl). In aspects, $R^{28}$ is independently $R^{29}$-substituted aryl (e.g., $C_6$-$C_{10}$ aryl, $C_{10}$ aryl, or phenyl). In aspects, $R^{28}$ is independently an unsubstituted aryl (e.g., $C_6$-$C_{10}$ aryl, $C_{10}$ aryl, or phenyl). In aspects, $R^{28}$ is independently $R^{29}$-substituted or unsubstituted heteroaryl (e.g., 5 to 10 membered heteroaryl, 5 to 9 membered heteroaryl, or 5 to 6 membered heteroaryl). In aspects, $R^{28}$ is independently $R^{29}$-substituted heteroaryl (e.g., 5 to 10 membered heteroaryl, 5 to 9 membered heteroaryl, or 5 to 6 membered heteroaryl). In aspects, $R^{28}$ is independently an unsubstituted heteroaryl (e.g., 5 to 10 membered heteroaryl, 5 to 9 membered heteroaryl, or 5 to 6 membered heteroaryl).

In aspects, $R^{28}$ is independently oxo. In aspects, $R^{28}$ is independently halogen. In aspects, $R^{28}$ is independently $-CCl_3$. In aspects, $R^{28}$ is independently $-CBr_3$. In aspects, $R^{28}$ is independently $-CF_3$. In aspects, $R^{28}$ is independently $-CI_3$. In aspects, $R^{28}$ is independently $-CHCl_2$. In aspects, $R^{28}$ is independently $-CHBr_2$. In aspects, $R^{28}$ is independently $-CHF_2$. In aspects, $R^{28}$ is independently $-CHI_2$. In aspects, $R^{28}$ is independently $-CH_2Cl$. In aspects, $R^{28}$ is independently $-CH_2Br$. In aspects, $R^{28}$ is independently $-CH_2F$. In aspects, $R^{28}$ is independently $-CH_2I$. In aspects, $R^{28}$ is independently $-CN$. In aspects, $R^{28}$ is independently $-OH$. In aspects, $R^{28}$ is independently $-NH_2$. In aspects, $R^{28}$ is independently $-COOH$. In aspects, $R^{28}$ is independently $-CONH_2$. In aspects, $R^{28}$ is independently $-NO_2$. In aspects, $R^{28}$ is independently $-SH$. In aspects, $R^{28}$ is independently $-SO_3H$. In aspects, $R^{28}$ is independently $-SO_4H$. In aspects, $R^{28}$ is independently $-SO_2NH_2$. In aspects, $R^{28}$ is independently $-NHNH_2$. In aspects, $R^{28}$ is independently $-ONH_2$. In aspects, $R^{28}$ is independently $-NHC(O)NHNH_2$. In aspects, $R^{28}$ is independently $-NHC(O)NH_2$. In aspects, $R^{28}$ is independently $-NHC(O)CH_3$. In aspects, $R^{28}$ is independently $-NHSO_2H$. In aspects, $R^{28}$ is independently $-NHC(O)H$. In aspects, $R^{28}$ is independently $-NHC(O)OH$. In aspects, $R^{28}$ is independently $-NHOH$. In aspects, $R^{28}$ is independently $-OCCl_3$. In aspects, $R^{28}$ is independently $-OCF_3$. In aspects, $R^{28}$ is independently $-OCBr_3$. In aspects, $R^{28}$ is independently $-OCI_3$. In aspects, $R^{28}$ is independently $-OCHCl_2$. In aspects, $R^{28}$ is independently $-OCHBr_2$. In aspects, $R^{28}$ is independently $-OCHI_2$. In aspects, $R^{28}$ is independently $-OCHF_2$. In aspects, $R^{28}$ is independently $-OCH_2Cl$. In aspects, $R^{28}$ is independently $-OCH_2Br$. In aspects, $R^{28}$ is independently $-OCH_2I$. In aspects, $R^{28}$ is independently $-OCH_2F$. In aspects, $R^{28}$ is independently $-N_3$. In aspects, $R^{28}$ is independently $-OCH_3$. In aspects, $R^{28}$ is independently $-CH_3$. In aspects, $R^{28}$ is independently $-CH_2CH_3$. In aspects, $R^{28}$ is independently unsubstituted propyl. In aspects, $R^{28}$ is independently unsubstituted isopropyl. In aspects, $R^{28}$ is independently unsubstituted butyl. In aspects, $R^{28}$ is independently unsubstituted tert-butyl. In aspects, $R^{28}$ is independently $-F$. In aspects, $R^{28}$ is independently $-Cl$. In aspects, $R^{28}$ is independently $-Br$. In aspects, $R^{28}$ is independently $-I$.

$R^{29}$ is independently oxo, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{29}$ is independently an unsubstituted alkyl (e.g., $C_1$-$C_8$ alkyl, $C_1$-$C_6$ alkyl, or $C_1$-$C_4$ alkyl). In aspects, $R^{29}$ is independently an unsubstituted heteroalkyl (e.g., 2 to 8 membered heteroalkyl, 2 to 6 membered heteroalkyl, or 2 to 4 membered heteroalkyl). In aspects, $R^{29}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{29}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{29}$ is independently an unsubstituted aryl (e.g., $C_6$-$C_{10}$ aryl, $C_{10}$ aryl, or phenyl). In aspects, $R^{29}$ is independently an unsubstituted heteroaryl (e.g., 5 to 10 membered heteroaryl, 5 to 9 membered heteroaryl, or 5 to 6 membered heteroaryl).

In aspects, $R^{29}$ is independently oxo. In aspects, $R^{29}$ is independently halogen. In aspects, $R^{29}$ is independently $—CCl_3$. In aspects, $R^{29}$ is independently $—CBr_3$. In aspects, $R^{29}$ is independently $—CF_3$. In aspects, $R^{29}$ is independently $—CI_3$. In aspects, $R^{29}$ is independently $—CHCl_2$. In aspects, $R^{29}$ is independently $—CHBr_2$. In aspects, $R^{29}$ is independently $—CHF_2$. In aspects, $R^{29}$ is independently $—CHI_2$. In aspects, $R^{29}$ is independently $—CH_2Cl$. In aspects, $R^{29}$ is independently $—CH_2Br$. In aspects, $R^{29}$ is independently $—CH_2F$. In aspects, $R^{29}$ is independently $—CH_2I$. In aspects, $R^{29}$ is independently —CN. In aspects, $R^{29}$ is independently —OH. In aspects, $R^{29}$ is independently $—NH_2$. In aspects, $R^{29}$ is independently —COOH. In aspects, $R^{29}$ is independently $—CONH_2$. In aspects, $R^{29}$ is independently $—NO_2$. In aspects, $R^{29}$ is independently —SH. In aspects, $R^{29}$ is independently $—SO_3H$. In aspects, $R^{29}$ is independently $—SO_4H$. In aspects, $R^{29}$ is independently $—SO_2NH_2$. In aspects, $R^{29}$ is independently $—NHNH_2$. In aspects, $R^{29}$ is independently $—ONH_2$. In aspects, $R^{29}$ is independently $—NHC(O)NHNH_2$. In aspects, $R^{29}$ is independently $—NHC(O)NH_2$. In aspects, $R^{29}$ is independently $—NHSO_2H$. In aspects, $R^{29}$ is independently —NHC(O)H. In aspects, $R^{29}$ is independently —NHC(O)OH. In aspects, $R^{29}$ is independently —NHOH. In aspects, $R^{29}$ is independently $—OCCl_3$. In aspects, $R^{29}$ is independently $—OCF_3$. In aspects, $R^{29}$ is independently $—OCBr_3$. In aspects, $R^{29}$ is independently $—OCI_3$. In aspects, $R^{29}$ is independently $—OCHCl_2$. In aspects, $R^{29}$ is independently $—OCHBr_2$. In aspects, $R^{29}$ is independently $—OCHI_2$. In aspects, $R^{29}$ is independently $—OCHF_2$. In aspects, $R^{29}$ is independently $—OCH_2Cl$. In aspects, $R^{29}$ is independently $—OCH_2Br$. In aspects, $R^{29}$ is independently $—OCH_2I$. In aspects, $R^{29}$ is independently $—OCH_2F$. In aspects, $R^{29}$ is independently $—N_3$. In aspects, $R^{29}$ is independently $—OCH_3$. In aspects, $R^{29}$ is independently $—CH_3$. In aspects, $R^{29}$ is independently $—CH_2CH_3$. In aspects, $R^{29}$ is independently unsubstituted propyl. In aspects, $R^{29}$ is independently unsubstituted isopropyl. In aspects, $R^{29}$ is independently unsubstituted butyl. In aspects, $R^{29}$ is independently unsubstituted tert-butyl. In aspects, $R^{29}$ is independently —F. In aspects, $R^{29}$ is independently —Cl. In aspects, $R^{29}$ is independently —Br. In aspects, $R^{29}$ is independently —I.

In aspects, $R^{3A}$ is independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{3A}$ is independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

In aspects, $R^{3A}$ is independently $R^{27}$-substituted or unsubstituted alkyl (e.g., $C_1$-$C_8$ alkyl, $C_1$-$C_6$ alkyl, or $C_1$-$C_4$ alkyl). In aspects, $R^{3A}$ is independently $R^{27}$-substituted alkyl (e.g., $C_1$-$C_8$ alkyl, $C_1$-$C_6$ alkyl, or $C_1$-$C_4$ alkyl). In aspects, $R^{3A}$ is independently an unsubstituted alkyl (e.g., $C_1$-$C_8$ alkyl, $C_1$-$C_6$ alkyl, or $C_1$-$C_4$ alkyl). In aspects, $R^{3A}$ is independently $R^{27}$-substituted or unsubstituted heteroalkyl (e.g., 2 to 8 membered heteroalkyl, 2 to 6 membered heteroalkyl, or 2 to 4 membered heteroalkyl). In aspects, $R^{3A}$ is independently $R^{27}$-substituted heteroalkyl (e.g., 2 to 8 membered heteroalkyl, 2 to 6 membered heteroalkyl, or 2 to 4 membered heteroalkyl). In aspects, $R^{3A}$ is independently an unsubstituted heteroalkyl (e.g., 2 to 8 membered heteroalkyl, 2 to 6 membered heteroalkyl, or 2 to 4 membered heteroalkyl). In aspects, $R^{3A}$ is independently $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{3A}$ is independently $R^{27}$-substituted cycloalkyl (e.g., $C_3$-$C_8$ cycloalkyl, $C_3$-$C_6$ cycloalkyl, or $C_5$-$C_6$ cycloalkyl). In aspects, $R^{3A}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{3A}$ is independently $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{3A}$ is independently $R^{27}$-substituted heterocycloalkyl (e.g., 3 to 8 membered heterocycloalkyl, 3 to 6 membered heterocycloalkyl, or 5 to 6 membered heterocycloalkyl). In aspects, $R^{3A}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{3A}$ is independently $R^{27}$-substituted or unsubstituted aryl (e.g., $C_6$-$C_{10}$ aryl, $C_{10}$ aryl, or phenyl). In aspects, $R^{3A}$ is independently $R^{27}$-substituted aryl (e.g., $C_6$-$C_{10}$ aryl, $C_{10}$ aryl, or phenyl). In aspects, $R^{3A}$ is independently an unsubstituted aryl (e.g., $C_6$-$C_{10}$ aryl, $C_{10}$ aryl, or phenyl). In aspects, $R^{3A}$ is independently $R^{27}$-substituted or unsubstituted heteroaryl (e.g., 5 to 10 membered heteroaryl, 5 to 9 membered heteroaryl, or 5 to 6 membered heteroaryl). In aspects, $R^{3A}$ is independently $R^{27}$-substituted heteroaryl (e.g., 5 to 10 membered heteroaryl, 5 to 9 membered heteroaryl, or 5 to 6 membered heteroaryl). In aspects, $R^{3A}$ is independently an unsubstituted heteroaryl (e.g., 5 to 10 membered heteroaryl, 5 to 9 membered heteroaryl, or 5 to 6 membered heteroaryl).

In aspects, $R^{3A}$ is independently —$CCl_3$. In aspects, $R^{3A}$ is independently —$CBr_3$. In aspects, $R^{3A}$ is independently —$CF_3$. In aspects, $R^{3A}$ is independently —$CI_3$. In aspects, $R^{3A}$ is independently —$CHCl_2$. In aspects, $R^{3A}$ is independently —$CHBr_2$. In aspects, $R^{3A}$ is independently —$CHF_2$. In aspects, $R^{3A}$ is independently —$CHI_2$. In aspects, $R^{3A}$ is independently —$CH_2Cl$. In aspects, $R^{3A}$ is independently —$CH_2Br$. In aspects, $R^{3A}$ is independently —$CH_2F$. In aspects, $R^{3A}$ is independently —$CH_2I$. In aspects, $R^{3A}$ is independently —CN. In aspects, $R^{3A}$ is independently —OH. In aspects, $R^{3A}$ is independently —COOH. In aspects, $R^{3A}$ is independently —$CONH_2$. In aspects, $R^{3A}$ is independently —$OCCl_3$. In aspects, $R^{3A}$ is independently —$OCF_3$. In aspects, $R^{3A}$ is independently —$OCBr_3$. In aspects, $R^{3A}$ is independently —$OCI_3$. In aspects, $R^{3A}$ is independently —$OCHCl_2$. In aspects, $R^{3A}$ is independently —$OCHBr_2$. In aspects, $R^{3A}$ is independently —$OCHI_2$. In aspects, $R^{3A}$ is independently —$OCHF_2$. In aspects, $R^{3A}$ is independently —$OCH_2Cl$. In aspects, $R^{3A}$ is independently —$OCH_2Br$. In aspects, $R^{3A}$ is independently —$OCH_2I$. In aspects, $R^{3A}$ is independently —$OCH_2F$. In aspects, $R^{3A}$ is independently —$OCH_3$. In aspects, $R^{3A}$ is independently —$CH_3$. In aspects, $R^{3A}$ is independently —$CH_2CH_3$. In aspects, $R^{3A}$ is independently unsubstituted propyl. In aspects, $R^{3A}$ is independently unsubstituted isopropyl. In aspects, $R^{3A}$ is independently unsubstituted butyl. In aspects, $R^{3A}$ is independently unsubstituted tert-butyl. In aspects, $R^{3A}$ is independently hydrogen.

In aspects, $R^{3B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{3B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

In aspects, $R^{3B}$ is independently $R^{27}$-substituted or unsubstituted alkyl (e.g., $C_1$-$C_8$ alkyl, $C_1$-$C_6$ alkyl, or $C_1$-$C_4$ alkyl). In aspects, $R^{3B}$ is independently $R^{27}$-substituted alkyl (e.g., $C_1$-$C_8$ alkyl, $C_1$-$C_6$ alkyl, or $C_1$-$C_4$ alkyl). In aspects, $R^{3B}$ is independently an unsubstituted alkyl (e.g., $C_1$-$C_8$ alkyl, $C_1$-$C_6$ alkyl, or $C_1$-$C_4$ alkyl). In aspects, $R^{3B}$ is independently $R^{27}$-substituted or unsubstituted heteroalkyl (e.g., 2 to 8 membered heteroalkyl, 2 to 6 membered heteroalkyl, or 2 to 4 membered heteroalkyl). In aspects, $R^{3B}$ is independently $R^{27}$-substituted heteroalkyl (e.g., 2 to 8 membered heteroalkyl, 2 to 6 membered heteroalkyl, or 2 to 4 membered heteroalkyl). In aspects, $R^{3B}$ is independently an unsubstituted heteroalkyl (e.g., 2 to 8 membered heteroalkyl, 2 to 6 membered heteroalkyl, or 2 to 4 membered heteroalkyl). In aspects, $R^{3B}$ is independently $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{3B}$ is independently $R^{27}$-substituted cycloalkyl (e.g., $C_3$-$C_8$ cycloalkyl, $C_3$-$C_6$ cycloalkyl, or $C_5$-$C_6$ cycloalkyl). In aspects, $R^{3B}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{3B}$ is independently $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{3B}$ is independently $R^{27}$-substituted heterocycloalkyl (e.g., 3 to 8 membered heterocycloalkyl, 3 to 6 membered heterocycloalkyl, or 5 to 6 membered heterocycloalkyl). In aspects, $R^{3B}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{3B}$ is independently $R^{27}$-substituted or unsubstituted aryl (e.g., $C_6$-$C_{10}$ aryl, $C_{10}$ aryl, or phenyl). In aspects, $R^{3B}$ is independently $R^{27}$-substituted aryl (e.g., $C_6$-$C_{10}$ aryl, $C_{10}$ aryl, or phenyl). In aspects, $R^{3B}$ is independently an unsubstituted aryl (e.g., $C_6$-$C_{10}$ aryl, $C_{10}$ aryl, or phenyl). In aspects, $R^{3B}$ is independently $R^{27}$-substituted or unsubstituted heteroaryl (e.g., 5 to 10 membered heteroaryl, 5 to 9 membered heteroaryl, or 5 to 6 membered heteroaryl). In aspects, $R^{3B}$ is independently $R^{27}$-substituted heteroaryl (e.g., 5 to 10 membered heteroaryl, 5 to 9 membered heteroaryl, or 5 to 6 membered heteroaryl). In aspects, $R^{3B}$ is independently an unsubstituted heteroaryl (e.g., 5 to 10 membered heteroaryl, 5 to 9 membered heteroaryl, or 5 to 6 membered heteroaryl).

In aspects, $R^{3B}$ is independently —$CCl_3$. In aspects, $R^{3B}$ is independently —$CBr_3$. In aspects, $R^{3B}$ is independently —$CF_3$. In aspects, $R^{3B}$ is independently —$CI_3$. In aspects, $R^{3B}$ is independently —$CHCl_2$. In aspects, $R^{3B}$ is independently —$CHBr_2$. In aspects, $R^{3B}$ is independently —$CHF_2$. In aspects, $R^{3B}$ is independently —$CHI_2$. In aspects, $R^{3B}$ is independently —$CH_2Cl$. In aspects, $R^{3B}$ is independently —$CH_2Br$. In aspects, $R^{3B}$ is independently —$CH_2F$. In aspects, $R^{3B}$ is independently —$CH_2I$. In aspects, $R^{3B}$ is independently —CN. In aspects, $R^{3B}$ is independently —OH. In aspects, $R^{3B}$ is independently —COOH. In aspects, $R^{3B}$ is independently —$CONH_2$. In aspects, $R^{3B}$ is independently —$OCCl_3$. In aspects, $R^{3B}$ is independently —$OCF_3$. In aspects, $R^{3B}$ is independently —$OCBr_3$. In aspects, $R^{3B}$ is independently —$OCI_3$. In aspects, $R^{3B}$ is independently —$OCHCl_2$. In aspects, $R^{3B}$ is independently —$OCHBr_2$. In aspects, $R^{3B}$ is independently —$OCHI_2$. In aspects, $R^{3B}$ is independently —$OCHF_2$. In aspects, $R^{3B}$ is independently —$OCH_2Cl$. In aspects, $R^{3B}$ is independently —$OCH_2Br$. In aspects, $R^{3B}$ is independently —$OCH_2I$. In aspects, $R^{3B}$ is independently —$OCH_2F$. In aspects, $R^{3B}$ is independently —$OCH_3$. In aspects, $R^{3B}$ is independently —$CH_3$. In aspects, $R^{3B}$ is independently —$CH_2CH_3$. In aspects, $R^{3B}$ is independently unsubstituted propyl. In aspects, $R^{3B}$ is independently unsubstituted isopropyl. In aspects, $R^{3B}$ is independently unsubstituted butyl. In aspects, $R^{3B}$ is independently unsubstituted tert-butyl. In aspects, $R^{3B}$ is independently hydrogen.

In embodiments, $R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —NHC(O)$NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —NC(O)$NHNR^{4A}R^{4B}$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

In aspects, $R^4$ is hydrogen, halogen, —$CF_3$, —$CBr_3$, —$CCl_3$, —$CI_3$, —$CHF_2$, —$CHBr_2$, —$CHCl_2$, —$CH_2F$, —$CH_2Br$, —$CH_2Cl$, —$OCF_3$, —$OCBr_3$, —$OCCl_3$, —$OCI_3$, —$OCHF_2$, —$OCHBr_2$, —$OCHCl_2$, —$OCH_2F$, —$OCH_2Br$, —$OCH_2Cl$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^4$ is $R^{30}$-substituted or unsubstituted alkyl (e.g., $C_1$-$C_8$ alkyl, $C_1$-$C_6$ alkyl, or $C_1$-$C_4$ alkyl). In aspects, $R^4$ is $R^{30}$-substituted alkyl (e.g., $C_1$-$C_8$ alkyl, $C_1$-$C_6$ alkyl, or $C_1$-$C_4$ alkyl). In aspects, $R^4$ is an unsubstituted alkyl (e.g., $C_1$-$C_8$ alkyl, $C_1$-$C_6$ alkyl, or $C_1$-$C_4$ alkyl). In aspects, $R^4$ is $R^{30}$-substituted or unsubstituted heteroalkyl (e.g., 2 to 8 membered heteroalkyl, 2 to 6 membered heteroalkyl, or 2 to 4 membered heteroalkyl). In aspects, $R^4$ is $R^{30}$-substituted heteroalkyl (e.g., 2 to 8 membered heteroalkyl, 2 to 6 membered heteroalkyl, or 2 to 4 membered heteroalkyl). In aspects, $R^4$ is an unsubstituted heteroalkyl (e.g., 2 to 8 membered heteroalkyl, 2 to 6 membered heteroalkyl, or 2 to 4 membered heteroalkyl). In aspects, $R^4$ is $R^+$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^4$ is $R^{30}$-substituted cycloalkyl (e.g., $C_3$-$C_8$ cycloalkyl, $C_3$-$C_6$ cycloalkyl, or $C_5$-$C_6$ cycloalkyl). In aspects, $R^4$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^4$ is $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^4$ is $R^+$-substituted heterocycloalkyl (e.g., 3 to 8 membered heterocycloalkyl, 3 to 6 membered heterocycloalkyl, or 5 to 6 membered heterocycloalkyl). In aspects, $R^4$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^4$ is $R^{30}$-substituted or unsubstituted aryl (e.g., $C_6$-$C_{10}$ aryl, $C_{10}$ aryl, or phenyl). In aspects, $R^4$ is $R^+$-substituted aryl (e.g., $C_6$-$C_{10}$ aryl, $C_{10}$ aryl, or phenyl). In aspects, $R^4$ is an unsubstituted aryl (e.g., $C_6$-$C_{10}$ aryl, $C_{10}$ aryl, or phenyl). In aspects, $R^4$ is $R^+$-substituted or unsubstituted heteroaryl (e.g., 5 to 10 membered heteroaryl, 5 to 9 membered heteroaryl, or 5 to 6 membered heteroaryl). In aspects, $R^4$ is $R^{30}$-substituted heteroaryl (e.g., 5 to 10 membered heteroaryl, 5 to 9 membered heteroaryl, or 5 to 6 membered heteroaryl). In aspects, $R^4$ is an unsubstituted heteroaryl (e.g., 5 to 10 membered heteroaryl, 5 to 9 membered heteroaryl, or 5 to 6 membered heteroaryl).

In aspects, $R^4$ is —$CX^4_3$. In aspects, $R^4$ is —$CHX^4_2$. In aspects, $R^4$ is —$CH_2X^4$. In aspects, $R^4$ is —$OCX^4_3$. In aspects, $R^4$ is —$OCH_2X^4$. In aspects, $R^4$ is —$OCHX^4_2$. In aspects, $R^4$ is —CN. In aspects, $R^4$ is —$SR^{4A}$. In aspects, $R^4$ is —$SOR^{4A}$. In aspects, $R^4$ is —$SO_2R^{4A}$. In aspects, $R^4$ is —$SO_3R^{4A}$. In aspects, $R^4$ is —$SO_4R^{4A}$. In aspects, $R^4$ is —$SONR^{4A}R^{4B}$. In aspects, $R^4$ is —$SO_2NR^{4A}R^{4B}$. In aspects, $R^4$ is —NHC(O)$NR^{4A}R^{4B}$. In aspects, $R^4$ is —N(O). In aspects, $R^4$ is —$N(O)_2$. In aspects, $R^4$ is —$NR^{4A}R^{4B}$. In aspects, $R^4$ is —C(O)$R^{4A}$. In aspects, $R^4$ is —C(O)—$OR^{4A}$. In aspects, $R^4$ is —C(O)$NR^{4A}R^{4B}$. In aspects, $R^4$ is —$OR^{4A}$. In aspects, $R^4$ is —$NR^{4A}SO_2R^{4B}$. In aspects, $R^4$ is —$NR^{4A}$C(O)$R^{4B}$. In aspects, $R^4$ is —$NR^{4A}$C(O)$OR^{4B}$. In aspects, $R^4$ is —$NR^{4A}OR^{4B}$. In aspects, $R^4$ is hydrogen. In aspects, $X^4$ is independently —F. In aspects, $X^4$ is independently —Cl. In aspects, $X^4$ is independently —Br. In aspects, $X^4$ is independently —I.

In aspects, $R^4$ is hydrogen. In aspects, $R^4$ is halogen. In aspects, $R^4$ is —$CCl_3$. In aspects, $R^4$ is —$CBr_3$. In aspects, $R^4$ is —$CF_3$. In aspects, $R^4$ is —$CI_3$. In aspects, $R^4$ is —$CHCl_2$. In aspects, $R^4$ is —$CHBr_2$. In aspects, $R^4$ is —$CHF_2$. In aspects, $R^4$ is —$CHI_2$. In aspects, $R^4$ is —$CH_2Cl$. In aspects, $R^4$ is —$CH_2Br$. In aspects, $R^4$ is —$CH_2F$. In aspects, $R^4$ is —$CH_2I$. In aspects, $R^4$ is —CN. In aspects, $R^4$ is —OH. In aspects, $R^4$ is —$NH_2$. In aspects, $R^4$ is —COOH. In aspects, $R^4$ is —$CONH_2$. In aspects, $R^4$ is —$NO_2$. In aspects, $R^4$ is —SH. In aspects, $R^4$ is —$SO_3H$. In aspects, $R^4$ is —$SO_4H$. In aspects, $R^4$ is —$SO_2NH_2$. In aspects, $R^4$ is —$NHNH_2$. In aspects, $R^4$ is —$ONH_2$. In aspects, $R^4$ is —NHC(O)$NHNH_2$. In aspects, $R^4$ is —NHC(O)$NH_2$. In aspects, $R^4$ is —$NHSO_2H$. In aspects, $R^4$ is —NHC(O)H. In aspects, $R^4$ is —NHC(O)OH. In aspects, $R^4$ is —NHOH. In aspects, $R^4$ is —$OCCl_3$. In aspects, $R^4$ is —$OCF_3$. In aspects, $R^4$ is —$OCBr_3$. In aspects, $R^4$ is —$OCI_3$. In aspects, $R^4$ is —$OCHCl_2$. In aspects, $R^4$ is —$OCHBr_2$. In aspects, $R^4$ is —$OCHI_2$. In aspects, $R^4$ is —$OCHF_2$. In aspects, $R^4$ is —$OCH_2Cl$. In aspects, $R^4$ is —$OCH_2Br$. In aspects, $R^4$ is —$OCH_2I$. In aspects, $R^4$ is —$OCH_2F$. In aspects, $R^4$ is —$N_3$. In aspects, $R^4$ is —$OCH_3$. In aspects, $R^4$ is —$CH_3$. In aspects, $R^4$ is —$CH_2CH_3$. In aspects, $R^4$ is unsubstituted propyl. In aspects, $R^4$ is unsubstituted isopropyl. In aspects, $R^4$ is unsubstituted butyl. In aspects, $R^4$ is unsubstituted tert-butyl. In aspects, $R^4$ is —F. In aspects, $R^4$ is —Cl. In aspects, $R^4$ is —Br. In aspects, $R^4$ is —I.

In embodiments, $R^4$ is hydrogen, halogen, —$CF_3$, —$CBr_3$, —$CCl_3$, —$CI_3$, —$CHBr_2$, —$CHCl_2$, —$CHI_2$, —$CH_2Br$, —$CH_2Cl$, —$CH_2I$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In aspects, $R^4$ is substituted or unsubstituted alkyl (e.g., $C_1$-$C_8$ alkyl, $C_1$-$C_6$ alkyl, or $C_1$-$C_4$ alkyl). In aspects, $R^4$ is substituted alkyl (e.g., $C_1$-$C_8$ alkyl, $C_1$-$C_6$ alkyl, or $C_1$-$C_4$ alkyl). In aspects, $R^4$ is an unsubstituted alkyl (e.g., $C_1$-$C_8$ alkyl, $C_1$-$C_6$ alkyl, or $C_1$-$C_4$ alkyl). In aspects, $R^4$ is substituted or unsubstituted heteroalkyl (e.g., 2 to 8 membered heteroalkyl, 2 to 6 membered heteroalkyl, or 2 to 4 membered heteroalkyl). In aspects, $R^4$ is substituted heteroalkyl (e.g., 2 to 8 membered heteroalkyl, 2 to 6 membered heteroalkyl, or 2 to 4 membered heteroalkyl). In aspects, $R^4$ is an unsubstituted heteroalkyl (e.g., 2 to 8 membered heteroalkyl, 2 to 6 membered heteroalkyl, or 2 to 4 membered heteroalkyl). In aspects, $R^4$ is substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^4$ is substituted cycloalkyl (e.g., $C_3$-$C_8$ cycloalkyl, $C_3$-$C_6$ cycloalkyl, or $C_5$-$C_6$ cycloalkyl). In aspects, $R^4$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^4$ is substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^4$ is substituted heterocycloalkyl (e.g., 3 to 8 membered heterocycloalkyl, 3 to 6 membered heterocycloalkyl, or 5 to 6 membered heterocycloalkyl). In aspects, $R^4$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^4$ is substituted or unsubstituted aryl (e.g., $C_6$-$C_{10}$ aryl, $C_{10}$ aryl, or phenyl). In aspects, $R^4$ is substituted aryl (e.g., $C_6$-$C_{10}$ aryl, $C_{10}$ aryl, or phenyl). In aspects, $R^4$ is an unsubstituted aryl (e.g., $C_6$-$C_{10}$ aryl, $C_{10}$ aryl, or phenyl). In aspects, $R^4$ is substituted or unsubstituted heteroaryl (e.g., 5 to 10 membered heteroaryl, 5 to 9 membered heteroaryl, or 5 to 6 membered heteroaryl). In aspects, $R^4$ is substituted heteroaryl (e.g., 5 to 10 membered heteroaryl, 5 to 9 membered heteroaryl, or 5 to 6 membered heteroaryl). In aspects, $R^4$ is an unsubstituted heteroaryl (e.g., 5 to 10 membered heteroaryl, 5 to 9 membered heteroaryl, or 5 to 6 membered heteroaryl).

$R^{30}$ is independently oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $R^{31}$-substituted or unsubstituted alkyl (e.g., $C_1$-$C_8$ alkyl, $C_1$-$C_6$ alkyl, or $C_1$-$C_4$ alkyl), $R^{31}$-substituted or unsubstituted heteroalkyl (e.g., 2 to 8 membered heteroalkyl, 2 to 6 membered heteroalkyl, or 2 to 4 membered heteroalkyl), $R^{31}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31}$-substituted or unsubstituted aryl (e.g., $C_6$-$C_{10}$ aryl, $C_{10}$ aryl, or phenyl), or $R^{31}$-substituted or unsubstituted heteroaryl (e.g., 5 to 10 membered heteroaryl, 5 to 9 membered heteroaryl, or 5 to 6 membered heteroaryl). In aspects, $R^{30}$ is independently oxo, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{30}$ is independently oxo. In aspects, $R^{30}$ is independently halogen. In aspects, $R^{30}$ is independently $-CCl_3$. In aspects, $R^{30}$ is independently $-CBr_3$. In aspects, $R^{30}$ is independently $-CF_3$. In aspects, $R^{30}$ is independently $-CI_3$. In aspects, $R^{30}$ is independently $-CHCl_2$. In aspects, $R^{30}$ is independently $-CHBr_2$. In aspects, $R^{30}$ is independently $-CHF_2$. In aspects, $R^{30}$ is independently $-CHI_2$. In aspects, $R^{30}$ is independently $-CH_2Cl$. In aspects, $R^{30}$ is independently $-CH_2Br$. In aspects, $R^{30}$ is independently $-CH_2F$. In aspects, $R^{30}$ is independently $-CH_2I$. In aspects, $R^{30}$ is independently $-CN$. In aspects, $R^{30}$ is independently $-OH$. In aspects, $R^{30}$ is independently $-NH_2$. In aspects, $R^{30}$ is independently $-COOH$. In aspects, $R^{30}$ is independently $-CONH_2$. In aspects, $R^{30}$ is independently $-NO_2$. In aspects, $R^{30}$ is independently $-SH$. In aspects, $R^{30}$ is independently $-SO_3H$. In aspects, $R^{30}$ is independently $-SO_4H$. In aspects, $R^{30}$ is independently $-SO_2NH_2$. In aspects, $R^{30}$ is independently $-NHNH_2$. In aspects, $R^{30}$ is independently $-ONH_2$. In aspects, $R^{30}$ is independently $-NHC(O)NHNH_2$. In aspects, $R^{30}$ is independently $-NHC(O)NH_2$. In aspects, $R^{30}$ is independently $-NHSO_2H$. In aspects, $R^{30}$ is independently $-NHC(O)H$. In aspects, $R^{30}$ is independently $-NHC(O)OH$. In aspects, $R^{30}$ is independently $-NHOH$. In aspects, $R^{30}$ is independently $-OCCl_3$. In aspects, $R^{30}$ is independently $-OCF_3$. In aspects, $R^{30}$ is independently $-OCBr_3$. In aspects, $R^{30}$ is independently $-OCI_3$. In aspects, $R^{30}$ is independently $-OCHCl_2$. In aspects, $R^{30}$ is independently $-OCHBr_2$. In aspects, $R^{30}$ is independently $-OCHI_2$. In aspects, $R^{30}$ is independently $-OCHF_2$. In aspects, $R^{30}$ is independently $-OCH_2Cl$. In aspects, $R^{30}$ is independently $-OCH_2Br$. In aspects, $R^{30}$ is independently $-OCH_2I$. In aspects, $R^{30}$ is independently $-OCH_2F$. In aspects, $R^{30}$ is independently $-N_3$. In aspects, $R^{30}$ is independently $-OCH_3$. In aspects, $R^{30}$ is independently $-CH_3$. In aspects, $R^{30}$ is independently $-CH_2CH_3$. In aspects, $R^{30}$ is independently unsubstituted propyl. In aspects, $R^{30}$ is independently unsubstituted isopropyl. In aspects, $R^{30}$ is independently unsubstituted butyl. In aspects, $R^{30}$ is independently unsubstituted tert-butyl. In aspects, $R^{30}$ is independently $-F$. In aspects, $R^{30}$ is independently $-Cl$. In aspects, $R^{30}$ is independently $-Br$. In aspects, $R^{30}$ is independently $-I$.

In aspects, $R^{30}$ is independently $R^{31}$-substituted or unsubstituted alkyl (e.g., $C_1$-$C_8$ alkyl, $C_1$-$C_6$ alkyl, or $C_1$-$C_4$ alkyl). In aspects, $R^{30}$ is independently $R^{31}$-substituted alkyl (e.g., $C_1$-$C_8$ alkyl, $C_1$-$C_6$ alkyl, or $C_1$-$C_4$ alkyl). In aspects, $R^{30}$ is independently an unsubstituted alkyl (e.g., $C_1$-$C_8$ alkyl, $C_1$-$C_6$ alkyl, or $C_1$-$C_4$ alkyl). In aspects, $R^{30}$ is independently $R^{31}$-substituted or unsubstituted heteroalkyl (e.g., 2 to 8 membered heteroalkyl, 2 to 6 membered heteroalkyl, or 2 to 4 membered heteroalkyl). In aspects, $R^{30}$ is independently $R^{31}$-substituted heteroalkyl (e.g., 2 to 8 membered heteroalkyl, 2 to 6 membered heteroalkyl, or 2 to 4 membered heteroalkyl). In aspects, $R^{30}$ is independently an unsubstituted heteroalkyl (e.g., 2 to 8 membered heteroalkyl, 2 to 6 membered heteroalkyl, or 2 to 4 membered heteroalkyl). In aspects, $R^{30}$ is independently $R^{31}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{30}$ is independently $R^{31}$-substituted cycloalkyl (e.g., $C_3$-$C_8$ cycloalkyl, $C_3$-$C_6$ cycloalkyl, or $C_5$-$C_6$ cycloalkyl). In aspects, $R^{30}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{30}$ is independently $R^{31}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{30}$ is independently $R^{31}$-substituted heterocycloalkyl (e.g., 3 to 8 membered heterocycloalkyl, 3 to 6 membered heterocycloalkyl, or 5 to 6 membered heterocycloalkyl). In aspects, $R^{30}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{30}$ is independently $R^{31}$-substituted or unsubstituted aryl (e.g., $C_6$-$C_{10}$ aryl, $C_{10}$ aryl, or phenyl). In aspects, $R^{30}$ is independently $R^{31}$-substituted aryl (e.g., $C_6$-$C_{10}$ aryl, $C_{10}$ aryl, or phenyl). In aspects, $R^{30}$ is independently an unsubstituted aryl (e.g., $C_6$-$C_{10}$ aryl, $C_{10}$ aryl, or phenyl). In aspects, $R^{30}$ is independently $R^{31}$-substituted or unsubstituted heteroaryl (e.g., 5 to 10 membered heteroaryl, 5 to 9 membered heteroaryl, or 5 to 6 membered heteroaryl). In aspects, $R^{30}$ is independently $R^{31}$-substituted heteroaryl (e.g., 5 to 10 membered heteroaryl, 5 to 9 membered heteroaryl, or 5 to 6 membered heteroaryl). In aspects, $R^{30}$ is independently an unsubstituted heteroaryl (e.g., 5 to 10 membered heteroaryl, 5 to 9 membered heteroaryl, or 5 to 6 membered heteroaryl).

$R^{31}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)$NHNH_2$, —NHC(O)$NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl). In aspects, $R^{31}$ is independently oxo, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{31}$ is independently $R^{32}$-substituted or unsubstituted alkyl (e.g., $C_1$-$C_8$ alkyl, $C_1$-$C_6$ alkyl, or $C_1$-$C_4$ alkyl). In aspects, $R^{31}$ is independently $R^{32}$-substituted alkyl (e.g., $C_1$-$C_8$ alkyl, $C_1$-$C_6$ alkyl, or $C_1$-$C_4$ alkyl). In aspects, $R^{31}$ is independently an unsubstituted alkyl (e.g., $C_1$-$C_8$ alkyl, $C_1$-$C_6$ alkyl, or $C_1$-$C_4$ alkyl). In aspects, $R^{31}$ is independently $R^{32}$-substituted or unsubstituted heteroalkyl (e.g., 2 to 8 membered heteroalkyl, 2 to 6 membered heteroalkyl, or 2 to 4 membered heteroalkyl). In aspects, $R^{31}$ is independently $R^{32}$-substituted heteroalkyl (e.g., 2 to 8 membered heteroalkyl, 2 to 6 membered heteroalkyl, or 2 to 4 membered heteroalkyl). In aspects, $R^{31}$ is independently an unsubstituted heteroalkyl (e.g., 2 to 8 membered heteroalkyl, 2 to 6 membered heteroalkyl, or 2 to 4 membered heteroalkyl). In aspects, $R^{31}$ is independently $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{31}$ is independently $R^{32}$-substituted cycloalkyl (e.g., $C_3$-$C_8$ cycloalkyl, $C_3$-$C_6$ cycloalkyl, or $C_5$-$C_6$ cycloalkyl). In aspects, $R^{31}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{31}$ is independently $R^{32}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{31}$ is independently $R^{32}$-substituted heterocycloalkyl (e.g., 3 to 8 membered heterocycloalkyl, 3 to 6 membered heterocycloalkyl, or 5 to 6 membered heterocycloalkyl). In aspects, $R^{31}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{31}$ is independently $R^{32}$-substituted or unsubstituted aryl (e.g., $C_6$-$C_{10}$ aryl, $C_{10}$ aryl, or phenyl). In aspects, $R^{31}$ is independently $R^{32}$-substituted aryl (e.g., $C_6$-$C_{10}$ aryl, $C_{10}$ aryl, or phenyl). In aspects, $R^{31}$ is independently an unsubstituted aryl (e.g., $C_6$-$C_{10}$ aryl, $C_{10}$ aryl, or phenyl). In aspects, $R^{31}$ is independently $R^{32}$-substituted or unsubstituted heteroaryl (e.g., 5 to 10 membered heteroaryl, 5 to 9 membered heteroaryl, or 5 to 6 membered heteroaryl). In aspects, $R^{31}$ is independently $R^{32}$-substituted heteroaryl (e.g., 5 to 10 membered heteroaryl, 5 to 9 membered heteroaryl, or 5 to 6 membered heteroaryl). In aspects, $R^{31}$ is independently an unsubstituted heteroaryl (e.g., 5 to 10 membered heteroaryl, 5 to 9 membered heteroaryl, or 5 to 6 membered heteroaryl).

In aspects, $R^{31}$ is independently oxo. In aspects, $R^{31}$ is independently halogen. In aspects, $R^{31}$ is independently $—CCl_3$. In aspects, $R^{31}$ is independently $—CBr_3$. In aspects, $R^{31}$ is independently $—CF_3$. In aspects, $R^{31}$ is independently $—CI_3$. In aspects, $R^{31}$ is independently $—CHCl_2$. In aspects, $R^{31}$ is independently $—CHBr_2$. In aspects, $R^{31}$ is independently $—CHF_2$. In aspects, $R^{31}$ is independently $—CHI_2$. In aspects, $R^{31}$ is independently $—CH_2Cl$. In aspects, $R^{31}$ is independently $—CH_2Br$. In aspects, $R^{31}$ is independently $—CH_2F$. In aspects, $R^{31}$ is independently $—CH_2I$. In aspects, $R^{31}$ is independently —CN. In aspects, $R^{31}$ is independently —OH. In aspects, $R^{31}$ is independently —$NH_2$. In aspects, $R^{31}$ is independently —COOH. In aspects, $R^{31}$ is independently —$CONH_2$. In aspects, $R^{31}$ is independently —$NO_2$. In aspects, $R^{31}$ is independently —SH. In aspects, $R^{31}$ is independently —$SO_3H$. In aspects, $R^{31}$ is independently —$SO_4H$. In aspects, $R^{31}$ is independently —$SO_2NH_2$. In aspects, $R^{31}$ is independently —$NHNH_2$. In aspects, $R^{31}$ is independently —$ONH_2$. In aspects, $R^{31}$ is independently —NHC(O)$NHNH_2$. In aspects, $R^{31}$ is independently —NHC(O)$NH_2$. In aspects, $R^{31}$ is independently —$NHSO_2H$. In aspects, $R^{31}$ is independently —NHC(O)H. In aspects, $R^{31}$ is independently —NHC(O)OH. In aspects, $R^{31}$ is independently —NHOH. In aspects, $R^{31}$ is independently —$OCCl_3$. In aspects, $R^{31}$ is independently —$OCF_3$. In aspects, $R^{31}$ is independently —$OCBr_3$. In aspects, $R^{31}$ is independently —$OCI_3$. In aspects, $R^{31}$ is independently —$OCHCl_2$. In aspects, $R^{31}$ is independently —$OCHBr_2$. In aspects, $R^{31}$ is independently —$OCHI_2$. In aspects, $R^{31}$ is independently —$OCHF_2$. In aspects, $R^{31}$ is independently —$OCH_2Cl$. In aspects, $R^{31}$ is independently —$OCH_2Br$. In aspects, $R^{31}$ is independently —$OCH_2I$. In aspects, $R^{31}$ is independently —$OCH_2F$. In aspects, $R^{31}$ is independently —$N_3$. In aspects, $R^{31}$ is independently —$OCH_3$. In aspects, $R^{31}$ is independently —$CH_3$. In aspects, $R^{31}$ is independently —$CH_2CH_3$. In aspects, $R^{31}$ is independently unsubstituted propyl. In aspects, $R^{31}$ is independently unsubstituted isopropyl. In aspects, $R^{31}$ is independently unsubstituted butyl. In aspects, $R^{31}$ is independently unsubstituted tert-butyl. In aspects, $R^{31}$ is independently —F. In aspects, $R^{31}$ is independently —Cl. In aspects, $R^{31}$ is independently —Br. In aspects, $R^{31}$ is independently —I.

$R^{32}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{32}$ is independently an unsubstituted alkyl (e.g., $C_1$-$C_8$ alkyl, $C_1$-$C_6$ alkyl, or $C_1$-$C_4$ alkyl). In aspects, $R^{32}$ is independently an unsubstituted heteroalkyl (e.g., 2 to 8 membered heteroalkyl, 2 to 6 membered heteroalkyl, or 2 to 4 membered heteroalkyl). In aspects, $R^{32}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{32}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{32}$ is independently an unsubstituted aryl (e.g., $C_6$-$C_{10}$ aryl, $C_{10}$ aryl, or phenyl). In aspects, $R^{32}$ is independently an unsubstituted heteroaryl (e.g., 5 to 10 membered heteroaryl, 5 to 9 membered heteroaryl, or 5 to 6 membered heteroaryl).

In aspects, $R^{32}$ is independently oxo. In aspects, $R^{32}$ is independently halogen. In aspects, $R^{32}$ is independently —$CCl_3$. In aspects, $R^{32}$ is independently —$CBr_3$. In aspects, $R^{32}$ is independently —$CF_3$. In aspects, $R^{32}$ is independently —$CI_3$. In aspects, $R^{32}$ is independently —$CHCl_2$. In aspects, $R^{32}$ is independently —$CHBr_2$. In aspects, $R^{32}$ is independently —$CHF_2$. In aspects, $R^{32}$ is independently —$CHI_2$. In aspects, $R^{32}$ is independently —$CH_2Cl$. In aspects, $R^{32}$ is independently —$CH_2Br$. In aspects, $R^{32}$ is independently —$CH_2F$. In aspects, $R^{32}$ is independently —$CH_2I$. In aspects, $R^{32}$ is independently —CN. In aspects, $R^{32}$ is independently —OH. In aspects, $R^{32}$ is independently —$NH_2$. In aspects, $R^{32}$ is independently —COOH. In aspects, $R^{32}$ is independently —$CONH_2$. In aspects, $R^{32}$ is independently —$NO_2$. In aspects, $R^{32}$ is independently —SH. In aspects, $R^{32}$ is independently —$SO_3H$. In aspects, $R^{32}$ is independently —$SO_4H$. In aspects, $R^{32}$ is independently —$SO_2NH_2$. In aspects, $R^{32}$ is independently —$NHNH_2$. In aspects, $R^{32}$ is independently —$ONH_2$. In aspects, $R^{32}$ is independently —NHC(O)$NHNH_2$. In aspects, $R^{32}$ is independently —NHC(O)$NH_2$. In aspects, $R^{32}$ is independently —$NHSO_2H$. In aspects, $R^{32}$ is independently —NHC(O)H. In aspects, $R^{32}$ is independently —NHC(O)OH. In aspects, $R^{32}$ is independently —NHOH. In aspects, $R^{32}$ is independently —$OCCl_3$. In aspects, $R^{32}$ is independently —$OCF_3$. In aspects, $R^{32}$ is independently —$OCBr_3$. In aspects, $R^{32}$ is independently —$OCI_3$. In aspects, $R^{32}$ is independently —$OCHCl_2$. In aspects, $R^{32}$ is independently —$OCHBr_2$. In aspects, $R^{32}$ is independently —$OCHI_2$. In aspects, $R^{32}$ is independently —$OCHF_2$. In aspects, $R^{32}$ is independently —$OCH_2Cl$. In aspects, $R^{32}$ is independently —$OCH_2Br$. In aspects, $R^{32}$ is independently —$OCH_2I$. In aspects, $R^{32}$ is independently —$OCH_2F$. In aspects, $R^{32}$ is independently —$N_3$. In aspects, $R^{32}$ is independently —$OCH_3$. In aspects, $R^{32}$ is independently —$CH_3$. In aspects, $R^{32}$ is independently —$CH_2CH_3$. In aspects, $R^{32}$ is independently unsubstituted propyl. In aspects, $R^{32}$ is independently unsubstituted isopropyl. In aspects, $R^{32}$ is independently unsubstituted butyl. In aspects, $R^{32}$ is independently unsubstituted tert-butyl. In aspects, $R^{32}$ is independently —F. In aspects, $R^{32}$ is independently —Cl. In aspects, $R^{32}$ is independently —Br. In aspects, $R^{32}$ is independently —I.

In aspects, $R^{4A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{4A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

In aspects, $R^{4A}$ is independently $R^{30}$-substituted or unsubstituted alkyl (e.g., $C_1$-$C_8$ alkyl, $C_1$-$C_6$ alkyl, or $C_1$-$C_4$ alkyl). In aspects, $R^{4A}$ is independently $R^{30}$-substituted alkyl (e.g., $C_1$-$C_8$ alkyl, $C_1$-$C_6$ alkyl, or $C_1$-$C_4$ alkyl). In aspects, $R^{4A}$ is independently an unsubstituted alkyl (e.g., $C_1$-$C_8$ alkyl, $C_1$-$C_6$ alkyl, or $C_1$-$C_4$ alkyl). In aspects, $R^{4A}$ is independently $R^{30}$-substituted or unsubstituted heteroalkyl (e.g., 2 to 8 membered heteroalkyl, 2 to 6 membered heteroalkyl, or 2 to 4 membered heteroalkyl). In aspects, $R^{4A}$ is independently $R^{30}$-substituted heteroalkyl (e.g., 2 to 8 membered heteroalkyl, 2 to 6 membered heteroalkyl, or 2 to 4 membered heteroalkyl). In aspects, $R^{4A}$ is independently an unsubstituted heteroalkyl (e.g., 2 to 8 membered heteroalkyl, 2 to 6 membered heteroalkyl, or 2 to 4 membered heteroalkyl). In aspects, $R^{4A}$ is independently $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{4A}$ is independently $R^{30}$-substituted cycloalkyl (e.g., $C_3$-$C_8$ cycloalkyl, $C_3$-$C_6$ cycloalkyl, or $C_5$-$C_6$ cycloalkyl). In aspects, $R^{4A}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{4A}$ is independently $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{4A}$ is independently $R^{30}$-substituted heterocycloalkyl (e.g., 3 to 8 membered heterocycloalkyl, 3 to 6 membered heterocycloalkyl, or 5 to 6 membered heterocycloalkyl). In aspects, $R^{4A}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{4A}$ is independently $R^{30}$-substituted or unsubstituted aryl (e.g., $C_6$-$C_{10}$ aryl, $C_{10}$ aryl, or phenyl). In aspects, $R^{4A}$ is independently $R^{30}$-substituted aryl (e.g., $C_6$-$C_{10}$ aryl, $C_{10}$ aryl, or phenyl). In aspects, $R^{4A}$ is independently an unsubstituted aryl (e.g., $C_6$-$C_{10}$ aryl, $C_{10}$ aryl, or phenyl). In aspects, $R^{4A}$ is independently $R^{30}$-substituted or unsubstituted heteroaryl (e.g., 5 to 10 membered heteroaryl, 5 to 9 membered heteroaryl, or 5 to 6 membered heteroaryl). In aspects, $R^{4A}$ is independently $R^{30}$-substituted heteroaryl (e.g., 5 to 10 membered heteroaryl, 5 to 9 membered heteroaryl, or 5 to 6 membered heteroaryl). In aspects, $R^{4A}$ is independently an unsubstituted heteroaryl (e.g., 5 to 10 membered heteroaryl, 5 to 9 membered heteroaryl, or 5 to 6 membered heteroaryl).

In aspects, $R^{4A}$ is independently $—CCl_3$. In aspects, $R^{4A}$ is independently $—CBr_3$. In aspects, $R^{4A}$ is independently $—CF_3$. In aspects, $R^{4A}$ is independently $—CI_3$. In aspects, $R^{4A}$ is independently $—CHCl_2$. In aspects, $R^{4A}$ is independently $—CHBr_2$. In aspects, $R^{4A}$ is independently $—CHF_2$. In aspects, $R^{4A}$ is independently $—CHI_2$. In aspects, $R^{4A}$ is independently $—CH_2Cl$. In aspects, $R^{4A}$ is independently $—CH_2Br$. In aspects, $R^{4A}$ is independently $—CH_2F$. In aspects, $R^{4A}$ is independently $—CH_2I$. In aspects, $R^{4A}$ is independently —CN. In aspects, $R^{4A}$ is independently —OH. In aspects, $R^{4A}$ is independently —COOH. In aspects, $R^{4A}$ is independently $—CONH_2$. In aspects, $R^{4A}$ is independently $—OCCl_3$. In aspects, $R^{4A}$ is independently $—OCF_3$. In aspects, $R^{4A}$ is independently $—OCBr_3$. In aspects, $R^{4A}$ is independently $—OCI_3$. In aspects, $R^{4A}$ is independently $—OCHCl_2$. In aspects, $R^{4A}$ is independently $—OCHBr_2$. In aspects, $R^{4A}$ is independently $—OCHI_2$. In aspects, $R^{4A}$ is independently $—OCHF_2$. In aspects, $R^{4A}$ is independently $—OCH_2Cl$. In aspects, $R^{4A}$ is independently $—OCH_2Br$. In aspects, $R^{4A}$ is independently $—OCH_2I$. In aspects, $R^{4A}$ is independently $—OCH_2F$. In aspects, $R^{4A}$ is independently $—OCH_3$. In aspects, $R^{4A}$ is independently $—CH_3$. In aspects, $R^{4A}$ is independently $—CH_2CH_3$. In aspects, $R^{4A}$ is independently unsubstituted propyl. In aspects, $R^{4A}$ is independently unsubstituted isopropyl. In aspects, $R^{4A}$ is independently unsubstituted butyl. In aspects, $R^{4A}$ is independently unsubstituted tert-butyl. In aspects, $R^{4A}$ is independently hydrogen.

In aspects, $R^{4B}$ is independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{4B}$ is independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

In aspects, $R^{4B}$ is independently $R^{30}$-substituted or unsubstituted alkyl (e.g., $C_1$-$C_8$ alkyl, $C_1$-$C_6$ alkyl, or $C_1$-$C_4$ alkyl). In aspects, $R^{4B}$ is independently $R^{30}$-substituted alkyl (e.g., $C_1$-$C_8$ alkyl, $C_1$-$C_6$ alkyl, or $C_1$-$C_4$ alkyl). In aspects, $R^{4B}$ is independently an unsubstituted alkyl (e.g., $C_1$-$C_8$ alkyl, $C_1$-$C_6$ alkyl, or $C_1$-$C_4$ alkyl). In aspects, $R^{4B}$ is independently $R^{30}$-substituted or unsubstituted heteroalkyl (e.g., 2 to 8 membered heteroalkyl, 2 to 6 membered heteroalkyl, or 2 to 4 membered heteroalkyl). In aspects, $R^{4B}$ is independently $R^{30}$-substituted heteroalkyl (e.g., 2 to 8 membered heteroalkyl, 2 to 6 membered heteroalkyl, or 2 to 4 membered heteroalkyl). In aspects, $R^{4B}$ is independently an unsubstituted heteroalkyl (e.g., 2 to 8 membered heteroalkyl, 2 to 6 membered heteroalkyl, or 2 to 4 membered heteroalkyl). In aspects, $R^{4B}$ is independently $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{4B}$ is independently $R^{30}$-substituted cycloalkyl (e.g., $C_3$-$C_8$ cycloalkyl, $C_3$-$C_6$ cycloalkyl, or $C_5$-$C_6$ cycloalkyl). In aspects, $R^{4B}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{4B}$ is independently $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{4B}$ is independently $R^{30}$-substituted heterocycloalkyl (e.g., 3 to 8 membered heterocycloalkyl, 3 to 6 membered heterocycloalkyl, or 5 to 6 membered heterocycloalkyl). In aspects, $R^{4B}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{4B}$ is independently $R^{30}$-substituted or unsubstituted aryl (e.g., $C_6$-$C_{10}$ aryl, $C_{10}$ aryl, or phenyl). In aspects, $R^{4B}$ is independently $R^{30}$-substituted aryl (e.g., $C_6$-$C_{10}$ aryl, $C_{10}$ aryl, or phenyl). In aspects, $R^{4B}$ is independently an unsubstituted aryl (e.g., $C_6$-$C_{10}$ aryl, $C_{10}$ aryl, or phenyl). In aspects, $R^{4B}$ is independently $R^{30}$-substituted or unsubstituted heteroaryl (e.g., 5 to 10 membered heteroaryl, 5 to 9 membered heteroaryl, or 5 to 6 membered heteroaryl). In aspects, $R^{4B}$ is independently $R^{30}$-substituted heteroaryl (e.g., 5 to 10 membered heteroaryl, 5 to 9 membered heteroaryl, or 5 to 6 membered heteroaryl). In aspects, $R^{4B}$ is independently an unsubstituted heteroaryl (e.g., 5 to 10 membered heteroaryl, 5 to 9 membered heteroaryl, or 5 to 6 membered heteroaryl).

In aspects, $R^{4B}$ is independently —$CCl_3$. In aspects, $R^{4B}$ is independently —$CBr_3$. In aspects, $R^{4B}$ is independently —$CF_3$. In aspects, $R^{4B}$ is independently —$CI_3$. In aspects, $R^{4B}$ is independently —$CHCl_2$. In aspects, $R^{4B}$ is independently —$CHBr_2$. In aspects, $R^{4B}$ is independently —$CHF_2$. In aspects, $R^{4B}$ is independently —$CHI_2$. In aspects, $R^{4B}$ is independently —$CH_2Cl$. In aspects, $R^{4B}$ is independently —$CH_2Br$. In aspects, $R^{4B}$ is independently —$CH_2F$. In aspects, $R^{4B}$ is independently —$CH_2I$. In aspects, $R^{4B}$ is independently —CN. In aspects, $R^{4B}$ is independently —OH. In aspects, $R^{4B}$ is independently —COOH. In aspects, $R^{4B}$ is independently —$CONH_2$. In aspects, $R^{4B}$ is independently —$OCCl_3$. In aspects, $R^{4B}$ is independently —$OCF_3$. In aspects, $R^{4B}$ is independently —$OCBr_3$. In aspects, $R^{4B}$ is independently —$OCI_3$. In aspects, $R^{4B}$ is independently —$OCHCl_2$. In aspects, $R^{4B}$ is independently —$OCHBr_2$. In aspects, $R^{4B}$ is independently —$OCHI_2$. In aspects, $R^{4B}$ is independently —$OCHF_2$. In aspects, $R^{4B}$ is independently —$OCH_2Cl$. In aspects, $R^{4B}$ is independently —$OCH_2Br$. In aspects, $R^{4B}$ is independently —$OCH_2I$. In aspects, $R^{4B}$ is independently —$OCH_2F$. In aspects, $R^{4B}$ is independently —$OCH_3$. In aspects, $R^{4B}$ is independently —$CH_3$. In aspects, $R^{4B}$ is independently —$CH_2CH_3$. In aspects, $R^{4B}$ is independently unsubstituted propyl. In aspects, $R^{4B}$ is independently unsubstituted isopropyl. In aspects, $R^{4B}$ is independently unsubstituted butyl. In aspects, $R^{4B}$ is independently unsubstituted tert-butyl. In aspects, $R^{4B}$ is independently hydrogen.

In embodiments, $R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —NHC(O)$NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In aspects, $R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —NHC(O)$NHNR^{5A}R^{5B}$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^5$ is $R^{33}$-substituted or unsubstituted alkyl (e.g., $C_1$-$C_8$ alkyl, $C_1$-$C_6$ alkyl, or $C_1$-$C_4$ alkyl). In aspects, $R^5$ is $R^{33}$-substituted alkyl (e.g., $C_1$-$C_8$ alkyl, $C_1$-$C_6$ alkyl, or $C_1$-$C_4$ alkyl). In aspects, $R^5$ is an unsubstituted alkyl (e.g., $C_1$-$C_8$ alkyl, $C_1$-$C_6$ alkyl, or $C_1$-$C_4$ alkyl). In aspects, $R^5$ is $R^{33}$-substituted or unsubstituted heteroalkyl (e.g., 2 to 8 membered heteroalkyl, 2 to 6 membered heteroalkyl, or 2 to 4 membered heteroalkyl). In aspects, $R^5$ is $R^{33}$-substituted heteroalkyl (e.g., 2 to 8 membered heteroalkyl, 2 to 6 membered heteroalkyl, or 2 to 4 membered heteroalkyl). In aspects, $R^5$ is an unsubstituted heteroalkyl (e.g., 2 to 8 membered heteroalkyl, 2 to 6 membered heteroalkyl, or 2 to 4 membered heteroalkyl). In aspects, $R^5$ is $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^5$ is $R^{33}$-substituted cycloalkyl (e.g., $C_3$-$C_8$ cycloalkyl, $C_3$-$C_6$ cycloalkyl, or $C_5$-$C_6$ cycloalkyl). In aspects, $R^5$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^5$ is $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^5$ is $R^{33}$-substituted heterocycloalkyl (e.g., 3 to 8 membered heterocycloalkyl, 3 to 6 membered heterocycloalkyl, or 5 to 6 membered heterocycloalkyl). In aspects, $R^5$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^5$ is $R^{33}$-substituted or unsubstituted aryl (e.g., $C_6$-$C_{10}$ aryl, $C_{10}$ aryl, or phenyl). In aspects, $R^5$ is $R^{33}$-substituted aryl (e.g., $C_6$-$C_{10}$ aryl, $C_{10}$ aryl, or phenyl). In aspects, $R^5$ is an unsubstituted aryl (e.g., $C_6$-$C_{10}$ aryl, $C_{10}$ aryl, or phenyl). In aspects, $R^5$ is $R^{33}$-substituted or unsubstituted heteroaryl (e.g., 5 to 10 membered heteroaryl, 5 to 9 membered heteroaryl, or 5 to 6 membered heteroaryl). In aspects, $R^5$ is $R^{33}$-substituted heteroaryl (e.g., 5 to 10 membered heteroaryl, 5 to 9 membered heteroaryl, or 5 to 6 membered heteroaryl). In aspects, $R^5$ is an unsubstituted heteroaryl (e.g., 5 to 10 membered heteroaryl, 5 to 9 membered heteroaryl, or 5 to 6 membered heteroaryl).

In aspects, $R^5$ is an unsubstituted alkyl. In aspects, $R^5$ is an unsubstituted $C_1$-$C_{12}$ alkyl. In aspects, $R^5$ is an unsubstituted $C_1$-$C_{10}$ alkyl. In aspects, $R^5$ is an unsubstituted $C_1$-$C_8$ alkyl. In aspects, $R^5$ is an unsubstituted $C_1$-$C_6$ alkyl. In aspects, $R^5$ is an unsubstituted $C_1$-$C_5$ alkyl. In aspects, $R^5$ is an unsubstituted $C_1$-$C_4$ alkyl. In aspects, $R^5$ is an unsubstituted $C_1$-$C_3$ alkyl. In aspects, $R^5$ is an unsubstituted $C_1$-$C_2$ alkyl. In aspects, $R^5$ is an unsubstituted $C_2$ alkyl. In aspects, $R^5$ is an unsubstituted $C_3$ alkyl. In aspects, $R^5$ is an unsubstituted $C_4$ alkyl. In aspects, $R^5$ is an unsubstituted $C_8$ alkyl. In aspects, $R^5$ is an unsubstituted $C_6$ alkyl.

In aspects, $R^5$ is a substituted alkyl. In aspects, $R^5$ is a substituted $C_1$-$C_{12}$ alkyl. In aspects, $R^5$ is a substituted $C_1$-$C_{10}$ alkyl. In aspects, $R^5$ is a substituted $C_1$-$C_8$ alkyl. In aspects, $R^5$ is a substituted $C_1$-$C_6$ alkyl. In aspects, $R^5$ is a substituted $C_1$-05 alkyl. In aspects, $R^5$ is a substituted $C_1$-$C_4$ alkyl. In aspects, $R^5$ is a substituted $C_1$-$C_3$ alkyl. In aspects, $R^5$ is a substituted $C_1$-$C_2$ alkyl. In aspects, $R^5$ is a substituted $C_2$ alkyl. In aspects, $R^5$ is a substituted $C_3$ alkyl. In aspects, $R^5$ is a substituted $C_4$ alkyl. In aspects, $R^5$ is a substituted $C_5$ alkyl. In aspects, $R^5$ is a substituted $C_6$ alkyl. In aspects, $R^5$ is an alkyl substituted with 1 to 4 substituents. In aspects, $R^5$ is an alkyl substituted with 1 to 3 substituents. In aspects, $R^5$ is an alkyl substituted with 1 or 2 substituents. In aspects, $R^5$ is an alkyl substituted with 1 substituent. In aspects, $R^5$ is an alkyl substituted with 2 substituents. In aspects, $R^5$ is an alkyl substituted with 3 substituents. In aspects, $R^5$ is an alkyl substituted with 4 substituents. In aspects, the substituent is any defined herein. In aspects, the substituent for the alkyl group of $R^5$ is halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In aspects, the substituent for the alkyl group of $R^5$ is halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted $C_1$-$C_4$ alkyl, unsubstituted 2 to 4 membered heteroalkyl. In aspects, the substituent for the alkyl group of $R^5$ is —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted $C_1$-$C_4$ alkyl, unsubstituted 2 to 4 membered heteroalkyl. In aspects, the substituent for the alkyl group of $R^5$ is —OH, $—NH_2$, —COOH, $—CONH_2$, $—NHNH_2$, or $—ONH_2$. In aspects, the substituent for the alkyl group of $R^5$ is —OH, —COOH, $—CONH_2$, or $—ONH_2$. In aspects, the substituent for the alkyl group of $R^5$ is —OH or —COOH. In aspects, the substituent for the alkyl group of $R^5$ is —OH.

In aspects, $R^5$ is $—CX^5_3$. In aspects, $R^5$ is $—CHX^5_2$. In aspects, $R^5$ is $—CH_2X^5$. In aspects, $R^5$ is $—OCX^5_3$. In aspects, $R^5$ is $—OCH_2X^5$. In aspects, $R^5$ is $—OCHX^5_2$. In aspects, $R^5$ is —CN. In aspects, $R^5$ is $—SR^{5A}$. In aspects, $R^5$ is $—SOR^{5A}$. In aspects, $R^5$ is $—SO_2R^{5A}$. In aspects, $R^5$ is $—SO_3R^{5A}$. In aspects, $R^5$ is $—SO_4R^{5A}$. In aspects, $R^5$ is $—SONR^{5A}R^{5B}$. In aspects, $R^5$ is $—SO_2NR^{5A}R^{5B}$. In aspects, $R^5$ is $—NHC(O)NR^{5A}R^{5B}$. In aspects, $R^5$ is —N(O). In aspects, $R^5$ is $—N(O)_2$. In aspects, $R^5$ is $—NR^{5A}R^{5B}$. In aspects, $R^5$ is $—C(O)R^{5A}$. In aspects, $R^5$ is $—C(O)—OR^{5A}$. In aspects, $R^5$ is $—C(O)NR^{5A}R^{5B}$. In aspects, $R^5$ is $—OR^{5A}$. In aspects, $R^5$ is $—NR^{5A}SO_2R^{5B}$. In aspects, $R^5$ is $—NR^{5A}C(O)R^{5B}$. In aspects, $R^5$ is $—NR^{5A}C(O)OR^{5B}$. In aspects, $R^5$ is $—NR^{5A}OR^{5B}$. In aspects, $R^5$ is hydrogen. In aspects, $X^5$ is independently —F. In aspects, $X^5$ is independently —Cl. In aspects, $X^5$ is independently —Br. In aspects, $X^5$ is independently —I.

In aspects, $R^5$ is hydrogen. In aspects, $R^5$ is oxo. In aspects, $R^5$ is halogen. In aspects, $R^5$ is $—CCl_3$. In aspects, $R^5$ is $—CBr_3$. In aspects, $R^5$ is $—CF_3$. In aspects, $R^5$ is $—CI_3$. In aspects, $R^5$ is $—CHCl_2$. In aspects, $R^5$ is $—CHBr_2$. In aspects, $R^5$ is $—CHF_2$. In aspects, $R^5$ is $—CHI_2$. In aspects, $R^5$ is $—CH_2Cl$. In aspects, $R^5$ is $—CH_2Br$. In aspects, $R^5$ is $—CH_2F$. In aspects, $R^5$ is $—CH_2I$. In aspects, $R^5$ is —CN. In aspects, $R^5$ is —OH. In aspects, $R^5$ is $—NH_2$. In aspects, $R^5$ is —COOH. In aspects, $R^5$ is $—CONH_2$. In aspects, $R^5$ is $—NO_2$. In aspects, $R^5$ is —SH. In aspects, $R^5$ is $—SO_3H$. In aspects, $R^5$ is $—SO_4H$. In aspects, $R^5$ is $—SO_2NH_2$. In aspects, $R^5$ is $—NHNH_2$. In aspects, $R^5$ is $—ONH_2$. In aspects, $R^5$ is $—NHC(O)NHNH_2$. In aspects, $R^5$ is $—NHC(O)NH_2$. In aspects, $R^5$ is $—NHSO_2H$. In aspects, $R^5$ is —NHC(O)H. In aspects, $R^5$ is —NHC(O)OH. In aspects, $R^5$ is —NHOH. In aspects, $R^5$ is $—OCCl_3$. In aspects, $R^5$ is $—OCF_3$. In aspects, $R^5$ is $—OCBr_3$. In aspects, $R^5$ is $—OCI_3$. In aspects, $R^5$ is $—OCHCl_2$. In aspects, $R^5$ is $—OCHBr_2$. In aspects, $R^5$ is $—OCHI_2$. In aspects, $R^5$ is $—OCHF_2$. In aspects, $R^5$ is $—OCH_2Cl$. In aspects, $R^5$ is $—OCH_2Br$. In aspects, $R^5$ is $—OCH_2I$. In aspects, $R^5$ is $—OCH_2F$. In aspects, $R^5$ is $—N_3$. In aspects, $R^5$ is $—OCH_3$. In aspects, $R^5$ is $—CH_3$. In aspects, $R^5$ is $—CH_2CH_3$. In aspects, $R^5$ is unsubstituted propyl. In aspects, $R^5$ is unsubstituted isopropyl. In aspects, $R^5$ is unsubstituted butyl. In aspects, $R^5$ is unsubstituted tert-butyl. In aspects, $R^5$ is —F. In aspects, $R^5$ is —Cl. In aspects, $R^5$ is —Br. In aspects, $R^5$ is —I.

In aspects, $R^5$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In aspects, $R^5$ is substituted or unsubstituted alkyl (e.g., $C_1$-$C_8$ alkyl, $C_1$-$C_6$ alkyl, or $C_1$-$C_4$ alkyl). In aspects, $R^5$ is substituted alkyl (e.g., $C_1$-$C_8$ alkyl, $C_1$-$C_6$ alkyl, or $C_1$-$C_4$ alkyl). In aspects, $R^5$ is an unsubstituted alkyl (e.g., $C_1$-$C_8$ alkyl, $C_1$-$C_6$ alkyl, or $C_1$-$C_4$ alkyl). In aspects, $R^5$ is substituted or unsubstituted heteroalkyl (e.g., 2 to 8 membered heteroalkyl, 2 to 6 membered heteroalkyl, or 2 to 4 membered heteroalkyl). In aspects, $R^5$ is substituted heteroalkyl (e.g., 2 to 8 membered heteroalkyl, 2 to 6 membered heteroalkyl, or 2 to 4 membered heteroalkyl). In aspects, $R^5$ is an unsubstituted heteroalkyl (e.g., 2 to 8 membered heteroalkyl, 2 to 6 membered heteroalkyl, or 2 to 4 membered heteroalkyl). In aspects, $R^5$ is substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^5$ is substituted cycloalkyl (e.g., $C_3$-$C_8$ cycloalkyl, $C_3$-$C_6$ cycloalkyl, or $C_5$-$C_6$ cycloalkyl). In aspects, $R^5$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^5$ is substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^5$ is substituted heterocycloalkyl (e.g., 3 to 8 membered heterocycloalkyl, 3 to 6 membered heterocycloalkyl, or 5 to 6 membered heterocycloalkyl). In aspects, $R^5$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^5$ is substituted or unsubstituted aryl (e.g., $C_6$-$C_{10}$ aryl, $C_{10}$ aryl, or phenyl). In aspects, $R^5$ is substituted aryl (e.g., $C_6$-$C_{10}$ aryl, $C_{10}$ aryl, or phenyl). In aspects, $R^5$ is an unsubstituted aryl (e.g., $C_6$-$C_{10}$ aryl, $C_{10}$ aryl, or phenyl). In aspects, $R^5$ is substituted or unsubstituted heteroaryl (e.g., 5 to 10 membered heteroaryl, 5 to 9 membered heteroaryl, or 5 to 6 membered heteroaryl). In aspects, $R^5$ is substituted heteroaryl (e.g., 5 to 10 membered heteroaryl, 5 to 9 membered heteroaryl, or 5 to 6 membered heteroaryl). In aspects, $R^5$ is an unsubstituted heteroaryl (e.g., 5 to 10 membered heteroaryl, 5 to 9 membered heteroaryl, or 5 to 6 membered heteroaryl).

$R^{33}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl). In aspects, $R^{33}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{33}$ is independently oxo. In aspects, $R^{33}$ is independently halogen. In aspects, $R^{33}$ is independently —$CCl_3$. In aspects, $R^{33}$ is independently —$CBr_3$. In aspects, $R^{33}$ is independently —$CF_3$. In aspects, $R^{33}$ is independently —$CI_3$. In aspects, $R^{33}$ is independently —$CHCl_2$. In aspects, $R^{33}$ is independently —$CHBr_2$. In aspects, $R^{33}$ is independently —$CHF_2$. In aspects, $R^{33}$ is independently —$CHI_2$. In aspects, $R^{33}$ is independently —$CH_2Cl$. In aspects, $R^{33}$ is independently —$CH_2Br$. In aspects, $R^{33}$ is independently —$CH_2F$. In aspects, $R^{33}$ is independently —$CH_2I$. In aspects, $R^{33}$ is independently —CN. In aspects, $R^{33}$ is independently —OH. In aspects, $R^{33}$ is independently —$NH_2$. In aspects, $R^{33}$ is independently —COOH. In aspects, $R^{33}$ is independently —$CONH_2$. In aspects, $R^{33}$ is independently —$NO_2$. In aspects, $R^{33}$ is independently —SH. In aspects, $R^{33}$ is independently —$SO_3H$. In aspects, $R^{33}$ is independently —$SO_4H$. In aspects, $R^{33}$ is independently —$SO_2NH_2$. In aspects, $R^{33}$ is independently —$NHNH_2$. In aspects, $R^{33}$ is independently —$ONH_2$. In aspects, $R^{33}$ is independently —NHC(O)$NHNH_2$. In aspects, $R^{33}$ is independently —NHC(O)$NH_2$. In aspects, $R^{33}$ is independently —$NHSO_2H$. In aspects, $R^{33}$ is independently —NHC(O)H. In aspects, $R^{33}$ is independently —NHC(O)OH. In aspects, $R^{33}$ is independently —NHOH. In aspects, $R^{33}$ is independently —$OCCl_3$. In aspects, $R^{33}$ is independently —$OCF_3$. In aspects, $R^{33}$ is independently —$OCBr_3$. In aspects, $R^{33}$ is independently —$OCI_3$. In aspects, $R^{33}$ is independently —$OCHCl_2$. In aspects, $R^{33}$ is independently —$OCHBr_2$. In aspects, $R^{33}$ is independently —$OCHI_2$. In aspects, $R^{33}$ is independently —$OCHF_2$. In aspects, $R^{33}$ is independently —$OCH_2Cl$. In aspects, $R^{33}$ is independently —$OCH_2Br$. In aspects, $R^{33}$ is independently —$OCH_2I$. In aspects, $R^{33}$ is independently —$OCH_2F$. In aspects, $R^{33}$ is independently —$N_3$. In aspects, $R^{33}$ is independently —$OCH_3$. In aspects, $R^{33}$ is independently —$CH_3$. In aspects, $R^{33}$ is independently —$CH_2CH_3$. In aspects, $R^{33}$ is independently unsubstituted propyl. In aspects, $R^{33}$ is independently unsubstituted isopropyl. In aspects, $R^{33}$ is independently unsubstituted butyl. In aspects, $R^{33}$ is independently unsubstituted tert-butyl. In aspects, $R^{33}$ is independently —F. In aspects, $R^{33}$ is independently —Cl. In aspects, $R^{33}$ is independently —Br. In aspects, $R^{33}$ is independently —I.

In aspects, $R^{33}$ is independently $R^{34}$-substituted or unsubstituted alkyl (e.g., $C_1$-$C_8$ alkyl, $C_1$-$C_6$ alkyl, or $C_1$-$C_4$ alkyl). In aspects, $R^{33}$ is independently $R^{34}$-substituted alkyl (e.g., $C_1$-$C_8$ alkyl, $C_1$-$C_6$ alkyl, or $C_1$-$C_4$ alkyl). In aspects, $R^{33}$ is independently an unsubstituted alkyl (e.g., $C_1$-$C_8$ alkyl, $C_1$-$C_6$ alkyl, or $C_1$-$C_4$ alkyl). In aspects, $R^{33}$ is independently $R^{34}$-substituted or unsubstituted heteroalkyl (e.g., 2 to 8 membered heteroalkyl, 2 to 6 membered heteroalkyl, or 2 to 4 membered heteroalkyl). In aspects, $R^{33}$ is independently $R^{34}$-substituted heteroalkyl (e.g., 2 to 8 membered heteroalkyl, 2 to 6 membered heteroalkyl, or 2 to 4 membered heteroalkyl). In aspects, $R^{33}$ is independently an unsubstituted heteroalkyl (e.g., 2 to 8 membered heteroalkyl, 2 to 6 membered heteroalkyl, or 2 to 4 membered heteroalkyl). In aspects, $R^{33}$ is independently $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{33}$ is independently $R^{34}$-substituted cycloalkyl (e.g., $C_3$-$C_8$ cycloalkyl, $C_3$-$C_6$ cycloalkyl, or $C_5$-$C_6$ cycloalkyl). In aspects, $R^{33}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{33}$ is independently $R^{34}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{33}$ is independently $R^{34}$-substituted heterocycloalkyl (e.g., 3 to 8 membered heterocycloalkyl, 3 to 6 membered heterocycloalkyl, or 5 to 6 membered heterocycloalkyl). In aspects, $R^{33}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{33}$ is independently $R^{34}$-substituted or unsubstituted aryl (e.g., $C_6$-$C_{10}$ aryl, $C_{10}$ aryl, or phenyl). In aspects, $R^{33}$ is independently $R^{34}$-substituted aryl (e.g., $C_6$-$C_{10}$ aryl, $C_{10}$ aryl, or phenyl).

In aspects, $R^{33}$ is independently an unsubstituted aryl (e.g., $C_6$-$C_{10}$ aryl, $C_{10}$ aryl, or phenyl). In aspects, $R^{33}$ is independently $R^{34}$-substituted or unsubstituted heteroaryl (e.g., 5 to 10 membered heteroaryl, 5 to 9 membered heteroaryl, or 5 to 6 membered heteroaryl). In aspects, $R^{33}$ is independently $R^{34}$-substituted heteroaryl (e.g., 5 to 10 membered heteroaryl, 5 to 9 membered heteroaryl, or 5 to 6 membered heteroaryl). In aspects, $R^{33}$ is independently an unsubstituted heteroaryl (e.g., 5 to 10 membered heteroaryl, 5 to 9 membered heteroaryl, or 5 to 6 membered heteroaryl).

$R^{34}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{35}$-substituted or unsubstituted alkyl (e.g., $C_1$-$C_8$ alkyl, $C_1$-$C_6$ alkyl, or $C_1$-$C_4$ alkyl), $R^{35}$-substituted or unsubstituted heteroalkyl (e.g., 2 to 8 membered heteroalkyl, 2 to 6 membered heteroalkyl, or 2 to 4 membered heteroalkyl), $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted or unsubstituted aryl (e.g., $C_6$-$C_{10}$ aryl, $C_{10}$ aryl, or phenyl), or $R^{35}$-substituted or unsubstituted heteroaryl (e.g., 5 to 10 membered heteroaryl, 5 to 9 membered heteroaryl, or 5 to 6 membered heteroaryl). In aspects, $R^{34}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{34}$ is independently $R^{35}$-substituted or unsubstituted alkyl (e.g., $C_1$-$C_8$ alkyl, $C_1$-$C_6$ alkyl, or $C_1$-$C_4$ alkyl). In aspects, $R^{34}$ is independently $R^{35}$-substituted alkyl (e.g., $C_1$-$C_8$ alkyl, $C_1$-$C_6$ alkyl, or $C_1$-$C_4$ alkyl). In aspects, $R^{34}$ is independently an unsubstituted alkyl (e.g., $C_1$-$C_8$ alkyl, $C_1$-$C_6$ alkyl, or $C_1$-$C_4$ alkyl). In aspects, $R^{34}$ is independently $R^{35}$-substituted or unsubstituted heteroalkyl (e.g., 2 to 8 membered heteroalkyl, 2 to 6 membered heteroalkyl, or 2 to 4 membered heteroalkyl). In aspects, $R^{34}$ is independently $R^{35}$-substituted heteroalkyl (e.g., 2 to 8 membered heteroalkyl, 2 to 6 membered heteroalkyl, or 2 to 4 membered heteroalkyl). In aspects, $R^{34}$ is independently an unsubstituted heteroalkyl (e.g., 2 to 8 membered heteroalkyl, 2 to 6 membered heteroalkyl, or 2 to 4 membered heteroalkyl). In aspects, $R^{34}$ is independently $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{34}$ is independently $R^{35}$-substituted cycloalkyl (e.g., $C_3$-$C_8$ cycloalkyl, $C_3$-$C_6$ cycloalkyl, or $C_5$-$C_6$ cycloalkyl). In aspects, $R^{34}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{34}$ is independently $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{34}$ is independently $R^{35}$-substituted heterocycloalkyl (e.g., 3 to 8 membered heterocycloalkyl, 3 to 6 membered heterocycloalkyl, or 5 to 6 membered heterocycloalkyl). In aspects, $R^{34}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{34}$ is independently $R^{35}$-substituted or unsubstituted aryl (e.g., $C_6$-$C_{10}$ aryl, $C_{10}$ aryl, or phenyl). In aspects, $R^{34}$ is independently $R^{35}$-substituted aryl (e.g., $C_6$-$C_{10}$ aryl, $C_{10}$ aryl, or phenyl). In aspects, $R^{34}$ is independently an unsubstituted aryl (e.g., $C_6$-$C_{10}$ aryl, $C_{10}$ aryl, or phenyl). In aspects, $R^{34}$ is independently $R^{35}$-substituted or unsubstituted heteroaryl (e.g., 5 to 10 membered heteroaryl, 5 to 9 membered heteroaryl, or 5 to 6 membered heteroaryl). In aspects, $R^{34}$ is independently $R^{35}$-substituted heteroaryl (e.g., 5 to 10 membered heteroaryl, 5 to 9 membered heteroaryl, or 5 to 6 membered heteroaryl). In aspects, $R^{34}$ is independently an unsubstituted heteroaryl (e.g., 5 to 10 membered heteroaryl, 5 to 9 membered heteroaryl, or 5 to 6 membered heteroaryl).

In aspects, $R^{34}$ is independently oxo. In aspects, $R^{34}$ is independently halogen. In aspects, $R^{34}$ is independently —$CCl_3$. In aspects, $R^{34}$ is independently —$CBr_3$. In aspects, $R^{34}$ is independently —$CF_3$. In aspects, $R^{34}$ is independently —$CI_3$. In aspects, $R^{34}$ is independently —$CHCl_2$. In aspects, $R^{34}$ is independently —$CHBr_2$. In aspects, $R^{34}$ is independently —$CHF_2$. In aspects, $R^{34}$ is independently —$CHI_2$. In aspects, $R^{34}$ is independently —$CH_2Cl$. In aspects, $R^{34}$ is independently —$CH_2Br$. In aspects, $R^{34}$ is independently —$CH_2F$. In aspects, $R^{34}$ is independently —$CH_2I$. In aspects, $R^{34}$ is independently —CN. In aspects, $R^{34}$ is independently —OH. In aspects, $R^{34}$ is independently —$NH_2$. In aspects, $R^{34}$ is independently —COOH. In aspects, $R^{34}$ is independently —$CONH_2$. In aspects, $R^{34}$ is independently —$NO_2$. In aspects, $R^{34}$ is independently —SH. In aspects, $R^{34}$ is independently —$SO_3H$. In aspects, $R^{34}$ is independently —$SO_4H$. In aspects, $R^{34}$ is independently —$SO_2NH_2$. In aspects, $R^{34}$ is independently —$NHNH_2$. In aspects, $R^{34}$ is independently —$ONH_2$. In aspects, $R^{34}$ is independently —NHC(O)$NHNH_2$. In aspects, $R^{34}$ is independently —NHC(O)$NH_2$. In aspects, $R^{34}$ is independently —$NHSO_2H$. In aspects, $R^{34}$ is independently —NHC(O)H. In aspects, $R^{34}$ is independently —NHC(O)OH. In aspects, $R^{34}$ is independently —NHOH. In aspects, $R^{34}$ is independently —$OCCl_3$. In aspects, $R^{34}$ is independently —$OCF_3$. In aspects, $R^{34}$ is independently —$OCBr_3$. In aspects, $R^{34}$ is independently —$OCI_3$. In aspects, $R^{34}$ is independently —$OCHCl_2$. In aspects, $R^{34}$ is independently —$OCHBr_2$. In aspects, $R^{34}$ is independently —$OCHI_2$. In aspects, $R^{34}$ is independently —$OCHF_2$. In aspects, $R^{34}$ is independently —$OCH_2Cl$. In aspects, $R^{34}$ is independently —$OCH_2Br$. In aspects, $R^{34}$ is independently —$OCH_2I$. In aspects, $R^{34}$ is independently —$OCH_2F$. In aspects, $R^{34}$ is independently —$N_3$. In aspects, $R^{34}$ is independently —$OCH_3$. In aspects, $R^{34}$ is independently —$CH_3$. In aspects, $R^{34}$ is independently —$CH_2CH_3$. In aspects, $R^{34}$ is independently unsubstituted propyl. In aspects, $R^{34}$ is independently unsubstituted isopropyl. In aspects, $R^{34}$ is independently unsubstituted butyl. In aspects, $R^{34}$ is independently unsubstituted tert-butyl. In aspects, $R^{34}$ is independently —F. In aspects, $R^{34}$ is independently —Cl. In aspects, $R^{34}$ is independently —Br. In aspects, $R^{34}$ is independently —I.

$R^{35}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{35}$ is independently an unsubstituted alkyl (e.g., $C_1$-$C_8$ alkyl, $C_1$-$C_6$ alkyl, or $C_1$-$C_4$ alkyl). In aspects, $R^{35}$ is independently an unsubstituted heteroalkyl (e.g., 2 to 8 membered heteroalkyl, 2 to 6 membered heteroalkyl, or 2 to 4 membered heteroalkyl). In aspects, $R^{35}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{35}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{35}$ is independently an unsubstituted aryl (e.g., $C_6$-$C_{10}$ aryl, $C_{10}$ aryl, or phenyl). In aspects, $R^{35}$ is independently an unsubstituted heteroaryl (e.g., 5 to 10 membered heteroaryl, 5 to 9 membered heteroaryl, or 5 to 6 membered heteroaryl).

In aspects, $R^{35}$ is independently oxo. In aspects, $R^{35}$ is independently halogen. In aspects, $R^{35}$ is independently —$CCl_3$. In aspects, $R^{35}$ is independently —$CBr_3$. In aspects, $R^{35}$ is independently —$CF_3$. In aspects, $R^{35}$ is independently —$CI_3$. In aspects, $R^{35}$ is independently —$CHCl_2$. In aspects, $R^{35}$ is independently —$CHBr_2$. In aspects, $R^{35}$ is independently —$CHF_2$. In aspects, $R^{35}$ is independently —$CHI_2$. In aspects, $R^{35}$ is independently —$CH_2Cl$. In aspects, $R^{35}$ is independently —$CH_2Br$. In aspects, $R^{35}$ is independently —$CH_2F$. In aspects, $R^{35}$ is independently —$CH_2I$. In aspects, $R^{35}$ is independently —CN. n aspects, $R^{35}$ is independently —OH. In aspects, $R^{35}$ is independently —$NH_2$. In aspects, $R^{35}$ is independently —COOH. In aspects, $R^{35}$ is independently —$CONH_2$. In aspects, $R^{35}$ is independently —$NO_2$. In aspects, $R^{35}$ is independently —SH. In aspects, $R^{35}$ is independently —$SO_3H$. In aspects, $R^{35}$ is independently —$SO_4H$. In aspects, $R^{35}$ is independently —$SO_2NH_2$. In aspects, $R^{35}$ is independently —$NHNH_2$. In aspects, $R^{35}$ is independently —$ONH_2$. In aspects, $R^{35}$ is independently —NHC(O)$NHNH_2$. In aspects, $R^{35}$ is independently —NHC(O)$NH_2$. In aspects, $R^{35}$ is independently —$NHSO_2H$. In aspects, $R^{35}$ is independently —NHC(O)H. In aspects, $R^{35}$ is independently —NHC(O)OH. In aspects, $R^{35}$ is independently —NHOH. In aspects, $R^{35}$ is independently —$OCCl_3$. In aspects, $R^{35}$ is independently —$OCF_3$. In aspects, $R^{35}$ is independently —$OCBr_3$. In aspects, $R^{35}$ is independently —$OCI_3$. In aspects, $R^{35}$ is independently —$OCHCl_2$. In aspects, $R^{35}$ is independently —$OCHBr_2$. In aspects, $R^{35}$ is independently —$OCHI_2$. In aspects, $R^{35}$ is independently —$OCHF_2$. In aspects, $R^{35}$ is independently —$OCH_2Cl$. In aspects, $R^{35}$ is independently —$OCH_2Br$. In aspects, $R^{35}$ is independently —$OCH_2I$. In aspects, $R^{35}$ is independently —$OCH_2F$. In aspects, $R^{35}$ is independently —$N_3$. In aspects, $R^{35}$ is independently —$OCH_3$. In aspects, $R^{35}$ is independently —$CH_3$. In aspects, $R^{35}$ is independently —$CH_2CH_3$. In aspects, $R^{35}$ is independently unsubstituted propyl. In aspects, $R^{35}$ is independently unsubstituted isopropyl. In aspects, $R^{35}$ is independently unsubstituted butyl. In aspects, $R^{35}$ is independently unsubstituted tert-butyl. In aspects, $R^{35}$ is independently —F. In aspects, $R^{35}$ is independently —Cl. In aspects, $R^{35}$ is independently —Br. In aspects, $R^{35}$ is independently —I.

In aspects, $R^{5A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{5A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In aspects, $R^{5A}$ is independently $R^{33}$-substituted or unsubstituted alkyl (e.g., $C_1$-$C_8$ alkyl, $C_1$-$C_6$ alkyl, or $C_1$-$C_4$ alkyl). In aspects, $R^{5A}$ is independently $R^{33}$-substituted alkyl (e.g., $C_1$-$C_8$ alkyl, $C_1$-$C_6$ alkyl, or $C_1$-$C_4$ alkyl). In aspects, $R^{5A}$ is independently an unsubstituted alkyl (e.g., $C_1$-$C_8$ alkyl, $C_1$-$C_6$ alkyl, or $C_1$-$C_4$ alkyl). In aspects, $R^{5A}$ is independently $R^{33}$-substituted or unsubstituted heteroalkyl (e.g., 2 to 8 membered heteroalkyl, 2 to 6 membered heteroalkyl, or 2 to 4 membered heteroalkyl). In aspects, $R^{5A}$ is independently $R^{33}$-substituted heteroalkyl (e.g., 2 to 8 membered heteroalkyl, 2 to 6 membered heteroalkyl, or 2 to 4 membered heteroalkyl). In aspects, $R^{5A}$ is independently an unsubstituted heteroalkyl (e.g., 2 to 8 membered heteroalkyl, 2 to 6 membered heteroalkyl, or 2 to 4 membered heteroalkyl). In aspects, $R^{5A}$ is independently $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{5A}$ is independently $R^{33}$-substituted cycloalkyl (e.g., $C_3$-$C_8$ cycloalkyl, $C_3$-$C_6$ cycloalkyl, or $C_5$-$C_6$ cycloalkyl). In aspects, $R^{5A}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{5A}$ is independently $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{5A}$ is independently $R^{33}$-substituted heterocycloalkyl (e.g., 3 to 8 membered heterocycloalkyl, 3 to 6 membered heterocycloalkyl, or 5 to 6 membered heterocycloalkyl). In aspects, $R^{5A}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{5A}$ is independently $R^{33}$-substituted or unsubstituted aryl (e.g., $C_6$-$C_{10}$ aryl, $C_{10}$ aryl, or phenyl). In aspects, $R^{5A}$ is independently $R^{33}$-substituted aryl (e.g., $C_6$-$C_{10}$ aryl, $C_{10}$ aryl, or phenyl). In aspects, $R^{5A}$ is independently an unsubstituted aryl (e.g., $C_6$-$C_{10}$ aryl, $C_{10}$ aryl, or phenyl). In aspects, $R^{5A}$ is independently $R^{33}$-substituted or unsubstituted heteroaryl (e.g., 5 to 10 membered heteroaryl, 5 to 9 membered heteroaryl, or 5 to 6 membered heteroaryl). In aspects, $R^{5A}$ is independently $R^{33}$-substituted heteroaryl (e.g., 5 to 10 membered heteroaryl, 5 to 9 membered heteroaryl, or 5 to 6 membered heteroaryl). In aspects, $R^{5A}$ is independently an unsubstituted heteroaryl (e.g., 5 to 10 membered heteroaryl, 5 to 9 membered heteroaryl, or 5 to 6 membered heteroaryl).

In aspects, $R^{5A}$ is independently —$CCl_3$. In aspects, $R^{5A}$ is independently —$CBr_3$. In aspects, $R^{5A}$ is independently —$CF_3$. In aspects, $R^{5A}$ is independently —$CI_3$. In aspects, $R^{5A}$ is independently —$CHCl_2$. In aspects, $R^{5A}$ is independently —$CHBr_2$. In aspects, $R^{5A}$ is independently —$CHF_2$. In aspects, $R^{5A}$ is independently —$CHI_2$. In aspects, $R^{5A}$ is independently —$CH_2Cl$. In aspects, $R^{5A}$ is independently —$CH_2Br$. In aspects, $R^{5A}$ is independently —$CH_2F$. In aspects, $R^{5A}$ is independently —$CH_2I$. In aspects, $R^{5A}$ is independently —CN. In aspects, $R^{5A}$ is independently —OH. In aspects, $R^{5A}$ is independently —COOH. In aspects, $R^{5A}$ is independently —$CONH_2$. In aspects, $R^{5A}$ is independently —$OCCl_3$. In aspects, $R^{5A}$ is independently —$OCF_3$. In aspects, $R^{5A}$ is independently —$OCBr_3$. In aspects, $R^{5A}$ is independently —$OCI_3$. In aspects, $R^{5A}$ is independently —$OCHCl_2$. In aspects, $R^{5A}$ is independently —$OCHBr_2$. In aspects, $R^{5A}$ is independently —$OCHI_2$. In aspects, $R^{5A}$ is independently —$OCHF_2$. In aspects, $R^{5A}$ is independently —$OCH_2Cl$. In aspects, $R^{5A}$ is independently —$OCH_2Br$. In aspects, $R^{5A}$ is independently —$OCH_2I$. In aspects, $R^{5A}$ is independently —$OCH_2F$. In aspects, $R^{5A}$ is independently —$OCH_3$. In aspects, $R^{5A}$ is independently —$CH_3$. In aspects, $R^{5A}$ is independently —$CH_2CH_3$. In aspects, $R^{5A}$ is independently unsubstituted propyl. In aspects, $R^{5A}$ is independently unsubstituted isopropyl. In aspects, $R^{5A}$ is independently unsubstituted butyl. In aspects, $R^{5A}$ is independently unsubstituted tert-butyl. In aspects, $R^{5A}$ is independently hydrogen.

In aspects, $R^{5B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{5B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In aspects, $R^{5B}$ is independently $R^{33}$-substituted or unsubstituted alkyl (e.g., $C_1$-$C_8$ alkyl, $C_1$-$C_6$ alkyl, or $C_1$-$C_4$ alkyl). In aspects, $R^{5B}$ is independently $R^{33}$-substituted alkyl (e.g., $C_1$-$C_8$ alkyl, $C_1$-$C_6$ alkyl, or $C_1$-$C_4$ alkyl). In aspects, $R^{5B}$ is independently an unsubstituted alkyl (e.g., $C_1$-$C_8$ alkyl, $C_1$-$C_6$ alkyl, or $C_1$-$C_4$ alkyl). In aspects, $R^{5B}$ is independently $R^{33}$-substituted or unsubstituted heteroalkyl (e.g., 2 to 8 membered heteroalkyl, 2 to 6 membered heteroalkyl, or 2 to 4 membered heteroalkyl). In aspects, $R^{5B}$ is independently $R^{33}$-substituted heteroalkyl (e.g., 2 to 8 membered heteroalkyl, 2 to 6 membered heteroalkyl, or 2 to 4 membered heteroalkyl). In aspects, $R^{5B}$ is independently an unsubstituted heteroalkyl (e.g., 2 to 8 membered heteroalkyl, 2 to 6 membered heteroalkyl, or 2 to 4 membered heteroalkyl). In aspects, $R^{5B}$ is independently $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{5B}$ is independently $R^{33}$-substituted cycloalkyl (e.g., $C_3$-$C_8$ cycloalkyl, $C_3$-$C_6$ cycloalkyl, or $C_5$-$C_6$ cycloalkyl). In aspects, $R^{5B}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{5B}$ is independently $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{5B}$ is independently $R^{33}$-substituted heterocycloalkyl (e.g., 3 to 8 membered heterocycloalkyl, 3 to 6 membered heterocycloalkyl, or 5 to 6 membered heterocycloalkyl). In aspects, $R^{5B}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{5B}$ is independently $R^{33}$-substituted or unsubstituted aryl (e.g., $C_6$-$C_{10}$ aryl, $C_{10}$ aryl, or phenyl). In aspects, $R^{5B}$ is independently $R^{33}$-substituted aryl (e.g., $C_6$-$C_{10}$ aryl, $C_{10}$ aryl, or phenyl). In aspects, $R^{5B}$ is independently an unsubstituted aryl (e.g., $C_6$-$C_{10}$ aryl, $C_{10}$ aryl, or phenyl). In aspects, $R^{5B}$ is independently $R^{33}$-substituted or unsubstituted heteroaryl (e.g., 5 to 10 membered heteroaryl, 5 to 9 membered heteroaryl, or 5 to 6 membered heteroaryl). In aspects, $R^{5B}$ is independently $R^{33}$-substituted heteroaryl (e.g., 5 to 10 membered heteroaryl, 5 to 9 membered heteroaryl, or 5 to 6 membered heteroaryl). In aspects, $R^{5B}$ is independently an unsubstituted heteroaryl (e.g., 5 to 10 membered heteroaryl, 5 to 9 membered heteroaryl, or 5 to 6 membered heteroaryl).

In aspects, $R^{5B}$ is independently —$CCl_3$. In aspects, $R^{5B}$ is independently —$CBr_3$. In aspects, $R^{5B}$ is independently —$CF_3$. In aspects, $R^{5B}$ is independently —$CI_3$. In aspects, $R^{5B}$ is independently —$CHCl_2$. In aspects, $R^{5B}$ is independently —$CHBr_2$. In aspects, $R^{5B}$ is independently —$CHF_2$. In aspects, $R^{5B}$ is independently —$CHI_2$. In aspects, $R^{5B}$ is independently —$CH_2Cl$. In aspects, $R^{5B}$ is independently —$CH_2Br$. In aspects, $R^{5B}$ is independently —$CH_2F$. In aspects, $R^{5B}$ is independently —$CH_2I$. In aspects, $R^{5B}$ is independently —CN. In aspects, $R^{5B}$ is independently —OH. In aspects, $R^{5B}$ is independently —COOH. In aspects, $R^{5B}$ is independently —$CONH_2$. In aspects, $R^{5B}$ is independently —$OCCl_3$. In aspects, $R^{5B}$ is independently —$OCF_3$. In aspects, $R^{5B}$ is independently —$OCBr_3$. In aspects, $R^{5B}$ is independently —$OCI_3$. In aspects, $R^{5B}$ is independently —$OCHCl_2$. In aspects, $R^{5B}$ is independently —$OCHBr_2$. In aspects, $R^{5B}$ is independently —$OCHI_2$. In aspects, $R^{5B}$ is independently —$OCHF_2$. In aspects, $R^{5B}$ is independently —$OCH_2Cl$. In aspects, $R^{5B}$ is independently —$OCH_2Br$. In aspects, $R^{5B}$ is independently —$OCH_2I$. In aspects, $R^{5B}$ is independently —$OCH_2F$. In aspects, $R^{5B}$ is independently —$OCH_3$. In aspects, $R^{5B}$ is independently —$CH_3$. In aspects, $R^{5B}$ is independently —$CH_2CH_3$. In aspects, $R^{5B}$ is independently unsubstituted propyl. In aspects, $R^{5B}$ is independently unsubstituted isopropyl. In aspects, $R^{5B}$ is independently unsubstituted butyl. In aspects, $R^{5B}$ is independently unsubstituted tert-butyl. In aspects, $R^{5B}$ is independently hydrogen.

In embodiments, $R^6$ is hydrogen, halogen, —$CF_3$, —$CBr_3$, —$CCl_3$, —$CI_3$, —$CHF_2$, —$CHBr_2$, —$CHCl_2$, —$CH_2F$, —$CH_2Br$, —$CH_2Cl$, —$OCF_3$, —$OCBr_3$, —$OCCl_3$, —$OCI_3$, —$OCHF_2$, —$OCHBr_2$, —$OCHCl_2$, —$OCH_2F$, —$OCH_2Br$, —$OCH_2Cl$, —CN, —$OR^{6A}$, —$NR^{6A}R^{6B}$, —$COOR^{6A}$, —$CONR^{6A}R^{6B}$, —$NO_2$, —$SR^{6A}$, —$SO_3R^{6A}$, —$SO_4R^{6A}$, —$SO_2NR^{6A}R^{6B}$, —$NHNR^{6A}R^{6B}$, —$ONR^{6A}R^{6B}$, —$NHC(O)NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^6$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —CN, —$OR^{6A}$, —$NR^{6A}R^{6B}$, —$COOR^{6A}$, —$CONR^{6A}R^{6B}$, 13 $NO_2$, —$SR^{6A}$, —$SO_3R^{6A}$, —$SO_4R^{6A}$, —$SO_2NR^{6A}R^{6B}$, —$NHNR^{6A}R^{6B}$, —$ONR^{6A}R^{6B}$, —$NHC(O)NHNR^{6A}R^{6B}$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

In aspects, $R^6$ is hydrogen, halogen, —$CF_3$, —$CBr_3$, —$CCl_3$, —$CI_3$, —$CHF_2$, —$CHBr_2$, —$CHCl_2$, —$CH_2F$, —$CH_2Br$, —$CH_2Cl$, —$OCF_3$, —$OCBr_3$, —$OCCl_3$, —$OCI_3$, —$OCHF_2$, —$OCHBr_2$, —$OCHCl_2$, —$OCH_2F$, —$OCH_2Br$, —$OCH_2Cl$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^6$ is $R^{36}$-substituted or unsubstituted alkyl (e.g., $C_1$-$C_8$ alkyl, $C_1$-$C_6$ alkyl, or $C_1$-$C_4$ alkyl). In aspects, $R^6$ is $R^{36}$-substituted alkyl (e.g., $C_1$-$C_8$ alkyl, $C_1$-$C_6$ alkyl, or $C_1$-$C_4$ alkyl). In aspects, $R^6$ is an unsubstituted alkyl (e.g., $C_1$-$C_8$ alkyl, $C_1$-$C_6$ alkyl, or $C_1$-$C_4$ alkyl). In aspects, $R^6$ is $R^{36}$-substituted or unsubstituted heteroalkyl (e.g., 2 to 8 membered heteroalkyl, 2 to 6 membered heteroalkyl, or 2 to 4 membered heteroalkyl). In aspects, $R^6$ is $R^{36}$-substituted heteroalkyl (e.g., 2 to 8 membered heteroalkyl, 2 to 6 membered heteroalkyl, or 2 to 4 membered heteroalkyl). In aspects, $R^6$ is an unsubstituted heteroalkyl (e.g., 2 to 8 membered heteroalkyl, 2 to 6 membered heteroalkyl, or 2 to 4 membered heteroalkyl). In aspects, $R^6$ is $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^6$ is $R^{36}$-substituted cycloalkyl (e.g., $C_3$-$C_8$ cycloalkyl, $C_3$-$C_6$ cycloalkyl, or $C_5$-$C_6$ cycloalkyl). In aspects, $R^6$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^6$ is $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^6$ is $R^{36}$-substituted heterocycloalkyl (e.g., 3 to 8 membered heterocycloalkyl, 3 to 6 membered heterocycloalkyl, or 5 to 6 membered heterocycloalkyl). In aspects, $R^6$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^6$ is $R^{36}$-substituted or unsubstituted aryl (e.g., $C_6$-$C_{10}$ aryl, $C_{10}$ aryl, or phenyl). In aspects, $R^6$ is $R^{36}$-substituted aryl (e.g., $C_6$-$C_{10}$ aryl, $C_{10}$ aryl, or phenyl). In aspects, $R^6$ is an unsubstituted aryl (e.g., $C_6$-$C_{10}$ aryl, $C_{10}$ aryl, or phenyl). In aspects, $R^6$ is $R^{36}$-substituted or unsubstituted heteroaryl (e.g., 5 to 10 membered heteroaryl, 5 to 9 membered heteroaryl, or 5 to 6 membered heteroaryl). In aspects, $R^6$ is $R^{36}$-substituted heteroaryl (e.g., 5 to 10 membered heteroaryl, 5 to 9 membered heteroaryl, or 5 to 6 membered heteroaryl). In aspects, $R^6$ is an unsubstituted heteroaryl (e.g., 5 to 10 membered heteroaryl, 5 to 9 membered heteroaryl, or 5 to 6 membered heteroaryl).

In aspects, $R^6$ is —$CX^6_3$. In aspects, $R^6$ is —$CHX^6_2$. In aspects, $R^6$ is —$CH_2X^6$. In aspects, $R^6$ is —$OCX^6_3$. In aspects, $R^6$ is —$OCH_2X^6$. In aspects, $R^6$ is —$OCHX^6_2$. In aspects, $R^6$ is —CN. In aspects, $R^6$ is —$SR^{6A}$. In aspects, $R^6$ is —$SOR^{6A}$. In aspects, $R^6$ is —$SO_2R^{6A}$. In aspects, $R^6$ is —$SO_3R^{6A}$. In aspects, $R^6$ is —$SO_4R^{6A}$. In aspects, $R^6$ is —$SONR^{6A}R^{6B}$. In aspects, $R^6$ is —$SO_2NR^{6A}R^{6B}$. In aspects, $R^6$ is —$NHC(O)NR^{6A}R^{6B}$. In aspects, $R^6$ is —N(O). In aspects, $R^6$ is —$N(O)_2$. In aspects, $R^6$ is —$NR^{6A}R^{6B}$. In aspects, $R^6$ is —$C(O)R^{6A}$. In aspects, $R^6$ is —C(O)—$OR^{6A}$. In aspects, $R^6$ is —$C(O)NR^{6A}R^{6B}$. In aspects, $R^6$ is —$OR^{6A}$. In aspects, $R^6$ is —$NR^{6A}SO_2R^{6B}$. In aspects, $R^6$ is —$NR^{6A}C(O)R^{6B}$. In aspects, $R^6$ is —$NR^{6A}C(O)OR^{6B}$. In aspects, $R^6$ is —$NR^{6A}OR^{6B}$. In aspects, $R^6$ is hydrogen. In aspects, $X^6$ is independently —F. In aspects, $X^6$ is independently —Cl. In aspects, $X^6$ is independently —Br. In aspects, $X^6$ is independently —I.

In aspects, $R^6$ is hydrogen. In aspects, $R^6$ is oxo. In aspects, $R^6$ is halogen. In aspects, $R^6$ is —$CCl_3$. In aspects, $R^6$ is —$CBr_3$. In aspects, $R^6$ is —$CF_3$. In aspects, $R^6$ is —$CI_3$. In aspects, $R^6$ is —$CHCl_2$. In aspects, $R^6$ is —$CHBr_2$. In aspects, $R^6$ is —$CHF_2$. In aspects, $R^6$ is —$CHI_2$. In aspects, $R^6$ is —$CH_2Cl$. In aspects, $R^6$ is —$CH_2Br$. In aspects, $R^6$ is —$CH_2F$. In aspects, $R^6$ is —$CH_2I$. In aspects, $R^6$ is —CN. In aspects, $R^6$ is —OH. In aspects, $R^6$ is —$NH_2$. In aspects, $R^6$ is —COOH. In aspects, $R^6$ is —$CONH_2$. In aspects, $R^6$ is —$NO_2$. In aspects, $R^6$ is —SH. In aspects, $R^6$ is —$SO_3H$. In aspects, $R^6$ is —$SO_4H$. In aspects, $R^6$ is —$SO_2NH_2$. In aspects, $R^6$ is —$NHNH_2$. In aspects, $R^6$ is —$ONH_2$. In aspects, $R^6$ is —$NHC(O)NHNH_2$. In aspects, $R^6$ is —$NHC(O)NH_2$. In aspects, $R^6$ is —$NHSO_2H$. In aspects, $R^6$ is —NHC(O)H. In aspects, $R^6$ is —NHC(O)OH. In aspects, $R^6$ is —NHOH. In aspects, $R^6$ is —$OCCl_3$. In aspects, $R^6$ is —$OCF_3$. In aspects, $R^6$ is —$OCBr_3$. In aspects, $R^6$ is —$OCI_3$. In aspects, $R^6$ is —$OCHCl_2$. In aspects, $R^6$ is —$OCHBr_2$. In aspects, $R^6$ is —$OCHI_2$. In aspects, $R^6$ is —$OCHF_2$. In aspects, $R^6$ is —$OCH_2Cl$. In aspects, $R^6$ is —$OCH_2Br$. In aspects, $R^6$ is —$OCH_2I$. In aspects, $R^6$ is —$OCH_2F$. In aspects, $R^6$ is —$N_3$. In aspects, $R^6$ is —$OCH_3$. In aspects, $R^6$ is —$CH_3$. In aspects, $R^6$ is —$CH_2CH_3$. In aspects, $R^6$ is unsubstituted propyl. In aspects, $R^6$ is unsubstituted isopropyl. In aspects, $R^6$ is unsubstituted butyl. In aspects, $R^6$ is unsubstituted tert-butyl. In aspects, $R^6$ is —F. In aspects, $R^6$ is —Cl. In aspects, $R^6$ is —Br. In aspects, $R^6$ is —I.

In aspects, $R^6$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In aspects, $R^6$ is substituted or unsubstituted alkyl (e.g., $C_1$-$C_8$ alkyl, $C_1$-$C_6$ alkyl, or $C_1$-$C_4$ alkyl). In aspects, $R^6$ is substituted alkyl (e.g., $C_1$-$C_8$ alkyl, $C_1$-$C_6$ alkyl, or $C_1$-$C_4$ alkyl). In aspects, $R^6$ is an unsubstituted alkyl (e.g., $C_1$-$C_8$ alkyl, $C_1$-$C_6$ alkyl, or $C_1$-$C_4$ alkyl). In aspects, $R^6$ is substituted or unsubstituted heteroalkyl (e.g., 2 to 8 membered heteroalkyl, 2 to 6 membered heteroalkyl, or 2 to 4 membered heteroalkyl). In aspects, $R^6$ is substituted heteroalkyl (e.g., 2 to 8 membered heteroalkyl, 2 to 6 membered heteroalkyl, or 2 to 4 membered heteroalkyl). In aspects, $R^6$ is an unsubstituted heteroalkyl (e.g., 2 to 8 membered heteroalkyl, 2 to 6 membered heteroalkyl, or 2 to 4 membered heteroalkyl). In aspects, $R^6$ is substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^6$ is substituted cycloalkyl (e.g., $C_3$-$C_8$ cycloalkyl, $C_3$-$C_6$ cycloalkyl, or $C_5$-$C_6$ cycloalkyl). In aspects, $R^6$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^6$ is substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^6$ is substituted heterocycloalkyl (e.g., 3 to 8 membered heterocycloalkyl, 3 to 6 membered heterocycloalkyl, or 5 to 6 membered heterocycloalkyl). In aspects, $R^6$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^6$ is substituted or unsubstituted aryl (e.g., $C_6$-$C_{10}$ aryl, $C_{10}$ aryl, or phenyl). In aspects, $R^6$ is substituted aryl (e.g., $C_6$-$C_{10}$ aryl, $C_{10}$ aryl, or phenyl). In aspects, $R^6$ is an unsubstituted aryl (e.g., $C_6$-$C_{10}$ aryl, $C_{10}$ aryl, or phenyl). In aspects, $R^6$ is substituted or unsubstituted heteroaryl (e.g., 5 to 10 membered heteroaryl, 5 to 9 membered heteroaryl, or 5 to 6 membered heteroaryl). In aspects, $R^6$ is substituted heteroaryl (e.g., 5 to 10 membered heteroaryl, 5 to 9 membered heteroaryl, or 5 to 6 membered heteroaryl). In aspects, $R^6$ is an unsubstituted heteroaryl (e.g., 5 to 10 membered heteroaryl, 5 to 9 membered heteroaryl, or 5 to 6 membered heteroaryl).

$R^{36}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $R^{37}$-substituted or unsubstituted alkyl (e.g., $C_1$-$C_8$ alkyl, $C_1$-$C_6$ alkyl, or $C_1$-$C_4$ alkyl), $R^{37}$-substituted or unsubstituted heteroalkyl (e.g., 2 to 8 membered heteroalkyl, 2 to 6 membered heteroalkyl, or 2 to 4 membered heteroalkyl), $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted or unsubstituted aryl (e.g., $C_6$-$C_{10}$ aryl, $C_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl). In aspects, $R^{36}$ is independently oxo, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{36}$ is independently oxo. In aspects, $R^{36}$ is independently halogen. In aspects, $R^{36}$ is independently $—CCl_3$. In aspects, $R^{36}$ is independently $—CBr_3$. In aspects, $R^{36}$ is independently $—CF_3$. In aspects, $R^{36}$ is independently $—CI_3$. In aspects, $R^{36}$ is independently $—CHCl_2$. In aspects, $R^{36}$ is independently $—CHBr_2$. In aspects, $R^{36}$ is independently $—CHF_2$. In aspects, $R^{36}$ is independently $—CHI_2$. In aspects, $R^{36}$ is independently $—CH_2Cl$. In aspects, $R^{36}$ is independently $—CH_2Br$. In aspects, $R^{36}$ is independently $—CH_2F$. In aspects, $R^{36}$ is independently $—CH_2I$. In aspects, $R^{36}$ is independently —CN. In aspects, $R^{36}$ is independently —OH. In aspects, $R^{36}$ is independently $—NH_2$. In aspects, $R^{36}$ is independently —COOH. In aspects, $R^{36}$ is independently $—CONH_2$. In aspects, $R^{36}$ is independently $—NO_2$. In aspects, $R^{36}$ is independently —SH. In aspects, $R^{36}$ is independently $—SO_3H$. In aspects, $R^{36}$ is independently $—SO_4H$. In aspects, $R^{36}$ is independently $—SO_2NH_2$. In aspects, $R^{36}$ is independently $—NHNH_2$. In aspects, $R^{36}$ is independently $—ONH_2$. In aspects, $R^{36}$ is independently $—NHC(O)NHNH_2$. In aspects, $R^{36}$ is independently $—NHC(O)NH_2$. In aspects, $R^{36}$ is independently $—NHSO_2H$. In aspects, $R^{36}$ is independently —NHC(O)H. In aspects, $R^{36}$ is independently —NHC(O)OH. In aspects, $R^{36}$ is independently —NHOH. In aspects, $R^{36}$ is independently $—OCCl_3$. In aspects, $R^{36}$ is independently $—OCF_3$. In aspects, $R^{36}$ is independently $—OCBr_3$. In aspects, $R^{36}$ is independently $—OCI_3$. In aspects, $R^{36}$ is independently $—OCHCl_2$. In aspects, $R^{36}$ is independently $—OCHBr_2$. In aspects, $R^{36}$ is independently $—OCHI_2$. In aspects, $R^{36}$ is independently $—OCHF_2$. In aspects, $R^{36}$ is independently $—OCH_2Cl$. In aspects, $R^{36}$ is independently $—OCH_2Br$. In aspects, $R^{36}$ is independently $—OCH_2I$. In aspects, $R^{36}$ is independently $—OCH_2F$. In aspects, $R^{36}$ is independently $—N_3$. In aspects, $R^{36}$ is independently $—OCH_3$. In aspects, $R^{36}$ is independently $—CH_3$. In aspects, $R^{36}$ is independently $—CH_2CH_3$. In aspects, $R^{36}$ is independently unsubstituted propyl. In aspects, $R^{36}$ is independently unsubstituted isopropyl. In aspects, $R^{36}$ is independently unsubstituted butyl. In aspects, $R^{36}$ is independently unsubstituted tert-butyl. In aspects, $R^{36}$ is independently —F. In aspects, $R^{36}$ is independently —Cl. In aspects, $R^{36}$ is independently —Br. In aspects, $R^{36}$ is independently —I.

In aspects, $R^{36}$ is independently $R^{37}$-substituted or unsubstituted alkyl (e.g., $C_1$-$C_8$ alkyl, $C_1$-$C_6$ alkyl, or $C_1$-$C_4$ alkyl). In aspects, $R^{36}$ is independently $R^{37}$-substituted alkyl (e.g., $C_1$-$C_8$ alkyl, $C_1$-$C_6$ alkyl, or $C_1$-$C_4$ alkyl). In aspects, $R^{36}$ is independently an unsubstituted alkyl (e.g., $C_1$-$C_8$ alkyl, $C_1$-$C_6$ alkyl, or $C_1$-$C_4$ alkyl). In aspects, $R^{36}$ is independently $R^{37}$-substituted or unsubstituted heteroalkyl (e.g., 2 to 8 membered heteroalkyl, 2 to 6 membered heteroalkyl, or 2 to 4 membered heteroalkyl). In aspects, $R^{36}$ is independently $R^{37}$-substituted heteroalkyl (e.g., 2 to 8 membered heteroalkyl, 2 to 6 membered heteroalkyl, or 2 to 4 membered heteroalkyl). In aspects, $R^{36}$ is independently an unsubstituted heteroalkyl (e.g., 2 to 8 membered heteroalkyl, 2 to 6 membered heteroalkyl, or 2 to 4 membered heteroalkyl). In aspects, $R^{36}$ is independently $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{36}$ is independently $R^{37}$-substituted cycloalkyl (e.g., $C_3$-$C_8$ cycloalkyl, $C_3$-$C_6$ cycloalkyl, or $C_5$-$C_6$ cycloalkyl). In aspects, $R^{36}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{36}$ is independently $R^{37}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{36}$ is independently $R^{37}$-substituted heterocycloalkyl (e.g., 3 to 8 membered heterocycloalkyl, 3 to 6 membered heterocycloalkyl, or 5 to 6 membered heterocycloalkyl). In aspects, $R^{36}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{36}$ is independently $R^{37}$-substituted or unsubstituted aryl (e.g., $C_6$-$C_{10}$ aryl, $C_{10}$ aryl, or phenyl). In aspects, $R^{36}$ is independently $R^{37}$-substituted aryl (e.g., $C_6$-$C_{10}$ aryl, $C_{10}$ aryl, or phenyl). In aspects, $R^{36}$ is independently an unsubstituted aryl (e.g., $C_6$-$C_{10}$ aryl, $C_{10}$ aryl, or phenyl). In aspects, $R^{36}$ is independently $R^{37}$-substituted or unsubstituted heteroaryl (e.g., 5 to 10 membered heteroaryl, 5 to 9 membered heteroaryl, or 5 to 6 membered heteroaryl). In aspects, $R^{36}$ is independently $R^{37}$-substituted heteroaryl (e.g., 5 to 10 membered heteroaryl, 5 to 9 membered heteroaryl, or 5 to 6 membered heteroaryl). In aspects, $R^{36}$ is independently an unsubstituted heteroaryl (e.g., 5 to 10 membered heteroaryl, 5 to 9 membered heteroaryl, or 5 to 6 membered heteroaryl).

$R^{37}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $R^{38}$-substituted or unsubstituted alkyl (e.g., $C_1$-$C_8$ alkyl, $C_1$-$C_6$ alkyl, or $C_1$-$C_4$ alkyl), $R^{38}$-substituted or unsubstituted heteroalkyl (e.g., 2 to 8 membered heteroalkyl, 2 to 6 membered heteroalkyl, or 2 to 4 membered heteroalkyl), $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted or unsubstituted aryl (e.g., $C_6$-$C_{10}$ aryl, $C_{10}$ aryl, or phenyl), or $R^{38}$-substituted or unsubstituted heteroaryl (e.g., 5 to 10 membered heteroaryl, 5 to 9 membered heteroaryl, or 5 to 6 membered heteroaryl). In aspects, $R^{37}$ is independently oxo, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{37}$ is independently $R^{38}$-substituted or unsubstituted alkyl (e.g., $C_1$-$C_8$ alkyl, $C_1$-$C_6$ alkyl, or $C_1$-$C_4$ alkyl). In aspects, $R^{37}$ is independently $R^{38}$-substituted alkyl (e.g., $C_1$-$C_8$ alkyl, $C_1$-$C_6$ alkyl, or $C_1$-$C_4$ alkyl). In aspects, $R^{37}$ is independently an unsubstituted alkyl (e.g., $C_1$-$C_8$ alkyl, $C_1$-$C_6$ alkyl, or $C_1$-$C_4$ alkyl). In aspects, $R^{37}$ is independently $R^{38}$-substituted or unsubstituted heteroalkyl (e.g., 2 to 8 membered heteroalkyl, 2 to 6 membered heteroalkyl, or 2 to 4 membered heteroalkyl). In aspects, $R^{37}$ is independently $R^{38}$-substituted heteroalkyl (e.g., 2 to 8 membered heteroalkyl, 2 to 6 membered heteroalkyl, or 2 to 4 membered heteroalkyl). In aspects, $R^{37}$ is independently an unsubstituted heteroalkyl (e.g., 2 to 8 membered heteroalkyl, 2 to 6 membered heteroalkyl, or 2 to 4 membered heteroalkyl). In aspects, $R^{37}$ is independently $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{37}$ is independently $R^{38}$-substituted cycloalkyl (e.g., $C_3$-$C_8$ cycloalkyl, $C_3$-$C_6$ cycloalkyl, or $C_5$-$C_6$ cycloalkyl). In aspects, $R^{37}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{37}$ is independently $R^{38}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{37}$ is independently $R^{38}$-substituted heterocycloalkyl (e.g., 3 to 8 membered heterocycloalkyl, 3 to 6 membered heterocycloalkyl, or 5 to 6 membered heterocycloalkyl). In aspects, $R^{37}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{37}$ is independently $R^{38}$-substituted or unsubstituted aryl (e.g., $C_6$-$C_{10}$ aryl, $C_{10}$ aryl, or phenyl). In aspects, $R^{37}$ is independently $R^{38}$-substituted aryl (e.g., $C_6$-$C_{10}$ aryl, $C_{10}$ aryl, or phenyl). In aspects, $R^{37}$ is independently an unsubstituted aryl (e.g., $C_6$-$C_{10}$ aryl, $C_{10}$ aryl, or phenyl). In aspects, $R^{37}$ is independently $R^{38}$-substituted or unsubstituted heteroaryl (e.g., 5 to 10 membered heteroaryl, 5 to 9 membered heteroaryl, or 5 to 6 membered heteroaryl). In aspects, $R^{37}$ is independently $R^{38}$-substituted heteroaryl (e.g., 5 to 10 membered heteroaryl, 5 to 9 membered heteroaryl, or 5 to 6 membered heteroaryl). In aspects, $R^{37}$ is independently an unsubstituted heteroaryl (e.g., 5 to 10 membered heteroaryl, 5 to 9 membered heteroaryl, or 5 to 6 membered heteroaryl).

In aspects, $R^{37}$ is independently oxo. In aspects, $R^{37}$ is independently halogen. In aspects, $R^{37}$ is independently —$CCl_3$. In aspects, $R^{37}$ is independently —$CBr_3$. In aspects, $R^{37}$ is independently —$CF_3$. In aspects, $R^{37}$ is independently —$CI_3$. In aspects, $R^{37}$ is independently —$CHCl_2$. In aspects, $R^{37}$ is independently —$CHBr_2$. In aspects, $R^{37}$ is independently —$CHF_2$. In aspects, $R^{37}$ is independently —$CHI_2$. In aspects, $R^{37}$ is independently —$CH_2Cl$. In aspects, $R^{37}$ is independently —$CH_2Br$. In aspects, $R^{37}$ is independently —$CH_2F$. In aspects, $R^{37}$ is independently —$CH_2I$. In aspects, $R^{37}$ is independently —CN. In aspects, $R^{37}$ is independently —OH. In aspects, $R^{37}$ is independently —$NH_2$. In aspects, $R^{37}$ is independently —COOH. In aspects, $R^{37}$ is independently —$CONH_2$. In aspects, $R^{37}$ is independently —$NO_2$. In aspects, $R^{37}$ is independently —SH. In aspects, $R^{37}$ is independently —$SO_3H$. In aspects, $R^{37}$ is independently —$SO_4H$. In aspects, $R^{37}$ is independently —$SO_2NH_2$. In aspects, $R^{37}$ is independently —$NHNH_2$. In aspects, $R^{37}$ is independently —$ONH_2$. In aspects, $R^{37}$ is independently —NHC(O)$NHNH_2$. In aspects, $R^{37}$ is independently —NHC(O)$NH_2$. In aspects, $R^{37}$ is independently —$NHSO_2H$. In aspects, $R^{37}$ is independently —NHC(O)H. In aspects, $R^{37}$ is independently —NHC(O)OH. In aspects, $R^{37}$ is independently —NHOH. In aspects, $R^{37}$ is independently —$OCCl_3$. In aspects, $R^{37}$ is independently —$OCF_3$. In aspects, $R^{37}$ is independently —$OCBr_3$. In aspects, $R^{37}$ is independently —$OCI_3$. In aspects, $R^{37}$ is independently —$OCHCl_2$. In aspects, $R^{37}$ is independently —$OCHBr_2$. In aspects, $R^{37}$ is independently —$OCHI_2$. In aspects, $R^{37}$ is independently —$OCHF_2$. In aspects, $R^{37}$ is independently —$OCH_2Cl$. In aspects, $R^{37}$ is independently —$OCH_2Br$. In aspects, $R^{37}$ is independently —$OCH_2I$. In aspects, $R^{37}$ is independently —$OCH_2F$. In aspects, $R^{37}$ is independently —$N_3$. In aspects, $R^{37}$ is independently —$OCH_3$. In aspects, $R^{37}$ is independently —$CH_3$. In aspects, $R^{37}$ is independently —$CH_2CH_3$. In aspects, $R^{37}$ is independently unsubstituted propyl. In aspects, $R^{37}$ is independently unsubstituted isopropyl. In aspects, $R^{37}$ is independently unsubstituted butyl. In aspects, $R^{37}$ is independently unsubstituted tert-butyl. In aspects, $R^{37}$ is independently —F. In aspects, $R^{37}$ is independently —Cl. In aspects, $R^{37}$ is independently —Br. In aspects, $R^{37}$ is independently —I.

$R^{38}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{38}$ is independently an unsubstituted alkyl (e.g., $C_1$-$C_8$ alkyl, $C_1$-$C_6$ alkyl, or $C_1$-$C_4$ alkyl). In aspects, $R^{38}$ is independently an unsubstituted heteroalkyl (e.g., 2 to 8 membered heteroalkyl, 2 to 6 membered heteroalkyl, or 2 to 4 membered heteroalkyl). In aspects, $R^{38}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{38}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{38}$ is independently an unsubstituted aryl (e.g., $C_6$-$C_{10}$ aryl, $C_{10}$ aryl, or phenyl). In aspects, $R^{38}$ is independently an unsubstituted heteroaryl (e.g., 5 to 10 membered heteroaryl, 5 to 9 membered heteroaryl, or 5 to 6 membered heteroaryl).

In aspects, $R^{38}$ is independently oxo. In aspects, $R^{38}$ is independently halogen. In aspects, $R^{38}$ is independently —$CCl_3$. In aspects, $R^{38}$ is independently —$CBr_3$. In aspects, $R^{38}$ is independently —$CF_3$. In aspects, $R^{38}$ is independently —$CI_3$. In aspects, $R^{38}$ is independently —$CHCl_2$. In aspects, $R^{38}$ is independently —$CHBr_2$. In aspects, $R^{38}$ is independently —$CHF_2$. In aspects, $R^{38}$ is independently —$CHI_2$. In aspects, $R^{38}$ is independently —$CH_2Cl$. In aspects, $R^{38}$ is independently —$CH_2Br$. In aspects, $R^{38}$ is independently —$CH_2F$. In aspects, $R^{38}$ is independently —$CH_2I$. In aspects, $R^{38}$ is independently —CN. In aspects, $R^{38}$ is independently —OH. In aspects, $R^{38}$ is independently —$NH_2$. In aspects, $R^{38}$ is independently —COOH. In aspects, $R^{38}$ is independently —$CONH_2$. In aspects, $R^{38}$ is independently —$NO_2$. In aspects, $R^{38}$ is independently —SH. In aspects, $R^{38}$ is independently —$SO_3H$. In aspects, $R^{38}$ is independently —$SO_4H$. In aspects, $R^{38}$ is independently —$SO_2NH_2$. In aspects, $R^{38}$ is independently —$NHNH_2$. In aspects, $R^{38}$ is independently —$ONH_2$. In aspects, $R^{38}$ is independently —NHC(O)$NHNH_2$. In aspects, $R^{38}$ is independently —NHC(O)$NH_2$. In aspects, $R^{38}$ is independently —$NHSO_2H$. In aspects, $R^{38}$ is independently —NHC(O)H. In aspects, $R^{38}$ is independently —NHC(O)OH. In aspects, $R^{38}$ is independently —NHOH. In aspects, $R^{38}$ is independently —$OCCl_3$. In aspects, $R^{38}$ is independently —$OCF_3$. In aspects, $R^{38}$ is independently —$OCBr_3$. In aspects, $R^{38}$ is independently —$OCI_3$. In aspects, $R^{38}$ is independently —$OCHCl_2$. In aspects, $R^{38}$ is independently —$OCHBr_2$. In aspects, $R^{38}$ is independently —$OCHI_2$. In aspects, $R^{38}$ is independently —$OCHF_2$. In aspects, $R^{38}$ is independently —$OCH_2Cl$. In aspects, $R^{38}$ is independently —$OCH_2Br$. In aspects, $R^{38}$ is independently —$OCH_2I$. In aspects, $R^{38}$ is independently —$OCH_2F$. In aspects, $R^{38}$ is independently —$N_3$. In aspects, $R^{38}$ is independently —$OCH_3$. In aspects, $R^{38}$ is independently —$CH_3$. In aspects, $R^{38}$ is independently —$CH_2CH_3$. In aspects, $R^{38}$ is independently unsubstituted propyl. In aspects, $R^{38}$ is independently unsubstituted isopropyl. In aspects, $R^{38}$ is independently unsubstituted butyl. In aspects, $R^{38}$ is independently unsubstituted tert-butyl. In aspects, $R^{38}$ is independently —F. In aspects, $R^{38}$ is independently —Cl. In aspects, $R^{38}$ is independently —Br. In aspects, $R^{38}$ is independently —I.

In aspects, $R^{6A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{6A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

In aspects, $R^{6A}$ is independently $R^{36}$-substituted or unsubstituted alkyl (e.g., $C_1$-$C_8$ alkyl, $C_1$-$C_6$ alkyl, or $C_1$-$C_4$ alkyl). In aspects, $R^{6A}$ is independently $R^{36}$-substituted alkyl (e.g., $C_1$-$C_8$ alkyl, $C_1$-$C_6$ alkyl, or $C_1$-$C_4$ alkyl). In aspects, $R^{6A}$ is independently an unsubstituted alkyl (e.g., $C_1$-$C_8$ alkyl, $C_1$-$C_6$ alkyl, or $C_1$-$C_4$ alkyl). In aspects, $R^{6A}$ is independently $R^{36}$-substituted or unsubstituted heteroalkyl (e.g., 2 to 8 membered heteroalkyl, 2 to 6 membered heteroalkyl, or 2 to 4 membered heteroalkyl). In aspects, $R^{6A}$ is independently $R^{36}$-substituted heteroalkyl (e.g., 2 to 8 membered heteroalkyl, 2 to 6 membered heteroalkyl, or 2 to 4 membered heteroalkyl). In aspects, $R^{6A}$ is independently an unsubstituted heteroalkyl (e.g., 2 to 8 membered heteroalkyl, 2 to 6 membered heteroalkyl, or 2 to 4 membered heteroalkyl). In aspects, $R^{6A}$ is independently $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{6A}$ is independently $R^{36}$-substituted cycloalkyl (e.g., $C_3$-$C_8$ cycloalkyl, $C_3$-$C_6$ cycloalkyl, or $C_5$-$C_6$ cycloalkyl). In aspects, $R^{6A}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{6A}$ is independently $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{6A}$ is independently $R^{36}$-substituted heterocycloalkyl (e.g., 3 to 8 membered heterocycloalkyl, 3 to 6 membered heterocycloalkyl, or 5 to 6 membered heterocycloalkyl). In aspects, $R^{6A}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{6A}$ is independently $R^{36}$-substituted or unsubstituted aryl (e.g., $C_6$-$C_{10}$ aryl, $C_{10}$ aryl, or phenyl). In aspects, $R^{6A}$ is independently $R^{36}$-substituted aryl (e.g., $C_6$-$C_{10}$ aryl, $C_{10}$ aryl, or phenyl). In aspects, $R^{6A}$ is independently an unsubstituted aryl (e.g., $C_6$-$C_{10}$ aryl, $C_{10}$ aryl, or phenyl). In aspects, $R^{6A}$ is independently $R^{36}$-substituted or unsubstituted heteroaryl (e.g., 5 to 10 membered heteroaryl, 5 to 9 membered heteroaryl, or 5 to 6 membered heteroaryl). In aspects, $R^{6A}$ is independently $R^{36}$-substituted heteroaryl (e.g., 5 to 10 membered heteroaryl, 5 to 9 membered heteroaryl, or 5 to 6 membered heteroaryl). In aspects, $R^{6A}$ is independently an unsubstituted heteroaryl (e.g., 5 to 10 membered heteroaryl, 5 to 9 membered heteroaryl, or 5 to 6 membered heteroaryl).

In aspects, $R^{6A}$ is independently —$CCl_3$. In aspects, $R^{6A}$ is independently —$CBr_3$. In aspects, $R^{6A}$ is independently —$CF_3$. In aspects, $R^{6A}$ is independently —$CI_3$. In aspects, $R^{6A}$ is independently —$CHCl_2$. In aspects, $R^{6A}$ is independently —$CHBr_2$. In aspects, $R^{6A}$ is independently —$CHF_2$. In aspects, $R^{6A}$ is independently —$CHI_2$. In aspects, $R^{6A}$ is independently —$CH_2Cl$. In aspects, $R^{6A}$ is independently —$CH_2Br$. In aspects, $R^{6A}$ is independently —$CH_2F$. In aspects, $R^{6A}$ is independently —$CH_2I$. In aspects, $R^{6A}$ is independently —CN. In aspects, $R^{6A}$ is independently —OH. In aspects, $R^{6A}$ is independently —COOH. In aspects, $R^{6A}$ is independently —$CONH_2$. In aspects, $R^{6A}$ is independently —$OCCl_3$. In aspects, $R^{6A}$ is independently —$OCF_3$. In aspects, $R^{6A}$ is independently —$OCBr_3$. In aspects, $R^{6A}$ is independently —$OCI_3$. In aspects, $R^{6A}$ is independently —$OCHCl_2$. In aspects, $R^{6A}$ is independently —$OCHBr_2$. In aspects, $R^{6A}$ is independently —$OCHI_2$. In aspects, $R^{6A}$ is independently —$OCHF_2$. In aspects, $R^{6A}$ is independently —$OCH_2Cl$. In aspects, $R^{6A}$ is independently —$OCH_2Br$. In aspects, $R^{6A}$ is independently —$OCH_2I$. In aspects, $R^{6A}$ is independently —$OCH_2F$. In aspects, $R^{6A}$ is independently —$OCH_3$. In aspects, $R^{6A}$ is independently —$CH_3$. In aspects, $R^{6A}$ is independently —$CH_2CH_3$. In aspects, $R^{6A}$ is independently unsubstituted propyl. In aspects, $R^{6A}$ is independently unsubstituted isopropyl. In aspects, $R^{6A}$ is independently unsubstituted butyl. In aspects, $R^{6A}$ is independently unsubstituted tert-butyl. In aspects, $R^{6A}$ is independently hydrogen.

In aspects, $R^{6B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{6B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

In aspects, $R^{6B}$ is independently $R^{36}$-substituted or unsubstituted alkyl (e.g., $C_1$-$C_8$ alkyl, $C_1$-$C_6$ alkyl, or $C_1$-$C_4$ alkyl). In aspects, $R^{6B}$ is independently $R^{36}$-substituted alkyl (e.g., $C_1$-$C_8$ alkyl, $C_1$-$C_6$ alkyl, or $C_1$-$C_4$ alkyl). In aspects, $R^{6B}$ is independently an unsubstituted alkyl (e.g., $C_1$-$C_8$ alkyl, $C_1$-$C_6$ alkyl, or $C_1$-$C_4$ alkyl). In aspects, $R^{6B}$ is independently $R^{36}$-substituted or unsubstituted heteroalkyl (e.g., 2 to 8 membered heteroalkyl, 2 to 6 membered heteroalkyl, or 2 to 4 membered heteroalkyl). In aspects, $R^{6B}$ is independently $R^{36}$-substituted heteroalkyl (e.g., 2 to 8 membered heteroalkyl, 2 to 6 membered heteroalkyl, or 2 to 4 membered heteroalkyl). In aspects, $R^{6B}$ is independently an unsubstituted heteroalkyl (e.g., 2 to 8 membered heteroalkyl, 2 to 6 membered heteroalkyl, or 2 to 4 membered heteroalkyl). In aspects, $R^{6B}$ is independently $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{6B}$ is independently $R^{36}$-substituted cycloalkyl (e.g., $C_3$-$C_8$ cycloalkyl, $C_3$-$C_6$ cycloalkyl, or $C_5$-$C_6$ cycloalkyl). In aspects, $R^{6B}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{6B}$ is independently $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{6B}$ is independently $R^{36}$-substituted heterocycloalkyl (e.g., 3 to 8 membered heterocycloalkyl, 3 to 6 membered heterocycloalkyl, or 5 to 6 membered heterocycloalkyl). In aspects, $R^{6B}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{6B}$ is independently $R^{36}$-substituted or unsubstituted aryl (e.g., $C_6$-$C_{10}$ aryl, $C_{10}$ aryl, or phenyl). In aspects, $R^{6B}$ is independently $R^{36}$-substituted aryl (e.g., $C_6$-$C_{10}$ aryl, $C_{10}$ aryl, or phenyl). In aspects, $R^{6B}$ is independently an unsubstituted aryl (e.g., $C_6$-$C_{10}$ aryl, $C_{10}$ aryl, or phenyl). In aspects, $R^{6B}$ is independently $R^{36}$-substituted or unsubstituted heteroaryl (e.g., 5 to 10 membered heteroaryl, 5 to 9 membered heteroaryl, or 5 to 6 membered heteroaryl). In aspects, $R^{6B}$ is independently $R^{36}$-substituted heteroaryl (e.g., 5 to 10 membered heteroaryl, 5 to 9 membered heteroaryl, or 5 to 6 membered heteroaryl). In aspects, $R^{6B}$ is independently an unsubstituted heteroaryl (e.g., 5 to 10 membered heteroaryl, 5 to 9 membered heteroaryl, or 5 to 6 membered heteroaryl).

In aspects, $R^{6B}$ is independently —$CCl_3$. In aspects, $R^{6B}$ is independently —$CBr_3$. In aspects, $R^{6B}$ is independently —$CF_3$. In aspects, $R^{6B}$ is independently —$CI_3$. In aspects, $R^{6B}$ is independently —$CHCl_2$. In aspects, $R^{6B}$ is independently —$CHBr_2$. In aspects, $R^{6B}$ is independently —$CHF_2$. In aspects, $R^{6B}$ is independently —$CHI_2$. In aspects, $R^{6B}$ is independently —$CH_2Cl$. In aspects, $R^{6B}$ is independently —$CH_2Br$. In aspects, $R^{6B}$ is independently —$CH_2F$. In aspects, $R^{6B}$ is independently —$CH_2I$. In aspects, $R^{6B}$ is independently —CN. In aspects, $R^{6B}$ is independently —OH. In aspects, $R^{6B}$ is independently —COOH. In aspects, $R^{6B}$ is independently —$CONH_2$. In aspects, $R^{6B}$ is independently —$OCCl_3$. In aspects, $R^{6B}$ is independently —$OCF_3$. In aspects, $R^{6B}$ is independently —$OCBr_3$. In aspects, $R^{6B}$ is independently —$OCI_3$. In aspects, $R^{6B}$ is independently —$OCHCl_2$. In aspects, $R^{6B}$ is independently —$OCHBr_2$. In aspects, $R^{6B}$ is independently —$OCHI_2$. In aspects, $R^{6B}$ is independently —$OCHF_2$. In aspects, $R^{6B}$ is independently —$OCH_2Cl$. In aspects, $R^{6B}$ is independently —$OCH_2Br$. In aspects, $R^{6B}$ is independently —$OCH_2I$. In aspects, $R^{6B}$ is independently —$OCH_2F$. In aspects, $R^{6B}$ is independently —$OCH_3$. In aspects, $R^{6B}$ is independently —$CH_3$. In aspects, $R^{6B}$ is independently —$CH_2CH_3$. In aspects, $R^{6B}$ is independently unsubstituted propyl. In aspects, $R^{6B}$ is independently unsubstituted isopropyl. In aspects, $R^{6B}$ is independently unsubstituted butyl. In aspects, $R^{6B}$ is independently unsubstituted tert-butyl. In aspects, $R^{6B}$ is independently hydrogen.

In embodiments, $R^7$ is hydrogen, halogen, —$CF_3$, —$CBr_3$, —$CCl_3$, —$CI_3$, —$CHBr_2$, —$CHCl_2$, —$CHI_2$, —$CH_2Br$, —$CH_2Cl$, —$CH_2I$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{7A}$, —$NR^{7A}R^{7B}$, —$COOR^{7A}$, —$CONR^{7A}R^{7B}$, —$NO_2$, —$SR^{7A}$, —$SO_3R^{7A}$, —$SO_4R^{7A}$, —$SO_2NR^{7A}R^{7B}$, —$NHNR^{7A}R^{7B}$, —$ONR^{7A}R^{7B}$, —$NHC(O)NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^7$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{7A}$, —$NR^{7A}R^{7B}$, —$COOR^{7A}$, —$CONR^{7A}R^{7B}$, —$NO_2$, —$SR^{7A}$, —$SO_3R^{7A}$, —$SO_4R^{7A}$, —$SO_2NR^{7A}R^{7B}$, —$NHNR^{7A}R^{7B}$, —$ONR^{7A}R^{7B}$, —$NHC(O)NHNR^{7A}R^{7B}$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In aspects, $R^7$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^7$ is $R^{40}$-substituted or unsubstituted alkyl (e.g., $C_1$-$C_8$ alkyl, $C_1$-$C_6$ alkyl, or $C_1$-$C_4$ alkyl). In aspects, $R^7$ is $R^{40}$-substituted alkyl (e.g., $C_1$-$C_8$ alkyl, $C_1$-$C_6$ alkyl, or $C_1$-$C_4$ alkyl). In aspects, $R^7$ is an unsubstituted alkyl (e.g., $C_1$-$C_8$ alkyl, $C_1$-$C_6$ alkyl, or $C_1$-$C_4$ alkyl). In aspects, $R^7$ is $R^{40}$-substituted or unsubstituted heteroalkyl (e.g., 2 to 8 membered heteroalkyl, 2 to 6 membered heteroalkyl, or 2 to 4 membered heteroalkyl). In aspects, $R^7$ is $R^{40}$-substituted heteroalkyl (e.g., 2 to 8 membered heteroalkyl, 2 to 6 membered heteroalkyl, or 2 to 4 membered heteroalkyl). In aspects, $R^7$ is an unsubstituted heteroalkyl (e.g., 2 to 8 membered heteroalkyl, 2 to 6 membered heteroalkyl, or 2 to 4 membered heteroalkyl). In aspects, $R^7$ is $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^7$ is $R^{40}$-substituted cycloalkyl (e.g., $C_3$-$C_8$ cycloalkyl, $C_3$-$C_6$ cycloalkyl, or $C_5$-$C_6$ cycloalkyl). In aspects, $R^7$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^7$ is $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^7$ is $R^{40}$-substituted heterocycloalkyl (e.g., 3 to 8 membered heterocycloalkyl, 3 to 6 membered heterocycloalkyl, or 5 to 6 membered heterocycloalkyl). In aspects, $R^7$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^7$ is $R^{40}$-substituted or unsubstituted aryl (e.g., $C_6$-$C_{10}$ aryl, $C_{10}$ aryl, or phenyl). In aspects, $R^7$ is $R^{40}$-substituted aryl (e.g., $C_6$-$C_{10}$ aryl, $C_{10}$ aryl, or phenyl). In aspects, $R^7$ is an unsubstituted aryl (e.g., $C_6$-$C_{10}$ aryl, $C_{10}$ aryl, or phenyl). In aspects, $R^7$ is $R^{40}$-substituted or unsubstituted heteroaryl (e.g., 5 to 10 membered heteroaryl, 5 to 9 membered heteroaryl, or 5 to 6 membered heteroaryl). In aspects, $R^7$ is $R^{40}$-substituted heteroaryl (e.g., 5 to 10 membered heteroaryl, 5 to 9 membered heteroaryl, or 5 to 6 membered heteroaryl). In aspects, $R^7$ is an unsubstituted heteroaryl (e.g., 5 to 10 membered heteroaryl, 5 to 9 membered heteroaryl, or 5 to 6 membered heteroaryl).

In aspects, $R^7$ is —$CX^7_3$. In aspects, $R^7$ is —$CHX^7_2$. In aspects, $R^7$ is —$CH_2X^7$. In aspects, $R^7$ is —$OCX^7_3$. In aspects, $R^7$ is —$OCH_2X^7$. In aspects, $R^7$ is —$OCHX^7_2$. In aspects, $R^7$ is —CN. In aspects, $R^7$ is —$SR^{7A}$. In aspects, $R^7$ is —$SOR^{7A}$. In aspects, $R^7$ is —$SO_2R^{7A}$. In aspects, $R^7$ is —$SO_3R^{7A}$. In aspects, $R^7$ is —$SO_4R^{7A}$. In aspects, $R^7$ is —$SONR^{7A}R^{7B}$. In aspects, $R^7$ is —$SO_2NR^{7A}R^{7B}$. In aspects, $R^7$ is —$NHC(O)NR^{7A}R^{7B}$. In aspects, $R^7$ is —N(O). In aspects, $R^7$ is —$N(O)_2$. In aspects, $R^7$ is —$NR^{7A}R^{7B}$. In aspects, $R^7$ is —$C(O)R^{7A}$. In aspects, $R^7$ is —C(O)—$OR^{7A}$.

In aspects, $R^7$ is —C(O)$NR^{7A}R^{7B}$. In aspects, $R^7$ is —$OR^{7A}$. In aspects, $R^7$ is —$NR^{7A}SO_2R^{7B}$. In aspects, $R^7$ is —$NR^{7A}$C(O)$R^{7B}$. In aspects, $R^7$ is —$NR^{7A}$C(O)$OR^{7B}$. In aspects, $R^7$ is —$NR^{7A}OR^{7B}$. In aspects, $R^7$ is hydrogen. In aspects, $X^7$ is independently —F. In aspects, $X^7$ is independently —Cl. In aspects, $X^7$ is independently —Br. In aspects, $X^7$ is independently —I.

In aspects, $R^7$ is hydrogen. In aspects, $R^7$ is oxo. In aspects, $R^7$ is halogen. In aspects, $R^7$ is —$CCl_3$. In aspects, $R^7$ is —$CBr_3$. In aspects, $R^7$ is —$CF_3$. In aspects, $R^7$ is —$CI_3$. In aspects, $R^7$ is —$CHCl_2$. In aspects, $R^7$ is —$CHBr_2$. In aspects, $R^7$ is —$CHF_2$. In aspects, $R^7$ is —$CHI_2$. In aspects, $R^7$ is —$CH_2Cl$. In aspects, $R^7$ is —$CH_2Br$. In aspects, $R^7$ is —$CH_2F$. In aspects, $R^7$ is —$CH_2I$. In aspects, $R^7$ is —CN. In aspects, $R^7$ is —OH. In aspects, $R^7$ is —$NH_2$. In aspects, $R^7$ is —COOH. In aspects, $R^7$ is —$CONH_2$. In aspects, $R^7$ is —$NO_2$. In aspects, $R^7$ is —SH. In aspects, $R^7$ is —$SO_3H$. In aspects, $R^7$ is —$SO_4H$. In aspects, $R^7$ is —$SO_2NH_2$. In aspects, $R^7$ is —$NHNH_2$. In aspects, $R^7$ is —$ONH_2$. In aspects, $R^7$ is —NHC(O)$NHNH_2$. In aspects, $R^7$ is —NHC(O)$NH_2$. In aspects, $R^7$ is —$NHSO_2H$. In aspects, $R^7$ is —NHC(O)H. In aspects, $R^7$ is —NHC(O)OH. In aspects, $R^7$ is —NHOH. In aspects, $R^7$ is —$OCCl_3$. In aspects, $R^7$ is —$OCF_3$. In aspects, $R^7$ is —$OCBr_3$. In aspects, $R^7$ is —$OCI_3$. In aspects, $R^7$ is —$OCHCl_2$. In aspects, $R^7$ is —$OCHBr_2$. In aspects, $R^7$ is —$OCHI_2$. In aspects, $R^7$ is —$OCHF_2$. In aspects, $R^7$ is —$N_3$. In aspects, $R^7$ is —$OCH_2Cl$. In aspects, $R^7$ is —$OCH_2Br$. In aspects, $R^7$ is —$OCH_2I$. In aspects, $R^7$ is —$OCH_2F$. In aspects, $R^7$ is —$OCH_3$. In aspects, $R^7$ is —$CH_3$. In aspects, $R^7$ is —$CH_2CH_3$. In aspects, $R^7$ is unsubstituted propyl. In aspects, $R^7$ is unsubstituted isopropyl. In aspects, $R^7$ is unsubstituted butyl. In aspects, $R^7$ is unsubstituted tert-butyl. In aspects, $R^7$ is —F. In aspects, $R^7$ is —Cl. In aspects, $R^7$ is —Br. In aspects, $R^7$ is —I.

In aspects, $R^7$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In aspects, $R^7$ is substituted or unsubstituted alkyl (e.g., $C_1$-$C_8$ alkyl, $C_1$-$C_6$ alkyl, or $C_1$-$C_4$ alkyl). In aspects, $R^7$ is substituted alkyl (e.g., $C_1$-$C_8$ alkyl, $C_1$-$C_6$ alkyl, or $C_1$-$C_4$ alkyl). In aspects, $R^7$ is an unsubstituted alkyl (e.g., $C_1$-$C_8$ alkyl, $C_1$-$C_6$ alkyl, or $C_1$-$C_4$ alkyl). In aspects, $R^7$ is substituted or unsubstituted heteroalkyl (e.g., 2 to 8 membered heteroalkyl, 2 to 6 membered heteroalkyl, or 2 to 4 membered heteroalkyl). In aspects, $R^7$ is substituted heteroalkyl (e.g., 2 to 8 membered heteroalkyl, 2 to 6 membered heteroalkyl, or 2 to 4 membered heteroalkyl). In aspects, $R^7$ is an unsubstituted heteroalkyl (e.g., 2 to 8 membered heteroalkyl, 2 to 6 membered heteroalkyl, or 2 to 4 membered heteroalkyl). In aspects, $R^7$ is substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^7$ is substituted cycloalkyl (e.g., $C_3$-$C_8$ cycloalkyl, $C_3$-$C_6$ cycloalkyl, or $C_5$-$C_6$ cycloalkyl). In aspects, $R^7$ is an unsubstituted cycloalkyl (e.g., $C_3$-$C_8$ cycloalkyl, $C_3$-$C_6$ cycloalkyl, or $C_5$-$C_6$ cycloalkyl). In aspects, $R^7$ is substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^7$ is substituted heterocycloalkyl (e.g., 3 to 8 membered heterocycloalkyl, 3 to 6 membered heterocycloalkyl, or 5 to 6 membered heterocycloalkyl). In aspects, $R^7$ is an unsubstituted heterocycloalkyl (e.g., 3 to 8 membered heterocycloalkyl, 3 to 6 membered heterocycloalkyl, or 5 to 6 membered heterocycloalkyl). In aspects, $R^7$ is substituted or unsubstituted aryl (e.g., $C_6$-$C_{10}$ aryl, $C_{10}$ aryl, or phenyl). In aspects, $R^7$ is substituted aryl (e.g., $C_6$-$C_{10}$ aryl, $C_{10}$ aryl, or phenyl). In aspects, $R^7$ is an unsubstituted aryl (e.g., $C_6$-$C_{10}$ aryl, $C_{10}$ aryl, or phenyl). In aspects, $R^7$ is substituted or unsubstituted heteroaryl (e.g., 5 to 10 membered heteroaryl, 5 to 9 membered heteroaryl, or 5 to 6 membered heteroaryl). In aspects, $R^7$ is substituted heteroaryl (e.g., 5 to 10 membered heteroaryl, 5 to 9 membered heteroaryl, or 5 to 6 membered heteroaryl). In aspects, $R^7$ is an unsubstituted heteroaryl (e.g., 5 to 10 membered heteroaryl, 5 to 9 membered heteroaryl, or 5 to 6 membered heteroaryl).

$R^{40}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{41}$-substituted or unsubstituted alkyl (e.g., $C_1$-$C_8$ alkyl, $C_1$-$C_6$ alkyl, or $C_1$-$C_4$ alkyl), $R^{41}$-substituted or unsubstituted heteroalkyl (e.g., 2 to 8 membered heteroalkyl, 2 to 6 membered heteroalkyl, or 2 to 4 membered heteroalkyl), $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41}$-substituted or unsubstituted aryl (e.g., $C_6$-$C_{10}$ aryl, $C_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl). In aspects, $R^{40}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{40}$ is independently oxo. In aspects, $R^{40}$ is independently halogen. In aspects, $R^{40}$ is independently —$CCl_3$. In aspects, $R^{40}$ is independently —$CBr_3$. In aspects, $R^{40}$ is independently —$CF_3$. In aspects, $R^{40}$ is independently —$CI_3$. In aspects, $R^{40}$ is independently —$CHCl_2$. In aspects, $R^{40}$ is independently —$CHBr_2$. In aspects, $R^{40}$ is independently —$CHF_2$. In aspects, $R^{40}$ is independently —$CHI_2$. In aspects, $R^{40}$ is independently —$CH_2Cl$. In aspects, $R^{40}$ is independently —$CH_2Br$. In aspects, $R^{40}$ is independently —$CH_2F$. In aspects, $R^{40}$ is independently —$CH_2I$. In aspects, $R^{40}$ is independently —CN. In aspects, $R^{40}$ is independently —OH. In aspects, $R^{40}$ is independently —$NH_2$. In aspects, $R^{40}$ is independently —COOH. In aspects, $R^{40}$ is independently —$CONH_2$. In aspects, $R^{40}$ is independently —$NO_2$. In aspects, $R^{40}$ is independently —SH. In aspects, $R^{40}$ is independently —$SO_3H$. In aspects, $R^{40}$ is independently —$SO_4H$. In aspects, $R^{40}$ is independently —$SO_2NH_2$. In aspects, $R^{40}$ is independently —$NHNH_2$. In aspects, $R^{40}$ is independently —$ONH_2$. In aspects, $R^{40}$ is independently —NHC(O)$NHNH_2$. In aspects, $R^{40}$ is independently —NHC(O)$NH_2$. In aspects, $R^{40}$ is independently —$NHSO_2H$. In aspects, $R^{40}$ is independently —NHC(O)H. In aspects, $R^{40}$ is independently —NHC(O)OH. In aspects, $R^{40}$ is independently —NHOH. In aspects, $R^{40}$ is independently —$OCCl_3$. In aspects, $R^{40}$ is independently —$OCF_3$. In aspects, $R^{40}$ is independently —$OCBr_3$. In aspects, $R^{40}$ is independently —$OCI_3$. In aspects, $R^{40}$ is independently —$OCHCl_2$. In aspects, $R^{40}$ is independently —$OCHBr_2$. In aspects, $R^{40}$ is independently —$OCHI_2$. In aspects, $R^{40}$ is independently —$OCHF_2$. In aspects, $R^{40}$ is independently —$OCH_2Cl$. In aspects, $R^{40}$ is independently —$OCH_2Br$. In aspects, $R^{40}$ is independently —$OCH_2I$. In aspects, $R^{40}$ is independently —$OCH_2F$. In aspects, $R^{40}$ is independently —$N_3$. In aspects, $R^{40}$ is independently —$OCH_3$. In aspects, $R^{40}$ is independently —$CH_3$. In aspects, $R^{40}$ is independently —$CH_2CH_3$. In aspects, $R^{40}$ is independently unsubstituted propyl. In aspects, $R^{40}$ is independently unsubstituted isopropyl. In aspects, $R^{40}$ is independently unsubstituted butyl. In aspects, $R^{40}$ is independently unsubstituted tert-butyl. In aspects, $R^{40}$ is independently —F. In aspects, $R^{40}$ is independently —Cl. In aspects, $R^{40}$ is independently —Br. In aspects, $R^{40}$ is independently —I.

In aspects, $R^{40}$ is independently $R^{41}$-substituted or unsubstituted alkyl (e.g., $C_1$-$C_8$ alkyl, $C_1$-$C_6$ alkyl, or $C_1$-$C_4$ alkyl). In aspects, $R^{40}$ is independently $R^{41}$-substituted alkyl (e.g., $C_1$-$C_8$ alkyl, $C_1$-$C_6$ alkyl, or $C_1$-$C_4$ alkyl). In aspects, $R^{40}$ is independently an unsubstituted alkyl (e.g., $C_1$-$C_8$ alkyl, $C_1$-$C_6$ alkyl, or $C_1$-$C_4$ alkyl). In aspects, $R^{40}$ is independently $R^{41}$-substituted or unsubstituted heteroalkyl (e.g., 2 to 8 membered heteroalkyl, 2 to 6 membered heteroalkyl, or 2 to 4 membered heteroalkyl). In aspects, $R^{40}$ is independently $R^{41}$-substituted heteroalkyl (e.g., 2 to 8 membered heteroalkyl, 2 to 6 membered heteroalkyl, or 2 to 4 membered heteroalkyl). In aspects, $R^{40}$ is independently an unsubstituted heteroalkyl (e.g., 2 to 8 membered heteroalkyl, 2 to 6 membered heteroalkyl, or 2 to 4 membered heteroalkyl). In aspects, $R^{40}$ is independently $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{40}$ is independently $R^{41}$-substituted cycloalkyl (e.g., $C_3$-$C_8$ cycloalkyl, $C_3$-$C_6$ cycloalkyl, or $C_5$-$C_6$ cycloalkyl). In aspects, $R^{40}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{40}$ is independently $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{40}$ is independently $R^{41}$-substituted heterocycloalkyl (e.g., 3 to 8 membered heterocycloalkyl, 3 to 6 membered heterocycloalkyl, or 5 to 6 membered heterocycloalkyl). In aspects, $R^{40}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{40}$ is independently $R^{41}$-substituted or unsubstituted aryl (e.g., $C_6$-$C_{10}$ aryl, $C_{10}$ aryl, or phenyl). In aspects, $R^{40}$ is independently $R^{41}$-substituted aryl (e.g., $C_6$-$C_{10}$ aryl, $C_{10}$ aryl, or phenyl). In aspects, $R^{40}$ is independently an unsubstituted aryl (e.g., $C_6$-$C_{10}$ aryl, $C_{10}$ aryl, or phenyl). In aspects, $R^{40}$ is independently $R^{41}$-substituted or unsubstituted heteroaryl (e.g., 5 to 10 membered heteroaryl, 5 to 9 membered heteroaryl, or 5 to 6 membered heteroaryl). In aspects, $R^{40}$ is independently $R^{41}$-substituted heteroaryl (e.g., 5 to 10 membered heteroaryl, 5 to 9 membered heteroaryl, or 5 to 6 membered heteroaryl). In aspects, $R^{40}$ is independently an unsubstituted heteroaryl (e.g., 5 to 10 membered heteroaryl, 5 to 9 membered heteroaryl, or 5 to 6 membered heteroaryl).

$R^{41}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{42}$-substituted or unsubstituted alkyl (e.g., $C_1$-$C_8$ alkyl, $C_1$-$C_6$ alkyl, or $C_1$-$C_4$ alkyl), $R^{42}$-substituted or unsubstituted heteroalkyl (e.g., 2 to 8 membered heteroalkyl, 2 to 6 membered heteroalkyl, or 2 to 4 membered heteroalkyl), $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42}$-substituted or unsubstituted aryl (e.g., $C_6$-$C_{10}$ aryl, $C_{10}$ aryl, or phenyl), or $R^{42}$-substituted or unsubstituted heteroaryl (e.g., 5 to 10 membered heteroaryl, 5 to 9 membered heteroaryl, or 5 to 6 membered heteroaryl). In aspects, $R^{41}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{41}$ is independently $R^{42}$-substituted or unsubstituted alkyl (e.g., $C_1$-$C_8$ alkyl, $C_1$-$C_6$ alkyl, or $C_1$-$C_4$ alkyl). In aspects, $R^{41}$ is independently $R^{42}$-substituted alkyl (e.g., $C_1$-$C_8$ alkyl, $C_1$-$C_6$ alkyl, or $C_1$-$C_4$ alkyl). In aspects, $R^{41}$ is independently an unsubstituted alkyl (e.g., $C_1$-$C_8$ alkyl, $C_1$-$C_6$ alkyl, or $C_1$-$C_4$ alkyl). In aspects, $R^{41}$ is independently $R^{42}$-substituted or unsubstituted heteroalkyl (e.g., 2 to 8 membered heteroalkyl, 2 to 6 membered heteroalkyl, or 2 to 4 membered heteroalkyl). In aspects, $R^{41}$ is independently $R^{42}$-substituted heteroalkyl (e.g., 2 to 8 membered heteroalkyl, 2 to 6 membered heteroalkyl, or 2 to 4 membered heteroalkyl). In aspects, $R^{41}$ is independently an unsubstituted heteroalkyl (e.g., 2 to 8 membered heteroalkyl, 2 to 6 membered heteroalkyl, or 2 to 4 membered heteroalkyl). In aspects, $R^{41}$ is independently $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{41}$ is independently $R^{42}$-substituted cycloalkyl (e.g., $C_3$-$C_8$ cycloalkyl, $C_3$-$C_6$ cycloalkyl, or $C_5$-$C_6$ cycloalkyl). In aspects, $R^{41}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{41}$ is independently $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{41}$ is independently $R^{42}$-substituted heterocycloalkyl (e.g., 3 to 8 membered heterocycloalkyl, 3 to 6 membered heterocycloalkyl, or 5 to 6 membered heterocycloalkyl). In aspects, $R^{41}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{41}$ is independently $R^{42}$-substituted or unsubstituted aryl (e.g., $C_6$-$C_{10}$ aryl, $C_{10}$ aryl, or phenyl). In aspects, $R^{41}$ is independently $R^{42}$-substituted aryl (e.g., $C_6$-$C_{10}$ aryl, $C_{10}$ aryl, or phenyl). In aspects, $R^{41}$ is independently an unsubstituted aryl (e.g., $C_6$-$C_{10}$ aryl, $C_{10}$ aryl, or phenyl). In aspects, $R^{41}$ is independently $R^{42}$-substituted or unsubstituted heteroaryl (e.g., 5 to 10 membered heteroaryl, 5 to 9 membered heteroaryl, or 5 to 6 membered heteroaryl). In aspects, $R^{41}$ is independently $R^{42}$-substituted heteroaryl (e.g., 5 to 10 membered heteroaryl, 5 to 9 membered heteroaryl, or 5 to 6 membered heteroaryl). In aspects, $R^{41}$ is independently an unsubstituted heteroaryl (e.g., 5 to 10 membered heteroaryl, 5 to 9 membered heteroaryl, or 5 to 6 membered heteroaryl).

In aspects, $R^{41}$ is independently oxo. In aspects, $R^{41}$ is independently halogen. In aspects, $R^{41}$ is independently $-CCl_3$. In aspects, $R^{41}$ is independently $-CBr_3$. In aspects, $R^{41}$ is independently $-CF_3$. In aspects, $R^{41}$ is independently $-CI_3$. In aspects, $R^{41}$ is independently $-CHCl_2$. In aspects, $R^{41}$ is independently $-CHBr_2$. In aspects, $R^{41}$ is independently $-CHF_2$. In aspects, $R^{41}$ is independently $-CHI_2$. In aspects, $R^{41}$ is independently $-CH_2Cl$. In aspects, $R^{41}$ is independently $-CH_2Br$. In aspects, $R^{41}$ is independently $-CH_2F$. In aspects, $R^{41}$ is independently $-CH_2I$. In aspects, $R^{41}$ is independently $-CN$. In aspects, $R^{41}$ is independently $-OH$. In aspects, $R^{41}$ is independently $-NH_2$. In aspects, $R^{41}$ is independently $-COOH$. In aspects, $R^{41}$ is independently $-CONH_2$. In aspects, $R^{41}$ is independently $-NO_2$. In aspects, $R^{41}$ is independently $-SH$. In aspects, $R^{41}$ is independently $-SO_3H$. In aspects, $R^{41}$ is independently $-SO_4H$. In aspects, $R^{41}$ is independently $-SO_2NH_2$. In aspects, $R^{41}$ is independently $-NHNH_2$. In aspects, $R^{41}$ is independently $-ONH_2$. In aspects, $R^{41}$ is independently $-NHC(O)NHNH_2$. In aspects, $R^{41}$ is independently $-NHC(O)NH_2$. In aspects, $R^{41}$ is independently $-NHSO_2H$. In aspects, $R^{41}$ is independently $-NHC(O)H$. In aspects, $R^{41}$ is independently $-NHC(O)OH$. In aspects, $R^{41}$ is independently $-NHOH$. In aspects, $R^{41}$ is independently $-OCCl_3$. In aspects, $R^{41}$ is independently $-OCF_3$. In aspects, $R^{41}$ is independently $-OCBr_3$. In aspects, $R^{41}$ is independently $-OCI_3$. In aspects, $R^{41}$ is independently $-OCHCl_2$. In aspects, $R^{41}$ is independently $-OCHBr_2$. In aspects, $R^{41}$ is independently $-OCHI_2$. In aspects, $R^{41}$ is independently $-OCHF_2$. In aspects, $R^{41}$ is independently $-OCH_2Cl$. In aspects, $R^{41}$ is independently $-OCH_2Br$. In aspects, $R^{41}$ is independently $-OCH_2I$. In aspects, $R^{41}$ is independently $-OCH_2F$. In aspects, $R^{41}$ is independently $-N_3$. In aspects, $R^{41}$ is independently $-OCH_3$. In aspects, $R^{41}$ is independently $-CH_3$. In aspects, $R^{41}$ is independently $-CH_2CH_3$. In aspects, $R^{41}$ is independently unsubstituted propyl. In aspects, $R^{41}$ is independently unsubstituted isopropyl. In aspects, $R^{41}$ is independently unsubstituted butyl. In aspects, $R^{41}$ is independently unsubstituted tert-butyl. In aspects, $R^{41}$ is independently $-F$. In aspects, $R^{41}$ is independently $-Cl$. In aspects, $R^{41}$ is independently $-Br$. In aspects, $R^{41}$ is independently $-I$.

$R^{42}$ is independently oxo, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In aspects, $R^{42}$ is independently an unsubstituted alkyl (e.g., $C_1$-$C_8$ alkyl, $C_1$-$C_6$ alkyl, or $C_1$-$C_4$ alkyl). In aspects, $R^{42}$ is independently an unsubstituted heteroalkyl (e.g., 2 to 8 membered heteroalkyl, 2 to 6 membered heteroalkyl, or 2 to 4 membered heteroalkyl). In aspects, $R^{42}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{42}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{42}$ is independently an unsubstituted aryl (e.g., $C_6$-$C_{10}$ aryl, $C_{10}$ aryl, or phenyl). In aspects, $R^{42}$ is independently an unsubstituted heteroaryl (e.g., 5 to 10 membered heteroaryl, 5 to 9 membered heteroaryl, or 5 to 6 membered heteroaryl).

In aspects, $R^{42}$ is independently oxo. In aspects, $R^{42}$ is independently halogen. In aspects, $R^{42}$ is independently $-CCl_3$. In aspects, $R^{42}$ is independently $-CBr_3$. In aspects, $R^{42}$ is independently $-CF_3$. In aspects, $R^{42}$ is independently $-CI_3$. In aspects, $R^{42}$ is independently $-CHCl_2$. In aspects, $R^{42}$ is independently $-CHBr_2$. In aspects, $R^{42}$ is independently $-CHF_2$. In aspects, $R^{42}$ is independently $-CHI_2$. In aspects, $R^{42}$ is independently $-CH_2Cl$. In aspects, $R^{42}$ is independently $-CH_2Br$. In aspects, $R^{42}$ is independently $-CH_2F$. In aspects, $R^{42}$ is independently $-CH_2I$. In aspects, $R^{42}$ is independently $-CN$. In aspects, $R^{42}$ is independently $-OH$. In aspects, $R^{42}$ is independently $-NH_2$. In aspects, $R^{42}$ is independently $-COOH$. In aspects, $R^{38}$ is independently $-CONH_2$. In aspects, $R^{38}$ is independently $-NO_2$. In aspects, $R^{42}$ is independently $-SH$. In aspects, $R^{42}$ is independently $-SO_3H$. In aspects, $R^{42}$ is independently $-SO_4H$. In aspects, $R^{42}$ is independently $-SO_2NH_2$. In aspects, $R^{42}$ is independently $-NHNH_2$. In aspects, $R^{42}$ is independently $-ONH_2$. In aspects, $R^{42}$ is independently $-NHC(O)NHNH_2$. In aspects, $R^{42}$ is independently $-NHC(O)NH_2$. In aspects, $R^{42}$ is independently $-NHSO_2H$. In aspects, $R^{42}$ is independently —NHC(O)H. In aspects, $R^{42}$ is independently —NHC(O)OH. In aspects, $R^{42}$ is independently —NHOH. In aspects, $R^{42}$ is independently —$OCCl_3$. In aspects, $R^{42}$ is independently —$OCF_3$. In aspects, $R^{42}$ is independently —$OCBr_3$. In aspects, $R^{42}$ is independently —$OCI_3$. In aspects, $R^{42}$ is independently —$OCHCl_2$. In aspects, $R^{42}$ is independently —$OCHBr_2$. In aspects, $R^{42}$ is independently —$OCHI_2$. In aspects, $R^{42}$ is independently —$OCHF_2$. In aspects, $R^{42}$ is independently —$OCH_2Cl$. In aspects, $R^{42}$ is independently —$OCH_2Br$. In aspects, $R^{42}$ is independently —$OCH_2I$. In aspects, $R^{42}$ is independently —$OCH_2F$. In aspects, $R^{42}$ is independently —$N_3$. In aspects, $R^{42}$ is independently —$OCH_3$. In aspects, $R^{42}$ is independently —$CH_3$. In aspects, $R^{42}$ is independently —$CH_2CH_3$. In aspects, $R^{42}$ is independently unsubstituted propyl. In aspects, $R^{42}$ is independently unsubstituted isopropyl. In aspects, $R^{42}$ is independently unsubstituted butyl. In aspects, $R^{42}$ is independently unsubstituted tert-butyl. In aspects, $R^{42}$ is independently —F. In aspects, $R^{42}$ is independently —Cl. In aspects, $R^{42}$ is independently —Br. In aspects, $R^{42}$ is independently —I.

In aspects, $R^{7A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{7A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In aspects, $R^{7A}$ is independently $R^{40}$-substituted or unsubstituted alkyl (e.g., $C_1$-$C_8$ alkyl, $C_1$-$C_6$ alkyl, or $C_1$-$C_4$ alkyl). In aspects, $R^{7A}$ is independently $R^{40}$-substituted alkyl (e.g., $C_1$-$C_8$ alkyl, $C_1$-$C_6$ alkyl, or $C_1$-$C_4$ alkyl). In aspects, $R^{7A}$ is independently an unsubstituted alkyl (e.g., $C_1$-$C_8$ alkyl, $C_1$-$C_6$ alkyl, or $C_1$-$C_4$ alkyl). In aspects, $R^{7A}$ is independently $R^{40}$-substituted or unsubstituted heteroalkyl (e.g., 2 to 8 membered heteroalkyl, 2 to 6 membered heteroalkyl, or 2 to 4 membered heteroalkyl). In aspects, $R^{7A}$ is independently $R^{40}$-substituted heteroalkyl (e.g., 2 to 8 membered heteroalkyl, 2 to 6 membered heteroalkyl, or 2 to 4 membered heteroalkyl). In aspects, $R^{7A}$ is independently an unsubstituted heteroalkyl (e.g., 2 to 8 membered heteroalkyl, 2 to 6 membered heteroalkyl, or 2 to 4 membered heteroalkyl). In aspects, $R^{7A}$ is independently $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{7A}$ is independently $R^{40}$-substituted cycloalkyl (e.g., $C_3$-$C_8$ cycloalkyl, $C_3$-$C_6$ cycloalkyl, or $C_5$-$C_6$ cycloalkyl). In aspects, $R^{7A}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{7A}$ is independently $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{7A}$ is independently $R^{40}$-substituted heterocycloalkyl (e.g., 3 to 8 membered heterocycloalkyl, 3 to 6 membered heterocycloalkyl, or 5 to 6 membered heterocycloalkyl). In aspects, $R^{7A}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{7A}$ is independently $R^{40}$-substituted or unsubstituted aryl (e.g., $C_6$-$C_{10}$ aryl, $C_{10}$ aryl, or phenyl). In aspects, $R^{7A}$ is independently $R^{40}$-substituted aryl (e.g., $C_6$-$C_{10}$ aryl, $C_{10}$ aryl, or phenyl). In aspects, $R^{7A}$ is independently an unsubstituted aryl (e.g., $C_6$-$C_{10}$ aryl, $C_{10}$ aryl, or phenyl). In aspects, $R^{7A}$ is independently $R^{40}$-substituted or unsubstituted heteroaryl (e.g., 5 to 10 membered heteroaryl, 5 to 9 membered heteroaryl, or 5 to 6 membered heteroaryl). In aspects, $R^{7A}$ is independently $R^{40}$-substituted heteroaryl (e.g., 5 to 10 membered heteroaryl, 5 to 9 membered heteroaryl, or 5 to 6 membered heteroaryl). In aspects, $R^{7A}$ is independently an unsubstituted heteroaryl (e.g., 5 to 10 membered heteroaryl, 5 to 9 membered heteroaryl, or 5 to 6 membered heteroaryl).

In aspects, $R^{7A}$ is independently —$CCl_3$. In aspects, $R^{7A}$ is independently —$CBr_3$. In aspects, $R^{7A}$ is independently —$CF_3$. In aspects, $R^{7A}$ is independently —$CI_3$. In aspects, $R^{7A}$ is independently —$CHCl_2$. In aspects, $R^{7A}$ is independently —$CHBr_2$. In aspects, $R^{7A}$ is independently —$CHF_2$. In aspects, $R^{7A}$ is independently —$CHI_2$. In aspects, $R^{7A}$ is independently —$CH_2Cl$. In aspects, $R^{7A}$ is independently —$CH_2Br$. In aspects, $R^{7A}$ is independently —$CH_2F$. In aspects, $R^{7A}$ is independently —$CH_2I$. In aspects, $R^{7A}$ is independently —CN. In aspects, $R^{7A}$ is independently —OH. In aspects, $R^{7A}$ is independently —COOH. In aspects, $R^{7A}$ is independently —$CONH_2$. In aspects, $R^{7A}$ is independently —$OCCl_3$. In aspects, $R^{7A}$ is independently —$OCF_3$. In aspects, $R^{7A}$ is independently —$OCBr_3$. In aspects, $R^{7A}$ is independently —$OCI_3$. In aspects, $R^{7A}$ is independently —$OCHCl_2$. In aspects, $R^{7A}$ is independently —$OCHBr_2$. In aspects, $R^{7A}$ is independently —$OCHI_2$. In aspects, $R^{7A}$ is independently —$OCHF_2$. In aspects, $R^{7A}$ is independently —$OCH_2Cl$. In aspects, $R^{7A}$ is independently —$OCH_2Br$. In aspects, $R^{7A}$ is independently —$OCH_2I$. In aspects, $R^{7A}$ is independently —$OCH_2F$. In aspects, $R^{7A}$ is independently —$OCH_3$. In aspects, $R^{7A}$ is independently —$CH_3$. In aspects, $R^{7A}$ is independently —$CH_2CH_3$. In aspects, $R^{7A}$ is independently unsubstituted propyl. In aspects, $R^{7A}$ is independently unsubstituted isopropyl. In aspects, $R^{7A}$ is independently unsubstituted butyl. In aspects, $R^{7A}$ is independently unsubstituted tert-butyl. In aspects, $R^{7A}$ is independently hydrogen.

In aspects, $R^{7B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In aspects, $R^{7B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In aspects, $R^{7B}$ is independently $R^{40}$-substituted or unsubstituted alkyl (e.g., $C_1$-$C_8$ alkyl, $C_1$-$C_6$ alkyl, or $C_1$-$C_4$ alkyl). In aspects, $R^{7B}$ is independently $R^{40}$-substituted alkyl (e.g., $C_1$-$C_8$ alkyl, $C_1$-$C_6$ alkyl, or $C_1$-$C_4$ alkyl). In aspects, $R^{7B}$ is independently an unsubstituted alkyl (e.g., $C_1$-$C_8$ alkyl, $C_1$-$C_6$ alkyl, or $C_1$-$C_4$ alkyl). In aspects, $R^{7B}$ is independently $R^{40}$-substituted or unsubstituted heteroalkyl (e.g., 2 to 8 membered heteroalkyl, 2 to 6 membered heteroalkyl, or 2 to 4 membered heteroalkyl). In aspects, $R^{7B}$ is independently $R^{40}$-substituted heteroalkyl (e.g., 2 to 8 membered heteroalkyl, 2 to 6 membered heteroalkyl, or 2 to 4 membered heteroalkyl). In aspects, $R^{7B}$ is independently an unsubstituted heteroalkyl (e.g., 2 to 8 membered heteroalkyl, 2 to 6 membered heteroalkyl, or 2 to 4 membered heteroalkyl). In aspects, $R^{7B}$ is independently $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In aspects, $R^{7B}$ is independently $R^{40}$-substituted cycloalkyl (e.g., $C_3$-$C_8$ cycloalkyl, $C_3$-$C_6$ cycloalkyl, or $C_5$-$C_6$ cycloalkyl). In aspects, $R^{7B}$ is independently an unsubstituted cycloalkyl (e.g., $C_3$-$C_8$ cycloalkyl, $C_3$-$C_6$ cycloalkyl, or $C_5$-$C_6$ cycloalkyl). In aspects, $R^{7B}$ is independently $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In aspects, $R^{7B}$ is independently $R^{40}$-substituted heterocycloalkyl (e.g., 3 to 8 membered heterocycloalkyl, 3 to 6 membered heterocycloalkyl, or 5 to 6 membered heterocycloalkyl). In aspects, $R^{7B}$ is independently an unsubstituted heterocycloalkyl (e.g., 3 to 8 membered heterocycloalkyl, 3 to 6 membered heterocycloalkyl, or 5 to 6 membered heterocycloalkyl). In aspects, $R^{7B}$ is independently $R^{40}$-substituted or unsubstituted aryl (e.g., $C_6$-$C_{10}$ aryl, $C_{10}$ aryl, or phenyl). In aspects, $R^{7B}$ is independently $R^{40}$-substituted aryl (e.g., $C_6$-$C_{10}$ aryl, $C_{10}$ aryl, or phenyl). In aspects, $R^{7B}$ is independently an unsubstituted aryl (e.g., $C_6$-$C_{10}$ aryl, $C_{10}$ aryl, or phenyl). In aspects, $R^{7B}$ is independently $R^{40}$-substituted or unsubstituted heteroaryl (e.g., 5 to 10 membered heteroaryl, 5 to 9 membered heteroaryl, or 5 to 6 membered heteroaryl). In aspects, $R^{7B}$ is independently $R^{40}$-substituted heteroaryl (e.g., 5 to 10 membered heteroaryl, 5 to 9 membered heteroaryl, or 5 to 6 membered heteroaryl). In aspects, $R^{7B}$ is independently an unsubstituted heteroaryl (e.g., 5 to 10 membered heteroaryl, 5 to 9 membered heteroaryl, or 5 to 6 membered heteroaryl).

In aspects, $R^{7B}$ is independently —$CCl_3$. In aspects, $R^{7B}$ is independently —$CBr_3$. In aspects, $R^{7B}$ is independently —$CF_3$. In aspects, $R^{7B}$ is independently —$CI_3$. In aspects, $R^{7B}$ is independently —$CHCl_2$. In aspects, $R^{7B}$ is independently —$CHBr_2$. In aspects, $R^{7B}$ is independently —$CHF_2$. In aspects, $R^{7B}$ is independently —$CHI_2$. In aspects, $R^{7B}$ is independently —$CH_2Cl$. In aspects, $R^{7B}$ is independently —$CH_2Br$. In aspects, $R^{7B}$ is independently —$CH_2F$. In aspects, $R^{7B}$ is independently —$CH_2I$. In aspects, $R^{7B}$ is independently —CN. In aspects, $R^{7B}$ is independently —OH. In aspects, $R^{7B}$ is independently —COOH. In aspects, $R^{7B}$ is independently —$CONH_2$. In aspects, $R^{7B}$ is independently —$OCCl_3$. In aspects, $R^{7B}$ is independently —$OCF_3$. In aspects, $R^{7B}$ is independently —$OCBr_3$. In aspects, $R^{7B}$ is independently —$OCI_3$. In aspects, $R^{7B}$ is independently —$OCHCl_2$. In aspects, $R^{7B}$ is independently —$OCHBr_2$. In aspects, $R^{7B}$ is independently —$OCHI_2$. In aspects, $R^{7B}$ is independently —$OCHF_2$. In aspects, $R^{7B}$ is independently —$OCH_2Cl$. In aspects, $R^{7B}$ is independently —$OCH_2Br$. In aspects, $R^{7B}$ is independently —$OCH_2I$. In aspects, $R^{7B}$ is independently —$OCH_2F$. In aspects, $R^{7B}$ is independently —$OCH_3$. In aspects, $R^{7B}$ is independently —$CH_3$. In aspects, $R^{7B}$ is independently —$CH_2CH_3$. In aspects, $R^{7B}$ is independently unsubstituted propyl. In aspects, $R^{7B}$ is independently unsubstituted isopropyl. In aspects, $R^{7B}$ is independently unsubstituted butyl. In aspects, $R^{7B}$ is independently unsubstituted tert-butyl. In aspects, $R^{7B}$ is independently hydrogen.

In aspects of the compound of Formula (I), $R^1$, $R^2$, and $R^4$ are hydrogen. In aspects of the compound of Formula (I), $R^1$, $R^2$, and $R^4$ are hydrogen; and $R^3$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or halogen. In aspects of the compound of Formula (I), $R^1$, $R^2$, and $R^4$ are hydrogen; $R^3$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or halogen; and $R^5$ is $C_1$-$C_4$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl and halogen. In aspects of the compound of Formula (I), $R^1$, $R^2$, and $R^4$ are hydrogen; $R^3$, $R^6$, and $R^7$ are each independently —OH, —$NH_2$, —COOH, —$CONH_2$, —$ONH_2$, or unsubstituted $C_1$-$C_4$ alkyl; and $R^5$ is $C_1$-$C_4$ alkyl substituted with 1 or 2 substituents independently selected from the group consisting of —OH, —$NH_2$, —COOH, —$CONH_2$, —$ONH_2$, and unsubstituted $C_1$-$C_4$ alkyl. In aspects of the compound of Formula (I), $R^1$, $R^2$, and $R^4$ are hydrogen; and $R^3$, $R^6$, and $R^7$ are each independently OH, —$NH_2$, —COOH, —$CONH_2$, —$NO_2$, —$NHNH_2$, or —$ONH_2$. In aspects of the compound of Formula (I), $R^1$, $R^2$, and $R^4$ are hydrogen; $R^3$, $R^6$, and $R^7$ are each independently OH, —$NH_2$, —COOH, —$CONH_2$, or —$ONH_2$; and $R^5$ is $C_1$-$C_4$ alkyl substituted with —OH, —$NH_2$, —COOH, —$CONH_2$, or —$ONH_2$.

The substituents for the compound of Formula (I) are those described herein. In aspects $R^1$, $R^3$, and $R^4$ are hydrogen. In aspects, $R^1$, $R^3$, and $R^4$ are hydrogen; and $R^3$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or halogen. In aspects, $R^1$, $R^3$, and $R^4$ are hydrogen; $R^3$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or halogen; and $R^5$ is $C_1$-$C_4$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, and unsubstituted $C_1$-$C_4$ alkyl. In aspects, $R^1$, $R^3$, and $R^4$ are hydrogen; and $R^3$, $R^6$, and $R^7$ are each independently OH, —$NH_2$, —COOH, —$CONH_2$, or —$ONH_2$. In aspects, $R^1$, $R^3$, and $R^4$ are hydrogen; $R^3$, $R^6$, and $R^7$ are each independently —OH, —$NH_2$, —COOH, —$CONH_2$, or —$ONH_2$; and $R^5$ is $C_1$-$C_4$ alkyl substituted with —OH, —$NH_2$, —COOH, —$CONH_2$, or —$ONH_2$.

The substituents for the compound of Formula (II) are those described herein. In aspects, $R^1$, $R^3$, and $R^4$ are hydrogen. In aspects, $R^1$, $R^3$, and $R^4$ are hydrogen; and $R^5$ is $C_1$-$C_4$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, and halogen. In aspects, $R^{2A}$, $R^{2B}$, $R^{6A}$, $R^{6B}$, $R^{7A}$, and $R^{7B}$ are hydrogen. In aspects, $R^1$, $R^3$, $R^4$, $R^{2A}$, $R^{2B}$, $R^{6A}$, $R^{6B}$, $R^{7A}$, and $R^{7B}$ are hydrogen; and $R^5$ is $C_1$-$C_4$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, and halogen.

The substituents for the compound of Formula (III) are those described herein. In aspects, $R^1$, $R^2$, and $R^4$ are hydrogen. In aspects, $R^1$, $R^2$, and $R^4$ are hydrogen; and $R^5$ is $C_1$-$C_4$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, and halogen. In aspects, $R^{3A}$, $R^{3B}$, $R^{6A}$, $R^{6B}$, $R^{7A}$, and $R^{7B}$ are hydrogen. In aspects, $R^1$, $R^2$, $R^4$, $R^{3A}$, $R^{3B}$, $R^{6A}$, $R^{6B}$, $R^{7A}$, and $R^{7B}$ are hydrogen; and $R^5$ is $C_1$-$C_4$ alkyl substituted with 1 or 2 substituents independently selected from the group consisting of —OH, —$NH_2$, —COOH, —$CONH_2$, —$ONH_2$, and unsubstituted $C_1$-$C_4$ alkyl.

The substituents for the compound of Formula (IV) are those described herein. In aspects, $R^5$ is $C_1$-$C_4$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, and halogen. In aspects, $R^{2A}$, $R^{2B}$, $R^{6A}$, $R^{6B}$, $R^{7A}$, and $R^{7B}$ are hydrogen. In aspects, $R^{2A}$, $R^{2B}$, $R^{6A}$, $R^{6B}$, $R^{7A}$, and $R^{7B}$ are hydrogen; and $R^5$ is $C_1$-$C_4$ alkyl substituted with 1 or 2 substituents independently selected from the group consisting of —OH, —$NH_2$, —COOH, —$CONH_2$, —$ONH_2$, and unsubstituted $C_1$-$C_4$ alkyl.

The substituents for the compound of Formula (V) are those described herein. In aspects, $R^5$ is $C_1$-$C_4$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, and halogen. In aspects, $R^{3A}$, $R^{3B}$, $R^{6A}$, $R^{6B}$, $R^{7A}$, and $R^{7B}$ are hydrogen. In aspects, $R^{3A}$, $R^{3B}$, $R^{6A}$, $R^{6B}$, $R^{7A}$, and $R^{7B}$ are hydrogen; and $R^5$ is $C_1$-$C_4$ alkyl substituted with 1 or 2 substituents independently selected from the group consisting of —OH, —$NH_2$, —COOH, —$CONH_2$, —$ONH_2$, and unsubstituted $C_1$-$C_4$ alkyl.

The substituents for the compound of Formula (V) are those described herein. In aspects, $R^{3A}$ and $R^{3B}$ are each independently —$COCH_3$, —$COCH_2CH_3$, —$CO(CH_2)_2CH_3$, —$CO(CH_2)_3CH_3$, —CN, —OH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or unsubstituted $C_1$-$C_4$ heteroalkyl. In aspects, $R^{6A}$, $R^{6B}$, $R^{7A}$, and $R^{7B}$ are hydrogen. In aspects, $R^{3B}$, $R^{6A}$, $R^{6B}$, $R^{7A}$ and $R^{7B}$ are hydrogen; and $R^{3A}$ is —$COCH_3$, —$COCH_2CH_3$, —$CO(CH_2)_2CH_3$, —$CO(CH_2)_3CH_3$, —CN, —OH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or unsubstituted $C_1$-$C_4$ heteroalkyl. In aspects, $R^{6A}$, $R^{6B}$, $R^{7A}$, and $R^{7B}$ are hydrogen. In aspects, $R^{3B}$, $R^{6A}$, $R^{6B}$, $R^{7A}$, and $R^{7B}$ are hydrogen; and $R^{3A}$ is —$COCH_3$, —$COCH_2CH_3$, —$CO(CH_2)_2CH_3$, or —$CO(CH_2)_3CH_3$.

The substituents for the compounds of Formula (VI), (VIA), and (VIB) are those described herein. In aspects, $R^3$ is halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or unsubstituted $C_1$-$C_4$ heteroalkyl. In aspects, $R^3$ is halogen or —CN. In aspects, $R^{6A}$, $R^{6B}$, $R^{7A}$, and $R^{7B}$ are hydrogen. In aspects, $R^3$ is halogen, and $R^{6A}$, $R^{6B}$, $R^{7A}$, and $R^{7B}$ are hydrogen. In aspects, $R^3$ is —CN, and $R^{6A}$, $R^{6B}$, $R^{7A}$, and $R^{7B}$ are hydrogen.

The substituents for the compounds of Formula (VII) and (VIIA) are those described herein. In aspects, $R^3$ is halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or unsubstituted $C_1$-$C_4$ heteroalkyl. In aspects, $R^3$ is halogen or —CN. In aspects, $R^{6A}$, $R^{6B}$, $R^{7A}$, and $R^{7B}$ are hydrogen. In aspects, $R^3$ is halogen, and $R^{6A}$, $R^{6B}$, $R^{7A}$, and $R^{7B}$ are hydrogen. In aspects, $R^3$ is —CN, and $R^{6A}$, $R^{6B}$, $R^{7A}$, and $R^{7B}$ are hydrogen.

The substituents for the compounds of Formula (VIII) are those described herein. In aspects, $R^{6A}$, $R^{6B}$, $R^{7A}$, and $R^{7B}$ are hydrogen.

The disclosure provides Compound CDH24, which is also referred to herein as a compound of Formula (A) or a pharmaceutically acceptable salt thereof:

(A)

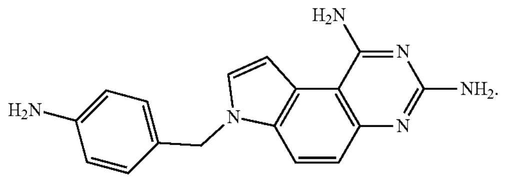

The disclosure provides Compound CDH24-6, which is also referred to herein as a compound of Formula (B) or a pharmaceutically acceptable salt thereof:

(B)

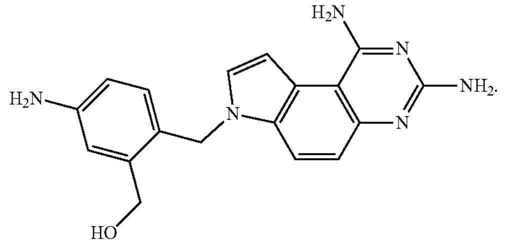

The disclosure provides Compound CDH24-7, which is also referred to herein as a compound of Formula (C) or a pharmaceutically acceptable salt thereof:

(C)

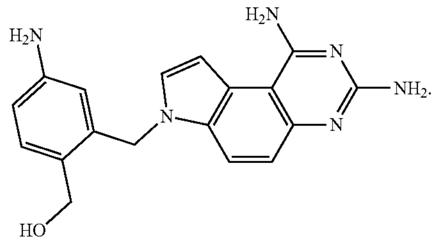

The disclosure provides Compound CDH24-16, which is also referred to herein as a compound of Formula (D) or a pharmaceutically acceptable salt thereof:

(D)

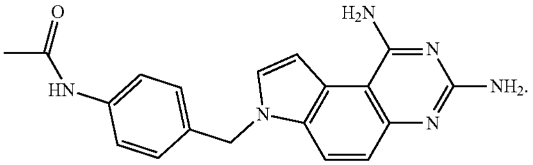

The disclosure provides Compound CDH24-18, which is also referred to herein as a compound of Formula (E) or a pharmaceutically acceptable salt thereof:

(E)

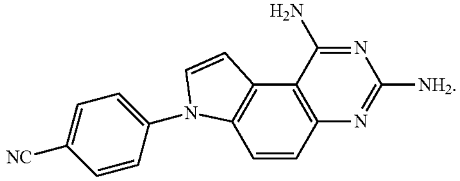

The disclosure provides Compound CDH24-20, which is also referred to herein as a compound of Formula (F) or a pharmaceutically acceptable salt thereof:

(F)

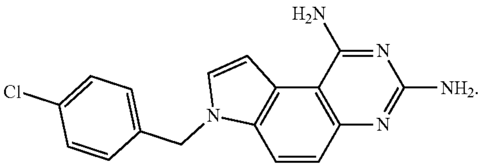

The disclosure provides Compound CDH24-21, which is also referred to herein as a compound of Formula (G) or a pharmaceutically acceptable salt thereof:

(G)

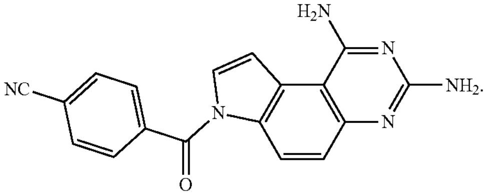

The disclosure provides Compound CDH24-17, which is also referred to herein as a compound of Formula (H) or a pharmaceutically acceptable salt thereof:

(H)

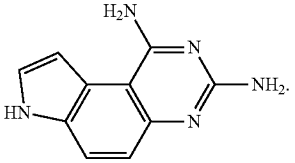

The disclosure provides compounds of Formula (IV), (V), (VI), or a pharmaceutically acceptable salt of any one thereof:

(IV)

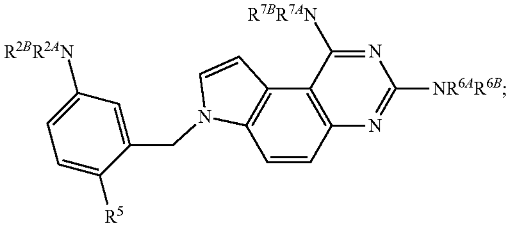

(V)

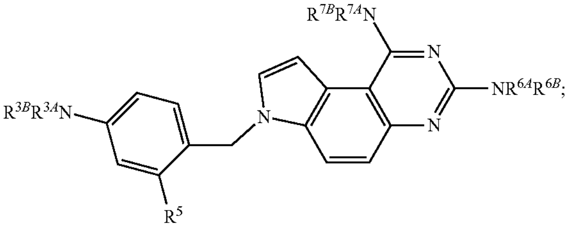

(VI)

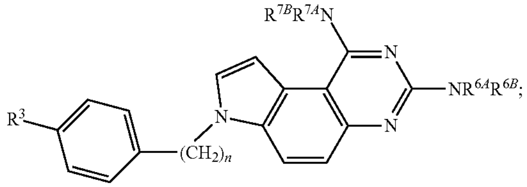

wherein n is 0 or 1; $R^{2A}$, $R^{2B}$, $R^{3A}$, $R^{3B}$, $R^{6A}$, $R^{6B}$, $R^{7A}$, and $R^{7B}$ are each independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl; and $R^3$ and $R^5$ are each independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl. In aspects, $R^3$ is halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or unsubstituted 2 to 4 membered heteroalkyl. In aspects, $R^5$ is $C_1$-$C_6$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, and unsubstituted $C_1$-$C_4$ alkyl. In aspects, $R^{2A}$, $R^{2B}$, $R^{3A}$, $R^{3B}$, $R^{6A}$, $R^{6B}$, $R^{7A}$, and $R^{7B}$ are hydrogen. In aspects, n is 1.

Methods of Treatment

The disclosure provides methods of treating a disease characterized by overexpression of METTL16 by administering to a patient an effective amount of any one of the METTL16 inhibitors described herein, including all embodiments and aspects thereof. In aspects, the disease overexpresses METTL16 when compared to a control. In aspects, the METTL16 inhibitor is a compound of Formula (I), (II), (III), (IV), (V), (VI), (VIA), (VIB), (VII), (VIIA), (VIII), (A), (B), (C), (D), (E), (F), (G), (H), or a pharmaceutically acceptable salt of any one of the foregoing. In aspects, the methods comprise administering a pharmaceutical composition comprising a METTL16 inhibitor and a pharmaceutically acceptable excipient.

The disclosure provides methods of treating cancer by administering to a patient an effective amount of any one of the compounds described herein, including all embodiments and aspects thereof. In aspects, the cancer overexpresses METTL16. In aspects, the cancer overexpresses METTL16 when compared to a control. In aspects, the compound is a compound of Formula (I) or a pharmaceutically acceptable salt thereof. In aspects, the compound is a compound of Formula (II) or a pharmaceutically acceptable salt thereof. In aspects, the compound is a compound of Formula (III) or a pharmaceutically acceptable salt thereof. In aspects, the compound is a compound of Formula (IV) or a pharmaceutically acceptable salt thereof. In aspects, the compound is a compound of Formula (V) or a pharmaceutically acceptable salt thereof. In aspects, the compound is a compound of Formula (VI) or a pharmaceutically acceptable salt thereof. In aspects, the compound is a compound of Formula (VIA) or a pharmaceutically acceptable salt thereof. In aspects, the compound is a compound of Formula (VIB) or a pharmaceutically acceptable salt thereof. In aspects, the compound is a compound of Formula (VII) or a pharmaceutically acceptable salt thereof. In aspects, the compound is a compound of Formula (VIIA) or a pharmaceutically acceptable salt thereof. In aspects, the compound is a compound of Formula (VIII) or a pharmaceutically acceptable salt thereof. In aspects, the compound is a compound of Formula (A) or a pharmaceutically acceptable salt thereof. In aspects, the compound is a compound of Formula (B) or a pharmaceutically acceptable salt thereof. In aspects, the compound is a compound of Formula (C) or a pharmaceutically acceptable salt thereof. In aspects, the compound is a compound of Formula (D) or a pharmaceutically acceptable salt thereof. In aspects, the compound is a compound of Formula (E) or a pharmaceutically acceptable salt thereof. In aspects, the compound is a compound of Formula (F) or a pharmaceutically acceptable salt thereof. In aspects, the compound is a compound of Formula (G) or a pharmaceutically acceptable salt thereof. In aspects, the compound is a compound of Formula (H) or a pharmaceutically acceptable salt thereof.

The disclosure provides methods of treating cancer by administering to a patient an effective amount of a pharmaceutical composition comprising a pharmaceutically acceptable excipient and any one of the compounds described herein, including all embodiments and aspects thereof. In aspects, the cancer overexpresses METTL16. In aspects, the pharmaceutical composition comprises a compound of Formula (I) or a pharmaceutically acceptable salt thereof. In aspects, the pharmaceutical composition comprises a compound of Formula (II) or a pharmaceutically acceptable salt thereof. In aspects, the pharmaceutical composition comprises a compound of Formula (III) or a pharmaceutically acceptable salt thereof. In aspects, the pharmaceutical composition comprises a compound of Formula (IV) or a pharmaceutically acceptable salt thereof. In aspects, the pharmaceutical composition comprises a compound of Formula (V) or a pharmaceutically acceptable salt thereof. In aspects, the pharmaceutical composition comprises a compound of Formula (VI) or a pharmaceutically acceptable salt thereof. In aspects, the pharmaceutical composition comprises a compound of Formula (VIA) or a pharmaceutically acceptable salt thereof. In aspects, the pharmaceutical composition comprises a compound of Formula (VIB) or a pharmaceutically acceptable salt thereof. In aspects, the pharmaceutical composition comprises a compound of Formula (VII) or a pharmaceutically acceptable salt thereof. In aspects, the pharmaceutical composition comprises a compound of Formula (VIIA) or a pharmaceutically acceptable salt thereof. In aspects, the pharmaceutical composition comprises a compound of Formula (VIII) or a pharmaceutically acceptable salt thereof. In aspects, the pharmaceutical composition comprises a compound of Formula (A) or a pharmaceutically acceptable salt thereof. In aspects, the pharmaceutical composition comprises a compound of Formula (B) or a pharmaceutically acceptable salt thereof. In aspects, the pharmaceutical composition comprises a compound of Formula (C) or a pharmaceutically acceptable salt thereof. In aspects, the pharmaceutical composition comprises a compound of Formula (D) or a pharmaceutically acceptable salt thereof. In aspects, the pharmaceutical composition comprises a compound of Formula (E) or a pharmaceutically acceptable salt thereof. In aspects, the pharmaceutical composition comprises a compound of Formula (F) or a pharmaceutically acceptable salt thereof. In aspects, the pharmaceutical composition comprises a compound of Formula (G) or a pharmaceutically acceptable salt thereof. In aspects, the pharmaceutical composition comprises a compound of Formula (H) or a pharmaceutically acceptable salt thereof. The pharmaceutically acceptable excipient may be any known in the art.

The compounds and pharmaceutical compositions described herein can be used to treat any cancer that overexpresses METTL16. In aspects, the cancer that overexpresses METTL16 is leukemia, glioma, glioblastoma, lung cancer, pancreatic cancer, liver cancer, thymoma, lymphoma, prostate cancer, head and neck cancer, fibrosarcoma, adrenocortical carcinoma, breast cancer, cervical cancer, ovarian cancer, bladder cancer, colorectal cancer, melanoma, multiple myeloma, thyroid cancer, cholangiocarcinoma, kidney cancer, or stomach cancer. In aspects, the leukemia is acute myeloid leukemia, acute lymphocytic leukemia, or chronic myeloid leukemia. In aspects, the cancer that overexpresses METTL16 is leukemia. In aspects, the cancer that overexpresses METTL16 is acute myeloid leukemia. In aspects, the cancer that overexpresses METTL16 is acute lymphocytic leukemia. In aspects, the cancer that overexpresses METTL16 is chronic myeloid leukemia. In aspects, the cancer that overexpresses METTL16 is glioblastoma. In aspects, the cancer that overexpresses METTL16 is lung cancer. In aspects, the cancer that overexpresses METTL16 is non-small cell lung cancer. In aspects, the cancer that overexpresses METTL16 is pancreatic cancer. In aspects, the cancer that overexpresses METTL16 is liver cancer. In aspects, the cancer that overexpresses METTL16 is thymoma. In aspects, the cancer that overexpresses METTL16 is lymphoma. In aspects, the cancer that overexpresses METTL16 is B cell lymphoma. In aspects, the cancer that overexpresses METTL16 is Burkitt's lymphoma. In aspects, the cancer that overexpresses METTL16 is prostate cancer. In aspects, the cancer that overexpresses METTL16 is head and neck cancer. In aspects, the cancer that overexpresses METTL16 is fibrosarcoma. In aspects, the cancer that overexpresses METTL16 is adrenocortical carcinoma. In aspects, the cancer that overexpresses METTL16 is breast cancer. In aspects, the cancer that overexpresses METTL16 is cervical cancer. In aspects, the cancer that overexpresses METTL16 is cholangiocarcinoma. In aspects, the cancer that overexpresses METTL16 is kidney cancer. In aspects, the cancer that overexpresses METTL16 is stomach cancer. In aspects, the cancer that overexpresses METTL16 is glioma. In aspects, the cancer that overexpresses METTL16 is ovarian cancer. In aspects, the cancer that overexpresses METTL16 is bladder cancer. In aspects, the cancer that overexpresses METTL16 is colorectal cancer. In aspects, the cancer that overexpresses METTL16 is melanoma. In aspects, the cancer that overexpresses METTL16 is multiple myeloma. In aspects, the cancer that overexpresses METTL16 is thyroid cancer. See, e.g., by Behan et al, Nature, 568:511-516 (2019); Barbieri et al, Nature, 552(7683):126-131 (2017).

In embodiments, the methods of treating cancer comprise administering to a patient an effective amount of any one of the compounds described herein, including all embodiments and aspects thereof, and co-administering one or more anti-cancer agents. In embodiments, the methods of treating cancer comprise administering to a patient an effective amount of a pharmaceutical composition comprising any one of the compounds described herein, including all embodiments and aspects thereof, and co-administering one or more anti-cancer agents. Any anti-cancer agent known in the art can be administered for combination therapy.

In embodiments, the methods comprise (i) detecting an expression level of METTL16 in a biological sample from a patient, and (ii) administering to the patient an effective amount of the compounds or pharmaceutical compositions described herein. In embodiments, the methods comprise (i) obtaining a biological sample from a patient; (ii) analyzing the biological sample for the expression level of METTL16; and (iii) administering to the patient an effective amount of the compounds or pharmaceutical compositions described herein. In aspects, the RNA expression level of METTL16 is detected and/or analyzed. In aspects, the protein expression level of METTL16 is detected and/or analyzed. In aspects, the methods further comprise co-administering one or more additional anti-cancer agents.

In embodiments, the methods comprise (i) detecting an expression level of METTL16 in a biological sample from a patient, (ii) comparing the expression level of METTL16 to a control; and (iii) administering to the patient an effective amount of the compounds or pharmaceutical compositions described herein when the expression level of METTL16 is increased relative to a control. In embodiments, the methods comprise (i) obtaining a biological sample from a patient; (ii) analyzing the biological sample for the expression level of METTL16; (iii) comparing the expression level of METTL16 to a control; and (iii) administering to the patient an effective amount of the compounds or pharmaceutical compositions described herein when the expression level of METTL16 is increased relative to a control. In aspects, the RNA expression level of METTL16 is detected and/or analyzed. In aspects, the protein expression level of METTL16 is detected and/or analyzed. In aspects, the control is a patient or patient population that does not have cancer. In aspects, the control is a patient or patient population that has a cancer that does not express or overexpress METTL16. In aspects, the methods further comprise co-administering one or more additional anti-cancer agents.

In embodiments, the methods comprise (i) detecting an expression level of METTL16 in a biological sample from a patient, (ii) comparing the expression level of METTL16 to a control; and (iii) administering to the patient an effective amount of the compounds or pharmaceutical compositions described herein when the expression level of METTL16 is similar to or increased relative to a control. In embodiments, the methods comprise (i) obtaining a biological sample from a patient; (ii) analyzing the biological sample for the expression level of METTL16; (iii) comparing the expression level of METTL16 to a control; and (iii) administering to the patient an effective amount of the compounds or pharmaceutical compositions described herein when the expression level of METTL16 is similar to or increased relative to a control. In aspects, the control is a patient or patient population that has a cancer that overexpresses METTL16. In aspects, the RNA expression level of METTL16 is analyzed. In aspects, the protein expression level of METTL16 is analyzed. In aspects, the methods further comprise co-administering one or more additional anti-cancer agents. In aspects "similar to" means "equal to."

In embodiments, the methods provided herein are useful for treating cancer in subjects who have an elevated level of METTL16 relative to a control. METTL16 levels may be detected at either the protein or gene expression level. METTL16 protein can be quantified by mass spectrometry, immunohistochemistry (IHC), high performance liquid chromatography (HPLC), Western blotting, enzyme-linked immunosorbent assay (ELISA), or flow cytometry with an antibody, or other detectable agent, that detects METTL16. METTL16 gene expression can be quantified by multiple platforms such as real-time polymerase chain reaction (rtPCR), RNA sequencing, microarray, Nanostring, or in situ hybridization. There is a range of METTL16 expression across and within tumor types that shows concordance when measured with either IHC or by Nanostring. One skilled in the art will understand the importance of selecting a threshold of METTL16 expression that constitutes an elevated level. Controls are also valuable for determining the significance of data. For example, if values for a given parameter are widely variant in controls, variation in test samples will not be considered as significant. In some examples of the disclosed methods, when the expression level of METTL16 is assessed, the level is compared with a control expression level of METTL16. By control expression level is meant the expression level of METTL16 from a sample or subject lacking cancer, a sample or subject at a selected stage of cancer or cancer state, or in the absence of a particular variable such as a therapeutic agent. Alternatively, the control level comprises a known amount of METTL16. Such a known amount correlates with an average level of subjects lacking cancer, at a selected stage of cancer or cancer state, or in the absence of a particular variable such as a therapeutic agent. A control level also includes the expression level of METTL16 from one or more selected samples or subjects as described herein. For example, a control level includes an assessment of the expression level of METTL16 in a sample from a subject that does not have cancer, is at a selected stage of cancer or cancer state, or have cancer but have not yet received treatment for the cancer. Another exemplary control level includes an assessment of the expression level of METTL16 in samples taken from multiple subjects that do not have cancer, are at a selected stage of cancer, or have cancer but have not yet received treatment for the cancer. In aspects, a threshold for elevated METTL16 may be above the median expression level of a group of control samples. In aspects, it is above the first quartile of METTL16 expression in a group of control samples. In aspects, it is above the 10th percentile of METTL16 expression for a group of control samples.

When the control level includes the expression level of METTL16 in a sample or subject in the absence of a therapeutic agent, the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

The elevated level of METTL16 may be determined using standard methods commonly known in the art. For example, the elevated level of METTL16 may be calculated by determining the percentage of cells that are positive for METTL16. The cells may be blood cells (e.g., peripheral blood cells) tumor cells, tumor infiltrating cells, stromal cells, vasculature cells, or a composite thereof. In aspects, the percentage of cells that are positive for METTL16 is greater than or equal to 1%. In aspects, the percentage of cells that are positive for METTL16 is greater than or equal to 5%. In aspects, the percentage of cells that are positive for METTL16 is greater than or equal to 10%. In aspects, the percentage of cells that are positive for METTL16 is greater than or equal to 15%. In aspects, the percentage of cells that are positive for METTL16 is greater than or equal to 20%. In aspects, the percentage of cells that are positive for METTL16 is greater than or equal to 25%.

In embodiments, METTL16 gene expression is used to assay for elevated METTL16. For example, quantitative rtPCR, RNA sequencing, microarray, Nanostring, and in situ hybridization are platforms to quantitate gene expression. For Nanostring, RNA is extracted from biological (e.g., tumor samples) and a known quantity of RNA is placed on the Nanostring machine for gene expression detection using gene specific probes.

In embodiments, quantitative rtPCR is used to quantitate the amount of METTL16 RNA within a sample. Known amounts of a synthetic template of METTL16 may be used to empirically derive a standard curve to compare METTL16 levels with the number of thermocycles required to detect METTL16. To determine a threshold for elevated METTL16, one skilled in the art could assess METTL16 levels in a control group of samples and select the 10th percentile of METTL16 expression. In embodiments, the 20th percentile or higher of METTL16 expression is selected as a threshold for elevated METTL16.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In aspects, an anti-cancer agent is an agent identified herein having utility in methods of treating cancer. In aspects, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomustine, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or $rlL_2$), interferon alfa-2a; interferon alfa-2b; interferon alfa-1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39. HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin Al (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCO, Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}In$, $^{90}Y$, or $^{131}I$, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

Dose and Dosing Regimens

The dosage and frequency (single or multiple doses) of the METTL16 inhibitors administered to a subject can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and METTL16 inhibitors described herein. Adjustment and manipulation of established dosages (e.g., frequency and duration) are well within the ability of those skilled in the art.

For any composition and METTL16 inhibitors described herein, the effective amount can be initially determined from cell culture assays. Target concentrations will be those concentrations of METTL16 inhibitors that are capable of achieving the methods described herein, as measured using the methods described herein or known in the art. As is known in the art, effective amounts of METTL16 inhibitors for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages of the METTL16 inhibitors may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Generally, treatment is initiated with smaller dosages which are less than the optimum dose of the METTL16 inhibitor. Thereafter, the dosage is increased by small increments until the optimum effect under circumstances is reached. Dosage amounts and intervals can be adjusted individually to provide levels of the METTL16 inhibitors effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of METTL16 inhibitors by considering factors such as compound potency, relative bioavailability, patient body weight, presence and severity of adverse side effects.

In embodiments, the METTL16 inhibitors is administered to a patient at an amount of about 0.1 mg/kg to about 500 mg/kg. In aspects, the METTL16 inhibitor is administered to a patient in an amount of about 0.5 mg/kg, 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, or 300 mg/kg. It is understood that where the amount is referred to as "mg/kg," the amount is milligram per kilogram body weight of the subject being administered with the METTL16 inhibitor. In aspects, the METTL16 inhibitor is administered to a patient in an amount from about 0.1 mg to about 1,000 mg per day, as a single dose, or in a dose administered two or three times per day. In aspects, the METTL16 inhibitor is administered to a patient in an amount from about 1 mg to about 500 mg per day, as a single dose, or in a dose administered two or three times per day.

Pharmaceutical Compositions

Provided herein are pharmaceutical compositions comprising a METTL16 inhibitor and a pharmaceutically acceptable excipient. The provided compositions are suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005).

"Pharmaceutically acceptable excipient" and "pharmaceutically acceptable carrier" refer to a substance that aids the administration of an active agent to and absorption by a subject and can be included in the compositions of the disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In aspects, oral pharmaceutical compositions will comprise an inert diluent or edible carrier, or they may be enclosed in hard or soft shell gelatin capsule, or they may be compressed into tablets, or they may be incorporated directly with the food. For oral therapeutic administration, the active compounds may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 1 to about 75% of the weight of the unit. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Detection, Assay, and Diagnostic Methods

In embodiments, methods described herein may include detecting a level of METTL16 with a specific binding agent (e.g., an agent that binds to a protein or nucleic acid molecule). Exemplary binding agents include an antibody or a fragment thereof, a detectable protein or a fragment thereof, a nucleic acid molecule such as an oligonucleotide/polynucleotide comprising a sequence that is complementary to patient genomic DNA, mRNA or a cDNA produced from patient mRNA, or any combination thereof. In aspects, an antibody is labeled with detectable moiety, e.g., a fluorescent compound, an enzyme or functional fragment thereof, or a radioactive agent. In aspects, an antibody is detectably labeled by coupling it to a chemiluminescent compound. In aspects, the presence of the chemiluminescent-tagged antibody is then determined by detecting the presence of luminescence that arises during the course of chemical reaction. Non-limiting examples of particularly useful chemiluminescent labeling compounds are luminol, isoluminol, theromatic acridinium ester, imidazole, acridinium salt and oxalate ester.

In embodiments, a specific binding agent is an agent that has greater than 10-fold, preferably greater than 100-fold, and most preferably, greater than 1000-fold affinity for the target molecule as compared to another molecule. As the skilled artisan will appreciate the term specific is used to indicate that other biomolecules present in the sample do not significantly bind to the binding agent specific for the target molecule. In aspects, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity. For example, in embodiments an antibody has a binding affinity (e.g., Kd) in the low micromolar ($10^{-6}$), nanomolar ($10^{-7}$-$10^{-9}$), with high affinity antibodies in the low nanomolar ($10^{-9}$) or pico molar ($10^{-12}$) range for its specific target ligand.

In embodiments, the present subject matter provides a composition comprising a binding agent, wherein the binding agent is attached to a solid support, (e.g., a strip, a polymer, a bead, a nanoparticle, a plate such as a multiwell plate, or an array such as a microarray). In embodiments relating to the use of a nucleic acid probe attached to a solid support (such as a microarray), a nucleic acid in a test sample may be amplified (e.g., using PCR) before or after the nucleic acid to be measured is hybridized with the probe. In aspects, reverse transcription polymerase chain reaction (RT-PCR) is used to detect mRNA levels. In aspects, a probe on a solid support is used, and mRNA (or a portion thereof) in a biological sample is converted to cDNA or partial cDNA and then the cDNA or partial cDNA is hybridized to a probe (e.g., on a microarray), hybridized to a probe and then amplified, or amplified and then hybridized to a probe. In aspects, a strip may be a nucleic acid-probe coated porous or non-porous solid support strip comprising linking a nucleic acid probe to a carrier to prepare a conjugate and immobilizing the conjugate on a porous solid support. In aspects, the support or carrier comprises glass, polystyrene, polypropylene, polyethylene, dextran, nylon, amylases, natural and modified celluloses, polyacrylamides, and magnetite. In aspects, the carrier can be either soluble to some extent or insoluble for the purposes of the disclosure. In aspects, the support material may have any structural configuration so long as the coupled molecule is capable of binding to a binding agent (e.g., an antibody). In aspects, the support configuration may be spherical, as in a bead, or cylindrical, as in the inside surface of a test tube, or the external surface of a rod. In aspects, the surface may be flat such as a plate (or a well within a multiwell plate), sheet, or test strip. The skilled artisan will know many other suitable carriers for binding antibody or antigen, or will be able to ascertain the same by use of routine experimentation.

In embodiments, a solid support comprises a polymer, to which an agent is chemically bound, immobilized, dispersed, or associated. In aspects, a polymer support may be, e.g., a network of polymers, and may be prepared in bead form (e.g., by suspension polymerization). In aspects, the location of active sites introduced into a polymer support depends on the type of polymer support. In aspects, in a swollen-gel-bead polymer support the active sites are distributed uniformly throughout the beads, whereas in a macroporous-bead polymer support they are predominantly on the internal surfaces of the macropores. In aspects, the solid support, e.g., a device, may contain a METTL16 binding agent.

In embodiments, detection is accomplished using an ELISA or Western blot format. In aspects, the binding agent comprises an nucleic acid (e.g., a probe or primers that are complementary for mRNA or cDNA), and the detecting step is accomplished using a polymerase chain reaction (PCR) or Northern blot format, or other means of detection. In aspects, a probe or primer is about 10-20, 15-25, 15-35, 15-25, 20-80, 50-100, or 10-100 nucleotides in length, e.g., about 10, 12, 15, 20, 25, 30, 35, 40, 45, 50, 55, 60, 70, 80, 90, or 100 nucleotides in length or less than about 30, 35, 40, 45, 50, 55, 60, 70, 80, 90, or 100 nucleotides in length.

As used herein, “assaying” means using an analytic procedure to qualitatively assess or quantitatively measure the presence or amount or the functional activity of a target entity. For example, assaying the level of a compound (such as a protein or an mRNA molecule) means using an analytic procedure (such as an in vitro procedure) to qualitatively assess or quantitatively measure the presence or amount of the compound.

In embodiments, the cells in a biological sample are lysed to release a protein or nucleic acid. Numerous methods for lysing cells and assessing protein and nucleic acid levels are known in the art. In aspects, cells are physically lysed, such as by mechanical disruption, liquid homogenization, high frequency sound waves, freeze/thaw cycles, with a detergent, or manual grinding. Non-limiting examples of detergents include Tween 20, Triton X-100, and sodium dodecyl sulfate. Non-limiting examples of assays for determining the level of a protein include HPLC, LC/MS, ELISA, immunoelectrophoresis, Western blot, immunohistochemistry, and radioimmuno assays. Non-limiting examples of assays for determining the level of an mRNA include Northern blotting, RT-PCR, RNA sequencing, and qRT-PCR.

In embodiments, the tumor sample can be obtained by a variety of procedures, such as surgical excision, aspiration or biopsy. In aspects, the tissue sample may be sectioned and assayed as a fresh specimen; alternatively, the tissue sample may be frozen for further sectioning. In aspects, the tissue sample is preserved by fixing and embedding in paraffin or the like.

In embodiments, once a suitable biological sample (e.g., tumor) has been obtained, it is analyzed to quantitate the expression level of each of the genes, e.g. METTL16. In aspects, determining the expression level of a gene comprises detecting and quantifying RNA transcribed from that gene or a protein translated from such RNA. In aspects, the RNA includes mRNA transcribed from the gene, and/or specific spliced variants thereof and/or fragments of such mRNA and spliced variants.

In embodiments, raw expression values are normalized by performing quantile normalization relative to the reference distribution and subsequent log 10-transformation. In aspects, when the gene expression is detected using the nCounter® Analysis System marketed by Nanostring Technologies, the reference distribution is generated by pooling reported (i.e., raw) counts for the test sample and one or more control samples (preferably at least 2 samples, more preferably at least any of 4, 8 or 16 samples) after excluding values for technical (both positive and negative control) probes and without performing intermediate normalization relying on negative (background-adjusted) or positive (synthetic sequences spiked with known titrations).

In embodiments, oligonucleotides in kits are capable of specifically hybridizing to a target region of a polynucleotide, such as for example, an RNA transcript or cDNA generated therefrom. As used herein, specific hybridization means the oligonucleotide forms an anti-parallel double-stranded structure with the target region under certain hybridizing conditions, while failing to form such a structure with non-target regions when incubated with the polynucleotide under the same hybridizing conditions. The composition and length of each oligonucleotide in the kit will depend on the nature of the transcript containing the target region as well as the type of assay to be performed with the oligonucleotide and is readily determined by the skilled artisan.

Embodiments 1 to 44

Embodiment 1. A compound of Formula (B) or a pharmaceutically acceptable salt thereof.

Embodiment 2. A compound of Formula (C) or a pharmaceutically acceptable salt thereof.

Embodiment 3. A pharmaceutical composition comprising the compound of Embodiment 1 or 2, and a pharmaceutically acceptable excipient.

Embodiment 4. A method of treating cancer in a patient in need thereof, the method comprising administering to the patient an effective amount of the compound of Embodiment 1 or 2, or the pharmaceutical composition of Embodiment 3.

Embodiment 5. The method of Embodiment 4, wherein the cancer is acute myeloid leukemia, acute lymphocytic leukemia, chronic myeloid leukemia, glioblastoma, lung cancer, pancreatic cancer, liver cancer, thymoma, lymphoma, prostate cancer, head and neck cancer, fibrosarcoma, adrenocortical carcinoma, breast cancer, cervical cancer, cholangiocarcinoma, kidney cancer, or stomach cancer.

Embodiment 6. A method of treating cancer in a patient in need thereof, wherein the cancer expresses an elevated level of METTL16 relative to a control, the method comprising administering to the patient an effective amount of the compound of Formula (I) or a pharmaceutically acceptable salt thereof:

(I)

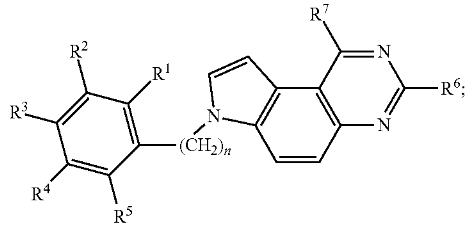

wherein: n is an integer from 0 to 6; $R^1$ is hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OR^{1A}$, $-NR^{1A}R^{1B}$, $-COOR^{1A}$, $-CONR^{1A}R^{1B}$, $-NO_2$, $-SR^{1A}$, $-SO_3R^{1A}$, $-SO_4R^{1A}$, $-SO_2NR^{1A}R^{1B}$, $-NHNR^{1A}R^{1B}$, 13 $ONR^{1A}R^{1B}$, $-NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{2A}$, —$NR^{2A}R^{2B}$, —$COOR^{2A}$, —$CONR^{2A}R^{2B}$, —$NO_2$, —$SR^{2A}$, —$SO_3R^{2A}$, —$SO_4R^{2A}$, —$SO_2NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{6A}$, —$NR^{6A}R^{6B}$, —$COOR^{6A}$, —$CONR^{6A}R^{6B}$, —$NO_2$, —$SR^{6A}$, —$SO_3R^{6A}$, —$SO_4R^{6A}$, —$SO_2NR^{6A}R^{6B}$, —$NHNR^{6A}R^{6B}$, —$ONR^{6A}R^{6B}$, —$NHC(O)NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$NR^{7A}R^{7B}$, —$COOR^{7A}$, —$CONR^{7A}R^{7B}$, —$NO_2$, —$SR^{7A}$, —$SO_3R^{7A}$, —$SO_4R^{7A}$, —$SO_2NR^{7A}R^{7B}$, —$NHNR^{7A}R^{7B}$, —$ONR^{7A}R^{7B}$, —$NHC(O)NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 7. A method of treating cancer in a patient in need thereof, the method comprising: (i) detecting an expression level of METTL16 in a biological sample from the subject; and (ii administering to the patient an effective amount of the compound of Formula (I) or a pharmaceutically acceptable salt thereof, wherein the compound of Formula (I) is as described in Embodiment 6.

Embodiment 8. The method of Embodiment 7, further comprising comparing the expression level of METTL16 to a control, and administering the compound of Formula (I) or the pharmaceutically acceptable salt thereof to the patient when the expression level of METTL16 is greater than the control.

Embodiment 9. The method of any one of Embodiments 6 to 8, wherein the cancer is acute myeloid leukemia, acute lymphocytic leukemia, chronic myeloid leukemia, glioblastoma, lung cancer, pancreatic cancer, liver cancer, thymoma, lymphoma, prostate cancer, head and neck cancer, fibrosarcoma, adrenocortical carcinoma, breast cancer, cervical cancer, cholangiocarcinoma, kidney cancer, or stomach cancer.

Embodiment 10. The method of any one of Embodiments 6 to 9, wherein: $R^1$ is hydrogen, halogen, —$OR^{1A}$, —$NR^{1A}R^{1B}$, —$COOR^{1A}$, —$CONR^{1A}R^{1B}$, —$NO_2$, —$NHNR^{1A}R^{1B}$, —$ONR^{1A}R^{1B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^2$ is hydrogen, halogen, —$OR^{2A}$, —$NR^{2A}R^{2B}$, —$COOR^{2A}$, —$CONR^{2A}R^{2B}$, —$NO_2$, —$NHNR^{2A}R^{2B}$, —$ONR^{2A}R^{2B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^3$ is hydrogen, halogen, —$OR^{3A}$, —$NR^{3A}R^{3B}$, —$COOR^{3A}$, —$CONR^{3A}R^{3B}$, —$NO_2$, —$NHNR^{3A}R^{3B}$, —$ONR^{3A}R^{3B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^4$ is hydrogen, halogen, —$OR^{4A}$, —$NR^{4A}R^{4B}$, —$COOR^{4A}$, —$CONR^{4A}R^{4B}$, —$NO_2$, —$NHNR^{4A}R^{4B}$, —$ONR^{4A}R^{4B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^5$ is hydrogen, halogen, —$OR^{5A}$, —$NR^{5A}R^{5B}$, —$COOR^{5A}$, —$CONR^{5A}R^{5B}$, —$NO_2$, —$NHNR^{5A}R^{5B}$, —$ONR^{5A}R^{5B}$, substituted or unsubstituted alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^6$ is hydrogen, halogen, —$OR^{6A}$, —$NR^{6A}R^{6B}$, —$COOR^{6A}$, —$CONR^{6A}R^{6B}$, —$NO_2$, —$NHNR^{6A}R^{6B}$, —$ONR^{6A}R^{6B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; and $R^7$ is hydrogen, halogen, —$OR^{7A}$, —$NR^{7A}R^{7B}$, —$COOR^{7A}$, —$CONR^{7A}R^{7B}$, —$NO_2$, —$NHNR^{7A}R^{7B}$, —$ONR^{7A}R^{7B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl.

Embodiment 11. The method of any one of Embodiments 6 to 10, wherein n is an integer from 1 to 3.

Embodiment 12. The method of Embodiment 11, wherein n is 1.

Embodiment 13. The method of any one of Embodiments 6 to 12, wherein $R^5$ is a substituted or unsubstituted alkyl.

Embodiment 14. The method of Embodiment 13, wherein $R^5$ is a substituted $C_1$-$C_8$ alkyl.

Embodiment 15. The method of Embodiment 14, wherein $R^5$ is $C_1$-$C_6$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, and unsubstituted $C_1$-$C_4$ alkyl.

Embodiment 16. The method of Embodiment 15, wherein $R^5$ is $C_1$-$C_4$ alkyl substituted with 1 or 2 substituents independently selected from the group consisting of —OH, —$NH_2$, —COOH, —$CONH_2$, —$ONH_2$, and unsubstituted $C_1$-$C_4$ alkyl.

Embodiment 17. The method of any one of Embodiments 6 to 16, wherein: $R^{1A}$ and $R^{1B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, or substituted or unsubstituted 2 to 6 membered heteroalkyl; $R^{2A}$ and $R^{2B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, or substituted or unsubstituted 2 to 6 membered heteroalkyl; $R^{3A}$ and $R^{3B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, or substituted or unsubstituted 2 to 6 membered heteroalkyl; $R^{4A}$ and $R^{4B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; $R^{5A}$ and $R^{5B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; $R^{6A}$ and $R^{6B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; and $R^{7A}$ and $R^{7B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl.

Embodiment 18. The method of any one of Embodiments 6 to 17, wherein $R^1$, $R^2$, and $R^4$ are hydrogen.

Embodiment 19. The method of any one of Embodiments 6 to 17, wherein $R^1$, $R^3$, and $R^4$ are hydrogen.

Embodiment 20. The method of any one of Embodiments 6 to 17, wherein $R^1$, $R^2$, and $R^4$ are hydrogen; and $R^3$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, or unsubstituted $C_1$-$C_4$ alkyl.

Embodiment 21. The method of Embodiment 20, wherein $R^1$, $R^2$, and $R^4$ are hydrogen; and $R^3$, $R^6$, and $R^7$ are each independently —OH, —$NH_2$, —COOH, —$CONH_2$, —$ONH_2$, or unsubstituted $C_1$-$C_4$ alkyl.

Embodiment 22. The method of any one of Embodiments 6 to 17, wherein $R^1$, $R^3$, and $R^4$ are hydrogen; and $R^2$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, or unsubstituted $C_1$-$C_4$ alkyl Embodiment 23. The method of Embodiment 22, wherein $R^1$, $R^3$, and $R^4$ are hydrogen; and $R^2$, $R^6$, and $R^7$ are each independently —OH, —$NH_2$, —COOH, —$CONH_2$, —$ONH_2$, or unsubstituted $C_1$-$C_4$ alkyl.

Embodiment 24. The method of any one of Embodiments 6 to 16, wherein the compound of Formula (I) is a compound of Formula (II) or a pharmaceutically acceptable salt thereof:

(II)

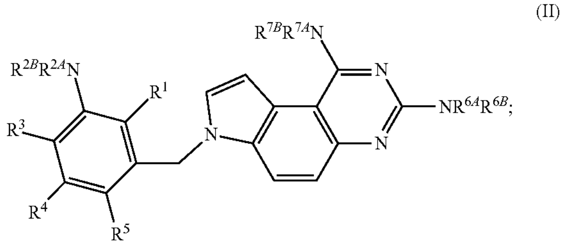

wherein $R^{2A}$, $R^{2B}$, $R^{6A}$, $R^{6B}$, $R^{7A}$, and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment 25. The method of Embodiment 24, wherein $R^{2A}$, $R^{2B}$, $R^{6A}$, $R^{6B}$, $R^{7A}$, and $R^{7B}$ are each independently hydrogen, —OH, —$NH_2$, —COOH, —$CONH_2$, —$ONH_2$, or substituted or unsubstituted $C_1$-$C_4$ alkyl.

Embodiment 26. The method of Embodiment 25, wherein $R^{2A}$, $R^{2B}$, $R^{6A}$, $R^{6B}$, $R^{7A}$, and $R^{7B}$ are hydrogen.

Embodiment 27. The method of any one of Embodiments 24 to 26, wherein $R^1$, $R^3$, and $R^4$ are hydrogen.

Embodiment 28. The method of Embodiment 27, wherein $R^5$ is hydrogen.

Embodiment 29. The method of any one of Embodiments 6 to 16, wherein the compound of Formula (I) is a compound of Formula (III) or a pharmaceutically acceptable salt thereof:

(III)

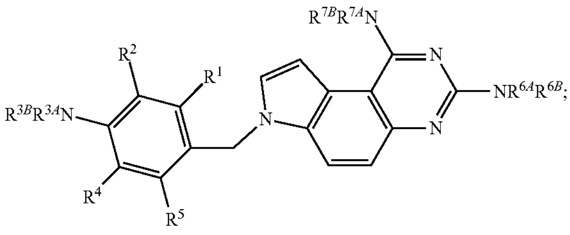

wherein $R^{3A}$, $R^{3B}$, $R^{6A}$, $R^{6B}$, $R^{7A}$, and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment 30. The method of Embodiment 29, wherein $R^{3A}$, $R^{3B}$, $R^{6A}$, $R^{6B}$, $R^{7A}$, and $R^{7B}$ are each independently hydrogen, —OH, —$NH_2$, —COOH, —$CONH_2$, —$ONH_2$, or substituted or unsubstituted $C_1$-$C_4$ alkyl.

Embodiment 31. The method of Embodiment 30, wherein $R^{3A}$, $R^{3B}$, $R^{6A}$, $R^{6B}$, $R^{7A}$, and $R^{7B}$ are hydrogen.

Embodiment 32. The method of any one of Embodiments 29 to 31, wherein $R^1$, $R^2$, and $R^4$ are hydrogen.

Embodiment 33. The method of Embodiment 32, wherein $R^5$ is hydrogen.

Embodiment 34. The method of any one of Embodiments 6 to 16, wherein the compound of Formula (I) is a compound of Formula (IV) or a pharmaceutically acceptable salt thereof:

(IV)

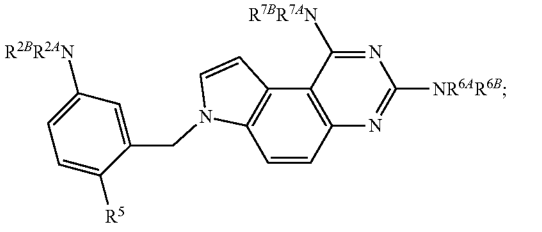

wherein $R^{2A}$, $R^{2B}$, $R^{6A}$, $R^{6B}$, $R^{7A}$, and $R^{7B}$ are each independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment 35. The method of Embodiment 34, wherein $R^{2A}$, $R^{2B}$, $R^{6A}$, $R^{6B}$, $R^{7A}$, and $R^{7B}$ are each independently hydrogen, —OH, $—NH_2$, —COOH, $—CONH_2$, $—ONH_2$, or substituted or unsubstituted $C_1$-$C_4$ alkyl.

Embodiment 36. The method of Embodiment 35, wherein $R^{2A}$, $R^{2B}$, $R^{6A}$, $R^{6B}$, $R^{7A}$, and $R^{7B}$ are hydrogen.

Embodiment 37. The method of any one of Embodiments 34 to 36, wherein $R^5$ is hydrogen.

Embodiment 38. The method of any one of Embodiments 6 to 16, wherein the compound of Formula (I) is a compound of Formula (V) or a pharmaceutically acceptable salt thereof:

(V)

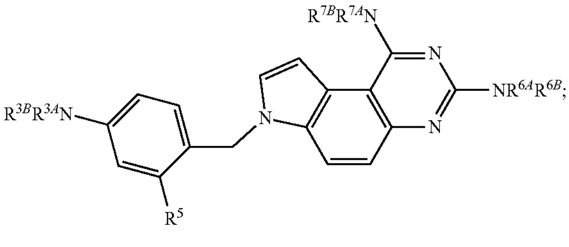

wherein $R^{3A}$, $R^{3B}$, $R^{6A}$, $R^{6B}$, $R^{7A}$, and $R^{7B}$ are each independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment 39. The method of Embodiment 38, wherein $R^{3A}$, $R^{3B}$, $R^{6A}$, $R^{6B}$, $R^{7A}$, and $R^{7B}$ are each independently hydrogen, —OH, $—NH_2$, —COOH, $—CONH_2$, $—ONH_2$, or substituted or unsubstituted $C_1$-$C_4$ alkyl.

Embodiment 40. The method of Embodiment 39, wherein $R^{3A}$, $R^{3B}$, $R^{6A}$, $R^{6B}$, $R^{7A}$, and $R^{7B}$ are hydrogen.

Embodiment 41. The method of any one of Embodiments 38 to 40, wherein $R^5$ is hydrogen.

Embodiment 42. The method of any one of Embodiments 6 to 9, wherein the compound of Formula (I) is a compound of Formula (A) or a pharmaceutically acceptable salt thereof.

Embodiment 43. The method of any one of Embodiments 6 to 9, wherein the compound of Formula (I) is a compound of Formula (B) or a pharmaceutically acceptable salt thereof.

Embodiment 44. The method of any one of Embodiments 6 to 9, wherein the compound of Formula (I) is a compound of Formula (C) or a pharmaceutically acceptable salt thereof.

Embodiments W1 to W50

Embodiment W1. A method of treating cancer in a patient in need thereof, wherein the cancer expresses an elevated level of METTL16 relative to a control, the method comprising administering to the patient an effective amount of the compound of Formula (I) or a pharmaceutically acceptable salt thereof:

(I)

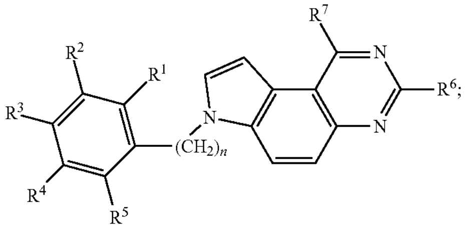

wherein: n is an integer from 0 to 6; $R^1$ is hydrogen, halogen, $—CF_3$, $—CBr_3$, $—CCl_3$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, $—OR^{1A}$, $—NR^{1A}R^{1B}$, $—COOR^{1A}$, $—CONR^{1A}R^{1B}$, $—NO_2$, $—SR^{1A}$, $—SO_3R^{1A}$, $—SO_4R^{1A}$, $—SO_2NR^{1A}R^{1B}$, $—NHNR^{1A}R^{1B}$, $—ONR^{1A}R^{1B}$, $—NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ are each independently hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $—CF_3$, $—CBr_3$, $—CCl_3$, $—CI_3$, $—CHF_2$, $—CHBr_2$, $—CHCl_2$, $—CHI_2$, $—CH_2F$, $—CH_2Br$, $—CH_2Cl$, $—CH_2I$, $—OCF_3$, $—OCBr_3$, $—OCCl_3$, $—OCI_3$, $—OCHF_2$, $—OCHBr_2$, $—OCHCl_2$, $—OCHI_2$, $—OCH_2F$, $—OCH_2Br$, $—OCH_2Cl$, $—OCH_2I$, —CN, $—OR^{2A}$, $—NR^{2A}R^{2B}$, —$COOR^{2A}$, —$CONR^{2A}R^{2B}$, —$NO_2$, —$SR^{2A}$, —$SO_3R^{2A}$, —$SO_4R^{2A}$, —$SO_2NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{6A}$, —$NR^{6A}R^{6B}$, —$COOR^{6A}$, —$CONR^{6A}R^{6B}$, —$NO_2$, —$SR^{6A}$, —$SO_3R^{6A}$, —$SO_4R^{6A}$, —$SO_2NR^{6A}R^{6B}$, —$NHNR^{6A}R^{6B}$, —$ONR^{6A}R^{6B}$, —$NHC(O)NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{7A}$, —$NR^{7A}R^{7B}$, —$COOR^{7A}$, —$CONR^{7A}R^{7B}$, —$NO_2$, —$SR^{7A}$, —$SO_3R^{7A}$, —$SO_4R^{7A}$, —$SO_2NR^{7A}R^{7B}$, —$NHNR^{7A}R^{7B}$, —$ONR^{7A}R^{7B}$, —$NHC(O)NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment W2. A method of treating cancer in a patient in need thereof, the method comprising: (i) detecting an expression level of METTL16 in a biological sample from the subject; and (ii) administering to the patient an effective amount of the compound of Formula (I) or a pharmaceutically acceptable salt thereof:

(I)

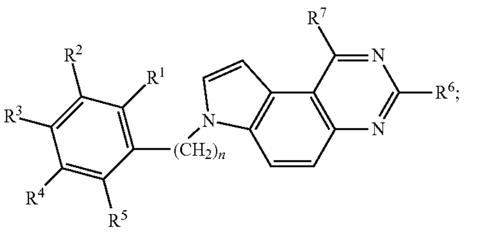

wherein: n is an integer from 0 to 6; $R^1$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{1A}$, —$NR^{1A}R^{1B}$, —$COOR^{1A}$, —$CONR^{1A}R^{1B}$, —$NO_2$, —$SR^{1A}$, —$SO_3R^{1A}$, —$SO_4R^{1A}$, —$SO_2NR^{1A}R^{1B}$, —$NHNR^{1A}R^{1B}$, —$ONR^{1A}R^{1B}$, —$NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{2A}$, —$NR^{2A}R^{2B}$, —$COOR^{2A}$, —$CONR^{2A}R^{2B}$, —$NO_2$, —$SR^{2A}$, —$SO_3R^{2A}$, —$SO_4R^{2A}$, —$SO_2NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{6A}$, —$NR^{6A}R^{6B}$, —$COOR^{6A}$, —$CONR^{6A}R^{6B}$, —$NO_2$, —$SR^{6A}$, —$SO_3R^{6A}$, —$SO_4R^{6A}$, —$SO_2NR^{6A}R^{6B}$, —$NHNR^{6A}R^{6B}$, —$ONR^{6A}R^{6B}$, —NHC(O)$NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{7A}$, —$NR^{7A}R^{7B}$, —$COOR^{7A}$, —$CONR^{7A}R^{7B}$, —$NO_2$, —$SR^{7A}$, —$SO_3R^{7A}$, —$SO_4R^{7A}$, —$SO_2NR^{7A}R^{7B}$, —$NHNR^{7A}R^{7B}$, —$ONR^{7A}R^{7B}$, —NHC(O)$NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment W3. The method of Embodiment W2, further comprising comparing the expression level of METTL16 to a control, and administering the compound of Formula (IA) or the pharmaceutically acceptable salt thereof to the patient when the expression level of METTL16 is greater than the control.

Embodiment W4. The method of any one of Embodiments W1 to W3, wherein the cancer is leukemia, lymphoma, or liver cancer.

Embodiment W5. The method of any one of Embodiments W1 to W3, wherein the cancer is acute myeloid leukemia, acute lymphocytic leukemia, or chronic myeloid leukemia.

Embodiment W6. The method of any one of Embodiments W1 to W3, wherein the cancer is leukemia, glioma, glioblastoma, lung cancer, pancreatic cancer, liver cancer, thymoma, lymphoma, prostate cancer, head and neck cancer, fibrosarcoma, adrenocortical carcinoma, breast cancer, cervical cancer, ovarian cancer, bladder cancer, colorectal cancer, melanoma, multiple myeloma, thyroid cancer, cholangiocarcinoma, kidney cancer, or stomach cancer.

Embodiment W7. The method of any one of Embodiments W1 to W6, wherein: $R^1$ is hydrogen, halogen, —CN, —$OR^{1A}$, —$NR^{1A}R^{1B}$, —$COOR^{1A}$, —$CONR^{1A}R^{1B}$, —$NO_2$, —$NHNR^{1A}R^{1B}$, —$ONR^{1A}R^{1B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^2$ is hydrogen, halogen, —CN, —$OR^{2A}$, —$NR^{2A}R^{2B}$, —$COOR^{2A}$, —$CONR^{2A}R^{2B}$, —$NO_2$, —$NHNR^{2A}R^{2B}$, —$ONR^{2A}R^{2B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^3$ is hydrogen, halogen, —CN, —$OR^{3A}$, —$NR^{3A}R^{3B}$, —$COOR^{3A}$, —$CONR^{3A}R^{3B}$, —$NO_2$, —$NHNR^{3A}R^{3B}$, —$ONR^{3A}R^{3B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^4$ is hydrogen, halogen, —CN, —$OR^{4A}$, —$NR^{4A}R^{4B}$, —$COOR^{4A}$, —$CONR^{4A}R^{4B}$, —$NO_2$, —$NHNR^{4A}R^{4B}$, —$ONR^{4A}R^{4B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^5$ is hydrogen, halogen, —CN, —$OR^{5A}$, —$NR^{5A}R^{5B}$, —$COOR^{5A}$, —$CONR^{5A}R^{5B}$, —$NO_2$, —$NHNR^{5A}R^{5B}$, —$ONR^{5A}R^{5B}$, substituted or unsubstituted alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^6$ is hydrogen, halogen, —$OR^{6A}$, —$NR^{6A}R^{6B}$, —$COOR^{6A}$, —$CONR^{6A}R^{6B}$, —$NO_2$, —$NHNR^{6A}R^{6B}$, —$ONR^{6A}R^{6B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl; $R^7$ is hydrogen, halogen, —$OR^{7A}$, —$NR^{7A}R^{7B}$, —$COOR^{7A}$, —$CONR^{7A}R^{7B}$, —$NO_2$, —$NHNR^{7A}R^{7B}$, —$ONR^{7A}R^{7B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl.

Embodiment W8. The method of any one of Embodiments W1 to W7, wherein n is an integer from 0 to 2.

Embodiment W9. The method of Embodiment W8, wherein n is 1.

Embodiment W10. The method of any one of Embodiments W1 to W9, wherein $R^5$ is a substituted or unsubstituted alkyl.

Embodiment W11. The method of Embodiment W10, wherein $R^5$ is a substituted $C_1$-$C_8$ alkyl.

Embodiment W12. The method of Embodiment W11, wherein $R^5$ is $C_1$-$C_6$ alkyl substituted with 1 or 2 substituents independently selected from the group consisting of —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, and unsubstituted $C_1$-$C_4$ alkyl.

Embodiment W13. The method of Embodiment W12, wherein $R^5$ is $C_1$-$C_4$ alkyl substituted with 1 or 2 substituents independently selected from the group consisting of —OH, —$NH_2$, —COOH, —$CONH_2$, —$ONH_2$, and unsubstituted $C_1$-$C_4$ alkyl.

Embodiment W14. The method of any one of Embodiments W1 to W13, wherein: $R^{1A}$ and $R^{1B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; $R^{2A}$ and $R^{2B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; $R^{3A}$ and $R^{3B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; $R^{4A}$ and $R^{4B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; $R^{5A}$ and $R^{5B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; $R^{6A}$ and $R^{6B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; and $R^{7A}$ and $R^{7B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl.

Embodiment W15. The method of any one of Embodiments W1 to W14, wherein $R^1$, $R^2$, and $R^4$ are hydrogen.

Embodiment W16. The method of any one of Embodiments W1 to W14, wherein $R^1$, $R^3$, and $R^4$ are hydrogen.

Embodiment W17. The method of any one of Embodiments W1 to W14, wherein $R^1$, $R^2$, and $R^4$ are hydrogen; and $R^3$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, or unsubstituted $C_1$-$C_4$ alkyl.

Embodiment W18. The method of Embodiment W17, wherein $R^1$, $R^2$, and $R^4$ are hydrogen; and $R^3$, $R^6$, and $R^7$ are each independently —OH, —$NH_2$, —COOH, —$CONH_2$, —$ONH_2$, or unsubstituted $C_1$-$C_4$ alkyl.

Embodiment W19. The method of any one of Embodiments W1 to W14, wherein $R^1$, $R^3$, and $R^4$ are hydrogen; and $R^2$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, or unsubstituted $C_1$-$C_4$ alkyl.

Embodiment W20. The method of Embodiment W19, wherein $R^1$, $R^3$, and $R^4$ are hydrogen; and $R^2$, $R^6$, and $R^7$ are each independently —OH, —$NH_2$, —COOH, —$CONH_2$, —$ONH_2$, or unsubstituted $C_1$-$C_4$ alkyl.

Embodiment W21. The method of any one of Embodiments W1 to W20, wherein the compound of Formula (I) is a compound of Formula (II) or a pharmaceutically acceptable salt thereof:

(II)

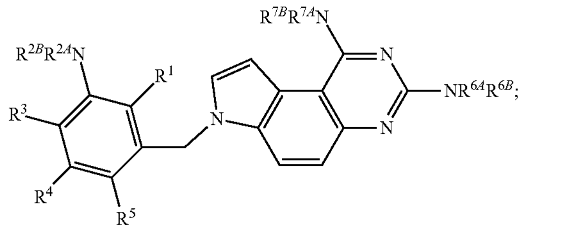

wherein $R^{2A}$, $R^{2B}$, $R^{6A}$, $R^{6B}$, $R^{7A}$, and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment W22. The method of Embodiment W21, wherein $R^{2A}$, $R^{2B}$, $R^{6A}$, $R^{6B}$, $R^{7A}$, and $R^{7B}$ are each independently hydrogen, —OH, —$NH_2$, —COOH, —$CONH_2$, —$ONH_2$, or substituted or unsubstituted $C_1$-$C_4$ alkyl.

Embodiment W23. The method of Embodiment W22, wherein $R^{2A}$, $R^{2B}$, $R^{6A}$, $R^{6B}$, $R^{7A}$, and $R^{7B}$ are hydrogen.

Embodiment W24. The method of any one of Embodiments W21 to W23, wherein $R^1$, $R^3$, and $R^4$ are hydrogen.

Embodiment W25. The method of Embodiment W24, wherein $R^5$ is hydrogen.

Embodiment W26. The method of any one of Embodiments W1 to W20, wherein the compound of Formula (I) is a compound of Formula (III) or a pharmaceutically acceptable salt thereof:

(III)

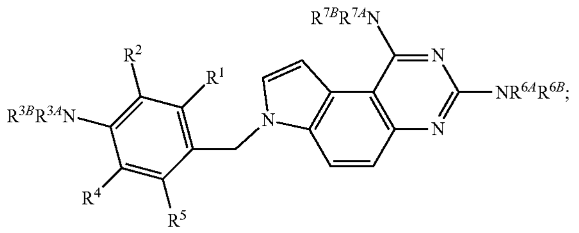

wherein $R^{3A}$, $R^{3B}$, $R^{6A}$, $R^{6B}$, $R^{7A}$, and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment W27. The method of Embodiment W26, wherein $R^{3A}$, $R^{3B}$, $R^{6A}$, $R^{6B}$, $R^{7A}$, and $R^{7B}$ are each independently hydrogen, —OH, —$NH_2$, —COOH, —$CONH_2$, —$ONH_2$, or substituted or unsubstituted $C_1$-$C_4$ alkyl.

Embodiment W28. The method of Embodiment W27, wherein $R^{3A}$, $R^{3B}$, $R^{6A}$, $R^{6B}$, $R^{7A}$, and $R^{7B}$ are hydrogen.

Embodiment W29. The method of any one of Embodiments W26 to W28, wherein $R^1$, $R^2$, and $R^4$ are hydrogen.

Embodiment W30. The method of Embodiment W29, wherein $R^5$ is hydrogen.

Embodiment W31. The method of any one of Embodiments 1 to 20, wherein the compound of Formula (I) is a compound of Formula (IV) or a pharmaceutically acceptable salt thereof:

(IV)

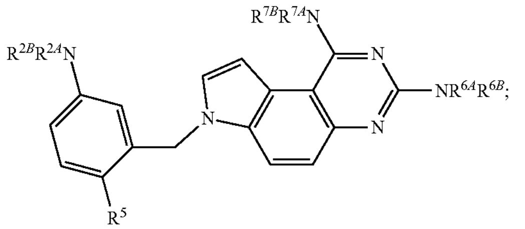

wherein $R^{2A}$, $R^{2B}$, $R^{6A}$, $R^{6B}$, $R^{7A}$, and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment W32. The method of Embodiment W31, wherein $R^{2A}$, $R^{2B}$, $R^{6A}$, $R^{6B}$, $R^{7A}$, and $R^{7B}$ are each independently hydrogen, —OH, —$NH_2$, —COOH, —$CONH_2$, —$ONH_2$, or substituted or unsubstituted $C_1$-$C_4$ alkyl Embodiment W33. The method of Embodiment W32, wherein $R^{2A}$, $R^{2B}$, $R^{6A}$, $R^{6B}$, $R^{7A}$, and $R^{7B}$ are hydrogen.

Embodiment W34. The method of any one of Embodiments W31 to W33, wherein $R^5$ is hydrogen.

Embodiment W35. The method of any one of Embodiments W1 to W20, wherein the compound of Formula (I) is a compound of Formula (V) or a pharmaceutically acceptable salt thereof:

(V)

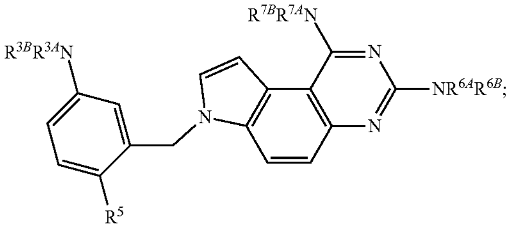

wherein $R^{3A}$, $R^{3B}$, $R^{6A}$, $R^{6B}$, $R^{7A}$, and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment W36. The method of Embodiment W35, wherein $R^{3A}$, $R^{3B}$, $R^{6A}$, $R^{6B}$, $R^{7A}$, and $R^{7B}$ are each independently hydrogen, —OH, —$NH_2$, —COOH, —$CONH_2$, —$ONH_2$, or substituted or unsubstituted $C_1$-$C_4$ alkyl.

Embodiment W37. The method of Embodiment W36, wherein $R^{3A}$, $R^{3B}$, $R^{6A}$, $R^{6B}$, $R^{7A}$, and $R^{7B}$ are hydrogen.

Embodiment W38. The method of any one of Embodiments W35 to W37, wherein $R^5$ is hydrogen.

Embodiment W39. The method of any one of Embodiments W1 to W20, wherein the compound of Formula (I) is a compound of Formula (VI) or a pharmaceutically acceptable salt thereof:

(VI)

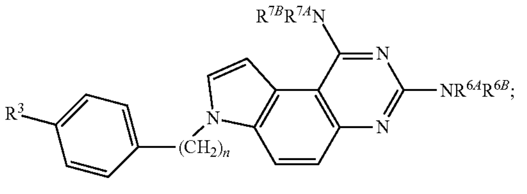

$R^{3A}$, $R^{3B}$, $R^{6A}$, $R^{6B}$, $R^{7A}$, and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

Embodiment W40. The method of Embodiment W39, wherein n is 1; $R^3$ is halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or unsubstituted $C_1$-$C_4$ heteroalkyl; and $R^{6A}$, $R^{6B}$, $R^{7A}$, and $R^{7B}$ are hydrogen.

Embodiment W41. The method of Embodiment W39, wherein n is 0; $R^3$ is halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted $C_1$-$C_4$ alkyl, or unsubstituted $C_1$-$C_4$ heteroalkyl; and $R^{6A}$, $R^{6B}$, $R^{7A}$, and $R^{7B}$ are hydrogen.

Embodiment W42. The method of any one of Embodiments W39 to W41, wherein $R^3$ is halogen or —CN. In embodiments, $R^3$ is chlorine.

Embodiment W43. The method of any one of Embodiments W1 to W6, wherein the compound of Formula (I) is a compound of any one of Formula (A)-(G) or a pharmaceutically acceptable salt of any one thereof:

(A)

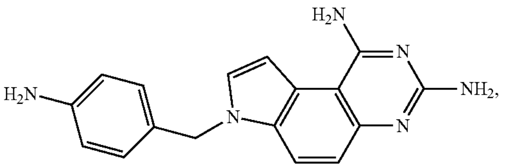

(B)

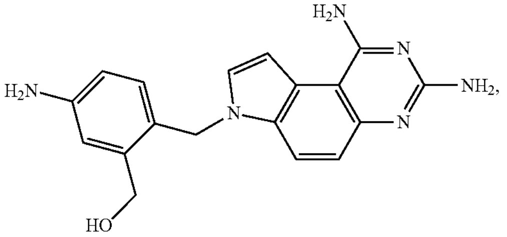

(C)

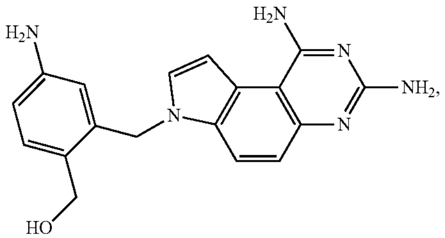

-continued (D)

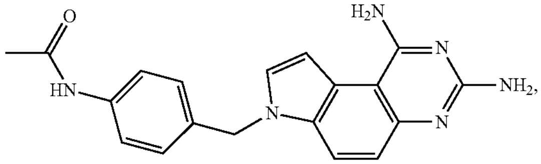

(E)

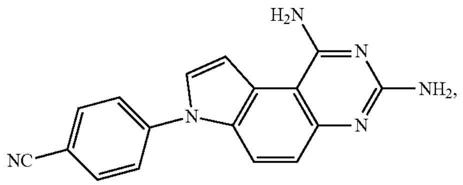

(F)

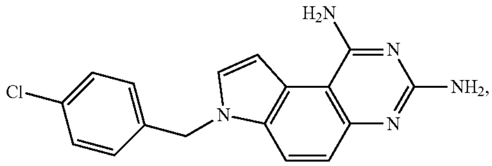

or (G)

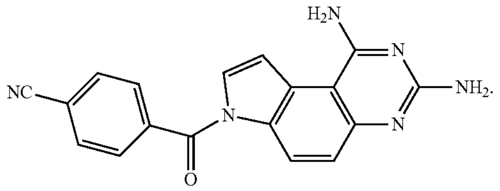

Embodiment W44. A compound of any one of Formula (B)-(G) or a pharmaceutically acceptable salt of any one thereof:

(B)

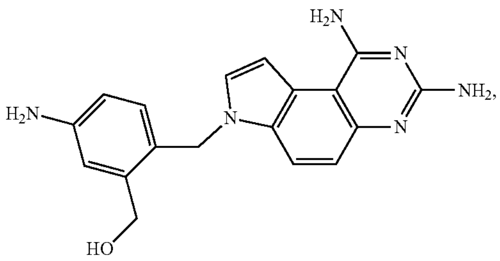

(C)

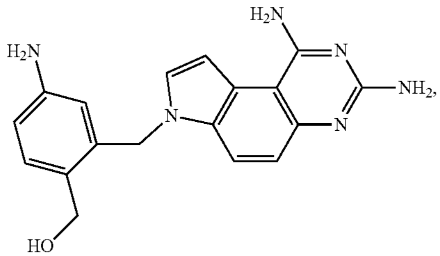

-continued (D)

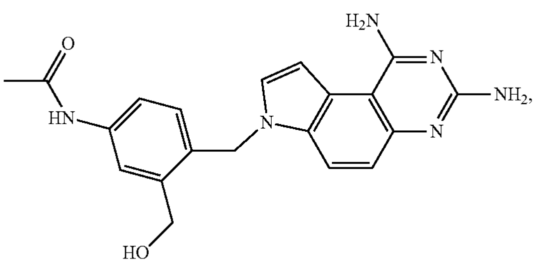

(E)

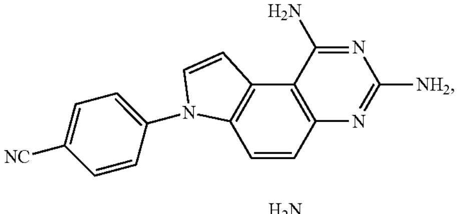

(F)

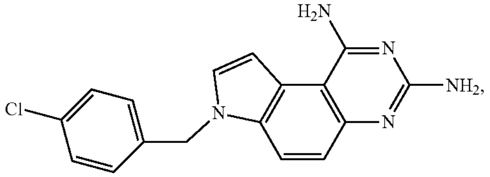

or (G)

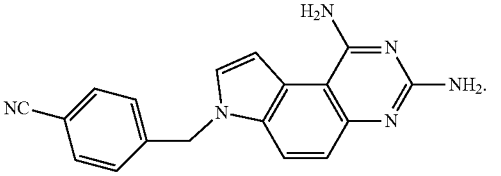

Embodiment W45. A pharmaceutical composition comprising the compound of Embodiment W44 and a pharmaceutically acceptable excipient.

Embodiment W46. A method of treating cancer in a patient in need thereof, the method comprising administering to the patient an effective amount of the compound of Embodiment W44 or the pharmaceutical composition of Embodiment W45.

Embodiment W47. A method of treating cancer in a patient in need thereof, wherein the cancer expresses an elevated level of METTL16 relative to a control, the method comprising administering to the patient an effective amount of the compound of Formula (VII) or a pharmaceutically acceptable salt thereof:

(VII)

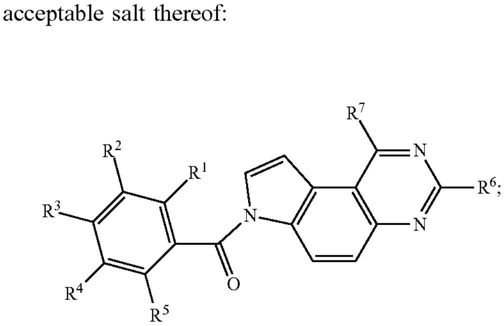

wherein: $R^1$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{1A}$, —$NR^{1A}R^{1B}$, —$COOR^{1A}$, —$CONR^{1A}R^{1B}$, —$NO_2$, —$SR^{1A}$, —$SO_3R^{1A}$, —$SO_4R^{1A}$, —$SO_2NR^{1A}R^{1B}$, —$NHNR^{1A}R^{1B}$, —$ONR^{1A}R^{1B}$, —$NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{2A}$, —$NR^{2A}R^{2B}$, —$COOR^{2A}$, —$CONR^{2A}R^{2B}$, —$NO_2$, —$SR^{2A}$, —$SO_3R^{2A}$, —$SO_4R^{2A}$, —$SO_2NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —NHC(O)$NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —NHC(O)$NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —NHC(O)$NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{6A}$, —$NR^{6A}R^{6B}$, —$COOR^{6A}$, —$CONR^{6A}R^{6B}$, —$NO_2$, —$SR^{6A}$, —$SO_3R^{6A}$, —$SO_4R^{6A}$, —$SO_2NR^{6A}R^{6B}$, —$NHNR^{6A}R^{6B}$, —$ONR^{6A}R^{6B}$, —NHC(O)$NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{7A}$, —$NR^{7A}R^{7B}$, —$COOR^{7A}$, —$CONR^{7A}R^{7B}$, —$NO_2$, —$SR^{7A}$, —$SO_3R^{7A}$, —$SO_4R^{7A}$, —$SO_2NR^{7A}R^{7B}$, —$NHNR^{7A}R^{7B}$, —$ONR^{7A}R^{7B}$, —NHC(O)$NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment W48. The method of Embodiment W47, wherein the compound of Formula (VII) is a compound of Formula (VIIA) or a pharmaceutically acceptable salt thereof:

(VIIA)

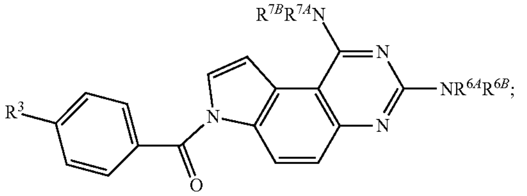

wherein $R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment W49. A method of treating cancer in a patient in need thereof, wherein the cancer expresses an elevated level of METTL16 relative to a control, the method comprising administering to the patient an effective amount of the compound of Formula (VIII) or a pharmaceutically acceptable salt thereof:

(VIII)

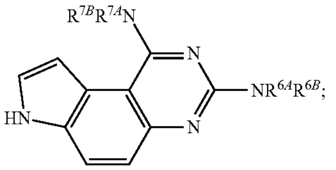

wherein: $R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment W50. The method of Embodiment W49, wherein $R^{6A}$, $R^{6B}$, $R^{7A}$, and $R^{7B}$ are hydrogen

EXAMPLES

The following examples are for purposes of illustration and are not intended to limit the spirit or scope of the disclosure or claims.

Example 1

Materials and Methods

Cell culture. For human leukemia cell lines, U937, HEL, THP1, NOMO-1, ML-2, NB4 and RS4-11 were maintained in RPMI1640 medium supplemented with 10% fetal bovine serum (FBS); KG-1A, MA9.3ITD, MA9.3RAS, kasumi-1 were cultured in IMDM supplemented with 20% FBS; MV4-11 and K562 were grown in IMDM medium with 10% FBS; MONOMAC-6 were maintained in RPMI1640 supplemented with 10% FBS, 2 mM L-glutamine, non-essential amino acid, 1 mM sodium pyruvate and 10 ug/ml human insulin. SUP-B15 was maintained in IMDM with 20% FBS, 4 mM L-glutamine adjusted to contain 1.5 g/L sodium bicarbonate and 0.05 mM 2-mercaptoethanol. U937, HEL, THP1, K562, MV4-11, RS4-11 and SUP-B15 were purchased from the American Type Culture Collection, and NOMO-1, ML-2, NB4 and MONOMAC-6 were obtained from DSMZ. MA9.3ITD (MLL-AF9 plus FLT3-ITD-transformed human CD34+ cord blood cell), MA9.3RAS (MLL-AF9 plus NRasG12D-transformed human CD34+ cord blood cell) were established by Dr. James Mulloy (Wunderlich et al, Blood, 121(12):e90-97 (2013). Human lymphoma cell line DG-75 was kept in RPMI1640 supplemented with 10% FBS, and CA-46 was kept in RPMI1640 supplemented with 20% FBS. These two cell lines were purchased from the American Type Culture Collection. Cervical cancer cell line Hela were obtained from the American Type Culture Collection and maintained in EMEM supplemented with 10% FBS. Pancreatic cancer cells co1o357 was kindly provided by Dr. Ravi Salgia from City of Hope, and cultured in RPMI1640 with 10% FBS. The glioblastoma cell lines, including T98G, LN229, A172 and U87MG were provided by Dr. David Plas from University of Cincinnati, and cultured in RPMI1640 with 10% FBS. HEK-293T obtained from the American Type Culture Collection and Lenti-X 293T obtained from Takara were maintained in DMEM with 10% FBS. Penicillin-Streptomycin (15140122, Life Technologies) and plasmocin prophylactic (Applied Biological Materials Inc.) were added into all the mediums to protect cells from potential contamination. All the cells are not among commonly misidentified cells lines, and were routinely tested for mycoplasma contamination using a PCR Mycoplasma Test Kit (PromoKine).

Retrovirus and lentivirus production. The retrovirus vectors and packaging vector pCL-ECO were co-transfected into HEK-293T cells using Effectene Transfection Reagent (301427, Qiagen, Valencia, CA). After 48 and 72 hours of transfection, the retrovirus were collected, and added into mouse progenitor cells in the presence of polybrene. The cells are spun for 2 hours at 1,800 rpm at 32° C.

Lentivirus was packaged with pMD2. G, pMDLg/pRRE and pRSV-Rev (purchased from Addgene). $3\times10^6$ Lenti-X 293T cells were seed in a 100 mm dish. When the dishes were 40-80% confluent, 5 μg plasmids were transfected into Lenti-X 293T cells with 1.5 μg pMD2. G, 0.9 μg pMDLg/pRRE, 2.1 μg pRSV-Rev in 100 mm cell culture dish with Effectene Transfection Reagent. The lentivirus particles were harvested at 48 and 72 hours after transfection, filtered with a low-protein binding 0.45 μM sterile filter and concentrated with PEG-it Virus Precipitation Solution (#LV810A-1, SBI), and infected cells with existence of polybrene.

RNA extraction, cDNA synthesis and qPCR. Total RNA was extracted from cultured cell lines using QIAzol regent (#79306, QIAGEN). RNA concentration and purity were detected using the Nanodrop 2000. From a starting amount of 200 ng-1000 ng of total RNA or immunoprecipitated RNA samples, cDNA was generated in 20 ul reaction volume using QuantiTect Rev. Transcription Kit (205314, Qiagen). Real-time PCR analysis were carried out with SYBR Green qPCR Master Mix (2×) (FEPK0253, Thermo Fisher) and results were normalized to reference gene, GAPDH or ACTB. The quantitative reverse transcription-PCR was performed on an AB 7900HT Fast Real-Time PCR system (Applied Biosystem). Each reaction was performed in triplicate. The relative gene expression level analysis was calculated using $2^{-\Delta\Delta Ct}$ method.

Protein extraction and Western Blot assay. Total protein were extracted by RIPA lysis buffer (R0278, Sigma-Aldrich) with Halt™ protease inhibitor cocktail (78429, Thermo Fisher Scientific) and Halt™ Phosphatase Inhibitor Cocktail (78420, Thermo Fisher Scientific). Protein concentration was measured using BCA method for Western blotting. Then protein sample were denatured at 99° C. for 10 min. Protein samples (20 ug/lane) were separated by 10% SDS-PAGE electrophoresis, and then transferred to 0.45 um PVDF Transfer Membranes (88518, Thermo Fisher Scientific), incubated with a specific primary antibody. Finally, the membranes were visualized using the pierce ECL Western blotting Substrate (PI32106, Thermo Fisher) or Amersham™ ECL™ Prime Western Blotting Detection Reagent (RPN2232, GE Healthcare). The primary antibodies used in this study as follows: METTL16 (HPA020352, Sigma-Aldrich), GAPDH (sc-47724, Santa Cruz Biotechnology), CRISPR-Cas9 (MBS1750147, MyBioSource), DHFR (15194-1-AP, Proteintech).

Cell viability and proliferation assay. Cell viability and proliferation were performed with CellTiter 96 Non-Radioactive Cell Proliferation Assay (MTT, G400, Promega). To verify the function of METTL16 inhibitor, cancer cells were seeded into 96-well plate and treated with a series of drug concentration in triplicates. For the cell proliferation with METTL16 knockdown stable cell lines were seeded into 96-well plates, and cultured in the incubator at 37° C. with 5% CO2. 15 μl of the Dye Solution was added into each well. After incubation of 2-4 h, 100 μl of the Solubilization Solution/Stop Mix was added to each well. Finally, the absorbance was determined at 570 nm on the next day.

Cell apoptosis assays. Cell apoptosis was detected by PE Annexin V Apoptosis Detection Kit I (559763, BD Biosciences). Briefly, $1\times10^6$ cells were collected, washed with PBS and re-suspended in 100 ul 1× binding buffer. Then, cells were stained in PE Annexin V and 7-AAD in room temperature for 15 min. Fortessa X20 was chosen to assess the apoptotic cells. FlowJo V10 software was chosen for statistical analysis.

Serial colony-forming assay. This assay was conducted as described previously with some modification. The primary murine leukemic cells were collected from bone marrow of AML mice induced by MLL-AF9. 20000 Cells for each dish were seeded into ColonyGEL methylcellulose medium (ReachBio, Seattle, WA) including 10 ng/ml of murine recombinant IL-3, IL-6, GM-CSF and 30 ng/ml of murine recombinant SCF, along with 1.0 mg/ml of G418 (GIBCO BRL, Gaithersburg, MD) and/or 2.5 μg/ml of puromycin (Sigma-Aldrich). The dishes were incubated at 37° C. in a humidified atmosphere of 5% CO2 for 6 to 7 days. Colony numbers were then counted and compared for each passage, and serial replating was performed for 3 passages.

Secondary bone marrow transplantation (BMT) assays with MLL-AF9 (MA9) AML. For primary BMT assays, 6- to 8-week-old C57BL/6J CD45.2 (B6) mice were treated with 5-fluorouracil (5-FU). After treatment for 5 days, bone marrow cells were collected. Then Lin (lineage positive cell-depleted) BM were isolated with Lineage Cell Depletion Kit (130-090-858, Miltenyi Biotec) and then transduced with a retrovirus encoding MLL-AF9 fusion gene. The transduced cells were maintained in ColonyGEL methylcellulose medium for 7 days with G418 selection. 6- to 8-week-old C57BL/6J CD45.1 (B6) recipient mice were prior to lethally irradiation at 960 rads. For each recipient mouse, $0.5\times10^6$ donor cells and $1\times10^6$ helper cells (isolated from bone marrow of healthy 6- to 8-week-old C57BL/6J CD45.1 (B6) mice) were transplanted by tail vein injection. For secondary BMT assays, primary leukemia BM cells ($CD45.2^+$) sorted by flow were re-injected into recipient mice (CD45.1). After 26 days of transplantation, the peripheral blood samples of all recipient mice were collected at the same time for a peripheral blood smear and analyzed for the engraftment of leukemia cells by FACS. Once the recipient mice exhibited classical AML symptoms including hunched posture, paralysis, and reduced body weight, the mice were euthanized by CO2 inhalation; the spleen, liver samples and BM cells were collected for further analysis.

Flow cytometry analysis. Stable METTL16 knockdown NB4 cells were induced to myeloid differentiation for 48 h by 200 nM ATRA (223018, Sigma-Aldrich). The cells were stained with PE-conjugated anti-CD11b (101208, BioLegend) and APC-conjugated anti-CD14 (17-0149-41, eBioscience) at 4° C. for 30 min, washed with PBS, and resuspended in IC Fixation Buffer (00-8222-49, eBioscience) before subjected to FACS analysis. The PB cells collected from mice were treated with ammonium Chloride Solution (07850, Stemcell technology) to deplete red blood cells. The cells were then blocked with anti-mouse CD16/32 (156612, BioLegend), stained with anti-CD45.1 (110706, BioLegend) and anti-CD45.2 (109806, BioLegend) at 4° C. in Flow Cytometry Staining Buffer (50-112-9748, Fisher Scientific) for 30 min and resuspended in IC Fixation Buffer (00-8222-49, eBioscience) before loaded for flow cytometry analysis.

$m^6A$ dot blot assay. Total RNA was purified with QIAzol regent, and mixed well with 3 volumes of RNA incubation buffer, then denatured at 65° C. for 5 minutes and cooling down on ice immediately. 200 ul of 10×SSC buffer (S6639, Sigma-Aldrich) was loaded onto the Amersham Hybond-N+ membrane for each well to pre-wet the membrane. Then one volume of 20×SSC buffer was added into the RNA samples before dotted onto the membrane. The UV irradiation was used to crosslink RNA to the membrane. After crosslink, the membrane was stained by 0.02% methylene blue and scanned as loading control. Then, the membrane was blocked with 5% nonfat dry milk at room temperature for 1 h and incubated with anti-m6A antibody (1:2000, Synaptic Systems) overnight at 4° C. Next day, the membrane was incubated with the HRP-conjugated goat anti-rabbit IgG (ab6721, abcam) at room temperature for 1 h and developed with pierce ECL Western blotting Substrate (PI32106, Thermo Fisher).

Drug Affinity Responsive Targets Stability (DARTS). DARTS was conducted as described previously with some modifications (Lomenick et al, Current Protocols in Chemical Biology, 3(4):163-180 (2011)) and aimed to identify the potential binding between METTL16 and molecular compound CDH24. In short, $4\times10^7$ U937 cells were collected, washed with chilled PBS, and lysed in 600 ul M-PER (78501, Thermo Fisher Scientific) supplement with protease inhibitor cocktail and phosphatase inhibitor cocktail. The cells were lysed on ice for 10 min, and centrifuged at 18,000 g for 10 min at 4° C. The supernatant was carefully transferred to a new tube. 10× TNC buffer (500 mM Tris-HCl with pH 8.0, 500 mM NaCl, 100 mM $CaCl_2$) was added into lysate, the protein concentration was then detected by BCA assay. The protein concentration diluted with 1× TNC buffer was adjusted to 5 ug/ul. The lysate was incubated with varying concentration of CDH24 or DMSO at room temperature for 2 h, and digested with Pronase (1:2000 for FTO) (10165921001, Roche) for 30 minutes. The reaction was quenched by addition of protease inhibitor cocktail and the sample was immediately placed on ice. 4× Laemmli Sample Buffer was added to lysate and denatured at 99° C. for 10 min. Finally, western blotting was used to determine the abundance of METTL16.

Cellular Thermal Shift Assay (CETSA). To validate the direct binding between CDH24 and METTL16 in cellular, CETSA was performed as previously described with some modification (Jafari et al, Nat Protoc., 9(9):21000-2122 (2014)). Briefly, $2\times10^7$ U937 cells were pretreated with 50 μM CDH24 or DMSO for 1 h; collected and washed with chilled PBS. Then, the cells were re-suspended in 1.5 ml PBS supplemented with protease inhibitor cocktail. And the cells were distributed into 10 different 200 ul 8-strip PCR tubes with 100 ul for each tube, heat shocked in the Bio-Rad T100 Thermal Cycler at indicated temperature for 3 min to denature proteins, and immediately cooled down at room temperature for 3 min. cells were lysed using dry ice and two repeated cycles of freeze-thaw, then centrifuged at 20,000 g for 20 min at 4° C. Soluble proteins, collected from the supernatant were denatured with 4× Laemmli Sample Buffer at 99° C. for 10 min. Finally, the protein samples were analyzed by western blot.

Gene-specific m6A qPCR. U937 and MA9.3RAS with high level of METTL16 were treated with CDH24 for 72 h. m6A RNA immunoprecipitation (MeRIP) was performed with Magna MeRIP m6A kit (17-10499, Millipore) according to the manufacturer's instructions with some modification. Total RNA was collected with QIAzol, fragmented to approximately 100 nt in length and purified with RNeasy MinElute Cleanup Kit (74204, QIAGEN). 1/10 of RNA was taken out as input control, the left RNA was distributed into two groups, and incubated with m6A antibody (1:2000, Synaptic Systems) or mouse IgG-conjugated Protein A/G Magnetic Beads at 4° C. overnight. The Methylated RNAs were competitively eluted by 20 uM m6A salt and purified with RNeasy MinElute Cleanup Kit. 1/3 immunoprecipitated RNA was used for reverse transcription PCR. Finally, we performed gene-specific $m^6A$ qPCR to determine the $m^6A$ abundance on the transcripts.

Quantification and statistical analysis. Data were analyzed with GrapPad Prism 7 and were presented as mean±SEM or mean±SD as indicated. Two-tailed Student's t test was used to compare means between groups as indicated; P<0.05 was considered significant. Kaplan-Meier survival curves were plotted with GraphPad Prism 7 and the P values were calculated using the log rank test. For Western blot results, representative figures from three biological replicates were shown. Densitometry analysis of the bands from Western blot were performed with Gel-Pro analyzer and normalized to the loading controls.

Figure 2A:
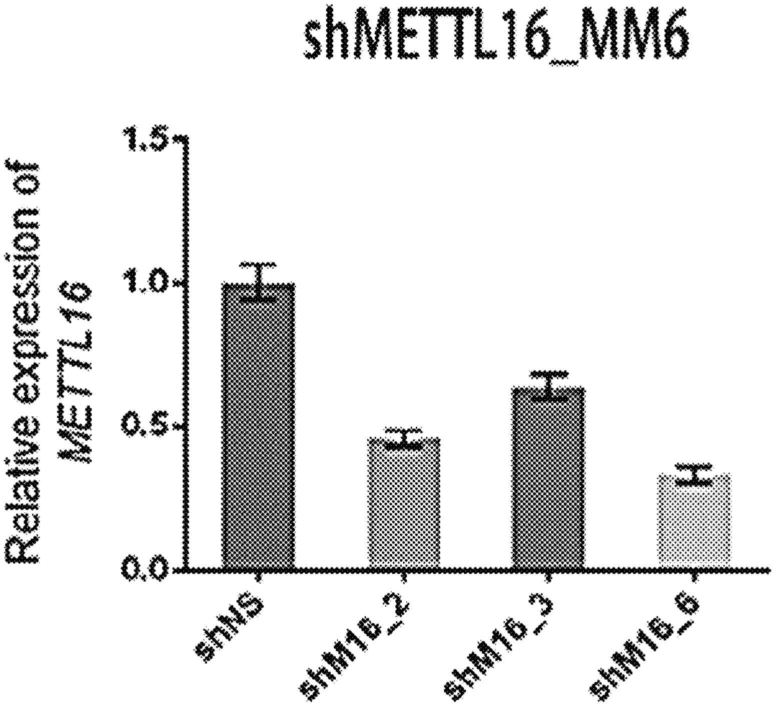
FIGS. 2A-2J show that knockdown of METTL16 suppresses AML cell growth and promotes apoptosis.
Figure 2B:
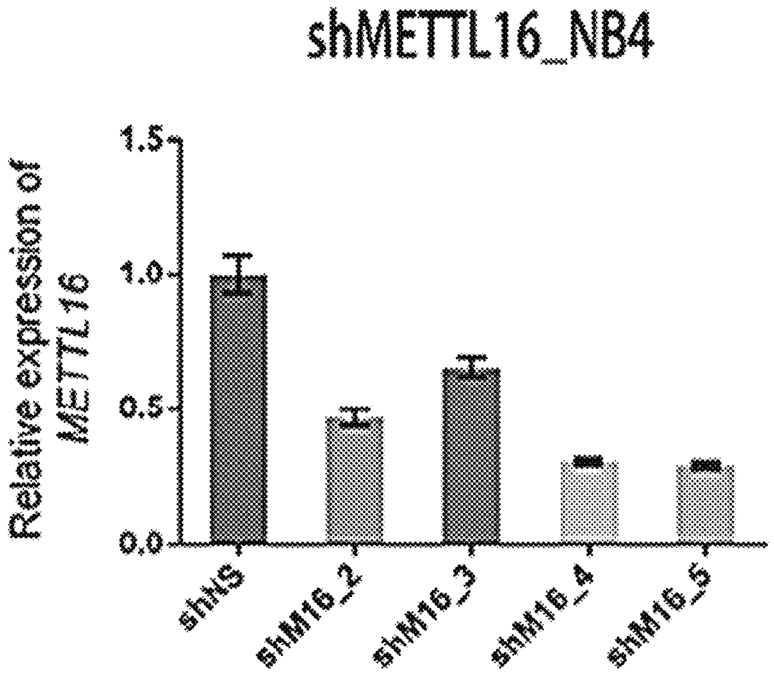
Figure 2C:
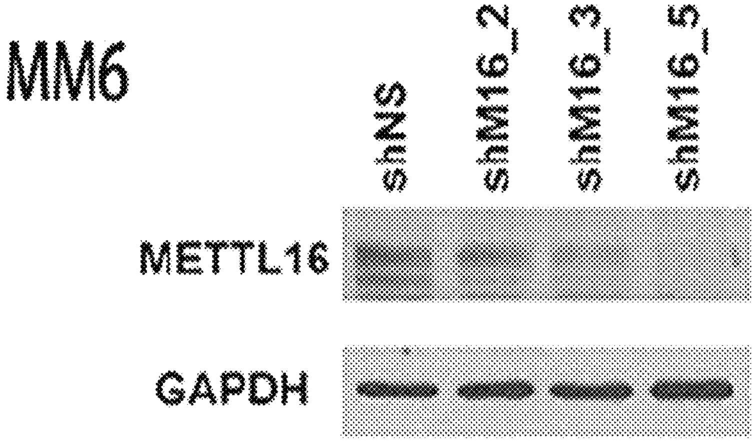
Figure 2D:
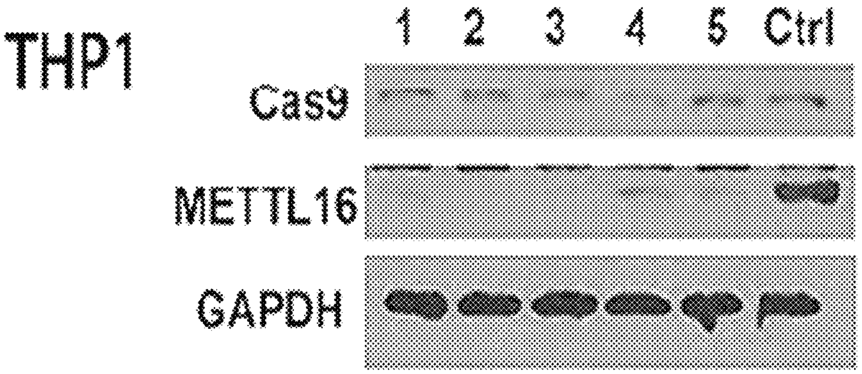
Figure 2E:
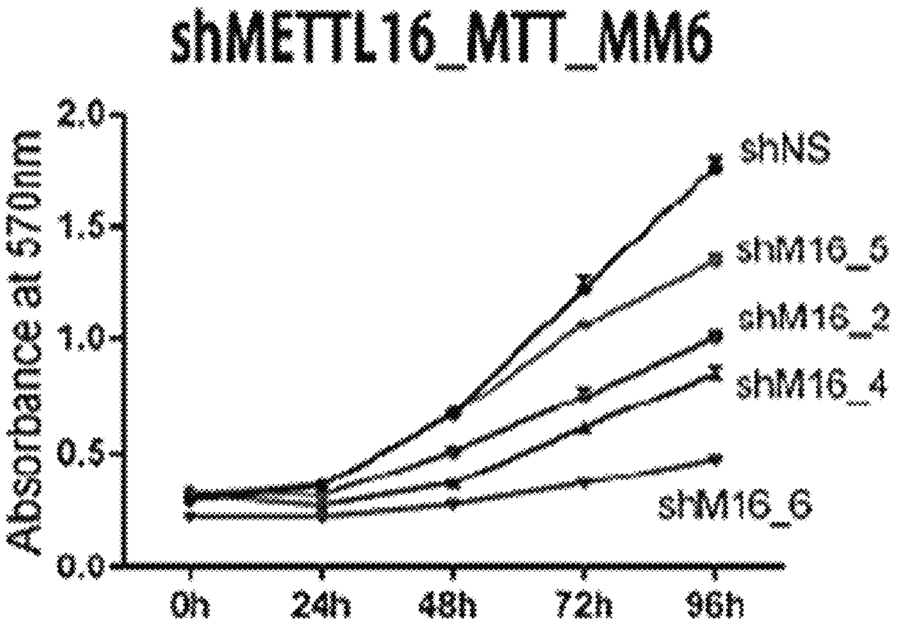
Figure 2F:
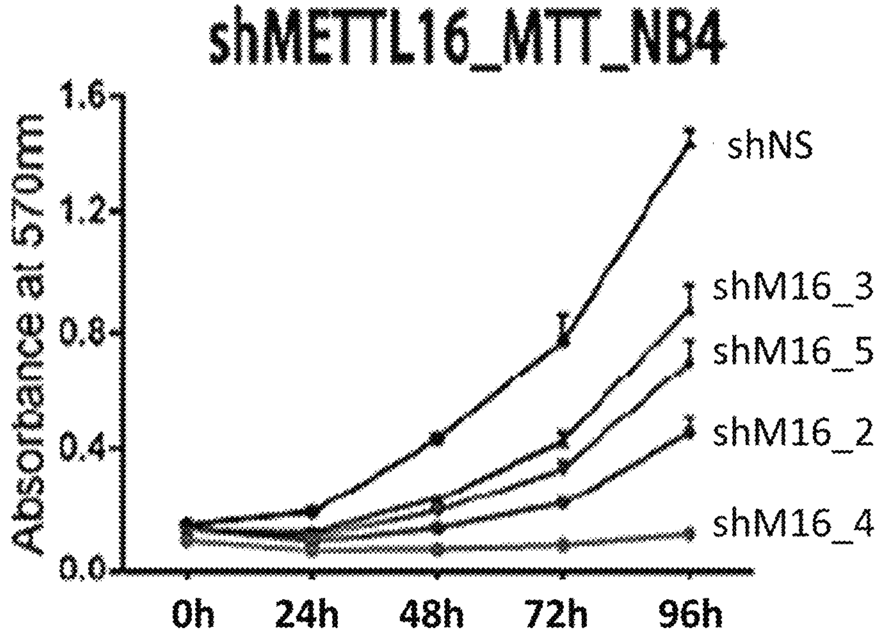
Figure 2G:
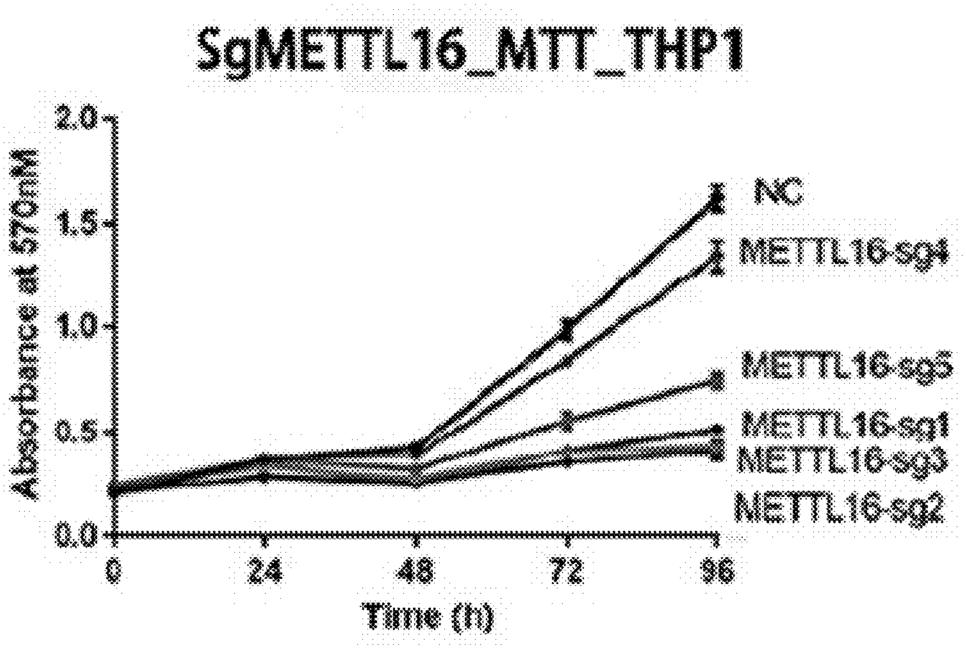
Figure 2H:
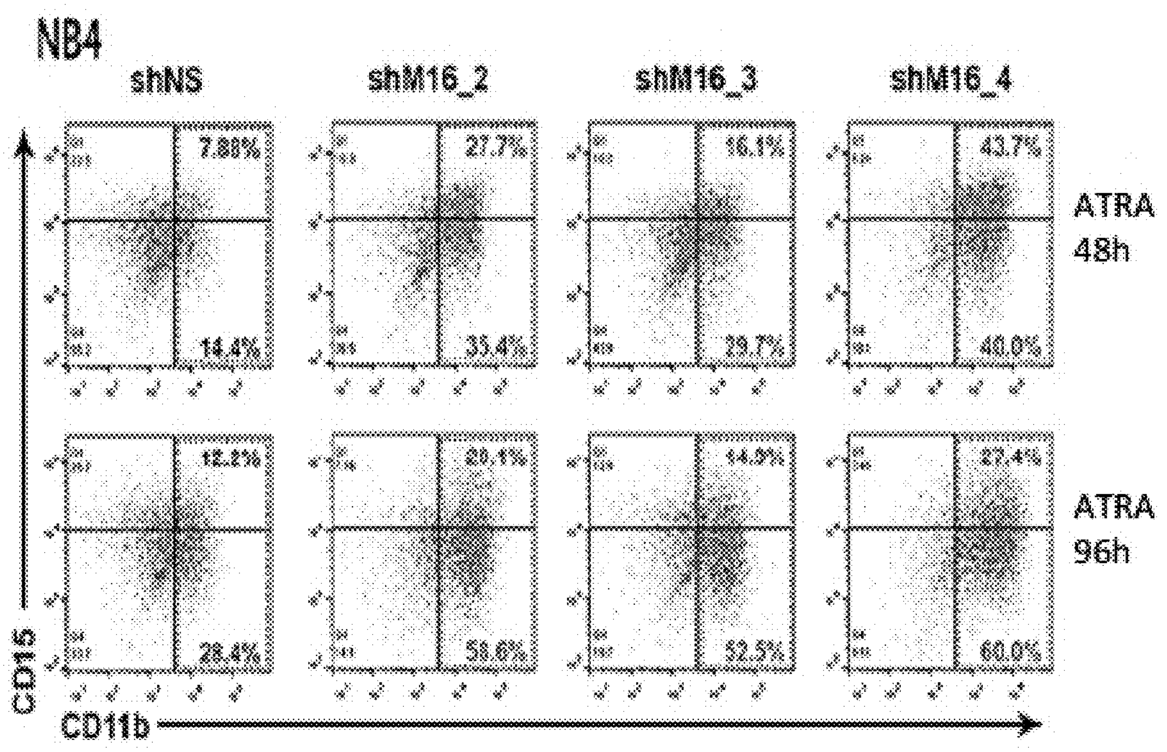
Figure 2I:
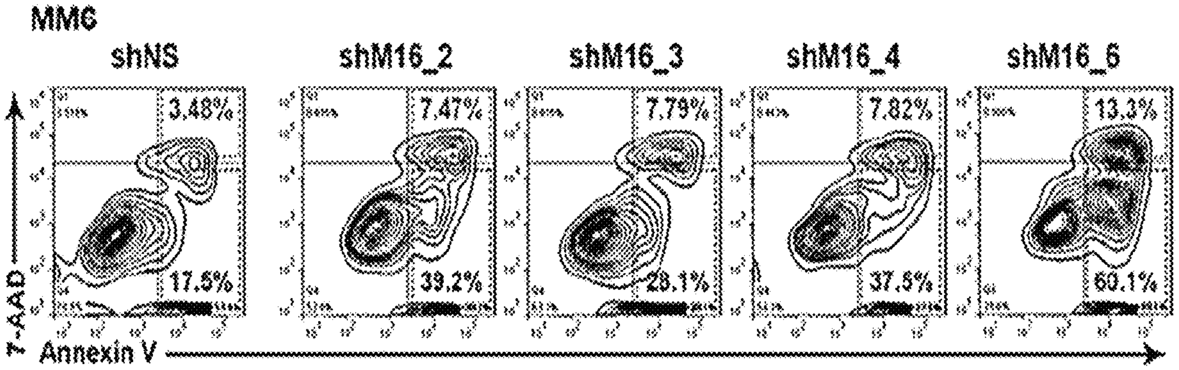
Figure 2J:
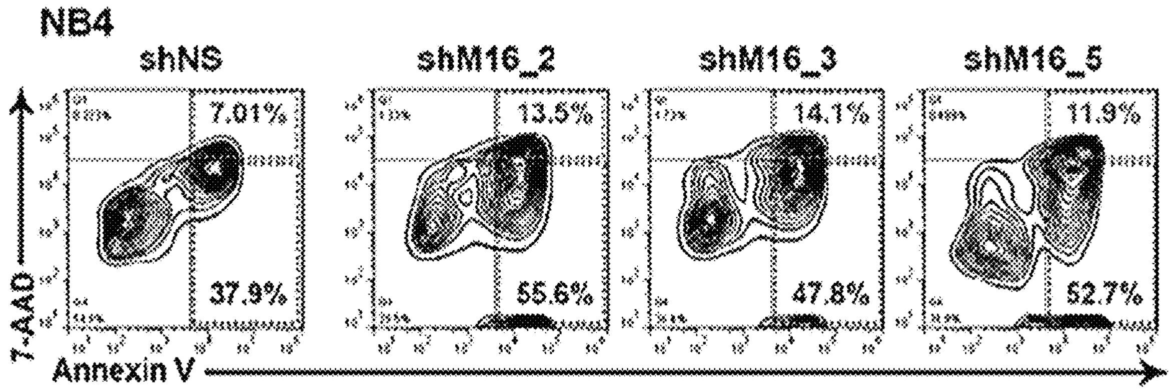
Figure 21:
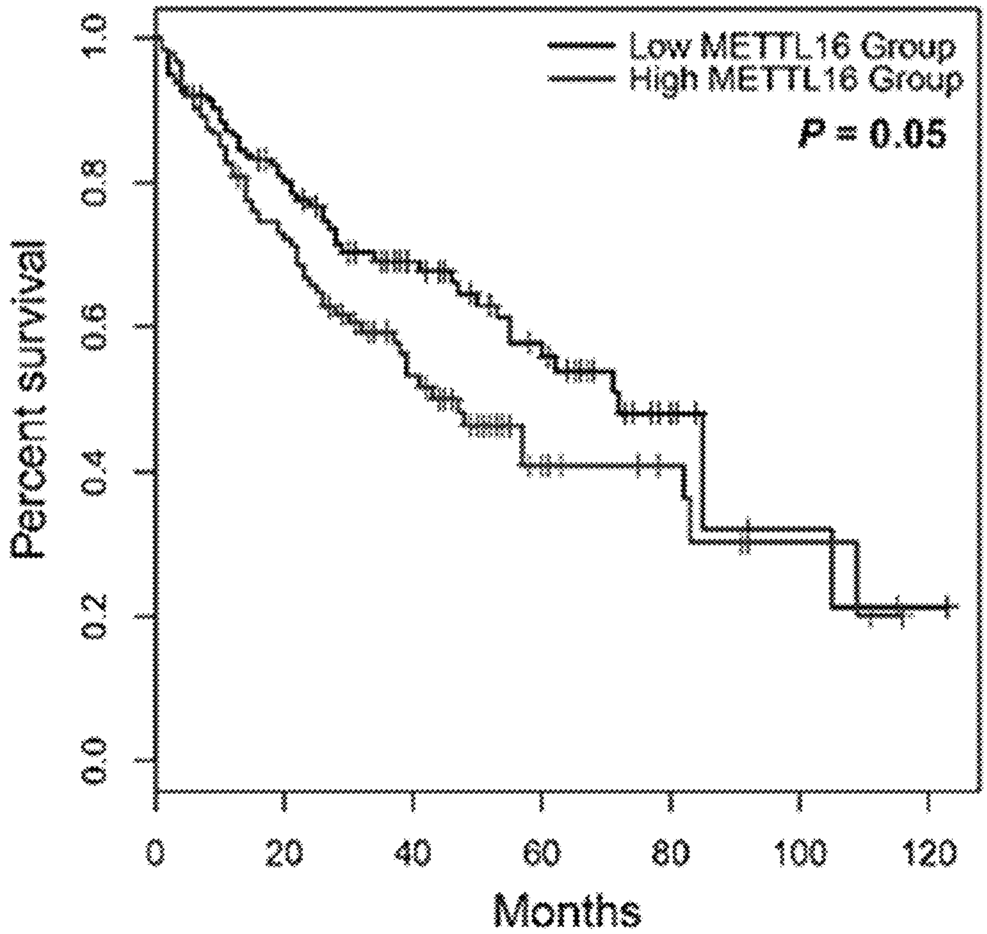
FIG. 21 shows that high expression of METTL16 relates to a poor survival in liver cancer patients. Overall survival analysis of METTL16 in patients with hepatocellular carcinoma (HCC) from the TCGA dataset. The raw data were derived from GEPIA2 (Gene Expression Profiling Interactive Analysis, http://gepia2. cancer-pku.cn/#survival).

FIGS. 2A-2B provide qRT-PCR confirmation of knockdown of METTL16 by shRNAs in MONOMAC-6 (MM6) (FIG. 2A) and NB4 AML cells (FIG. 2B). FIGS. 2C-2D provide a Western blot confirming the down-regulation of METTL16 protein induced by shRNA knockdown in MM6 cells (FIG. 2C) or CRISPR-Cas9 knockout in THP1 cells (FIG. 2D). FIGS. 2E-2G show the effects of depletion of METTL16 expression on AML cell growth/proliferation in MM6 (FIG. 2E), NB4 (FIG. 2F) and THP1 (FIG. 2G). AML cells as detected by MTT assays. FIGS. 2H-2J show the effect of METTL16 knockdown on cell differentiation in NB4 AML cells (FIG. 2H) or apoptosis in MM6 (FIG. 21) and NB4 AML cells (FIG. 2J). In FIGS. 2A-2J: *p<0.05; p<0.01; *p<0.001; t test. Error bars, mean±SEM (n≥3).

Figure 3A:
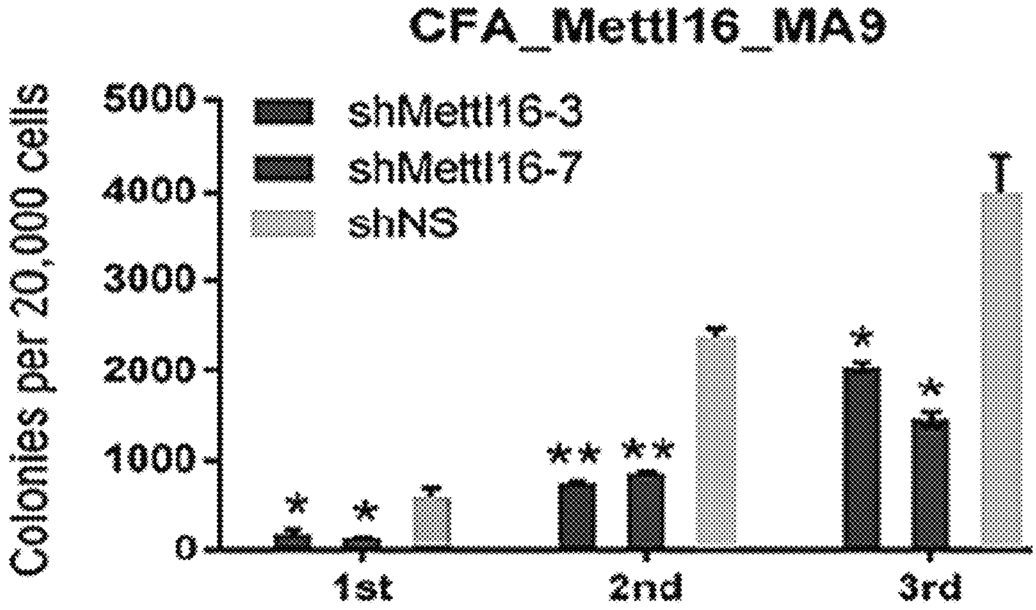
FIGS. 3A-3H show that METTL16 plays a critical role in AML development and maintenance.
Figure 3B:
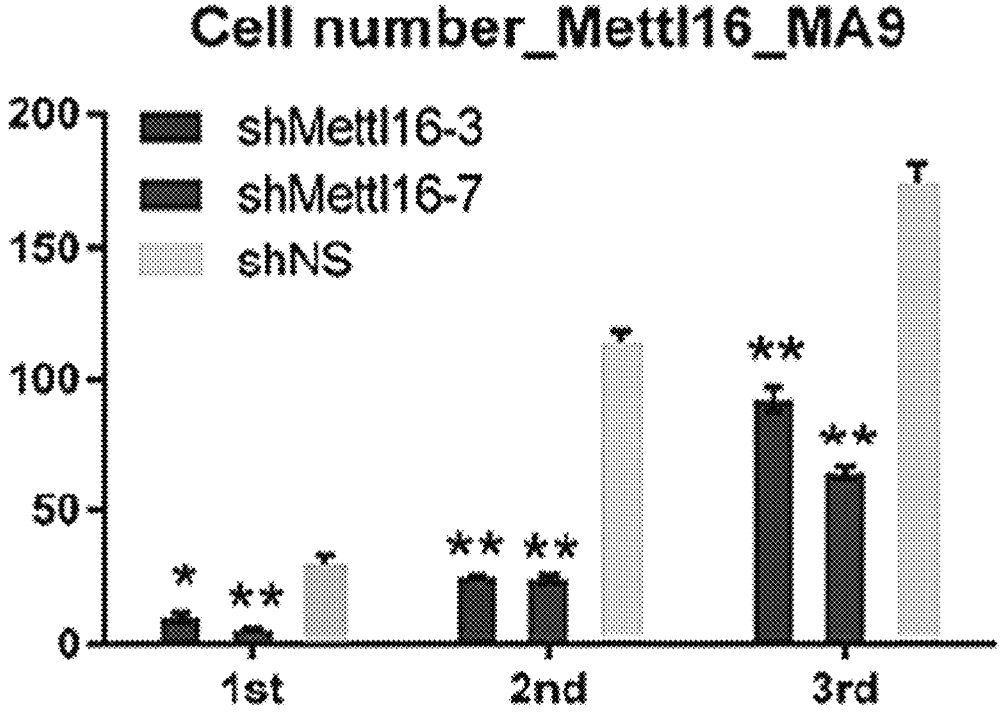
Figure 3C:
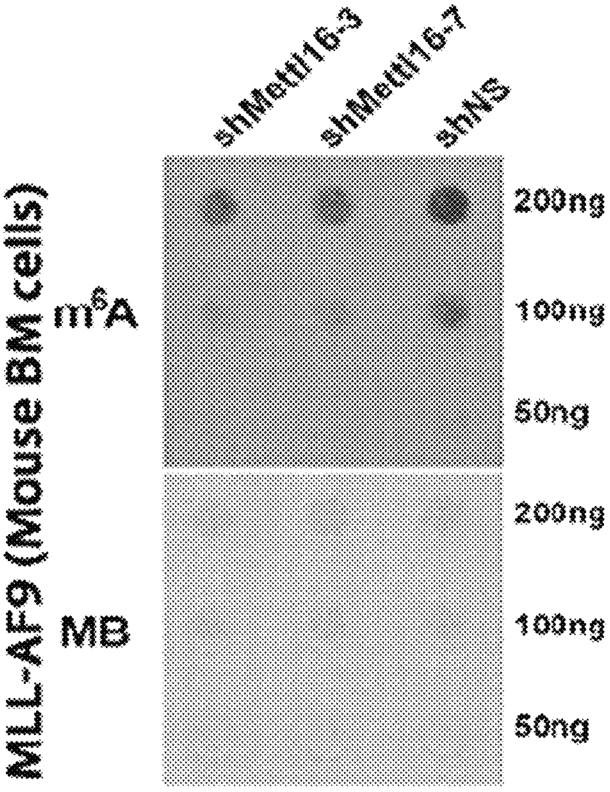
Figure 3D:
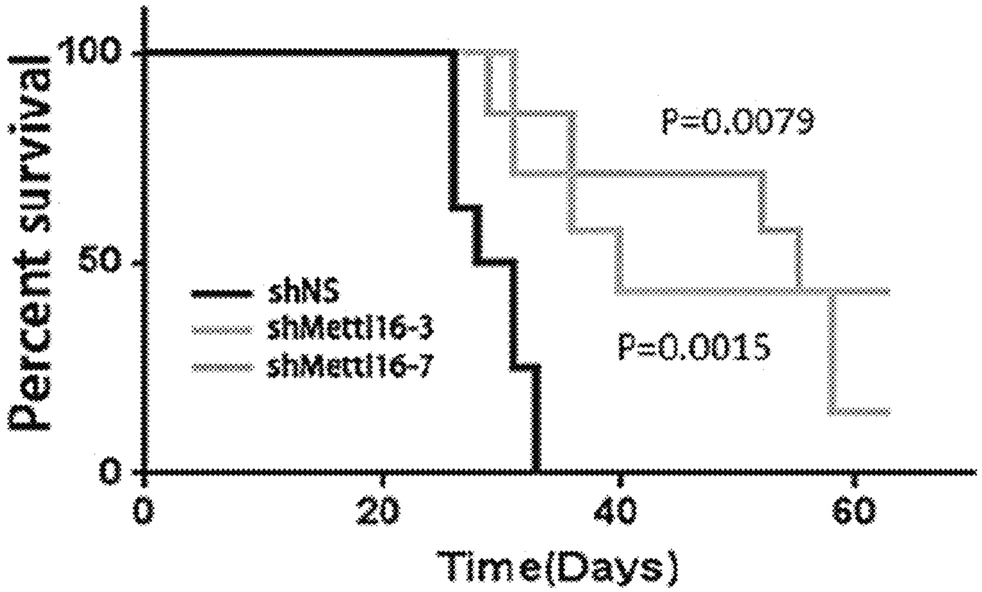
Figure 3E:
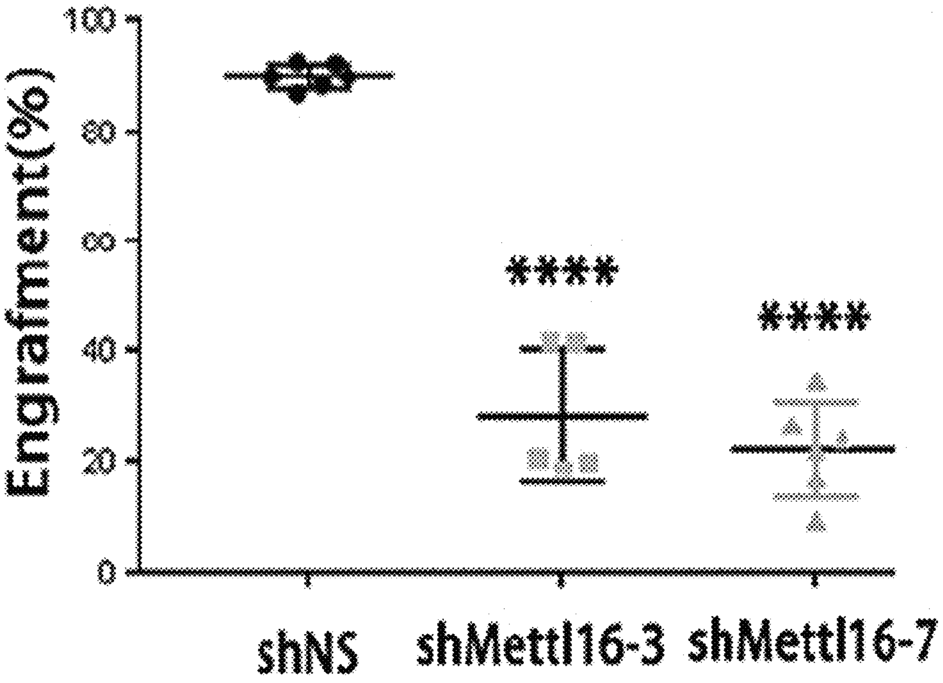
Figure 3F:
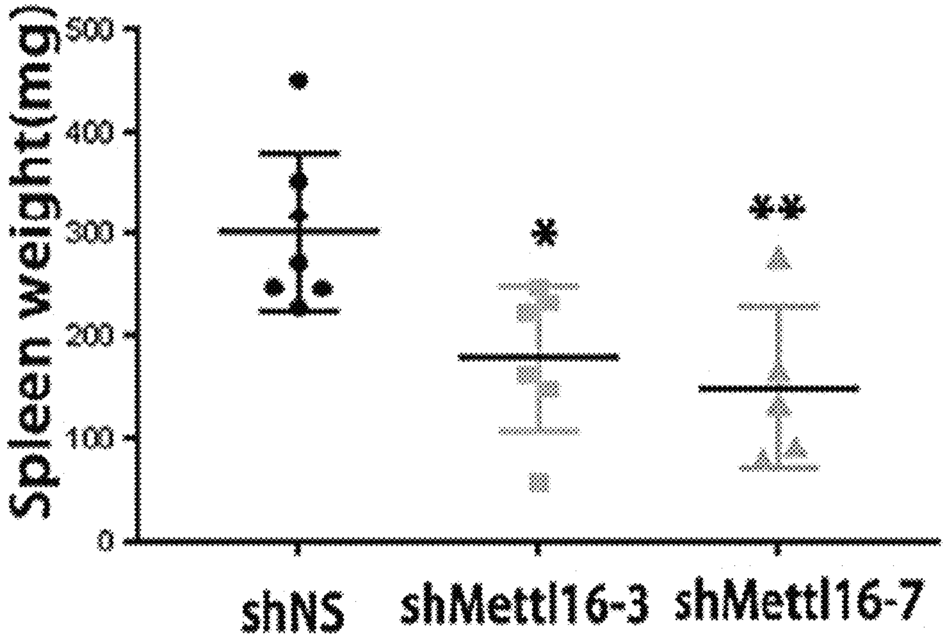
Figure 3G:
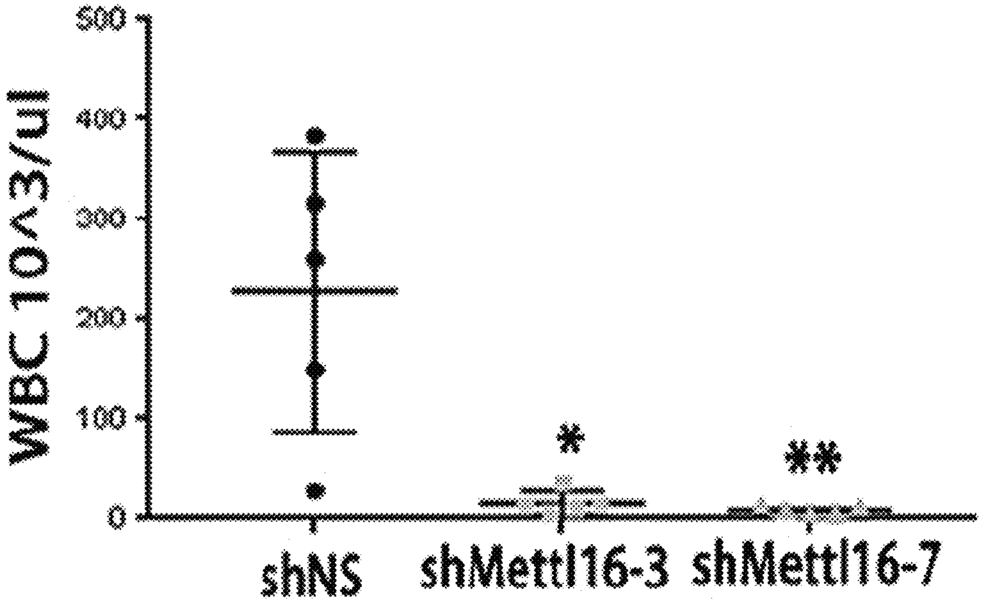
Figure 3H:
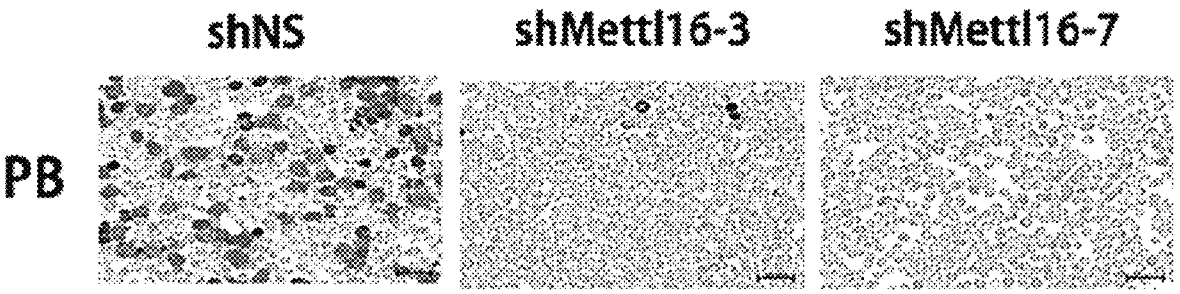

FIGS. 3A-3B show the effect of knockdown of Mettl16 on colony forming ability of primary murine MLL-AF9 (MA9) leukemic cells in vitro. $Lin^-$ BM cells from WT CD45.1 mice were transduced with MSCVneo-MLL-AF9 (MA9) plus shMettl16 (shMettl16-3 and -7) or control shRNA (shNS; control) and seeded for colony-forming/replating assays. Colony (FIG. 3A) or cell (FIG. 3B) numbers were compared between Mettl16 knockdown groups and the control group. FIG. 3C shows cells collected from the first round of plating in FIG. 3A were subjected to RNA extraction for detection of global $m^6A$ abundance with $m^6A$ dot blot assays. MB, a methylene blue staining served as loading control. FIGS. 3D-3G show the effect of Mettl16 knockout on the progression of MA9-induced AML in secondary bone marrow transplantation (BMT) recipient mice. Kaplan-Meier survival curves are shown in FIG. 3D, while engraftment is shown in FIG. 3E, spleen weight is shown in FIG. 3F, and white blood cell (WBC) is shown in FIG. 3G. FIG. 3H provides Wright-Giemsa staining of peripheral blood (PB) collected from the secondary BMT recipient mice on day 26 post-transplantation. Black bar represents 50 μm. With reference to FIGS. 3A-3H: *p<0.05; p<0.01 *p<0.001; t test. Error bars, mean±SEM (n≥3). For Kaplan-Meier curve, p values were calculated by log-rank test.

Figure 4A:
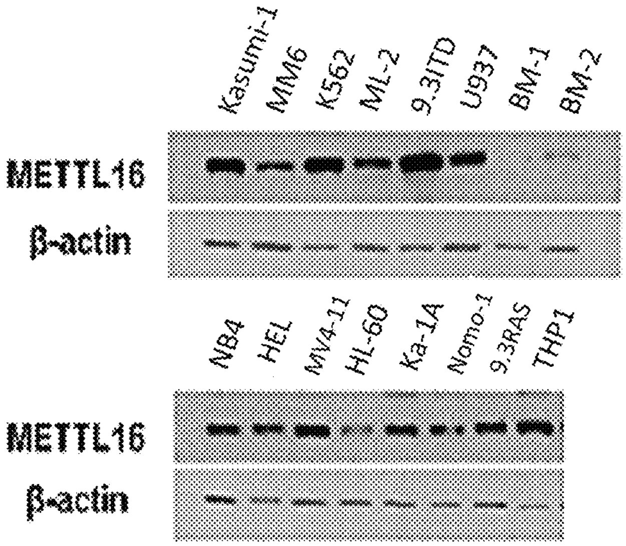
FIGS. 4A-4K show the inhibitory effect of CDH24 (compound of Formula (A)) on cell viability and growth in AML and other cancers.
Figure 4B:
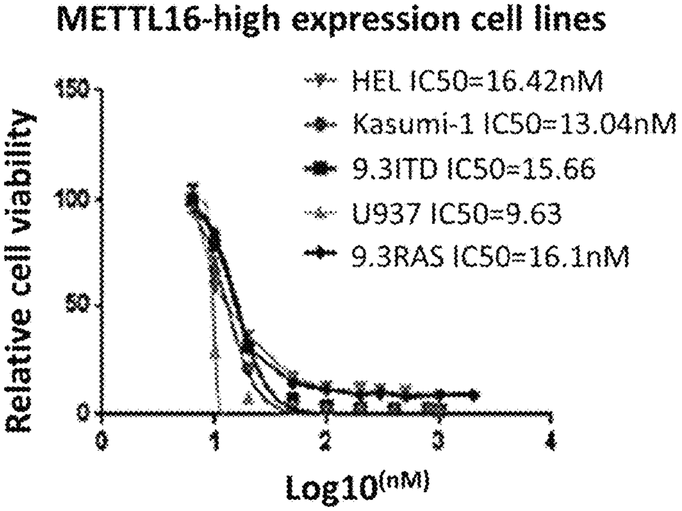
Figure 4C:
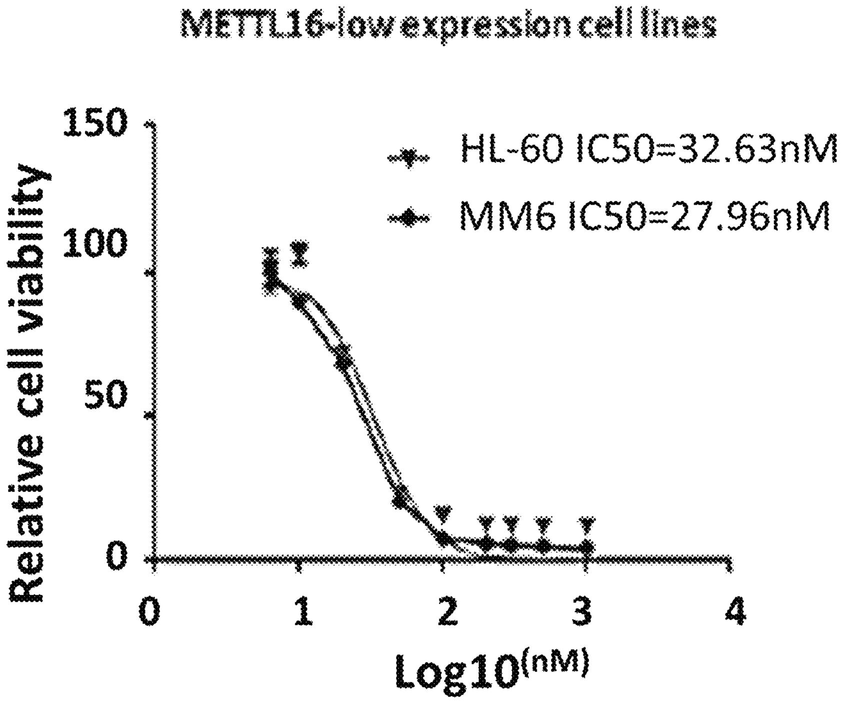
Figure 4D:
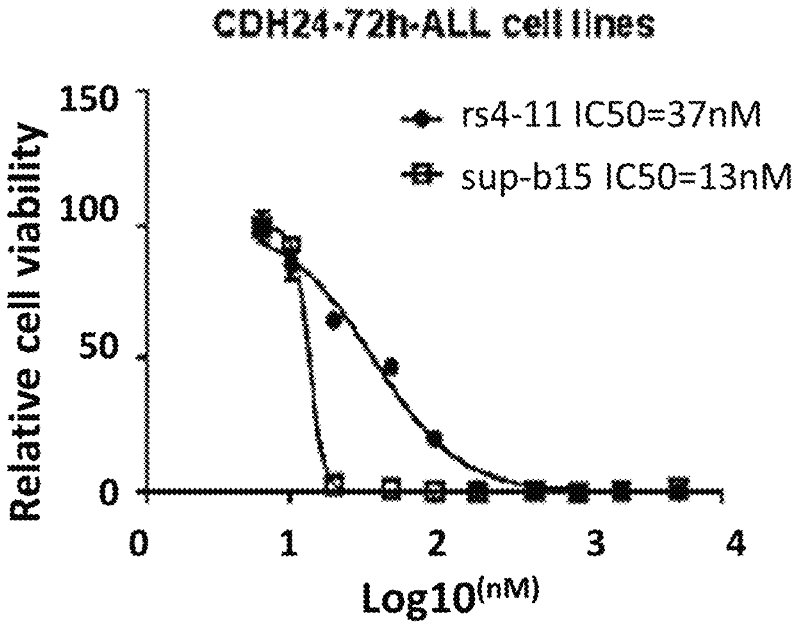
Figure 4E:
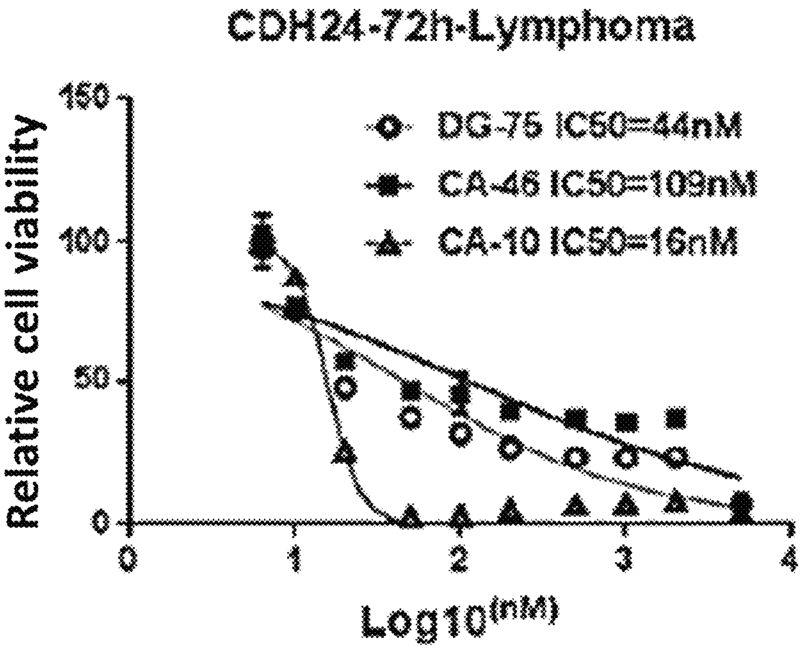
Figure 4F:
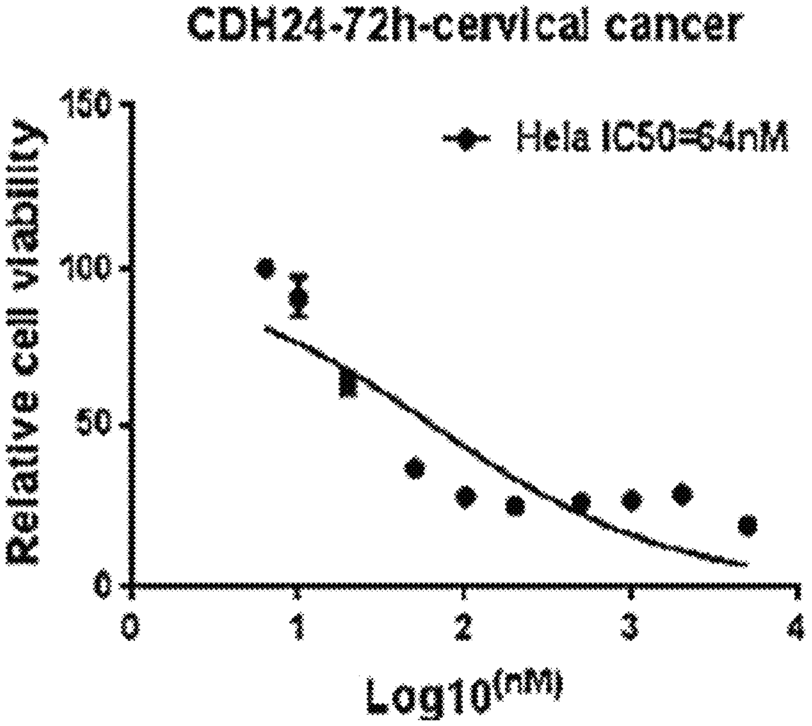
Figure 4G:
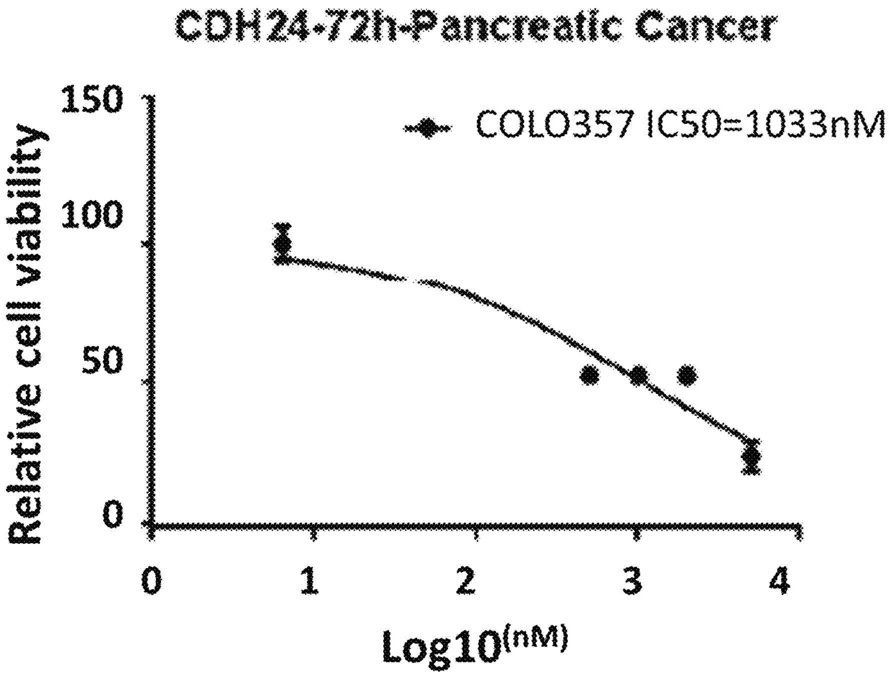
Figure 4H:
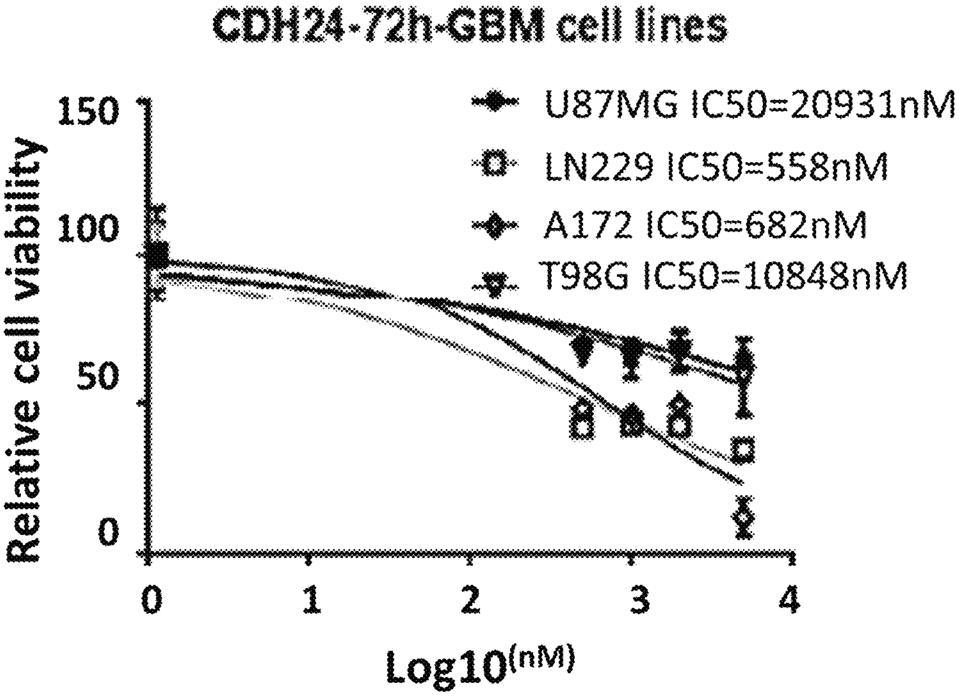
Figure 4I:
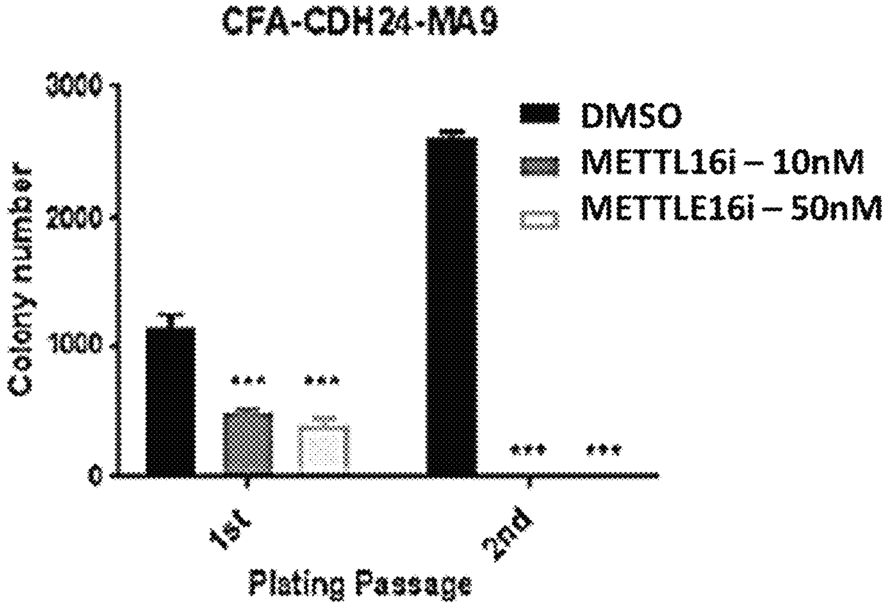
Figure 4J:
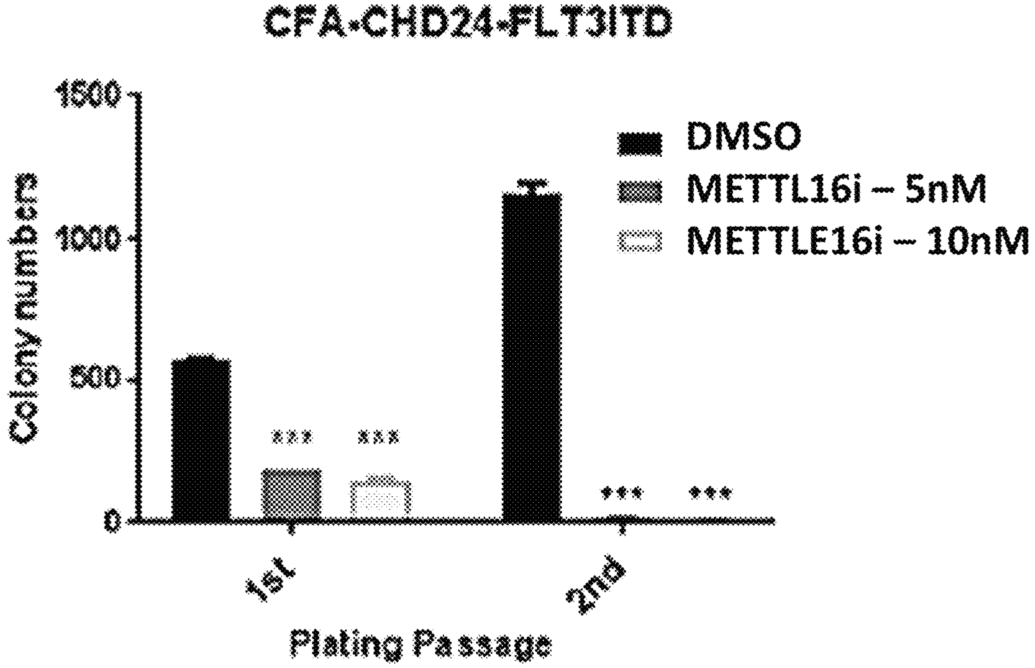
Figure 4K:
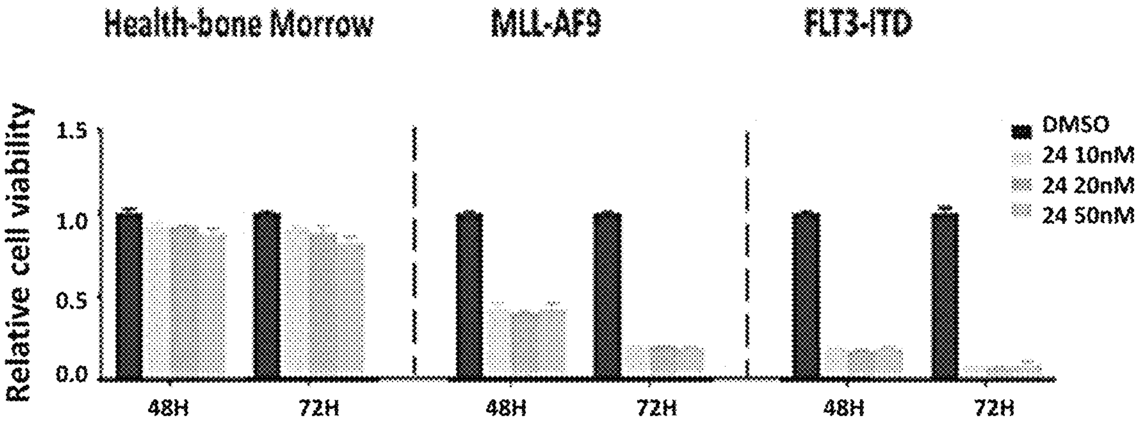

FIG. 4A provides a Western blots analysis showing the levels of METTL16 expression in various AML cell lines (Kasumi-1, MONOMAC6 (MM6), K562, ML-2, 9.3ITD, U937) and normal bone marrow (BM) mononuclear cells. Actin served as a loading control. FIGS. 4B-4C show the CDH24 $IC_{50}$ values on inhibition of cell viability in AML cell lines expressing relative high (FIG. 4B) or low (FIG. 4C) levels of METTL16. The values were detected by MTT assays 72 hours post treatment of CDH24 with a series of concentrations. FIGS. 4D-4H show the inhibitory effects of CDH24 treatment on cell viability in acute lymphoblastic leukemia (ALL) (FIG. 4D), lymphoma (FIG. 4E), cervical cancer (FIG. 4F), pancreatic cancer (FIG. 4G), and glioblastoma (GBM) (FIG. 4H) cell lines. The values were detected by MTT assay 72 hours post treatment of CDH24 with a series of concentrations. FIGS. 4I-4J show the effect of CDH24 treatment on colony forming ability of primary murine MLL-AF9 (MA9) AML cells (FIG. 4I), or primary murine FLT3-ITD/NPM1-mutant (FLT3/ITD) AML cells (FIG. 4J). The murine AML Cells were treated with CDH24 (with two different concentrations) or DMSO, and then colony numbers were compared between CDH24 treated group and control group in two passages of plating. FIG. 4K shows the effects of CDH24 treatment (with three different concentrations: 10 nM, 20 nM and 50 nM) on cell viability of healthy murine BM cells, murine MLL-AF9 (MA9) AML cells and murine FLT3-ITD/NPM1-mutant (FLT3-ITD) AML cells in vitro. The values were detected by MTT assays 48 or 72 hours post treatment. In FIGS. 4A-4K: *p<0.05; p<0.01; *p<0.001; t test. Error bars, mean±SEM (n≥3)

Figure 5A:
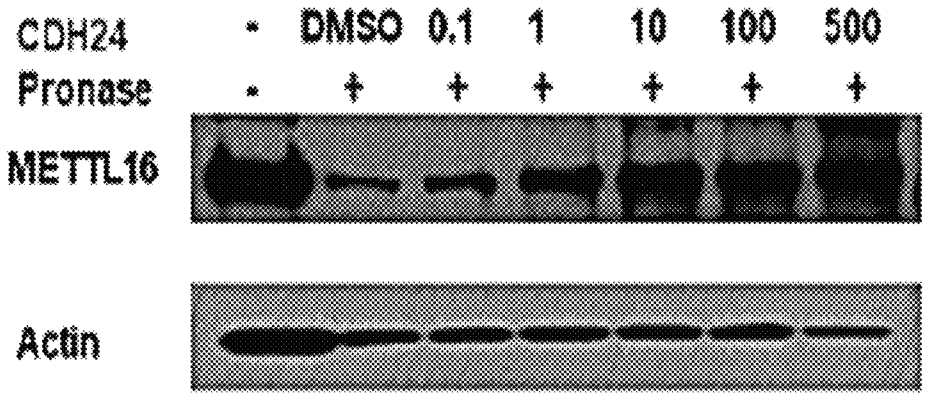
FIGS. 5A-5F show that METTL16 is a direct target of Formula (A) (i.e., CDH24).
Figure 5B:
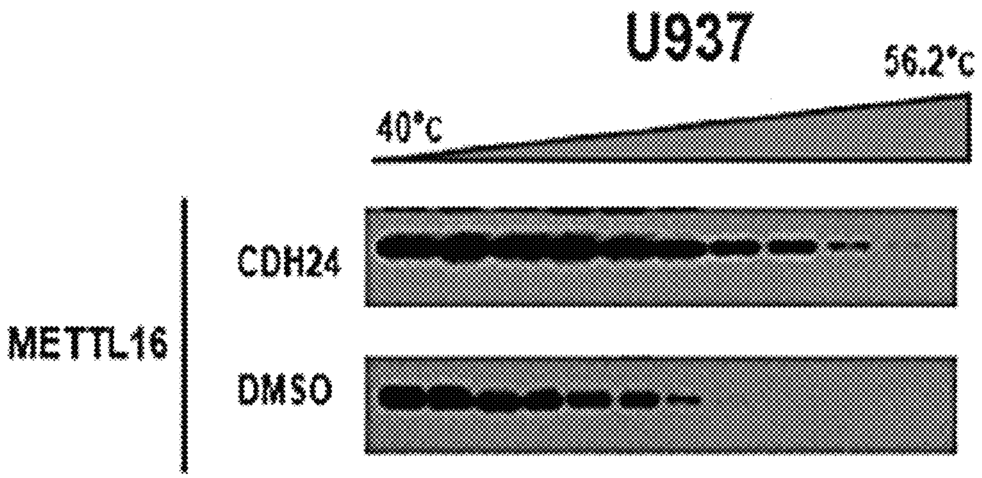
Figure 5C:
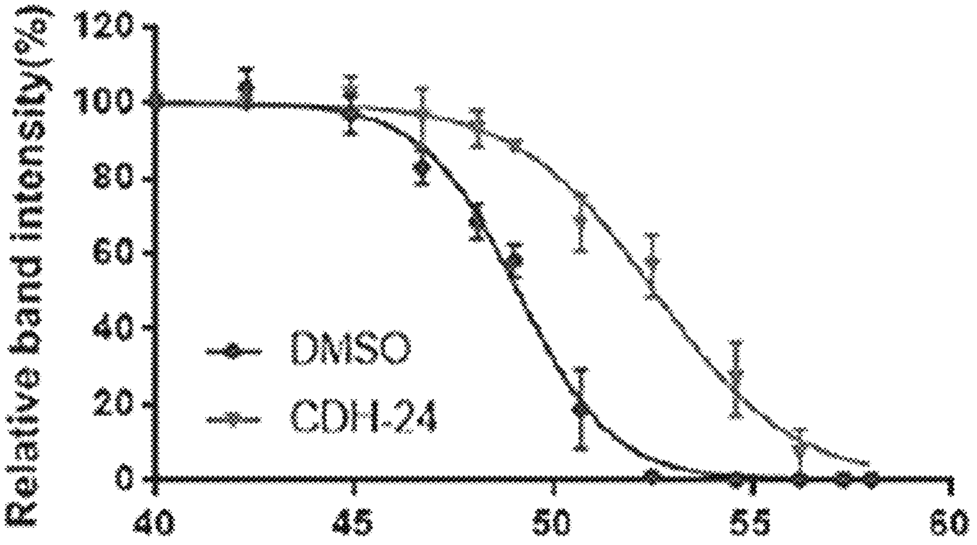
Figure 5D:
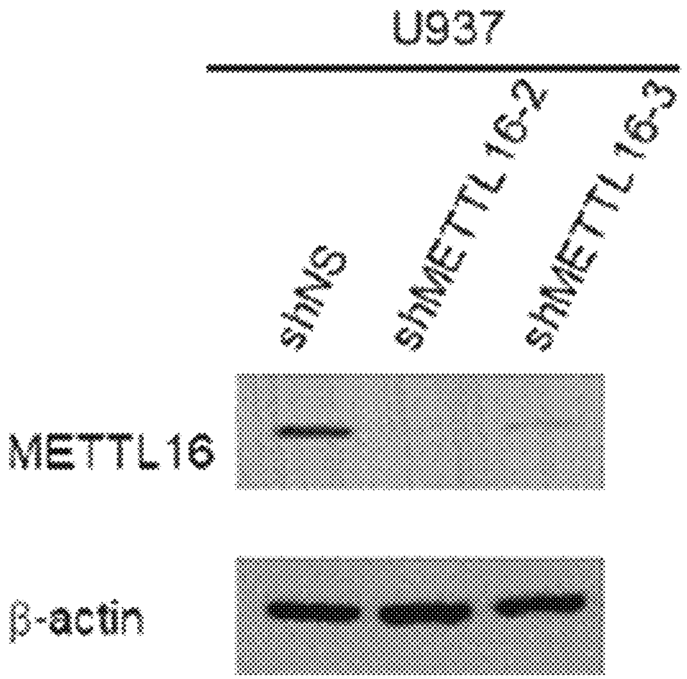
Figure 5E:
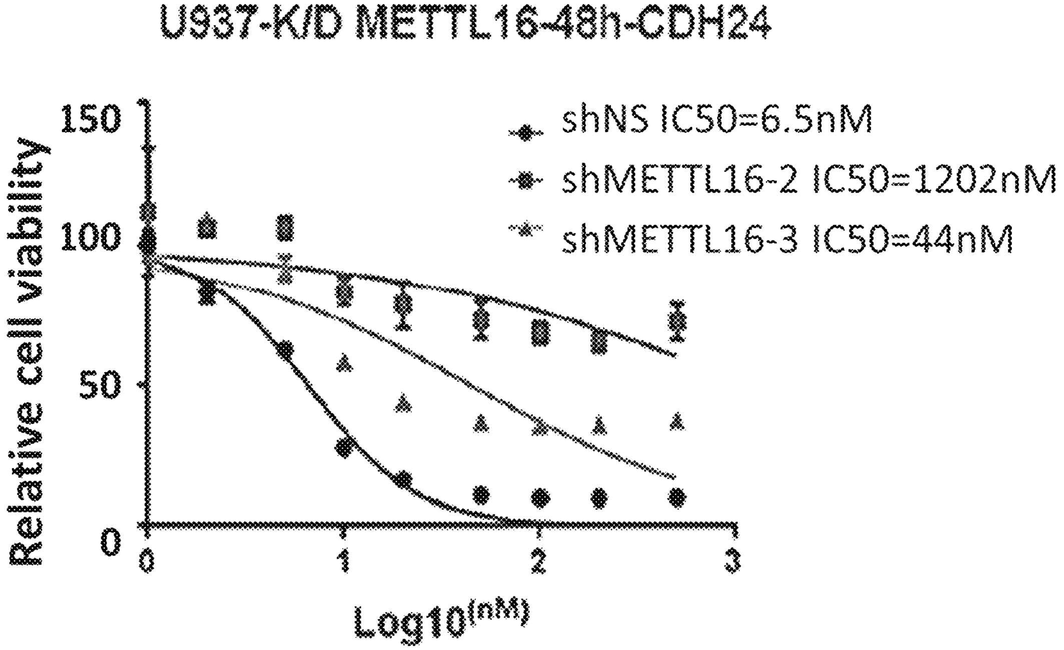
Figure 5F:
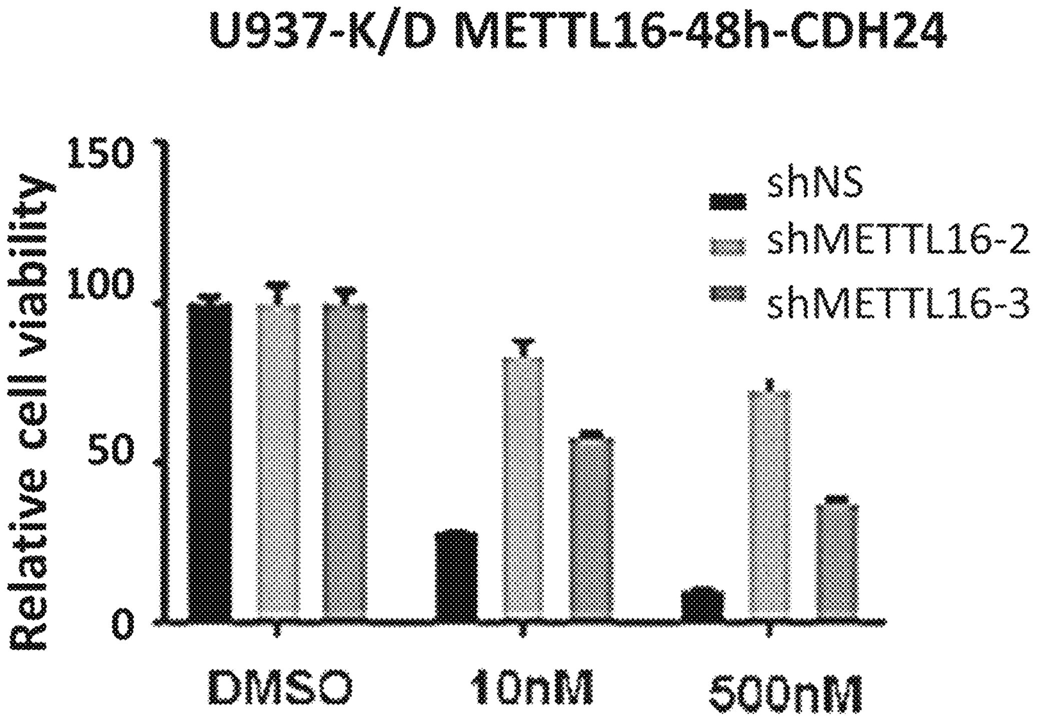

FIGS. 5A-5C provide confirmation of CDH24's direct binding to METTL16 by drug affinity responsive target stability (DARTS) assay (FIG. 5A) and cellular thermal shift assay (CETSA) (FIGS. 5B-5C). For DARTS, U937 cell lysates were treated with CDH-24 (from 0.1 uM to 500 uM) or DMSO; samples were subjected to pronase digestion and detected by immunoblotting. Actin was resistant to subtilizing under these conditions and served as a loading control. For CETSA, Densitometric analysis of immunoblot of METTL16 in U937 cells treated with CDH24 or DMSO and cultured at different temperatures. FIGS. 5D-5F show the effect of CDH24 treatment on cell viability of U937 AML cells with or without METTL16 knockdown. METTL16 knockdown by shRNAs was confirmed by western blots (FIG. 5D). The ICso values of CDH24 were detected by MTT assays 48 hours post treatment in U937 cells with or without METTL16 knockdown (FIG. 5E), and the relative cell viability of U937 cells with or without METTL16 knockdown upon treatment of 10 nM or 500 nM CDH24 or DMSO were shown as representatives (FIG. 5F). In FIGS. 5A-5F: *p<005; p<0.01: *p<0001; t test. Error bars, mean±SEM (n≥3).

Figure 6A:
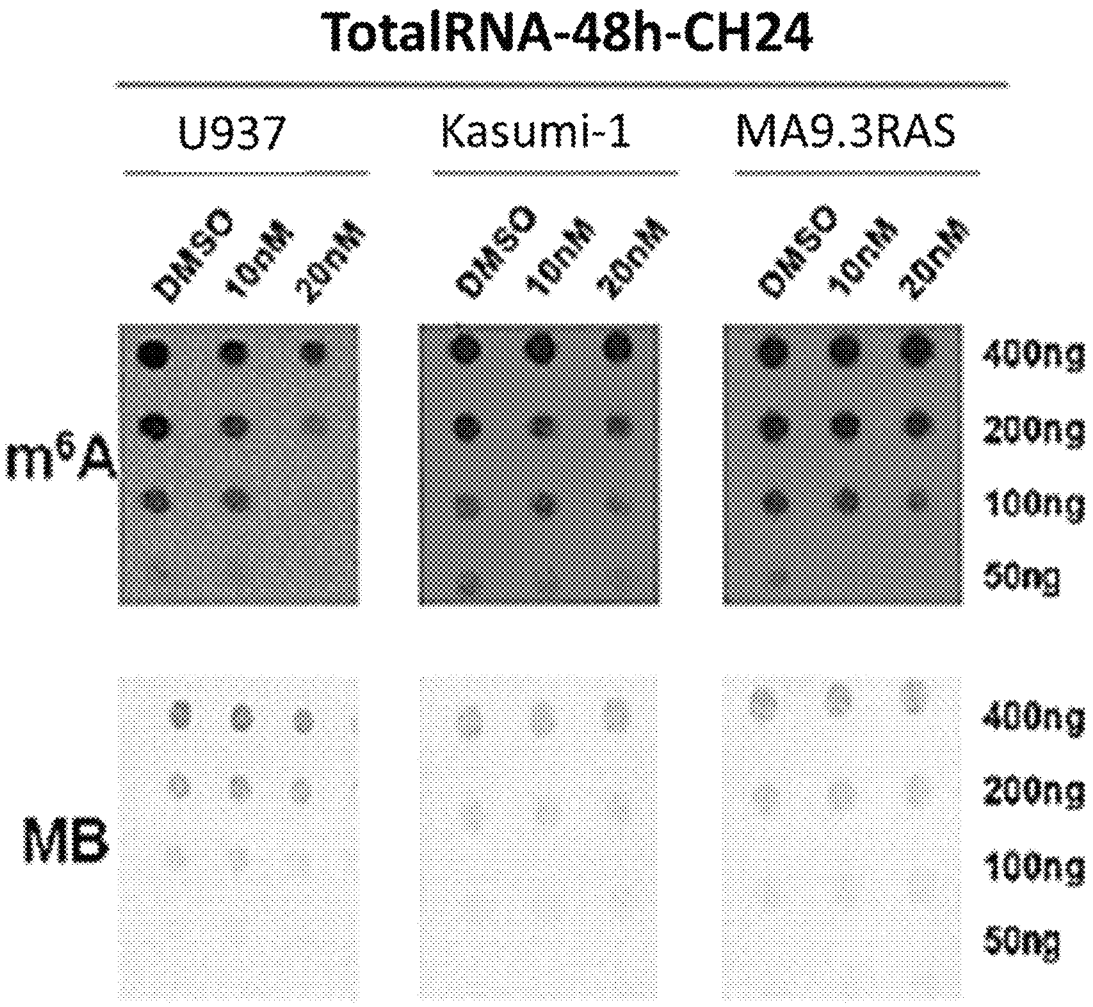
FIGS. 6A-6C show the inhibitory effect of Formula (A) (i.e., CDH24) on methyltransferase activity of METTL16 and on expression of METTL16 target genes.
Figure 6B:
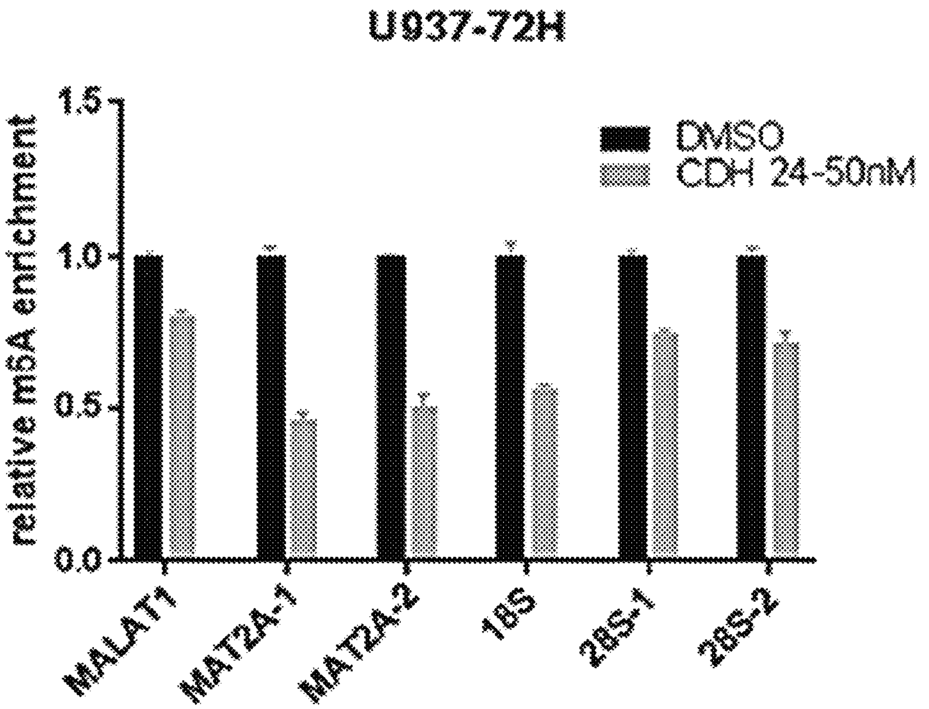
Figure 6C:
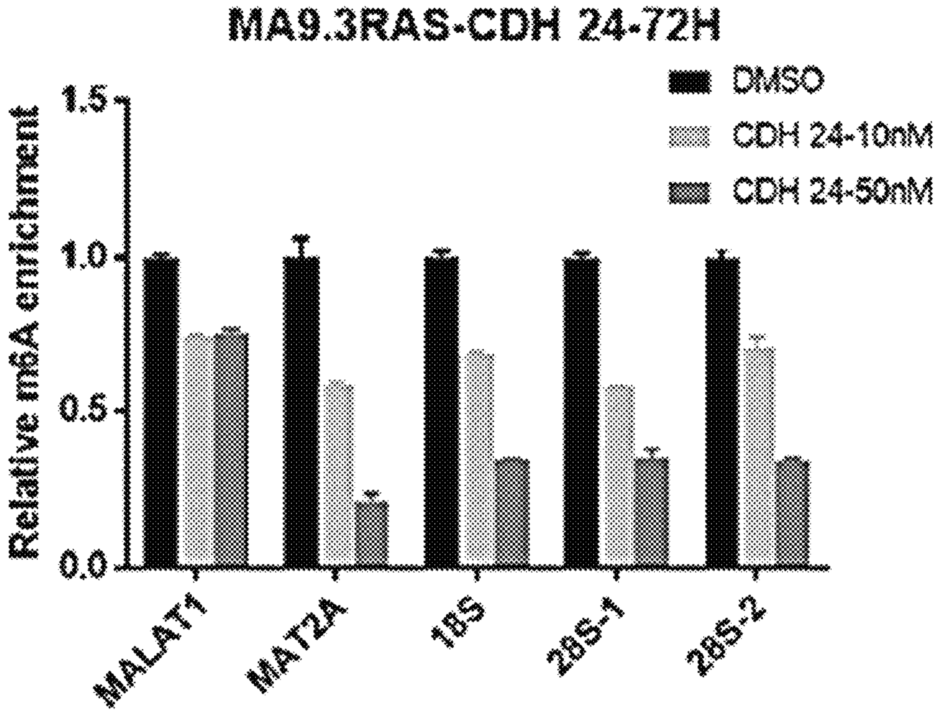

FIG. 6A shows that treatment of CDH24 (48 hours) increases levels of global $m^6A$ in U937, Kasumi-1 and MA9.3RAS (9.3RAS) AML cells. MB, methyl blue (as loading control). FIGS. 6B-6C show gene-specific $m^6A$ qPCR analysis of $m^6A$ level changes in mRNA transcripts of several known target transcripts of METTL16 in U937 (FIG. 6B) or MA9.3RAS (FIG. 6C) AML cells upon 72 hours treatment of CD-24, relative to cells treated with DMSO.

Figure 7A:
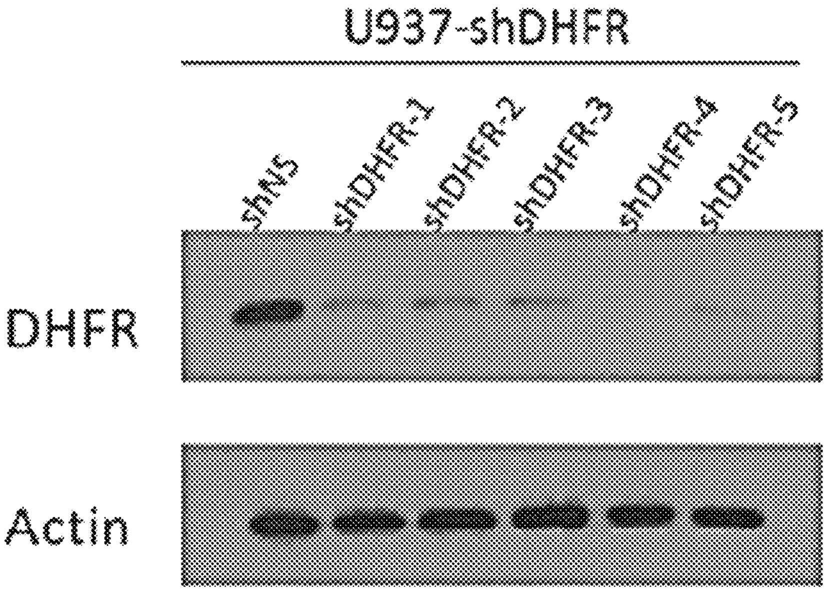
FIGS. 7A-7B demonstrate that knockdown of DHFR (a previously reported putative drug target of Formula (A) (i.e., CDH24)) showed no obvious effect on AML cell growth.
Figure 7B:
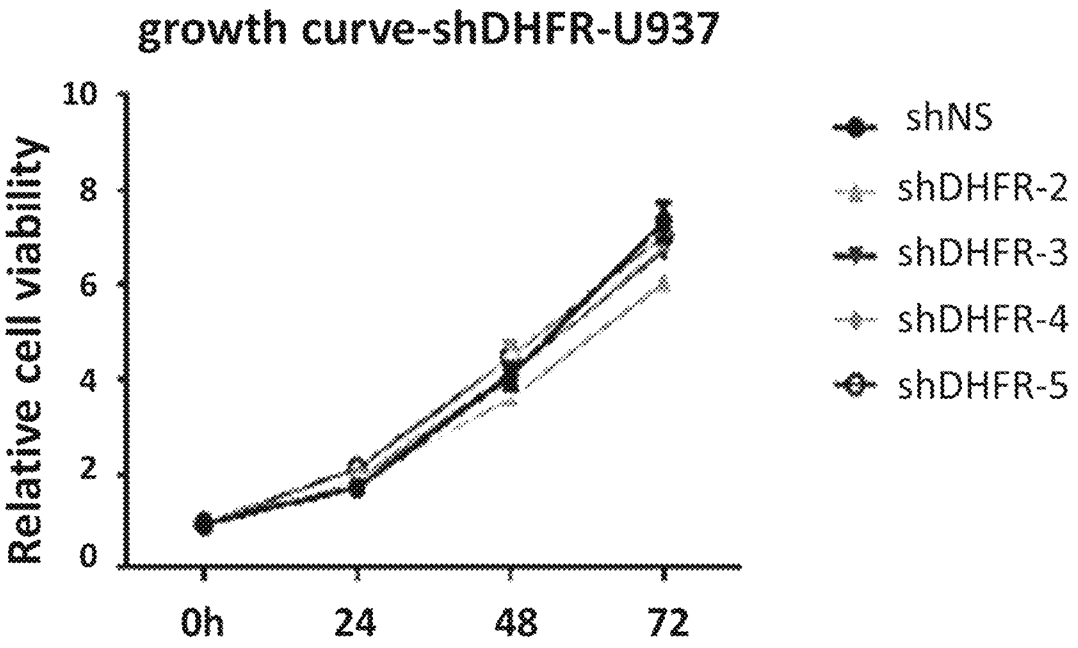
Figure 8:
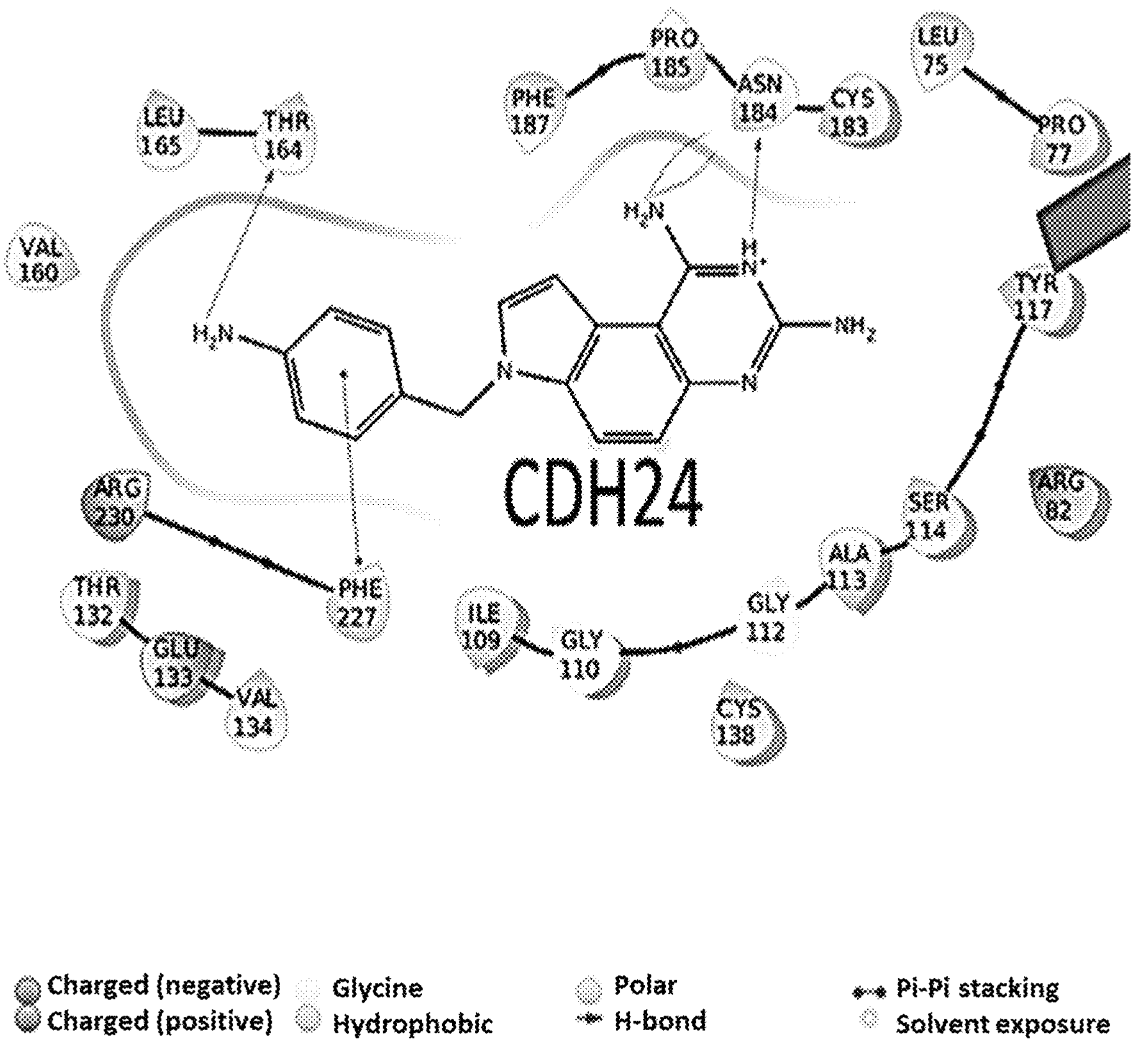
FIG. 8 shows the interaction between the compound of Formula (A) (i.e., CDH24) and METTL16.
Figure 9A:
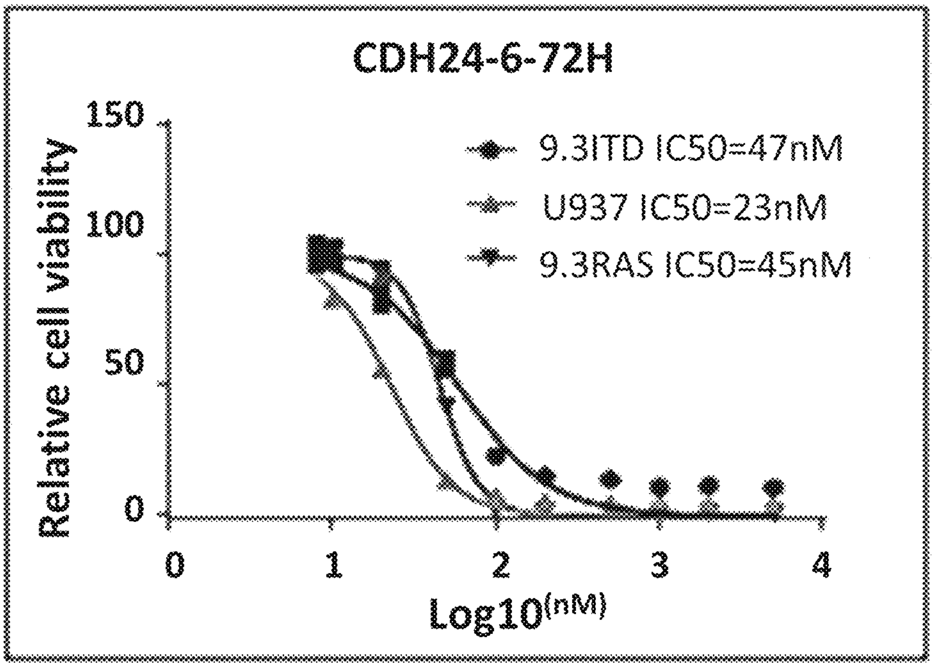
FIGS. 9A-9B shows that the compounds of Formula (B) (i.e., CDH24-6) and Formula (C) (i.e., CDH24-7) inhibit cell viability and growth in AML cells, following the assays described herein.
Figure 9B:
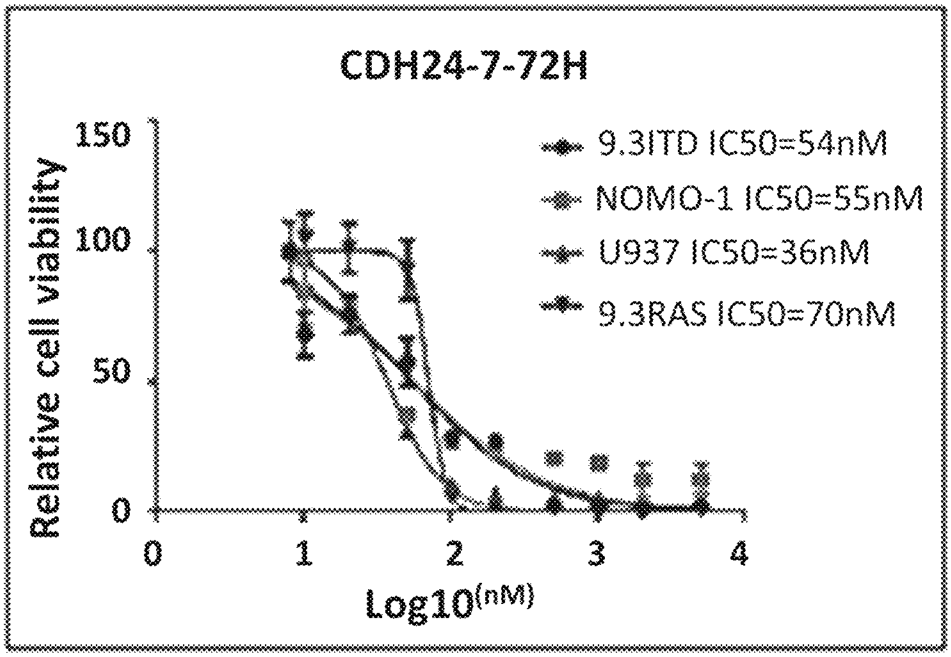
Figure 10:
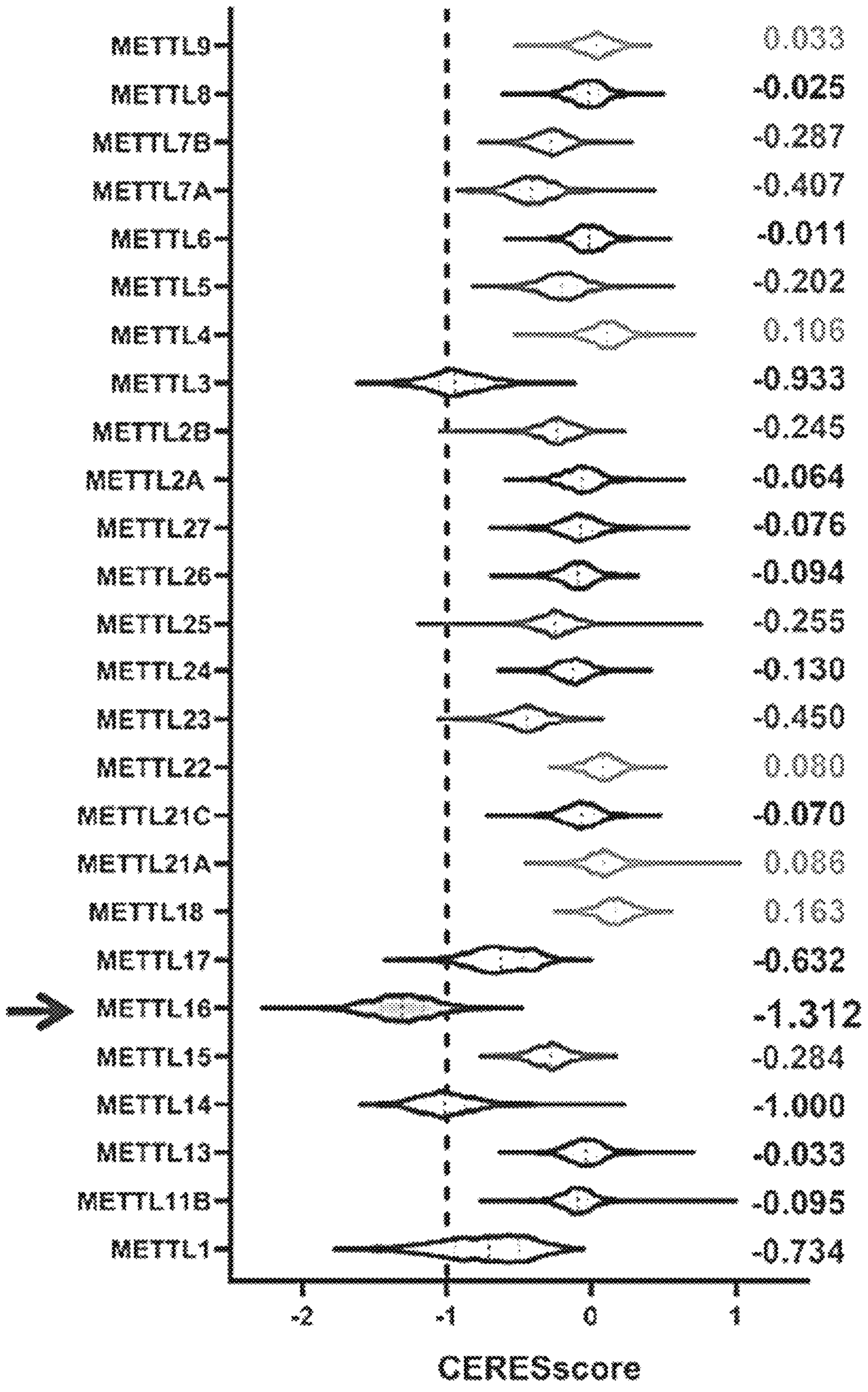
FIG. 10 provides CERES scores of METTL family members from genome-scale CRISPR-Cas9 essentiality screens across 769 cancer cell lines. The raw data were downloaded from DepMap (https://depmap.org/portal/—genes: 18333; cell lines: 739; primary diseases: 29; lineages: 26). As the CERES scores, 0 and −1 represent the median effects of nonessential genes and common core essential genes, respectively. The lower CERES score indicates the higher cancer dependency of the specific gene. For each violin, the minimum, first quartile, median, third quartile, and maximum were displayed. The average of CERES scores for each METTL family member was shown.
Figure 11:
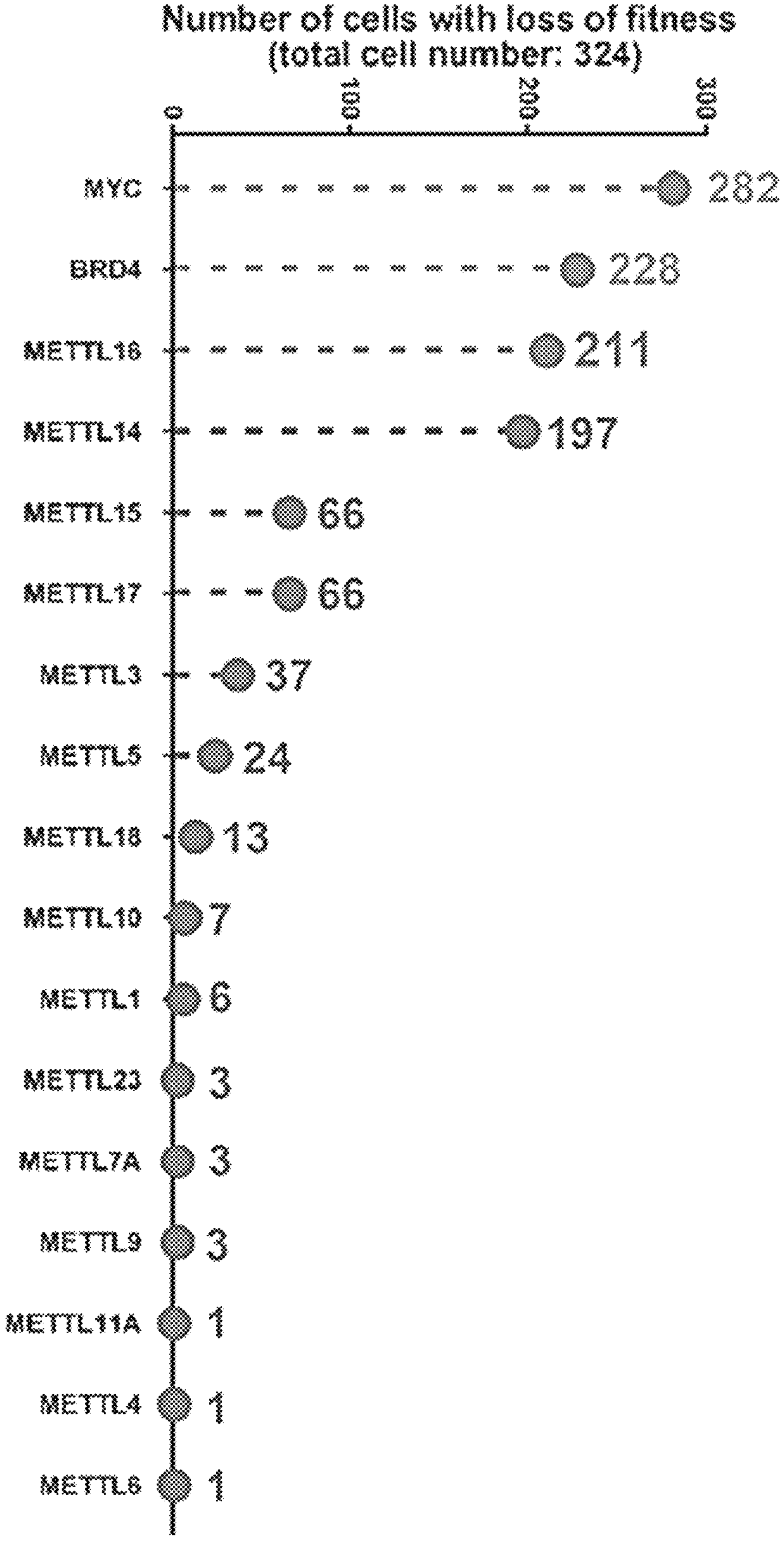
FIG. 11 shows the dependency of METTL16 in the majority of cancers from another genome-scale CRISPR-Cas9 screens with 324 cancer cell lines. The raw data were derived from https://score.depmap.sanger.ac.uk/. In this screen, 324 cancer cell lines from 13 cancer types were included. MYC and BRD4 were shown as positive controls, which represent the appealing cancer therapeutic targets. The number of cells with loss-of-fitness effects and the number of cancer type were highlighted for each gene. For example, METTL16 (211/13) indicates that knockout of METTL16 exhibits loss-of-fitness effects (essential function) in 211 of the 324 cancer cell lines and the 211 cancer cell lines belong to all the 13 cancer types.

DHFR was reported previously as a direct target of CDH24. The data shown herein indicates the DHFR is unlikely an important target of CDH24 that mediates the anti-tumor effects of CDH24. FIG. 7A shows that Western blot analysis confirmed shRNAs-mediated DHFR knockdown in U937 cells. FIG. 7B shows the effect of DHFR knockdown on proliferation of U937 cells.

Example 2

Figure 12A:
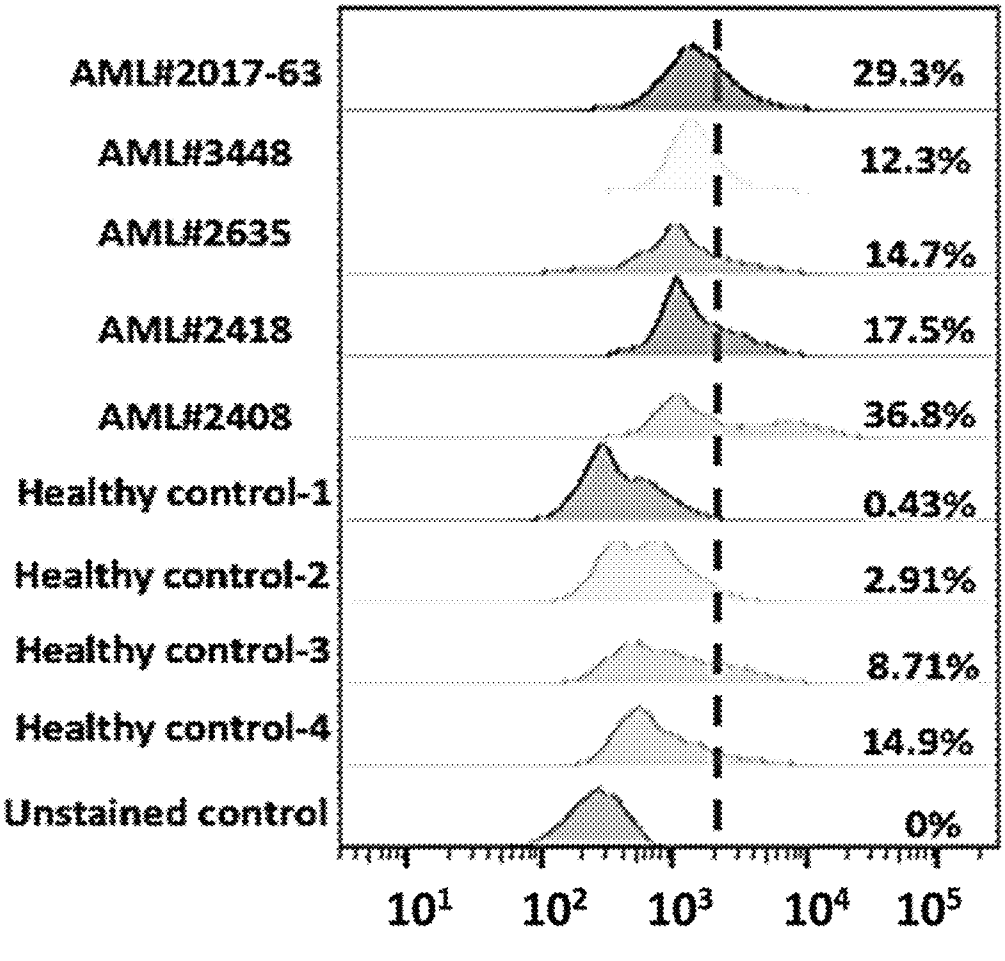
FIGS. 12A-12C show that METTL16 is aberrantly overexpressed in primary AML patient samples.
Figure 12B:
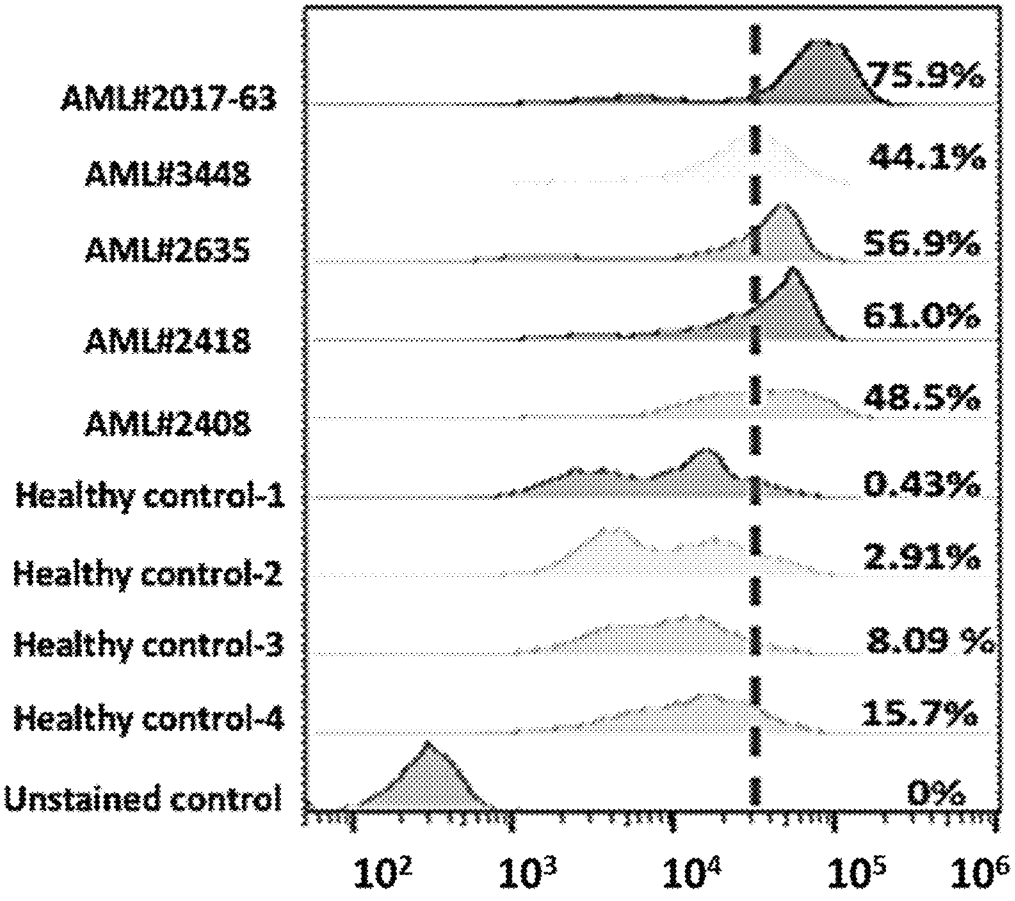
Figure 12C:
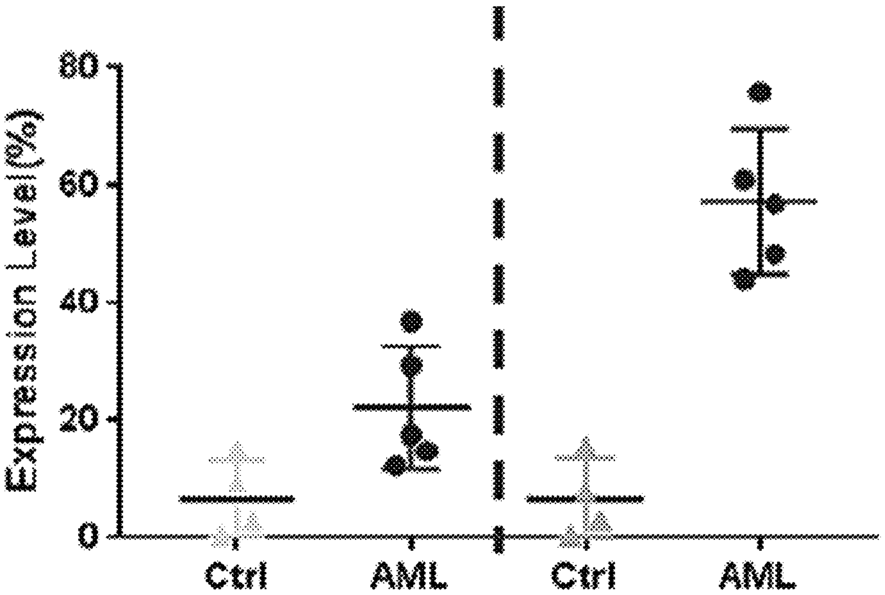
Figure 13A:
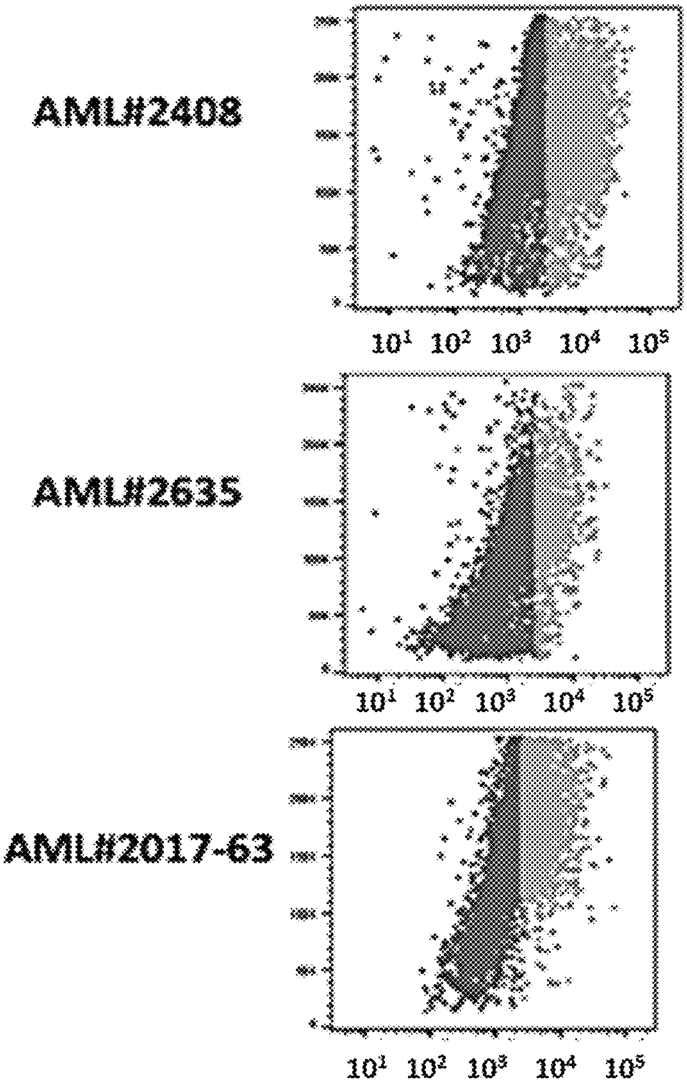
FIGS. 13A-13D compare METTL16 expression between CD34+ and CD34− cells in human primary AML.
Figure 13B:
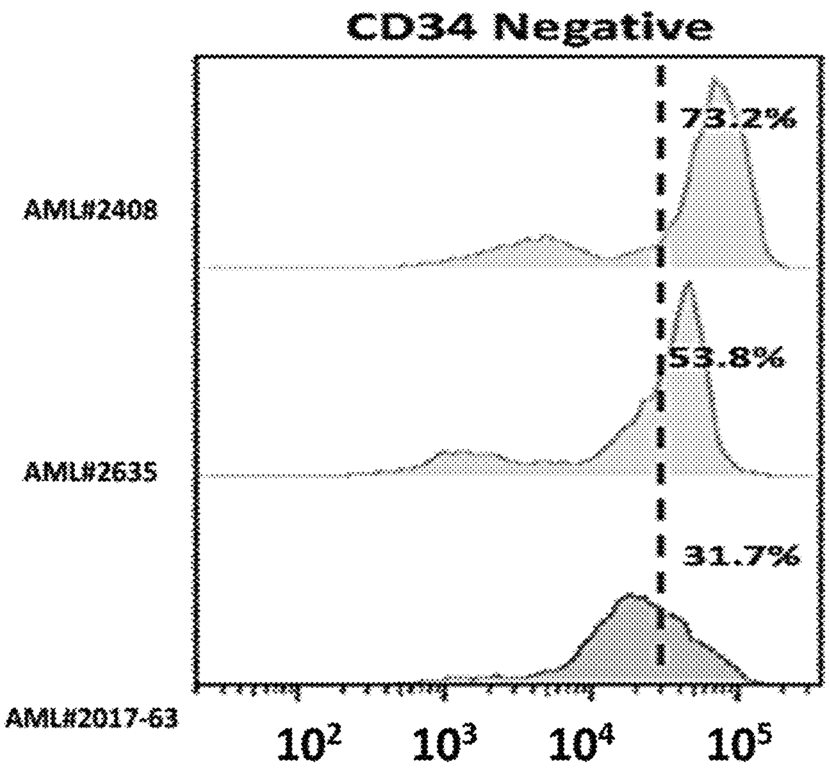
Figure 13C:
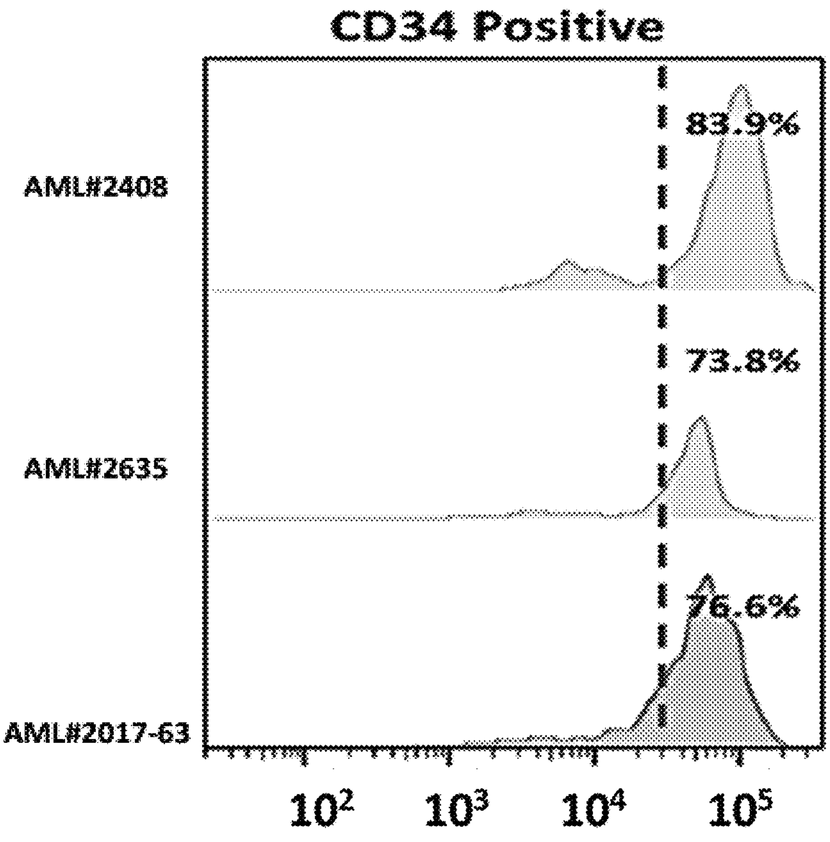
Figure 13D:
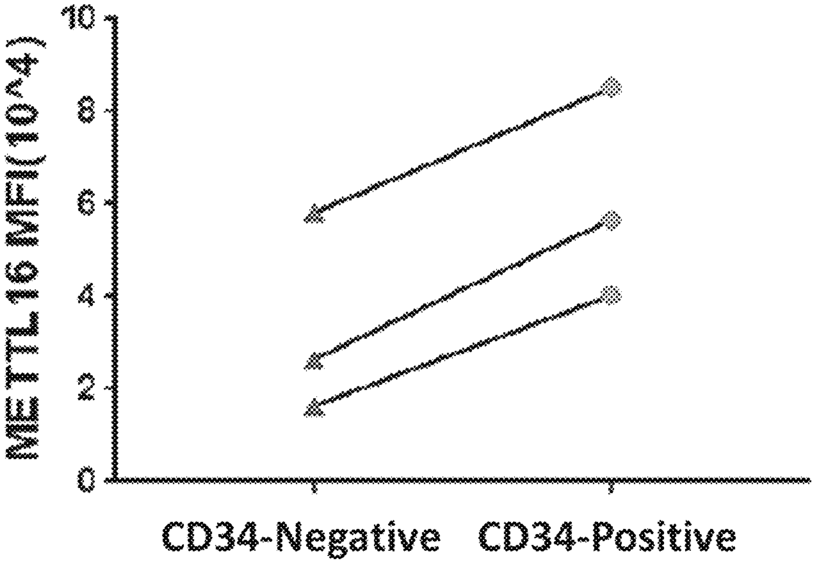
Figure 14A:
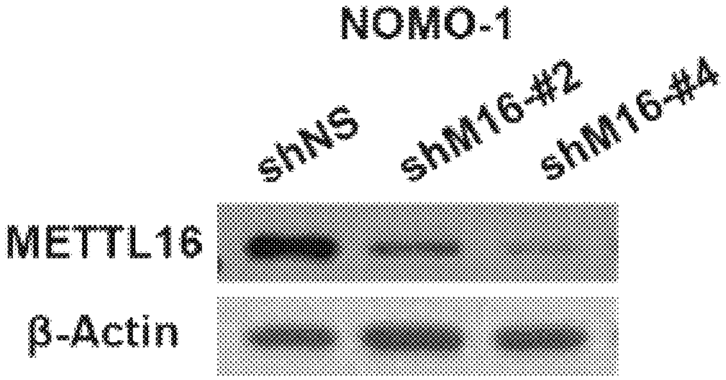
FIGS. 14A-14F show that knockdown of METTL16 significantly inhibited the growth and proliferation of human AML cells.
Figure 14B:
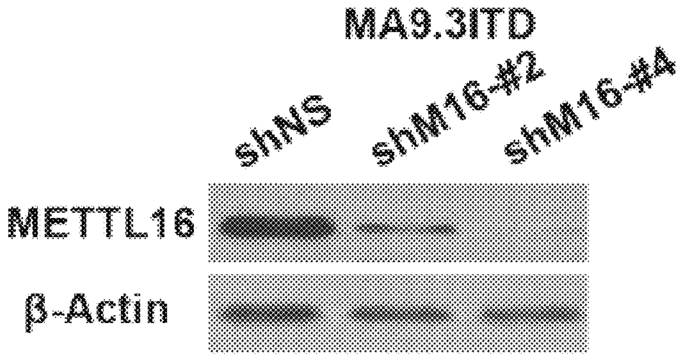
Figure 14C:
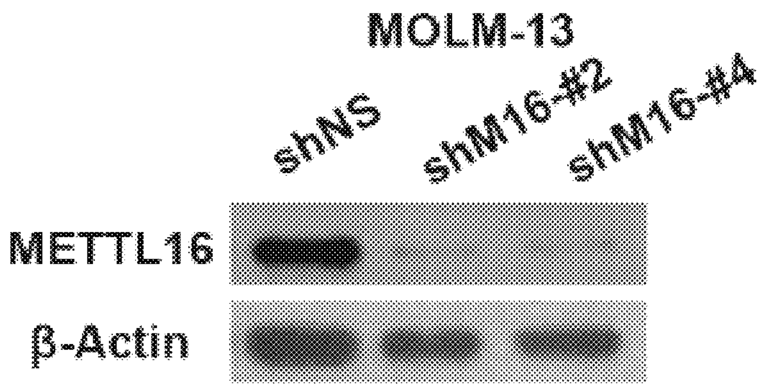
Figure 14D:
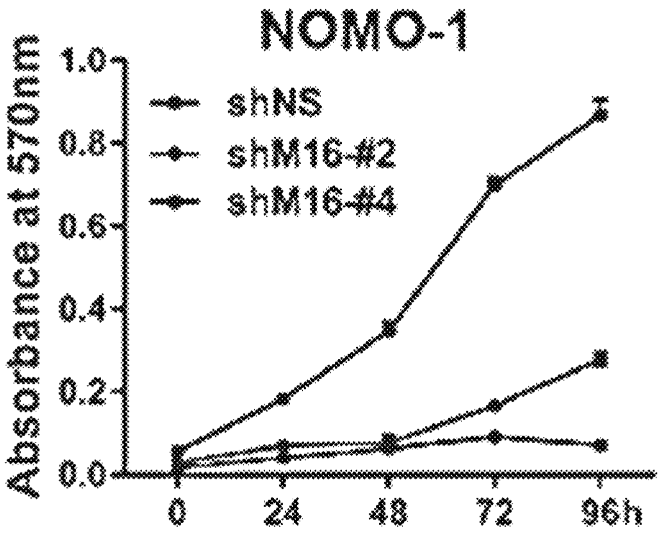
Figure 14E:
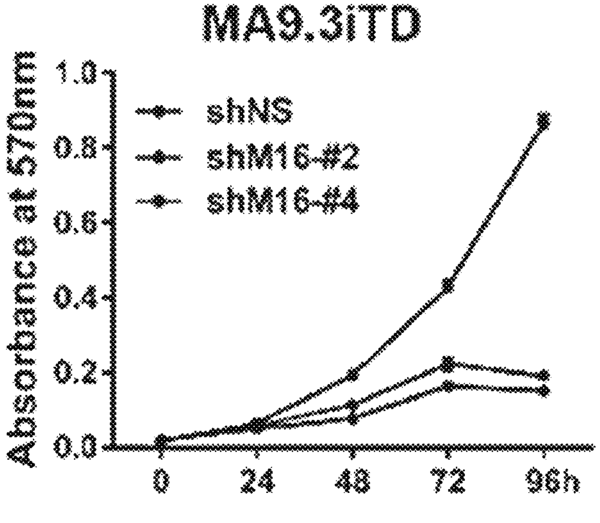
Figure 14F:
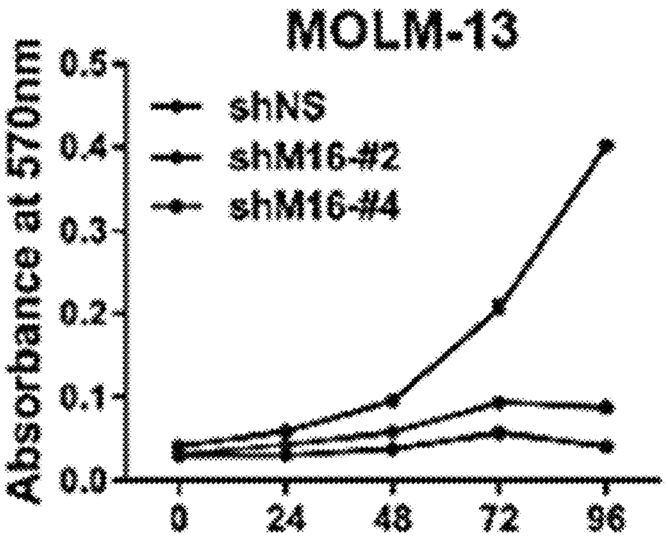

As shown in FIGS. 12A-12C, METTL16 is aberrantly overexpressed in primary AML patient samples compared to healthy controls as detected by flow cytometry (intracellular staining); and AML samples also have a higher CD34 level than the healthy controls. As shown in FIGS. 13A-13D, in each individual primary AML sample, METTL16 level is significantly higher (p<0.05; paired t-test) in CD34+ immature leukemia stem/initiating cells (LSCs/LICs) than in CD34− bulk AML cells.

Intracellular staining with METTL16 was performed as follows: human primary cells were incubated on ice for 5 min with Fc block and labeled with CD34 surface marker on ice for 30 min. Then the cells were washed with chilled PBS, fixated in 4% paraformaldehyde (158127, Sigma-Aldrich) at 4° C. for 20 min with rotation. After fixation, the cells were permeabilized in 5× Permeabilization buffer (00-8333-56, eBioscience) on ice for 20 min, and stained with rabbit anti-human METTL16 (1:100) for 1 hour on ice. After washing, cells were stained with goat anti-rabbit IgG (H+L) (Alexa Fluor 555 Conjugate, 4413S, Cell Signaling Technology) in 5× Permeabilization buffer for 30 minutes at room temperature protected from light, washed with FACS buffer and resuspended in 500 μl of FACS buffer for analysis.

Example 3

FIGS. 14A-14F show that knockdown of METTL16 significantly inhibited the growth and proliferation of human AML cells. Cells were seeded into 96-well plate in the concentration of 10,000 cells/well. Cell proliferation were assessed by CellTiter 96 Non-Radioactive Cell Proliferation Assay (MTT, G4100, Promega) following the manufacturer's protocols. For AML cells proliferation assays, AML cells were first infected with lentivirus, selected with 2 μg/ml puromycin (P8833, Sigma-Aldrich) for 3 days, and then seeded into 96-well in triplicated.

Example 4

Figure 15A:
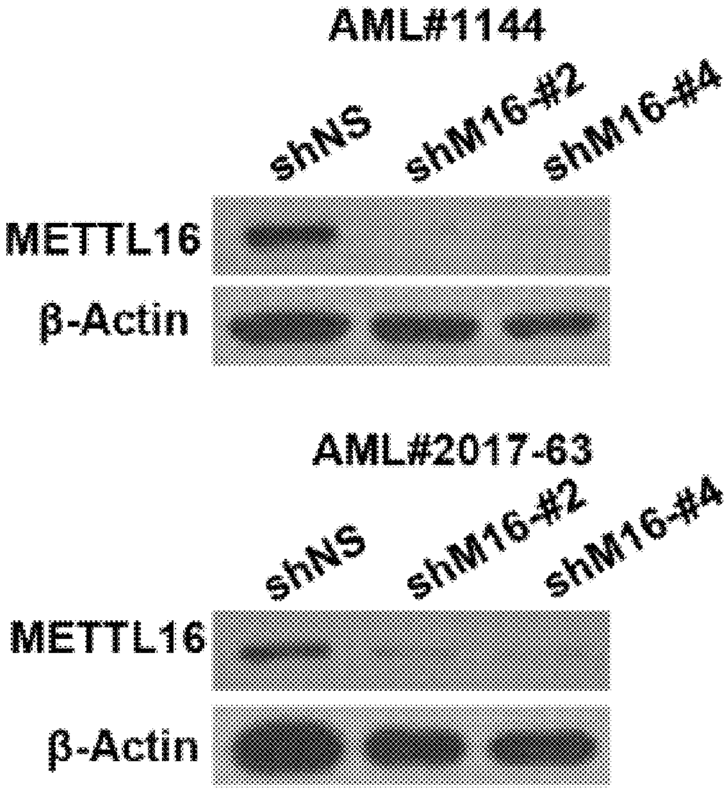
FIGS. 15A-15C show knockdown of METTL16 significantly promoted the apoptosis of human primary AML cells collected from patients. The top and bottom panels in FIG. 15A are immunoblot showing knockdown efficiency of METTL16 in AML patient samples. The top-middle-bottom panels in FIG. 15B show the effect of METTL16 knockdown on cell apoptosis in AML patient samples. The top and bottom panels in FIG. 15C show statistical results of the effects of METTL16 knockdown on the early stage (EA) and later stage (LA) apoptosis of primary AML cell samples. ***$p<0.001$
Figure 15B:
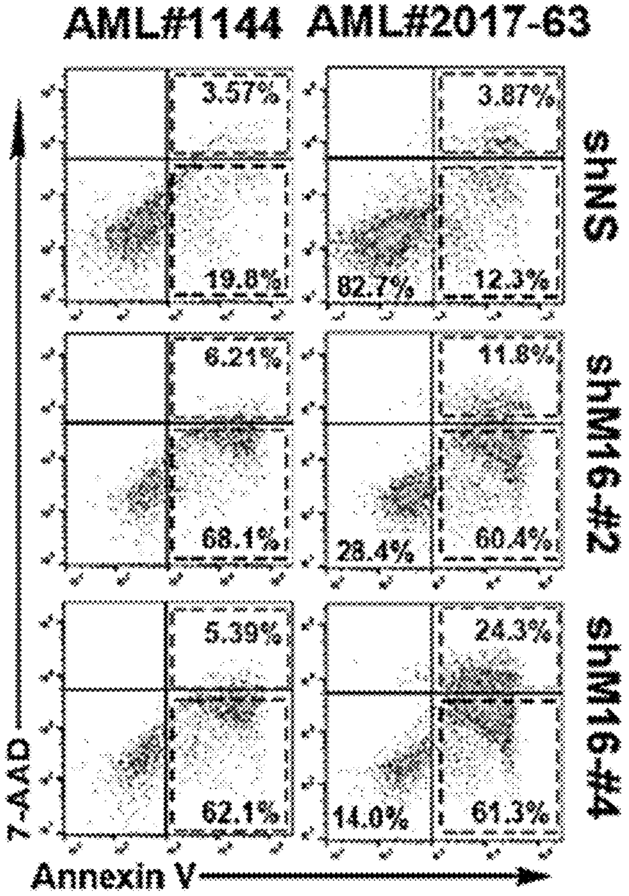
Figure 15C:
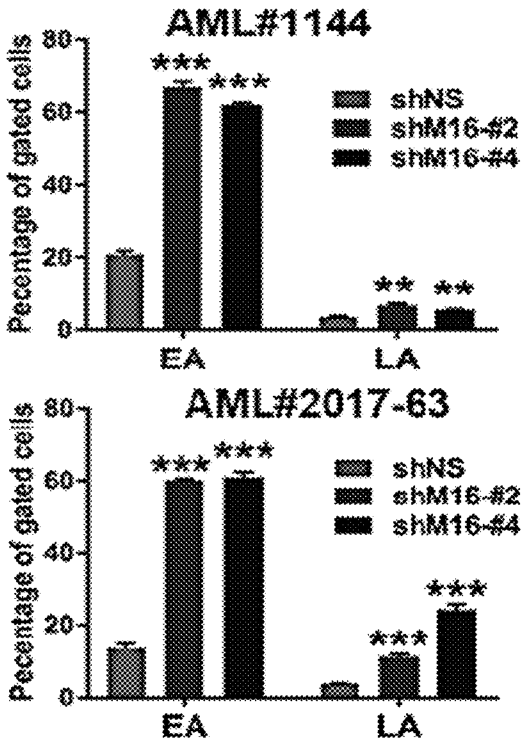

FIGS. 15A-15C show that knockdown of METTL16 significantly promoted the apoptosis of human primary AML cells collected from patients. For apoptosis assays, APC Annexin V apoptosis Detection Kit (88-8007-74, eBiosciences, San Diego, CA) was used according to the manufacturer's protocol. Cells were washed with chilled PBS, and then incubated in 100 μl 1× Binding buffer containing 5 ||l of PE Annexin V and 5 μl 7-AAD for 15 min at room temperature, protected from light. After that, cells were resuspended in 400 μl of 1× Binding Buffer and analyzed by flow cytometry within one hour.

Example 5

Figure 16:
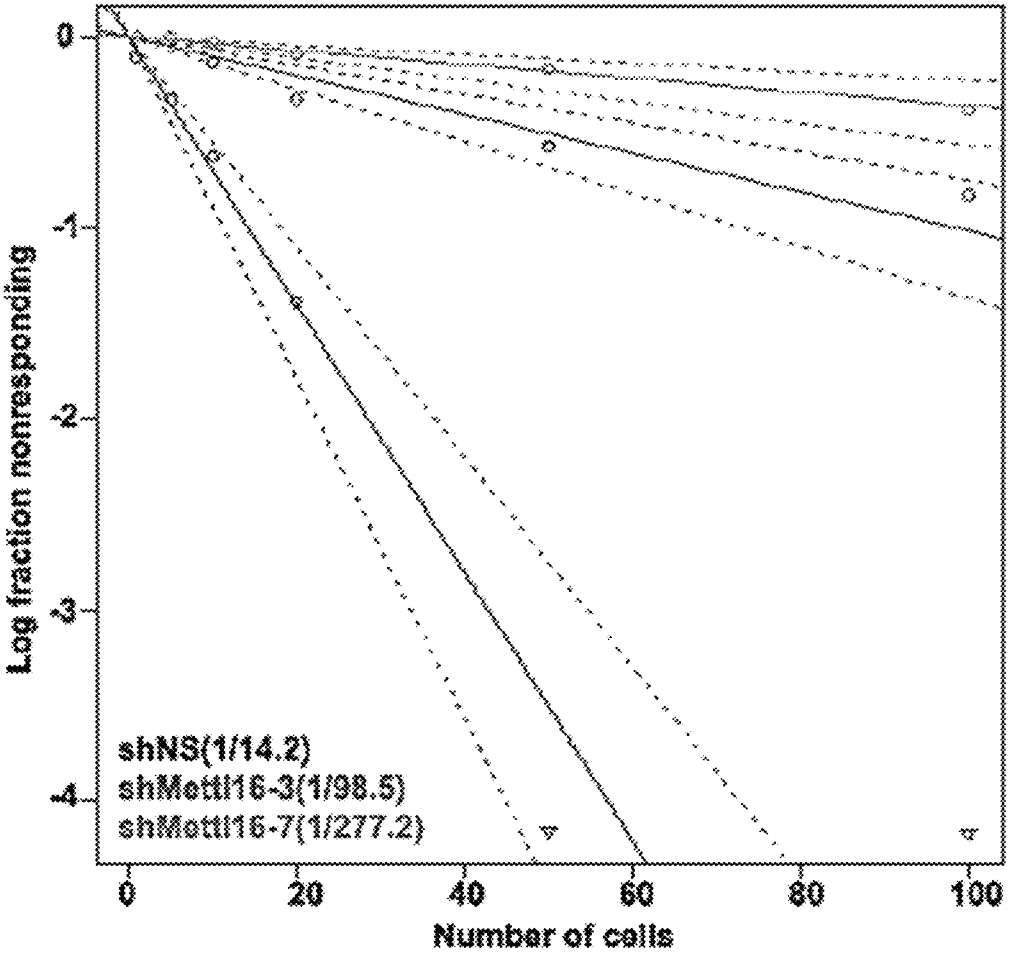
FIG. 16 shows knockdown of FTO significantly inhibited self-renewal of LSCs/LICs, resulting in a significantly lower LSC/LIC frequency. LSC/LIC frequency changes in MLL-AF9 (MA9) primary murine AML cells upon METTL16 KD were estimated by in vitro limiting dilution assays (LDAs).
Figure 17A:
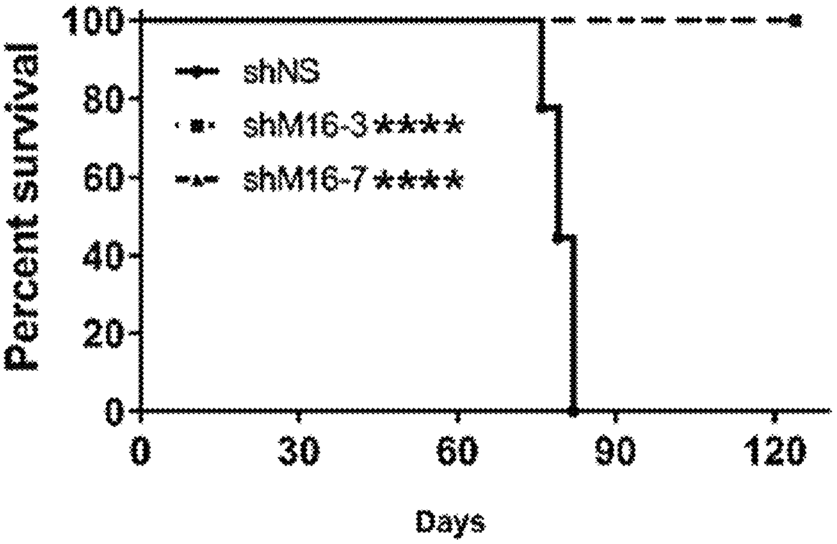
FIGS. 17A-17F show that METTL16 is required for murine AML development.
Figure 17B:
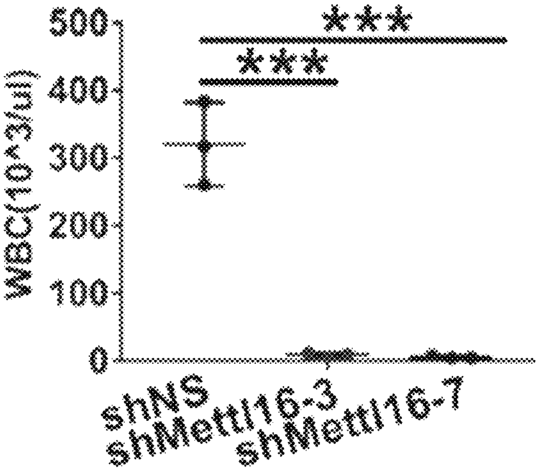
Figure 17C:
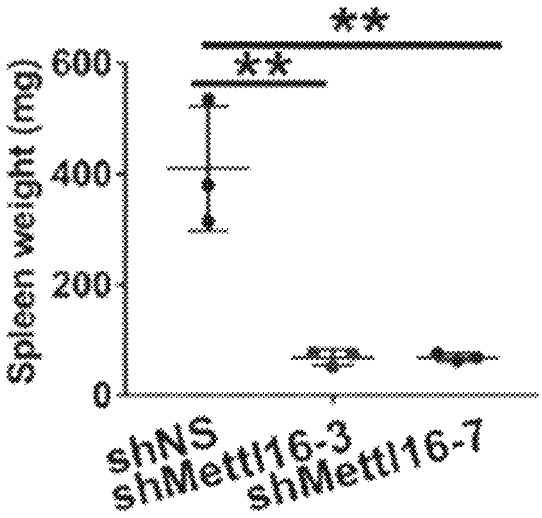
Figure 17D:
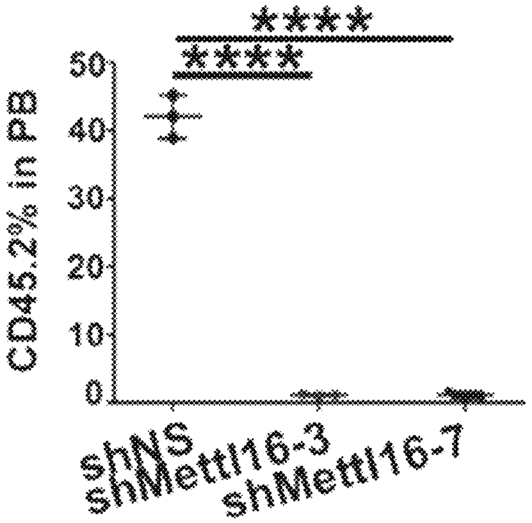
Figure 17E:
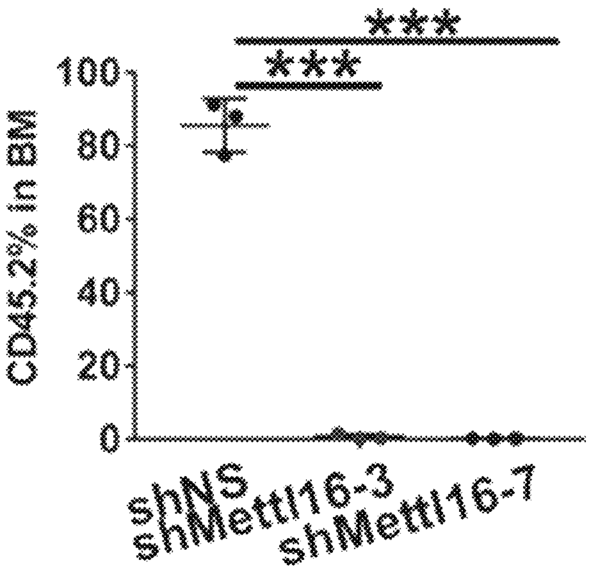
Figure 17F:
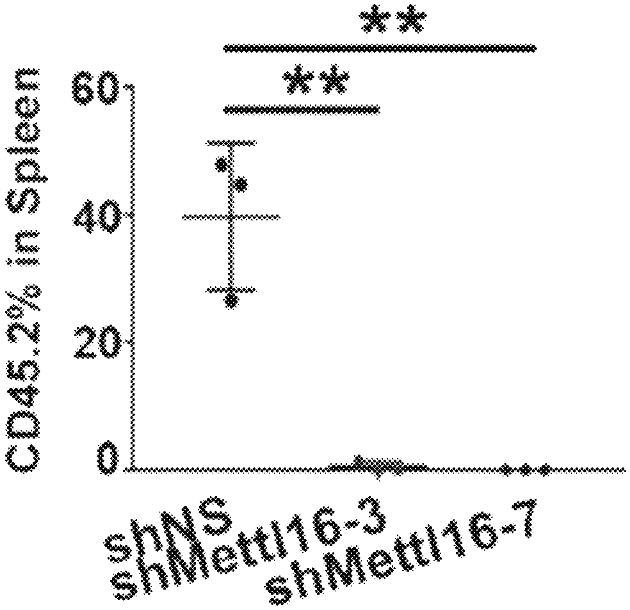
Figure 18A:
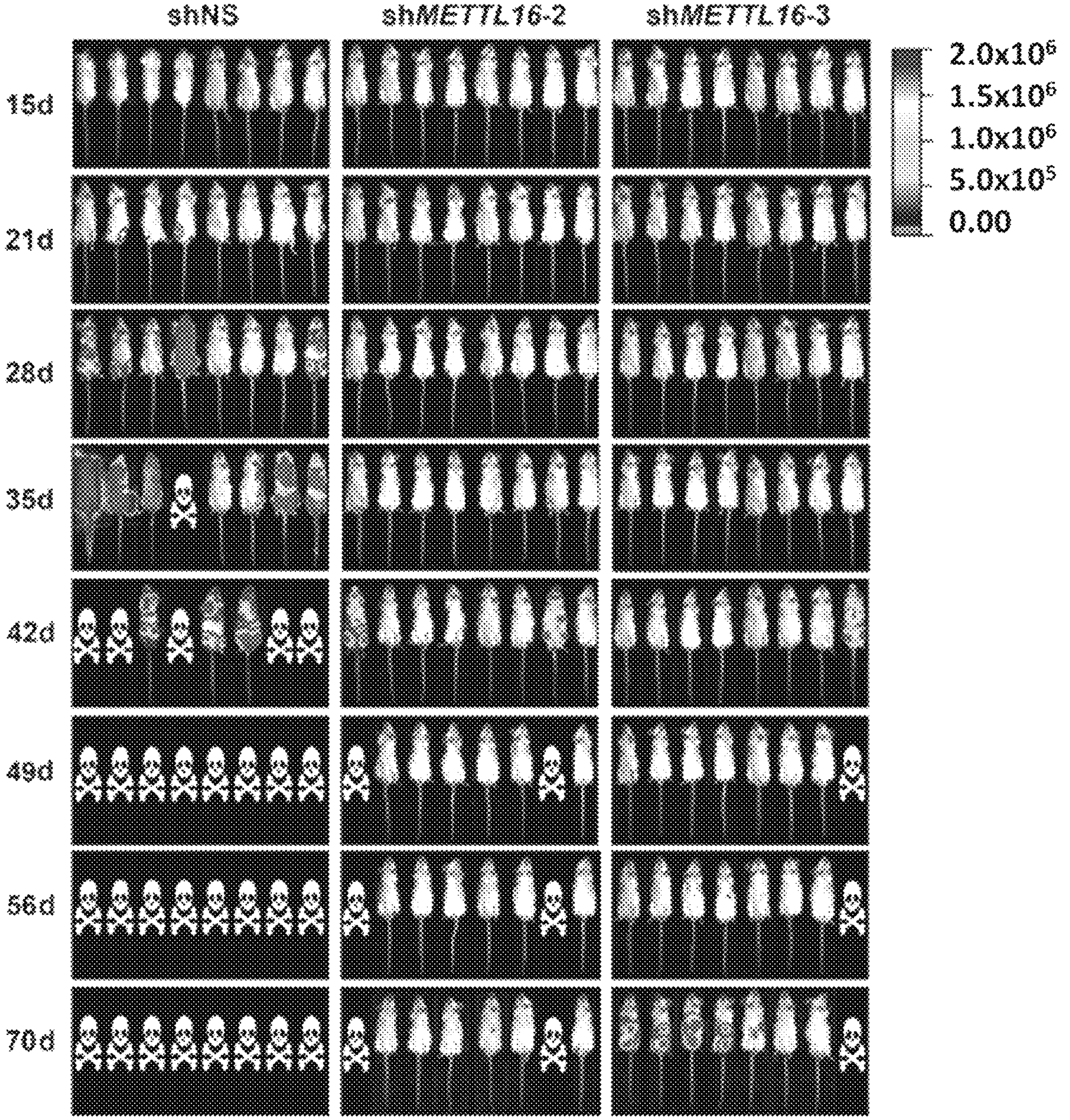
FIGS. 18A-18C show that METTL16 is required for human AML maintenance.
Figure 18B:
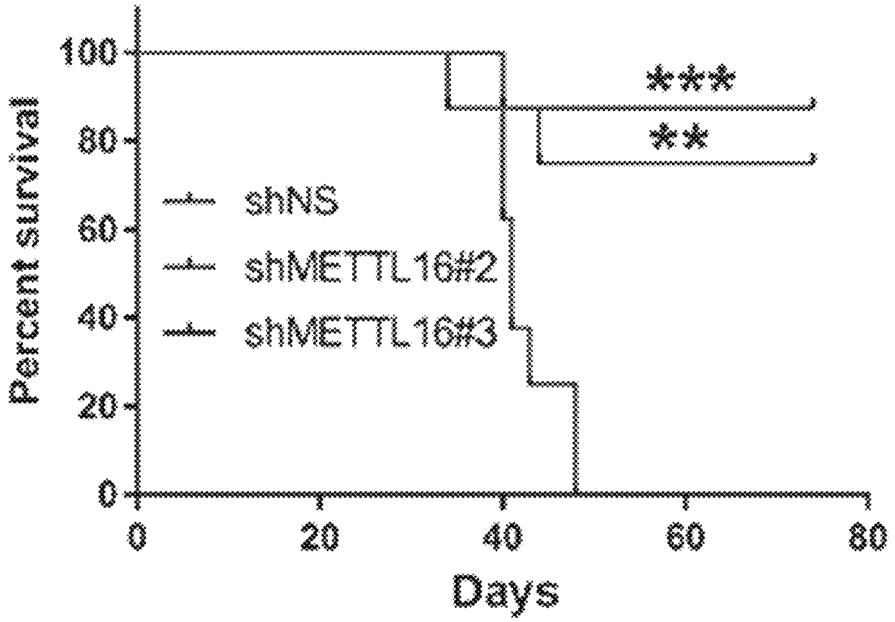
Figure 18C:
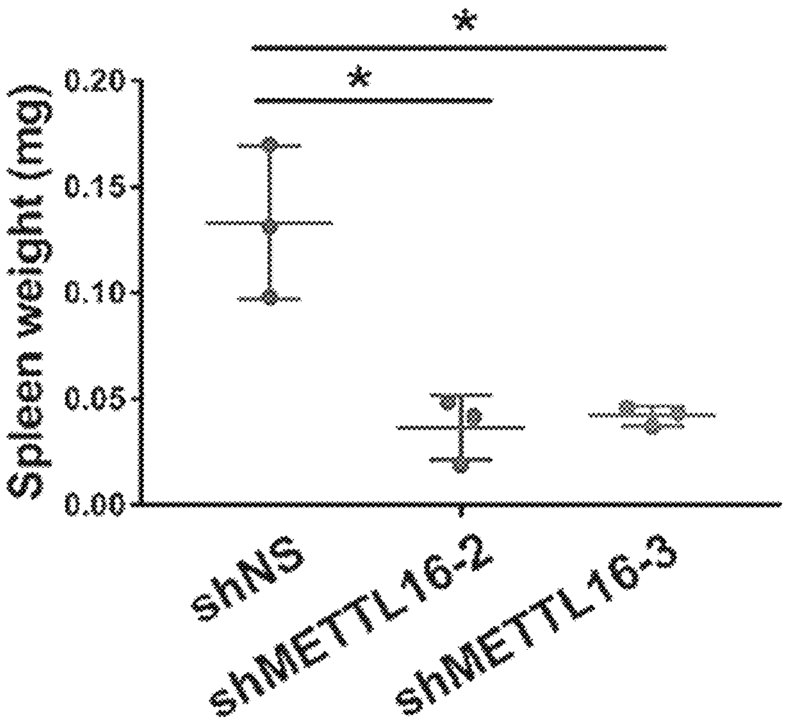

The knockdown of FTO significantly inhibited self-renewal of LSCs/LICs, resulting in a significantly lower LSC/LIC frequency, as shown in FIG. 16. Limiting Dilution Assays: the murine MA9 cells with or without METTL16 knockdown were suspended in ColonyGEL medium supplied with 10 ng/ml of murine recombinant IL-3, IL-6, GM-CSF and 50 ng/ml of murine recombinant SCF, 1 mg/ml Geneticin® Selective Antibiotic and 2.5 μg/ml of puromycin. Then plated in 48-well plates with six different doses of cell number for each group. For each dose, 12 wells were included. Frequency of stem cell was estimated after 7 days of culture. The number of wells containing colony-forming cells in shown in Table 1 below

TABLE 1

| Number of | Tested | Positive Response in Different Groups (MA9) | | |
|---|---|---|---|---|
| cells/well | Wells | shNS | shMETTL16-3 | shMETTL16-7 |
| 100 | 32 | 32 | 18 | 10 |
| 50 | 32 | 32 | 14 | 5 |
| 20 | 32 | 24 | 9 | 3 |
| 10 | 32 | 15 | 4 | 1 |
| 5 | 32 | 9 | 0 | 0 |
| 1 | 32 | 3 | 0 | 0 |

Example 6

As shown in FIGS. 17A-17F, METTL16 is required for murine AML development. Bone marrow (BM) cells were collected from 4- to 6-week-old C57BL/6 (CD45.2) mice five days after 5-fluorouracil (5-FU) treatment (150 mg/kg), and BM progenitor (i.e., lineage negative, Lin−) cells were enriched with the Mouse Lineage Cell Depletion Kit (Miltenyi Biotec Inc., Auburn, CA). BM progenitor cells were then co-transduced with combinations of MSCVneo-based retroviruses and shMettl16 lentivirus. cells were collected and washed twice then transplanted via tail vein injection into lethally irradiated (960 cGy, 96 cGy/min, γ-rays) 6 to 8 week-old B6. SJL (CD45.1) recipient mice. For each recipient mouse, 0.2-0.3x106 donor cells and whole bone marrow cells (1×106) freshly harvested from a B6. SJL (CD45.1) mouse were transplanted. Leukemic mice were euthanized by CO2 inhalation if they showed signs of systemic illness.

Example 7

Figure 19:
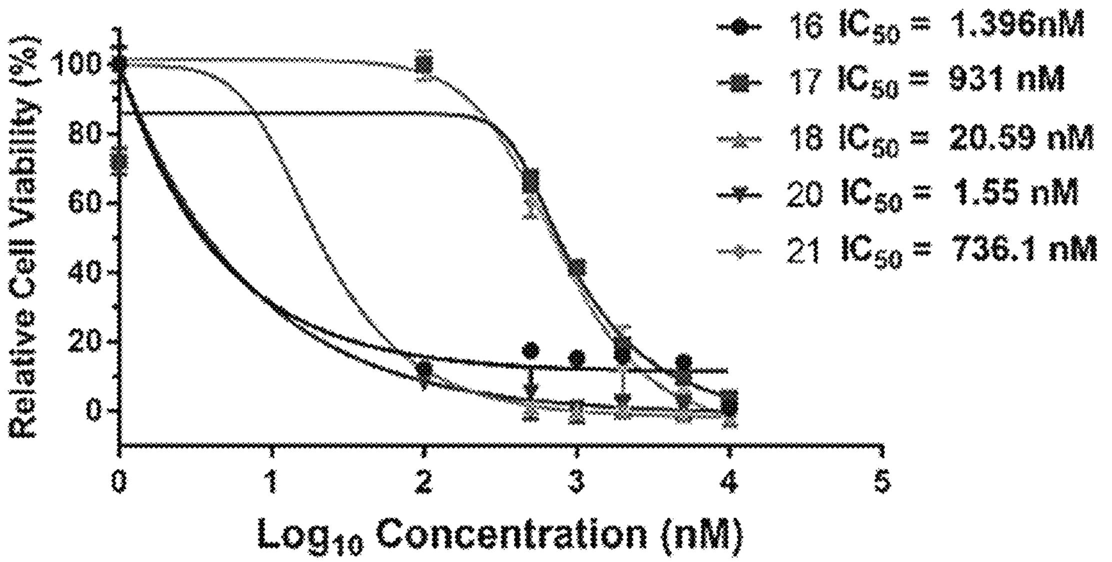
FIG. 19 shows the IC50 of compounds described herein in inhibiting the viability of human NOMO-1 AML cells. With reference to $Log_{10}$ concentration of 1.5 nM, the top line is Compound (G) ("21"; i.e., CDH24-21) (IC50=736.1 nM), the next line is Compound H ("17"; i.e., CDH24-17) (IC50=931 nM), the next line is Compound (E) ("18"; i.e., CDH24-18) (IC50=20.59 nM), the next line is Compound D ("16"; i.e., CDH24-16) (IC50=1.396 nM), and the bottom line is Compound (F) ("20"; i.e., CDH24-20) (IC50=1.55 nM).
Figure 20A:
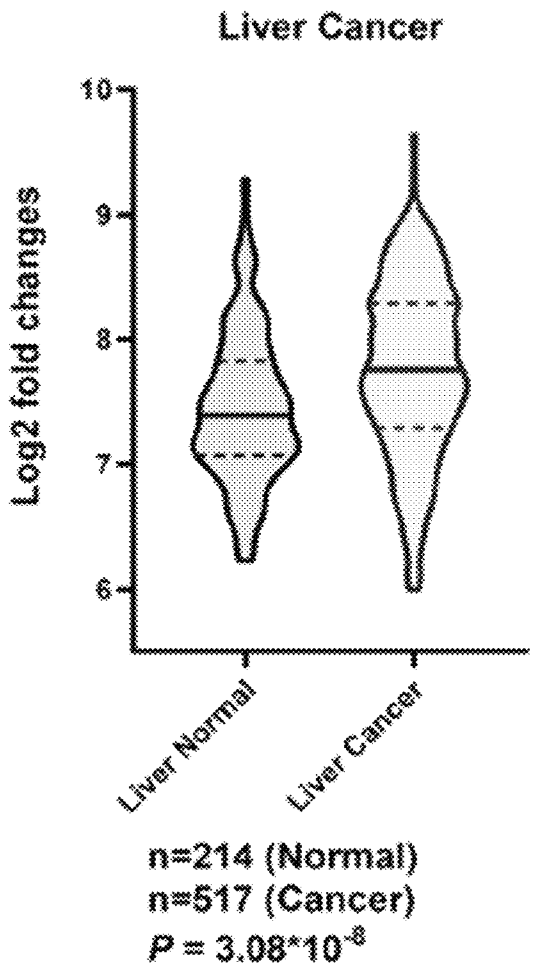
FIGS. 20A-20B show that METTL16 is highly expressed in liver cancers.
Figure 20B:
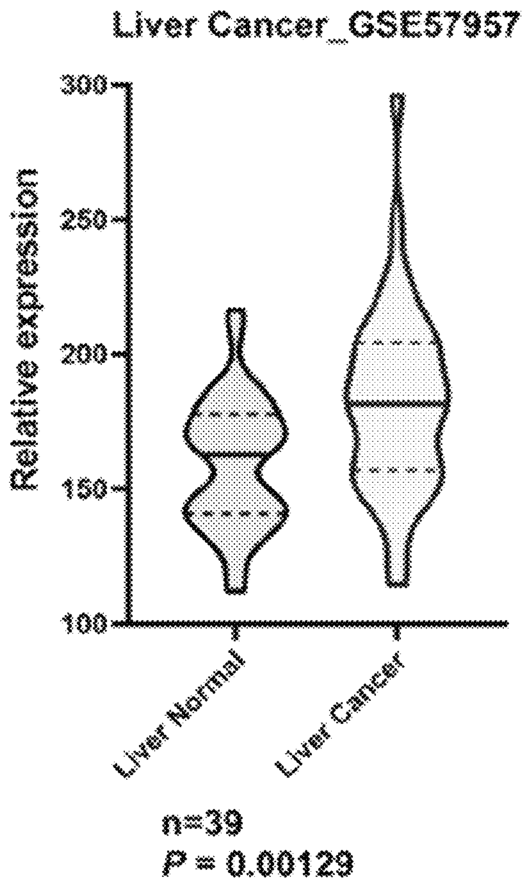

The compounds described herein were tested for their ability to inhibit the viability of human NOMO-1 AML cells. As shown in FIG. 19, Compound (G) had an IC50=736.1 nM. Compound H had an IC50=931 nM. Compound (E) had an IC50=20.59 nM. Compound D had an IC50=1.396 nM. Compound (F) had an IC50=1.55 nM. Cell viability. NOMO-1 cells were seeded into 96-well plate in the concentration of 10,000 cells/well and treated with compounds in triplicates for 72 h. Cell viability was assessed by CellTiter 96 Non-Radioactive Cell Proliferation Assay (MTT, G4100, Promega) following the manufacturer's protocols.

Example 8

Figure 22A:
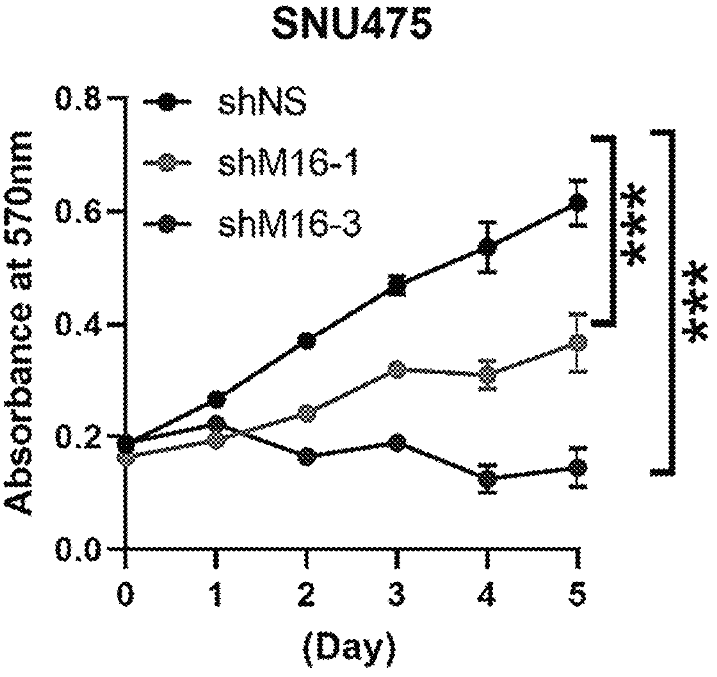
FIGS. 22A-22B show that knockdown of METTL16 significantly inhibited the proliferation/growth, migration and invasion of human liver cancer cells (in vitro studies).
Figure 22B:
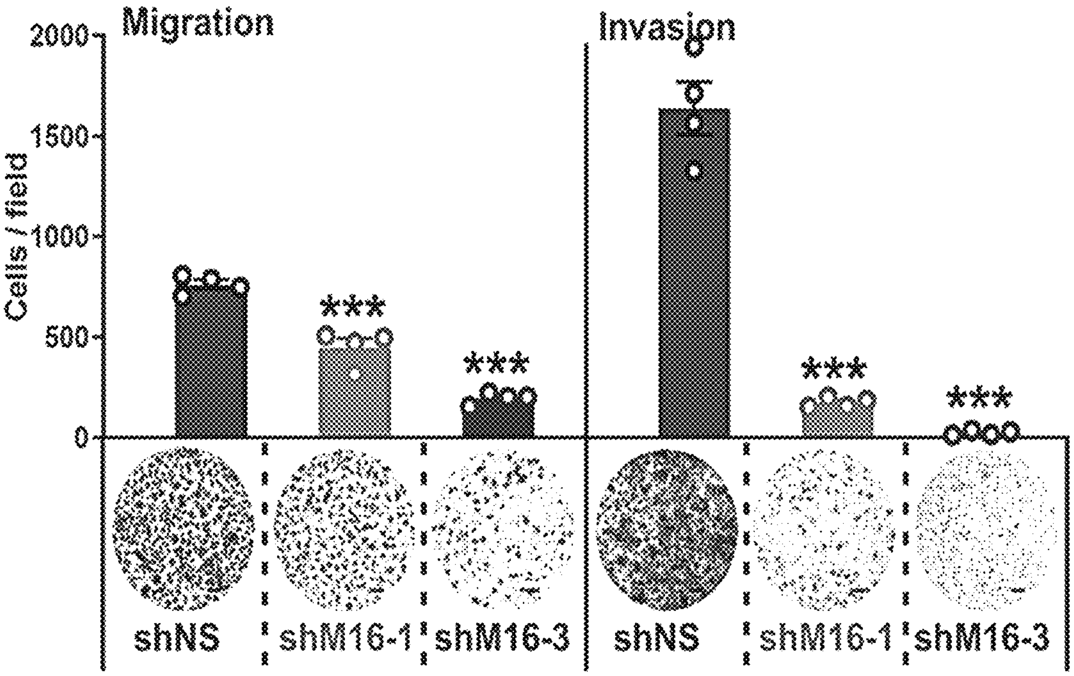
Figures 23A, 23B, 23C:
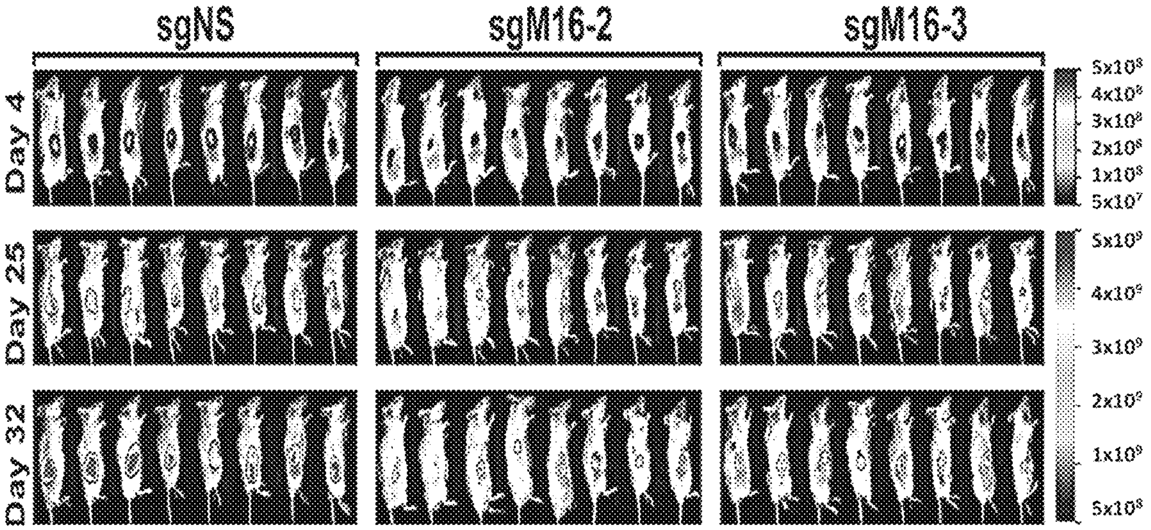
FIGS. 23A-23E Knockdown of METTL16 significantly inhibited human liver cancer progression in xenograft recipient mice in vivo.
Figure 23D:
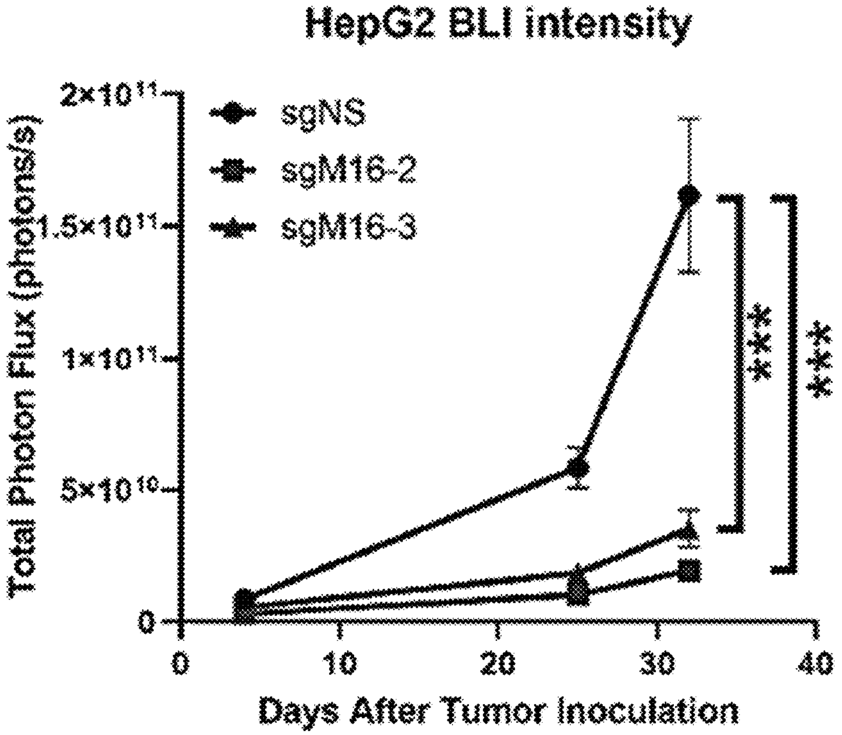
Figure 23E:
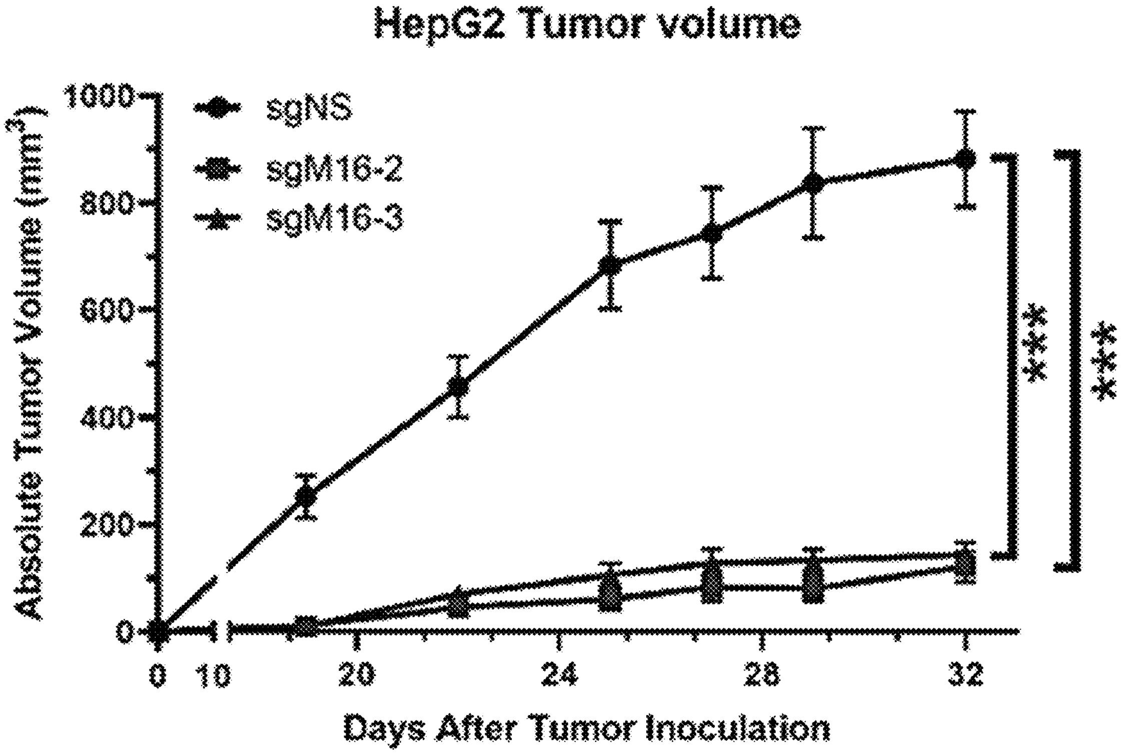

FIGS. 22A-22B show that knockdown of METTL16 significantly inhibited the proliferation/growth, migration and invasion of human liver cancer cells (in vitro studies).

Determination of cell proliferation via MTT assay. In vitro assessment of cell proliferation was measured by CellTiter 96 Non-Radioactive Cell Proliferation Assay (MTT, G400, Promega). SNU475 cells were infected with shMETTL16 lentivirus and selected with 2 μg/mL puromycin for 1 week to generate stable knockdown cells. The cells were seeded into 96-well tissue culture plates at a cell density of $5\times10^3$ cells per well, respectively. Based on the manufacture's recommendation, 15 μL of MTT solution was added into each well at a series of predetermined time points. After incubation at 37° C. for 3-4 hours, 100 μL solubilization/Stop solution was added to quench the reaction. Finally, the absorbance at 570 nm was recorded using a microplate reader.

Transwell migration and invasion assay. Transwell assays were carried out using Corning transwell permeable inserts (pore size, 8 μm, 07-200-150, Fisher Scientific) in 24-well plate. SNU475 cells with METTL16 knockdown were dissociated and resuspended in serum-free medium. For the migration assay, $5\times10^4$ cells were inoculated in the upper chamber in 200 μL serum-free medium, 600 μL completed medium with 10% FBS was added to the lower chamber. For the invasion assay, the permeable inserts were carefully pre-coated with 70 μL, 1:8 diluted Matrigel (356234, Corning), and incubated in 37° C. for three hours. Then $1\times10^5$ cells in serum-free medium were carefully layered onto the Matrigel matrix. The plates were incubated in a humidified tissue culture incubator at 37° C., 5% $CO_2$ atmosphere. After incubation of 24 hours for migration and 48 hours for invasion, the non-migrated cells were wiped and the upper chambers were immersed in 5% formaldehyde solution for 5 minutes. Each insert was stained with 0.1% crystal violet for 10 minutes and then rinsed with PBS. After the inserts dried completely, random fields were captured under a microscope and cells were counted. All the experiments were repeated at least three times.

Example 9

Figure 24A:
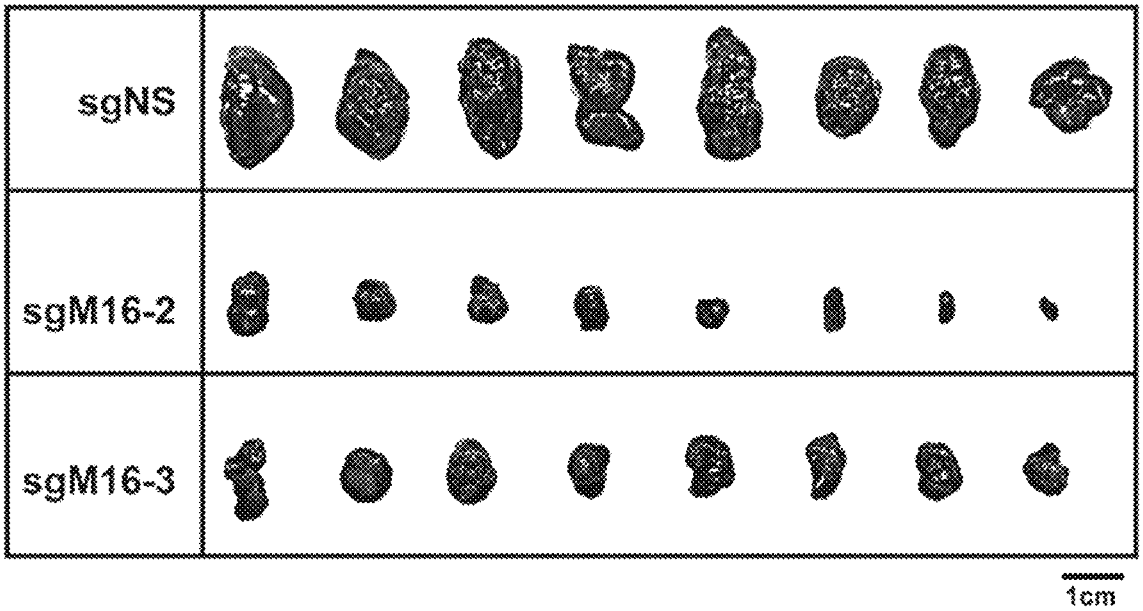
FIGS. 24A-24B show that knockdown of METTL16 significantly reduced tumor sizes in mice.
Figure 24B:
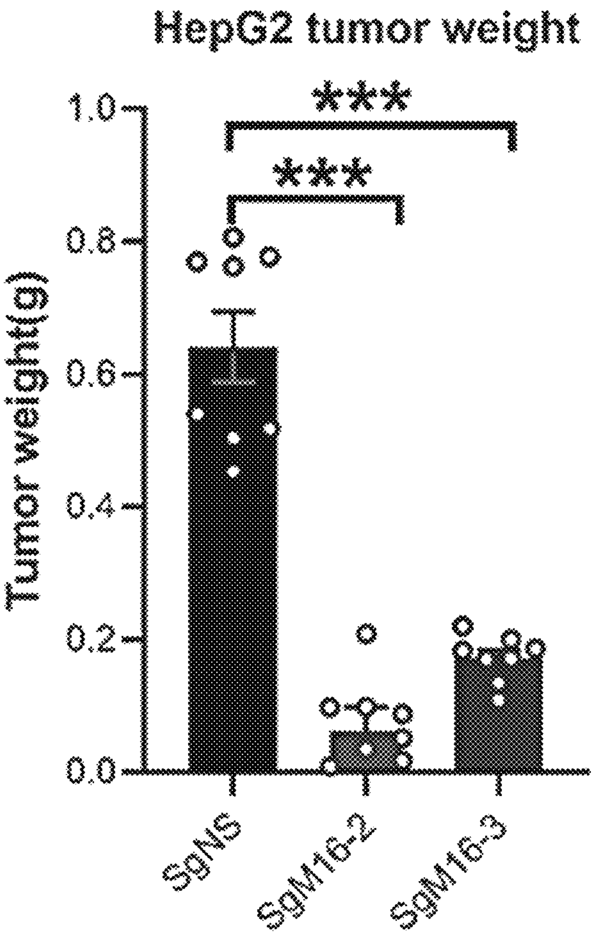

NSG mice model bearing subcutaneous tumors. NOD-SCID IL2Rγ-null (NSG) mice were purchased from the Jackson Laboratory (Stock No: 005557) and maintained at the core facilities of City of Hope. All animal care and procedures were conducted in congruent with federal and state government guidelines and Institutional Animal Care and Use Committee (IACUC) protocols approved by City of Hope. The single Cas9 clone of HepG2 cells was established and selected with 5 μg/mL blasticidin, and infected with pLenti-CMV-Puro-LUC to stably express luciferase gene via selection with 2 μg/mL puromycin. Then, the Cas9-LUC-HepG2 cells were infected with pLenti-sgMETTL16-hygromycin or scramble control and selected with 1 mg/mL hygromycin. The stable cell lines ($1\times10^6$) were injected subcutaneously into 5-8 weeks-old NSG mice. The size of tumor was measured using a caliper and the volume was calculated as (width×width×length/2) $mm^3$. In vivo bioluminescence imaging was applied to measure the tumor progression as previously described. Mice were euthanized when the tumor volume exceeded 1000 $mm^3$. As shown in FIGS. 24A-24B, the knockdown of METTL16 significantly reuded liver tumor sizes in mice.

The section headings used herein are for organizational purposes only and are not to be construed as limiting the subject matter described. All documents, or portions of documents, cited in the application are hereby expressly incorporated by reference in their entirety for any purpose.

While various embodiments and aspects are shown and described herein, it will be obvious to those skilled in the art that such embodiments and aspects are provided by way of example only. Numerous variations, changes, and substitutions will now occur to those skilled in the art. Various alternatives to the embodiments and aspects described herein may be used.

What is claimed is:

1. A method for treating liver cancer, lymphoma, cervical cancer, pancreatic cancer, or glioblastoma in a human patient in need thereof, the method comprising:

(i) detecting an elevated expression level of METTL16 relative to a control in a biological sample from the human patient, wherein the control is a human patient that does not have cancer, and wherein the METTL16 is expressed by the liver cancer, lymphoma, cervical cancer, pancreatic cancer, or glioblastoma; and (ii) administering an effective amount of the compound of Formula (I) or a pharmaceutically acceptable salt thereof to the human patient having the elevated expression level of METTL16 in the biological sample in step (i); wherein the compound of Formula (I) is:

(I)

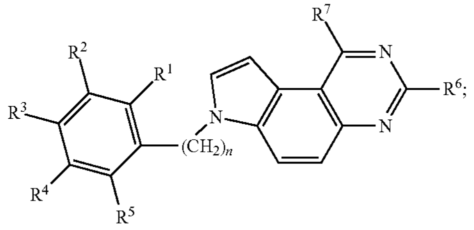

wherein:

n is an integer from 0 to 6;

$R^1$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{1A}$, —$NR^{1A}R^{1B}$, —$COOR^{1A}$, —$CONR^{1A}R^{1B}$, —$NO_2$, —$SR^{1A}$, —$SO_3R^{1A}$, —$SO_4R^{1A}$, —$SO_2NR^{1A}R^{1B}$, —$NHNR^{1A}R^{1B}$, —$ONR^{1A}R^{1B}$, —$NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{2A}$, —$NR^{2A}R^{2B}$, —$COOR^{2A}$, —$CONR^{2A}R^{2B}$, —$NO_2$, —$SR^{2A}$, —$SO_3R^{2A}$, —$SO_4R^{2A}$, —$SO_2NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{4A}$ and $R^{4B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3RSA$, —$SO_4R^{5A}$, —$SO_2NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{6A}$, —$NR^{6A}R^{6B}$, —$COOR^{6A}$, —$CONR^{6A}R^{6B}$, —$NO_2$, —$SR^{6A}$, —$SO_3R^{6A}$, —$SO_4R^{6A}$, —$SO_2NR^{6A}R^{6B}$, —$NHNR^{6A}R^{6B}$, —$ONR^{6A}R^{6B}$, —$NHC(O)NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OR^{7A}$, $-NR^{7A}R^{7B}$, $-COOR^{7A}$, $-CONR^{7A}R^{7B}$, $-NO_2$, $-SR^{7A}$, $-SO_3R^{7A}$, $-SO_4R^{7A}$, $-SO_2NR^{7A}R^{7B}$, $-NHNR^{7A}R^{7B}$, $-ONR^{7A}R^{7B}$, $-NHC(O)NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{7A}$ and $R^{7B}$ are each independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The method of claim 1, wherein:

$R^1$ is hydrogen, halogen, $-CN-OR^{1A}$, $-NR^{1A}R^{1B}$, $-COOR^{1A}$, $-CONR^{1A}R^{1B}$, $-NO_2$, $-NHNR^{1A}R^{1B}$, $-ONR^{1A}R^{1B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl;

$R^2$ is hydrogen, halogen, $-CN$, $-OR^{2A}$, $-NR^{2A}R^{2B}$, $-COOR^{2A}$, $-CONR^{2A}R^{2B}$, $-NO_2$, $-NHNR^{2A}R^{2B}$, $-ONR^{2A}R^{2B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl;

$R^3$ is hydrogen, halogen, $-CN$, $-OR^{3A}$, $-NR^{3A}R^{3B}$, $-COOR^{3A}$, $-CONR^{3A}R^{3B}$, $-NO_2$, $-NHNR^{3A}R^{3B}$, $-ONR^{3A}R^{3B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl;

$R^4$ is hydrogen, halogen, $-CN$, $-OR^{4A}$, $-NR^{4A}R^{4B}$, $-COOR^{4A}$, $-CONR^{4A}R^{4B}$, $-NO_2$, $-NHNR^{4A}R^{4B}$, $-ONR^{4A}R^{4B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl;

$R^5$ is hydrogen, halogen, $-CN$, $-OR^{5A}$, $-NR^{5A}R^{5B}$, $-COOR^{5A}$, $-CONR^{5A}R^{5B}$, $-NO_2$, $-NHNR^{5A}R^{5B}$, $-ONR^{5A}R^{5B}$, substituted or unsubstituted alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl;

$R^6$ is hydrogen, halogen, $-OR^{6A}$, $-NR^{6A}R^{6B}$, $-COOR^{6A}$, $-CONR^{6A}R^{6B}$, $-NO_2$, $-NHNR^{6A}R^{6B}$, $-ONR^{6A}R^{6B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl;

$R^7$ is hydrogen, halogen, $-OR^{7A}$, $-NR^{7A}R^{7B}$, $-COOR^{7A}$, $-CONR^{7A}R^{7B}$, $-NO_2$, $-NHNR^{7A}R^{7B}$, $-ONR^{7A}R^{7B}$, substituted or unsubstituted $C_1$-$C_6$ alkyl, substituted or unsubstituted 2 to 6 membered heteroalkyl, substituted or unsubstituted 5 or 6-membered cycloalkyl, substituted or unsubstituted 5 or 6-membered heterocycloalkyl, substituted or unsubstituted 5 or 6-membered aryl, or substituted or unsubstituted 5 or 6-membered heteroaryl.

3. The method of claim 1, wherein $R^5$ is $C_1$-$C_6$ alkyl substituted with 1 or 2 substituents independently selected from the group consisting of $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, and unsubstituted $C_1$-$C_4$ alkyl.

4. The method of claim 1, wherein:

$R^{1A}$ and $R^{1B}$ are each independently hydrogen, halogen, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted $C_1$-$C_6$ alkyl, or substituted or unsubstituted 2 to 6 membered heteroalkyl;

$R^{2A}$ and $R^{2B}$ are each independently hydrogen, halogen, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted $C_1$-$C_6$ alkyl, or substituted or unsubstituted 2 to 6 membered heteroalkyl;

$R^{3A}$ and $R^{3B}$ are each independently hydrogen, halogen, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted $C_1$-$C_6$ alkyl, or substituted or unsubstituted 2 to 6 membered heteroalkyl;

$R^{4A}$ and $R^{4B}$ are each independently hydrogen, halogen, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted $C_1$-$C_6$ alkyl, or substituted or unsubstituted 2 to 6 membered heteroalkyl;

$R^{5A}$ and $R^{5B}$ are each independently hydrogen, halogen, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted $C_1$-$C_6$ alkyl, or substituted or unsubstituted 2 to 6 membered heteroalkyl;

$R^{6A}$ and $R^{6B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl; and $R^{7A}$ and $R^{7B}$ are each independently hydrogen, halogen, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, or substituted or unsubstituted 2 to 6 membered heteroalkyl.

5. The method of claim 1, wherein:

(i) $R^1$, $R^2$, and $R^4$ are hydrogen; and $R^3$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, or unsubstituted $C_1$-$C_4$ alkyl; or (ii) $R^1$, $R^3$, and $R^4$ are hydrogen; and $R^2$, $R^6$, and $R^7$ are each independently —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, or unsubstituted $C_1$-$C_4$ alkyl.

6. The method of claim 1, wherein the compound of Formula (I) is a compound of Formula (II) or a pharmaceutically acceptable salt thereof; wherein the compound of Formula (II) is (II)

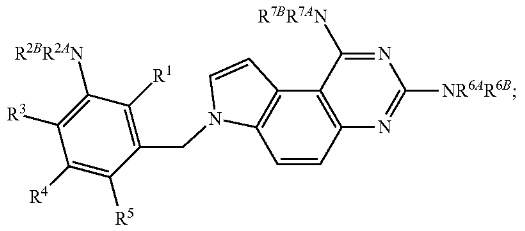

wherein $R^1$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{1A}$, —$NR^{1A}R^{1B}$, —$COOR^{1A}$, —$CONR^{1A}R^{1B}$, —$NO_2$, —$SR^{1A}$, —$SO_3R^{1A}$, —$SO_4R^{1A}$, —$SO_2NR^{1A}R^{1B}$, —$NHNR^{1A}R^{1B}$, —$ONR^{1A}R^{1B}$, —NHC(O)$NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl;

$R^3$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{3A}$, —$NR^{3A}R^{3B}$, —$COOR^{3A}$, —$CONR^{3A}R^{3B}$, —$NO_2$, —$SR^{3A}$, —$SO_3R^{3A}$, —$SO_4R^{3A}$, —$SO_2NR^{3A}R^{3B}$, —$NHNR^{3A}R^{3B}$, —$ONR^{3A}R^{3B}$, —NHC(O)$NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —NHC(O)$NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{4A}$ and $R^{4B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

7. The method of claim 1, wherein the compound of Formula (I) is a compound of Formula (III) or a pharmaceutically acceptable salt thereof; wherein the compound of Formula (III) is (III)

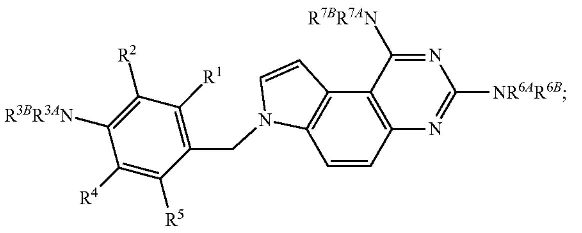

wherein $R^1$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{1A}$, —$NR^{1A}R^{1B}$, —$COOR^{1A}$, —$CONR^{1A}R^{1B}$, —$NO_2$, —$SR^{1A}$, —$SO_3R^{1A}$, —$SO_4R^{1A}$, —$SO_2NR^{1A}R^{1B}$, —$NHNR^{1A}R^{1B}$, —$ONR^{1A}R^{1B}$, —$NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{2A}$, —$NR^{2A}R^{2B}$, —$COOR^{2A}$, —$CONR^{2A}R^{2B}$, —$NO_2$, —$SR^{2A}$, —$SO_3R^{2A}$, —$SO_4R^{2A}$, —$SO_2NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl;

$R^4$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{4A}$, —$NR^{4A}R^{4B}$, —$COOR^{4A}$, —$CONR^{4A}R^{4B}$, —$NO_2$, —$SR^{4A}$, —$SO_3R^{4A}$, —$SO_4R^{4A}$, —$SO_2NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{4A}$ and $R^{4B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, -$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

8. The method of claim 1, wherein the compound of Formula (I) is a compound of Formula (IV) or a pharmaceutically acceptable salt thereof, wherein the compound of Formula (IV) is (IV)

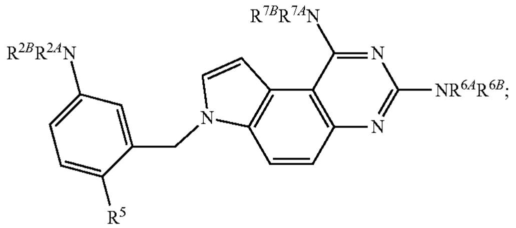

wherein $R^{2A}$ and $R^{2B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl;

$R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl; and $R^{7A}$ and $R^{7B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

9. The method of claim 1, wherein the compound of Formula (I) is a compound of Formula (V) or a pharmaceutically acceptable salt thereof; wherein the compound of Formula (V) is (V)

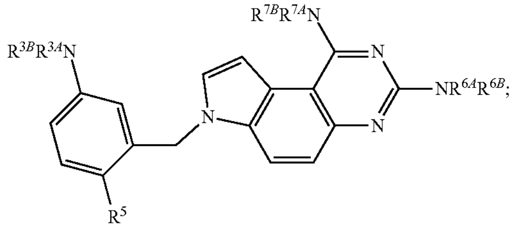

wherein $R^{3A}$ and $R^{3B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl;

$R^5$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —$OR^{5A}$, —$NR^{5A}R^{5B}$, —$COOR^{5A}$, —$CONR^{5A}R^{5B}$, —$NO_2$, —$SR^{5A}$, —$SO_3R^{5A}$, —$SO_4R^{5A}$, —$SO_2NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5A}$ and $R^{5B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6A}$ and $R^{6B}$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl;

$R^{7A}$ and $R^{7B}$ are each independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

10. The method of claim 1, wherein the compound of Formula (I) is a compound of Formula (VI) or a pharmaceutically acceptable salt thereof; wherein the compound of Formula (VI) is (VI)

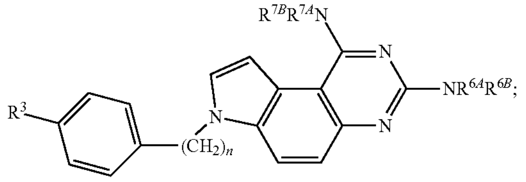

$R^{3A}$, $R^{3B}$, $R^{6A}$, $R^{6B}$, $R^{7A}$, and $R^{7B}$ are each independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted $C_1$-$C_6$ alkyl, substituted or unsubstituted 2 to 6 membered heteroalkyl, substituted or unsubstituted $C_5$-$C_6$ cycloalkyl, substituted or unsubstituted 5 or 6 membered heterocycloalkyl, substituted or unsubstituted $C_5$-$C_6$ aryl, or substituted or unsubstituted 5 to 6 membered heteroaryl.

11. The method of claim 1, wherein the compound of Formula (I) is a compound of Formula (A), a compound of Formula (B), a compound of Formula (C), a compound of Formula (D), a compound of Formula (E), a compound of Formula (F), or a pharmaceutically acceptable salt of one of the foregoing; wherein the compound of Formula (A) is (A)

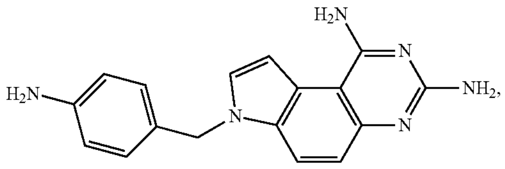

the compound of Formula (B) is (B)

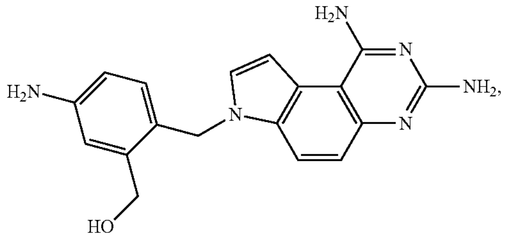

the compound of Formula (C) is (C)

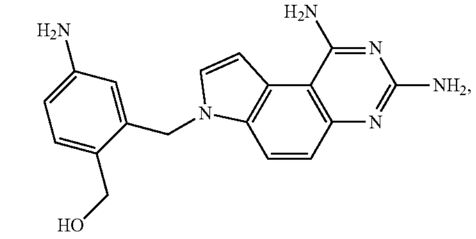

the compound of Formula (D) is (D)

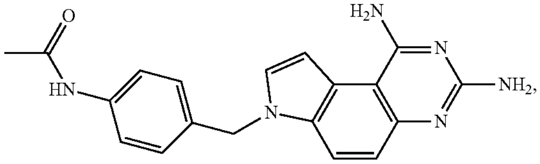

the compound of Formula (E) is, and (E)

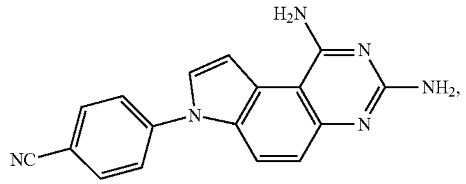

the compound of Formula (F) is (F)

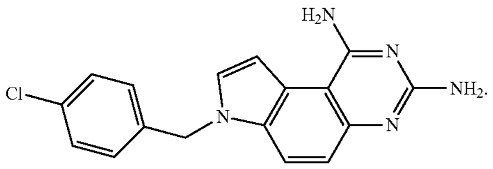

* * * * *